United States Patent [19]

Reitz et al.

[11] Patent Number: 5,238,952

[45] Date of Patent: Aug. 24, 1993

[54] N-SUBSTITUTED IMIDAZOL-2-ONE COMPOUNDS FOR TREATMENT OF CIRCULATORY DISORDERS

[75] Inventors: David B. Reitz, Chesterfield; Robert E. Manning, St. Louis, both of Mo.

[73] Assignee: G. D. Searle & Co., Chicago, Ill.

[21] Appl. No.: 828,546

[22] Filed: Jan. 28, 1992

Related U.S. Application Data

[62] Division of Ser. No. 606,806, Oct. 31, 1990, Pat. No. 5,087,634.

[51] Int. Cl.$^5$ .............. A61K 31/415; A61K 31/41; C07D 233/70; C07D 257/04
[52] U.S. Cl. ..................... 514/381; 514/392; 548/253; 548/316.4
[58] Field of Search ............. 548/250, 253, 316.4; 514/381, 392

[56] References Cited

U.S. PATENT DOCUMENTS

| | | | |
|---|---|---|---|
| 4,816,463 | 3/1989 | Blankley et al. | 514/293 |
| 4,880,804 | 11/1989 | Carini et al. | 514/234.5 |

FOREIGN PATENT DOCUMENTS

| | | | |
|---|---|---|---|
| 621842 | 2/1963 | Belgium | 548/263.2 |
| 806146 | 12/1974 | Belgium | 548/263.2 |
| 7180 | 10/1981 | European Pat. Off. | 548/263.2 |
| 253310 | 1/1988 | European Pat. Off. | 548/253 |
| 283310 | 9/1988 | European Pat. Off. | |
| 323841 | 7/1989 | European Pat. Off. | 548/253 |
| 412594 | 2/1991 | European Pat. Off. | 548/263.2 |
| 160447 | 8/1983 | German Democratic Rep. | 548/263.2 |

OTHER PUBLICATIONS

P. C. Wong et al, *J. Pharmacol. Exp. Ther.*, 247(1), 1-7 (1988).
A. T. Chiu et al, *European J. Pharmacol.*, 157, 13-21 (1988).
A. T. Chiu et al *J. Pharmacol. Exp. Ther.*, 250(3), 867-874 (1989).
Progress in Drug Research, vol. 10, Denkewalter et al., pp. 510-512. 1966.

*Primary Examiner*—Mary C. Lee
*Assistant Examiner*—Joseph K. McKane
*Attorney, Agent, or Firm*—J. Timothy Keane

[57] ABSTRACT

A class of N-substituted imidazol-2-one compounds is described for use in treatment of circulatory disorders. Compounds of particular interest are angiotensin II antagonists of the formula

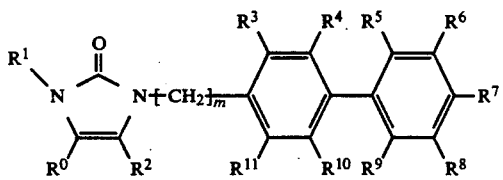

wherein m is one; wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, cyclohexylethyl, cyclohexanoyl, 1-oxo-2-cyclohexylethyl, benzoyl, 1-oxo-2-phenethyl, 1-oxopropyl, 1-oxobutyl, 1-oxopentyl and 2-hydroxybutyl; wherein $R^0$ is selected from hydrido, methyl, fluoro, chloro, monofluoromethyl, difluoromethyl, trifluoromethyl, formyl, carboxyl and dimethoxymethyl; wherein $R^2$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, propylthio, butylthio, and hydroxyalkyl; wherein each of $R^3$, $R^4$, $R^6$, $R^7$, $R^8$, $R^{10}$ and $R^{11}$ is hydrido; with the proviso that at least one of $R^5$ and $R^9$ must be selected from COOH, SH, $PO_3H_2$, $SO_3H$, $CONHNH_2$, $CONHNHSO_2CF_3$, OH,

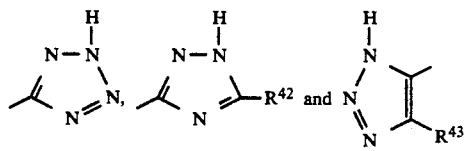

wherein each of $R^{42}$ and $R^{43}$ is independently selected from chloro, cyano, nitro, trifluoromethyl, methoxycarbonyl and trifluoromethylsulfonyl; or a tautomer thereof or a pharmaceutically-aceptable salt thereof. These compounds are particularly useful in treatment or control of hypertension and congestive heart failure.

10 Claims, No Drawings

N-SUBSTITUTED IMIDAZOL-2-ONE COMPOUNDS FOR TREATMENT OF CIRCULATORY DISORDERS

This is a divisional of application Ser. No. 07/606,806 filed Oct. 31, 1990 U.S. Pat. No. 5,087,634.

FIELD OF THE INVENTION

Non-peptidic N-substituted imidazol-2-one compounds are described for use in treatment of circulatory disorders such as hypertension and congestive heart failure. Of particular interest are angiotensin II antagonist compounds provided by imidazol-2-ones having a biphenylmethyl moiety attached to a nitrogen atom of the imidazol-2-one.

BACKGROUND OF THE INVENTION

The renin-angiotensin system is one of the hormonal mechanisms involved in regulation of pressure/volume homeostasis and in expression of hypertension. Activation of the renin-angiotensin cascade begins with renin secretion from the juxtaglomerular apparatus of the kidney and culminates in the formation of angiotensin II, the primary active species of this system. This octapeptide, angiotensin II, is a potent vasoconstrictor agent and also produces other physiological effects such as promoting aldosterone secretion, promoting sodium and fluid retention, inhibiting renin secretion, increasing sympathetic nervous system activity, increasing vasopressin secretion, causing positive cardiac inotropic effect and modulating other hormonal systems.

Previous studies have shown that antagonizing angiotensin II at its receptors is a viable approach to inhibit the renin-angiotensin system, given the pivotal role of this octapeptide which mediates the actions of the renin-angiotensin system through interaction with various tissue receptors. There are several known angiotensin II antagonists, most of which are peptidic in nature. Such peptidic compounds are of limited use due to their lack of oral bioavailability or their short duration of action. Also, commercially-available peptidic angiotensin II antagonists (e.g., Saralasin) have a significant residual agonist activity which further limit their therapeutic application.

Non-peptidic compounds with angiotensin II antagonist properties are known. For example, the sodium salt of 2-n-butyl-4-chloro-1-(2-chlorobenzyl)imidazole-5-acetic acid has specific competitive angiotensin II antagonist activity as shown in a series of binding experiments, functional assays and in vivo tests [P. C. Wong et al, *J. Pharmacol. Exp. Ther.*, 247 (1), 1-7 (1988)]. Also, the sodium salt of 2-butyl-4-chloro-1-(2-nitrobenzyl-)imidazole-5-acetic acid has specific competitive angiotensin II antagonist activity as shown in a series of binding experiments, functional assays and in vivo tests [A. T. Chiu et al, *European J. Pharmacol.*, 157, 1321 (1988)]. A family of 1-benzylimidazole-5-acetate derivatives has been shown to have competitive angiotensin II antagonist properties [A. T. Chiu et al, *J. Pharmacol. Exp. Ther.*, 250(3), 867-874 (1989)]. U.S. Pat. No. 4,816,463 to Blankey et al describes a family of 4,5,6,7-tetrahydro-1H-imidazo(4,5-c)-tetrahydro-pyridine derivatives useful as antihypertensives, some of which are reported to antagonize the binding of labelled angiotensin II to rat adrenal receptor preparation and thus cause a significant decrease in mean arterial blood pressure in conscious hypertensive rats. EP No. 253,310, published 20 Jan. 1988, describes a series of aralkyl imidazole compounds, including in particular a family of biphenylmethyl substituted imidazoles, as antagonists to the angiotensin II receptor. EP No. 323,841 published 12 Jul. 1989 describes four classes of angiotensin II antagonists, namely, biphenylmethylpyrroles, biphenylmethylpyrazoles, biphenylmethyl-1,2,3-triazoles and biphenylmethyl 4-substituted-4H-1,2,4-triazoles, including the compound 3,5-dibutyl-4-[(2'-carboxybiphenyl-4-yl)methyl]-4H-1,2,4-triazole. U.S. Pat. No. 4,880,804 to Carini et al describes a family of biphenylmethylbenzimidazole compounds as angiotensin II receptor blockers for use in treatment of hypertension and congestive heart failure.

There are several families of known compounds having one or two oxo substituents on a triazole ring. For example, East German Patent No. 160,447 published 3 Aug. 1983 describes a family of 1,2,4-triazolin-5-one compounds, specifically 2,4-dihydro-4,5-bis(phenylmethyl)-3H-1,2,4-triazol-3-one, for use as herbicides. Belgian Patent No. 806,146 published 16 Oct. 1972 describes a family of triazolinone compounds, including the compound (3-(4-m-chlorophenyl-1-piperazinyl)-propyl)-3,4-diethyl-1,2,4-triazolin-5-one, having tranquilizer, hypotensive and analgesic activities. Belgian Patent No. 631,842 published 28 Feb. 1963 describes a family of 1,2,4-triazolones having hypnotic, tranquilizer, narcotic, sedative and analgetic activities, which includes a class of 4-N-aralkyl-1,2,4-triazol-5-one compounds. EP #7,180 published 15 Jun. 1978 describes a family of 1,2-disubstituted-4-alkyl-1,2,4-triazolidine-3,5-dione compounds having a wide variety of activities, such as antiulcer, bronchodilator, antifertility and cardiovascular-related activities which include antihypertensive, antiarrhythmic, platelet aggregation inhibition and smooth muscle activities. EP #283,310 published 18 Mar. 1987 describes a family of $N^1$-diarylmethyl-$N^2$-aminoalkyl-diaza-heterocyclic derivatives for treating cerebral vascular and ischmic diseases and for protecting against anoxia.

DESCRIPTION OF THE INVENTION

A class of N-substituted biphenylalkyl imidazol-2-one compounds useful in treating circulatory disorders, particularly cardiovascular disorders, is defined by Formula I:

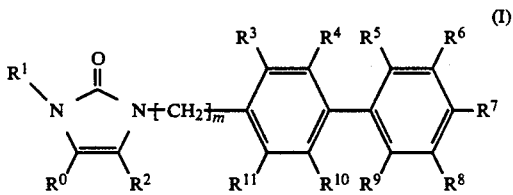

wherein m is a number selected from one to four, inclusive;

wherein $R^1$ is selected from alkyl, hydroxyalkyl, haloalkyl, cycloalkyl, cycloalkylalkyl, formyl, aralkyl, aryl, aroyl, alkoxyalkyl, alkylcarbonyl, alkylcarbonylalkyl, cycloalkylcarbonyl, cycloalkylalkylcarbonyl, aralkylcarbonyl, alkoxycarbonyl, alkenyl, cycloalkenyl, aralkoxycarbonyl, alkynyl, alkylthiocarbonyl, alkylthiothiocarbonyl, arylthiocarbonyl, arylthiothiocarbonyl, aralkylthiocarbonyl, alkylthiocarbonyl, alkylsulfinyl, alkylsulfonyl, aralkylsulfinyl, aralkylsulfonyl, arylsulfinyl, arylsulfonyl, heteroaryl having one or more ring atoms selected from oxygen, sulfur and nitrogen atoms, and amido radicals of the formula

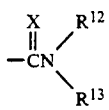

wherein X is oxygen atom or sulfur atom;

wherein each of $R^{12}$ and $R^{13}$ is independently selected from hydrido, alkyl, cycloalkyl, cyano, amino, monoalkylamino, dialkylamino, hydroxyalkyl, cycloalkylalkyl, alkoxyalkyl, aralkyl and aryl, and wherein $R^{12}$ and $R^{13}$ taken together may form a heterocyclic group having five to seven ring members including the nitrogen atom of said amido radical and which heterocyclic group may further contain one or more hetero atoms as ring members selected from oxygen, nitrogen and sulfur atoms and which heterocyclic group may be saturated or partially unsaturated; wherein each of $R^{12}$ and $R^{13}$ taken together may form an aromatic heterocyclic group having five ring members including the nitrogen atom of said amido radical and which aromatic heterocyclic group may further contain one or more additional nitrogen atoms;

wherein each of $R^0$ and $R^2$ through $R^{11}$ is independently selected from hydrido, alkyl, hydroxyalkyl, formyl, halo, haloalkyl, cycloalkyl, cycloalkylalkyl, cycloalkylhaloalkyl, cycloalkylcarbonyl, alkoxy, aralkyl, aralkylhaloalkyl, aryl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptothiocarbonyl, mercaptoalkyl, alkoxycarbonyloxy, alkylthio, cycloalkylthio, cycloalkylalkylthio, alkylthiocarbonyl, alkylcarbonylthio, alkylthiocarbonyloxy, alkylthiocarbonylthio, alkylthiothiocarbonyl, alkylthiothiocarbonylthio, arylthio, arylthiocarbonyl, arylcarbonylthio, arylthiocarbonyloxy, arylthiocarbonylthio, arylthiothiocarbonyl, arylthiothiocarbonylthio, aralkylthio, aralkylthiocarbonyl, aralkylcarbonylthio, aralkylthiocarbonyloxy, aralkylthiocarbonylthio, alkylthiocarbonyl, aralkylthiocarbonylthio, mercapto, alkylsulfinyl, alkylsulfonyl, aralkylsulfinyl, aralkylsulfonyl, arylsulfinyl, arylsulfonyl, phthalimido, phthalimidoalkyl, heteroaryl, heteroarylalkyl, cycloheteroalkyl, cycloheteroalkylalkyl and cycloheteroalkylcarbonylalkyl wherein each of said heteroaryl- and cyclohetero-containing groups has one or more ring atoms selected from oxygen, sulfur and nitrogen atoms, and wherein each of $R^0$ and $R^2$ through $R^{11}$ may be further independently selected from amino and amido radicals of the formula

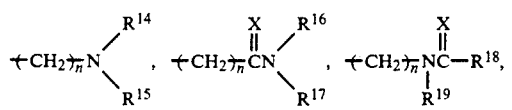

-continued

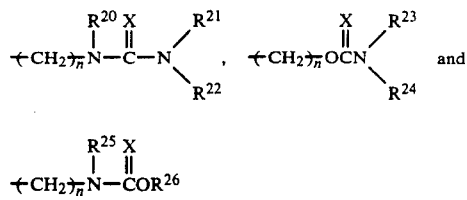

wherein X is oxygen atom or sulfur atom;

wherein each n is a number independently selected from zero to six, inclusive;

wherein each of $R^{14}$ through $R^{26}$ is independently selected from hydrido, alkyl, cycloalkyl, cyano, amino, monoalkylamino, dialkylamino, hydroxyalkyl, cycloalkylalkyl, alkoxyalkyl, aralkyl and aryl, and wherein $R^{14}$ and $R^{15}$ taken together, $R^{16}$ and $R^{17}$ taken together, $R^{18}$ and $R^{19}$ taken together, $R^{21}$ and $R^{22}$ taken together and $R^{23}$ and $R^{24}$ taken together may each form a heterocyclic group having five to seven ring members including the nitrogen atom of said amino or amido radical and which heterocyclic group may further contain one or more hetero atoms as ring members selected from oxygen, nitrogen and sulfur atoms and which heterocyclic group may be saturated or partially unsaturated; wherein $R^{14}$ and $R^{15}$ taken together, $R^{16}$ and $R^{17}$ taken together, $R^{21}$ and $R^{22}$ taken together and $R^{23}$ and $R^{24}$ taken together may each form an aromatic heterocyclic group having five ring members including the nitrogen atom of said amino or amido radical and which aromatic heterocyclic group may further contain one or more additional nitrogen atoms;

and wherein each of $R^0$ and $R^3$ through $R^{11}$ may be further independently selected from hydroxy and acidic moieties of the formula $$-Y_nA$$

wherein n is a number selected from zero through three, inclusive, and wherein A is an acidic group selected to contain at least one acidic hydrogen atom, and the amide, ester and salt derivatives of said acidic moieties; wherein Y is a spacer group independently selected from one or more of alkyl, cycloalkyl, cycloalkylalkyl, alkenyl, alkynyl, aryl, aralkyl and heteroaryl having one or more ring atoms selected from oxygen, sulfur and nitrogen atoms;

and wherein any of the foregoing $R^0$ through $R^{26}$, Y and A groups having a substitutable position may be substituted by one or more groups independently selected from hydroxy, alkyl, alkenyl, alkynyl, aralkyl, hydroxyalkyl, haloalkyl, halo, oxo, alkoxy, aryloxy, aralkoxy, aralkylthio, alkoxyalkyl, cycloalkyl, cycloalkylalkyl, aryl, aroyl, cycloalkenyl, cyano, cyanoamino, nitro, alkylcarbonyloxy, alkoxycarbonyloxy, alkylcarbonyl, alkoxycarbonyl, aralkoxycarbonyl, carboxyl, mercapto, mercaptocarbonyl, alkylthio, arylthio, alkylthiocarbonyl, alkylsulfinyl, alkylsulfonyl, haloalkylsulfonyl, aralkylsulfinyl, aralkylsulfonyl, arylsulfinyl, arylsulfonyl, heteroaryl having one or more ring atoms selected from oxygen, sulfur and nitrogen atoms, and amino and amido radicals of the formula

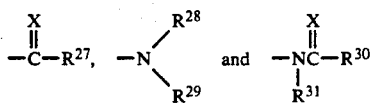

wherein X is oxygen atom or sulfur atom; wherein each of $R^{27}$ through $R^{31}$ is independently selected from hydrido, alkyl, cycloalkyl, cycloalkylalkyl, aralkyl, aryl, $DR^{32}$ and

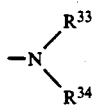

wherein D is selected from oxygen atom and sulfur atom and $R^{32}$ is selected from hydrido, alkyl, cycloalkyl, cycloalkylalkyl, aralkyl and aryl; wherein each of $R^{27}$, $R^{28}$, $R^{29}$, $R^{30}$, $R^{31}$, $R^{33}$ and $R^{34}$ is independently selected from hydrido, alkyl, cycloalkyl, cyano, hydroxyalkyl, haloalkyl, cycloalkylalkyl, alkoxyalkyl, alkylcarbonyl, alkoxycarbonyl, carboxyl, alkylsulfinyl, alkylsulfonyl, arylsulfinyl, arylsulfonyl, haloalkylsulfinyl, haloalkylsulfonyl, aralkyl and aryl, and wherein each of $R^{27}$, $R^{28}$, $R^{29}$, $R^{30}$, $R^{31}$, $R^{33}$ and $R^{34}$ is further independently selected from amino and amido radicals of the formula

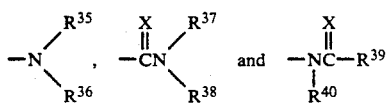

wherein X is oxygen atom or sulfur atom;
wherein each of $R^{35}$, $R^{36}$, $R^{37}$, $R^{38}$, $R^{39}$ and $R^{40}$ is independently selected from hydrido, alkyl, cycloalkyl, cyano, hydroxyalkyl, cycloalkylalkyl, alkoxyalkyl, haloalkylsulfinyl, haloalkylsulfonyl, aralkyl and aryl, and wherein each of $R^{28}$ and $R^{29}$ taken together and each of $R^{30}$ and $R^{31}$ taken together may form a heterocyclic group having five to seven ring members including the nitrogen atom of said amino or amido radical, which heterocyclic group may further contain one or more hetero atoms as ring members selected from oxygen, nitrogen and sulfur atoms and which heterocyclic group may be saturated or partially unsaturated; wherein each of $R^{28}$ and $R^{29}$ taken together and each of $R^{33}$ and $R^{34}$ taken together may form an aromatic heterocyclic group having five ring members including the nitrogen atom of said amino or amido radical and which aromatic heterocyclic group may further contain one or more additional nitrogen atoms; or a tautomer thereof or a pharmaceutically-acceptable salt thereof.

Compounds of Formula I would be useful in treating a variety of circulatory disorders, including cardiovascular disorders, such as hypertension, congestive heart failure and arteriosclerosis, and to treat other disorders such as glaucoma. These compounds would also be useful as adjunctive therapies. For example, compounds of Formula I may be used in combination with other drugs, such as a diuretic, to treat hypertension. Also, compounds of Formula I could be used in conjunction with certain surgical procedures. For example, these compounds could be used to prevent post-angioplasty re-stenosis. Compounds of Formula I are therapeutically effective in treatment of cardiovascular disorders by acting as antagonists to, or blockers of, the angiotensin II (AII) receptor. Compounds of Formula I would be therapeutically effective in treatment of the above-mentioned circulatory and cardiovascular disorders or would be precursors to, or prodrugs of, therapeutically-effective compounds.

The phrase "acidic group selected to contain at least one acidic hydrogen atom", as used to define the $-Y_nA$ moiety, is intended to embrace chemical groups which, when attached to any of the $R^0$ and $R^3$ through $R^{11}$ positions of Formula I, confers acidic character to the compound of Formula I. "Acidic character" means proton-donor capability, that is, the capacity of the compound of Formula I to be a proton donor in the presence of a proton-receiving substance such as water. Typically, the acidic group should be selected to have proton-donor capability such that the product compound of Formula I has a $pK_a$ in a range from about one to about twelve. More typically, the Formula I compound would have a $pK_a$ in a range from about two to about seven. An example of an acidic group containing at least one acidic hydrogen atom is carboxyl group (—COOH). Where n is zero and A is —COOH, in the $-Y_nA$ moiety, such carboxyl group would be attached directly to one of the $R^0$ and $R^3$ through $R^{11}$ positions. The Formula I compound may have one $-Y_nA$ moiety attached at one of the $R^3$ through $R^{11}$ positions, or may have a plurality of such $-Y_nA$ moieties attached at more than one of the $R^0$ and $R^3$ through $R^{11}$ positions, up to a maximum of ten such $-Y_nA$ moieties. There are many examples of acidic groups other than carboxyl group, selectable to contain at least one acidic hydrogen atom. Such other acidic groups may be collectively referred to as "bioisosteres of carboxylic acid" or referred to as "acidic bioisosteres". Specific examples of such acidic bioisosteres are described hereinafter. Compounds of Formula I having the $-Y_nA$ moiety attached at one of positions $R^0$, $R^5$, $R^6$, $R^8$ and $R^9$ would be expected to have preferred properties, while attachment at $R^5$ or $R^9$ would be more preferred.

A preferred class of compounds consists of those compounds of Formula I wherein m is one; wherein $R^1$ is selected from alkyl, hydroxyalkyl, haloalkyl, cycloalkyl, cycloalkylalkyl, aralkyl, aryl, aroyl, alkoxyalkyl, alkylcarbonyl, cycloalkylcarbonyl, cycloalkylalkylcarbonyl, aralkylcarbonyl, alkoxycarbonyl, alkenyl, cycloalkenyl, alkynyl, cycloalkynyl, alkylthiocarbonyl, arylthiocarbonyl, arylthiothiocarbonyl, aralkylthiocarbonyl, alkylsulfonyl, aralkylsulfonyl, arylsulfonyl, heteroaryl having one or more ring atoms selected from oxygen, sulfur and nitrogen atoms, and amido radicals of the formula

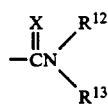

wherein X is oxygen atom or sulfur atom;
wherein each of $R^{12}$ and $R^{13}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;
wherein each of $R^0$ and $R^2$ is independently selected from hydrido, alkyl, hydroxyalkyl, formyl, halo, haloalkyl, cycloalkyl, cycloalkylalkyl, cycloalkylhaloalkyl, cycloalkylcarbonyl, alkoxy, aralkyl, aralkylhaloalkyl, aryl, aroyl, aryloxy, aryloxyalkyl, aralkoxy, alkoxyalkyl, alkylcarbonyl, alkoxycarbonyl, alkenyl, cycloalkenyl, alkynyl, cycloalkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptothiocarbonyl, mercaptoalkyl, alkoxycarbonyloxy, alkylthio, cycloalkylthio, cycloalkylalkylthio, alkylthiocarbonyl, alkylcarbonylthio, alkylthiocarbonyloxy, alkylthiocarbonylthio, alkylthiothiocarbonyl, alkylthiothiocarbonylthio, arylthio, arylthiocarbonyl, arylcarbonylthio, arylthiocarbonyloxy, arylthiocarbonylthio, arylthiothiocarbonyl, arylthiothiocarbonylthio, aralkylthio, aralkylthiocarbonyl, aralkylcarbonylthio, aralkylthiocarbonyloxy, aralkylthiocarbonylthio, aralkylthiothiocarbonyl, aralkylthiothiocarbonylthio, mercapto, alkylsulfinyl, alkylsulfonyl, aralkylsulfinyl, aralkylsulfonyl, arylsulfinyl, arylsulfonyl, phthalimido, phthalimidoalkyl, heteroaryl, heteroarylalkyl, cycloheteroalkyl, cycloheteroalkylalkyl and cycloheteroalkylcarbonylalkyl wherein each of said heteroaryl- and cycloheteroalkyl-containing groups has one or more hetero ring atoms selected from oxygen, sulfur and nitrogen atoms, and wherein each of $R^0$ and $R^2$ through $R^{11}$ may be further independently selected from amino and amido radicals of the formula

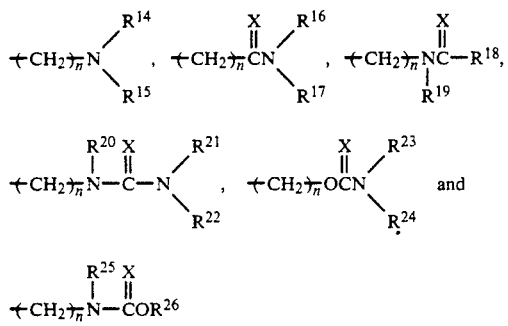

wherein X is selected from oxygen atom or sulfur atom;
wherein each n is a number independently selected from zero to six, inclusive;
wherein each of $R^{14}$ through $R^{26}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;
wherein each of $R^3$ through $R^{11}$ is independently selected from hydrido, hydroxy, alkyl, hydroxyalkyl, halo, haloalkyl, cycloalkyl, cycloalkylalkyl, alkoxy, aralkyl, aryl, aroyl, aryloxy, aralkoxy, alkoxyalkyl, alkylcarbonyl, alkoxycarbonyl, alkenyl, cycloalkenyl, alkynyl, cycloalkynyl, cyano, nitro, carboxyl, alkylcarbonyloxy, mercaptocarbonyl, mercaptothiocarbonyl, alkoxycarbonyloxy, alkylthio, alkylthiocarbonyl, alkylcarbonylthio, alkylthiocarbonyloxy, alkylthiocarbonylthio, alkylthiothiocarbonyl, arylthio, arylthiocarbonyl, arylcarbonylthio, arylthiocarbonyloxy, arylthiothiocarbonyl, aralkylthio, aralkylthiocarbonyl, aralkylcarbonylthio, aralkylthiocarbonyloxy, aralkylthiocarbonylthio, aralkylthiothiocarbonyl, aralkylthiothiocarbonylthio, mercapto, alkylsulfinyl, aralkylsulfonyl and arylsulfonyl, and amino and amido radicals of the formula

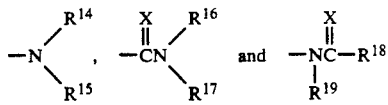

wherein X is oxygen atom or sulfur atom;
wherein each of $R^{14}$, $R^{15}$, $R^{16}$, $R^{17}$, $R^{18}$ and $R^{19}$ is independently selected from hydrido, alkyl, cycloalkyl, cyano, hydroxyalkyl, cycloalkylalkyl, alkoxyalkyl, aralkyl and aryl;
and wherein each of $R^0$ and $R^3$ through $R^{11}$ may be further independently selected from acidic moieties of the formula $$-Y_nA$$

wherein n is a number selected from zero through three, inclusive; wherein A is an acidic group selected from acids containing one or more atoms selected from oxygen, sulfur, phosphorus and nitrogen atoms, and wherein said acidic group is selected to contain at least one acidic hydrogen atom, and the amide, ester and salt derivatives of said acidic moieties; wherein Y is a spacer group independently selected from one or more of alkyl, cycloalkyl, cycloalkylalkyl, alkenyl, alkynyl, aryl, aralkyl and heteroaryl having one or more ring atoms selected from oxygen, sulfur and nitrogen atoms;
and wherein any of the foregoing $R^0$ through $R^{26}$, Y and A groups having a substitutable position may be substituted by one or more groups independently selected from hydroxy, alkyl, alkenyl, aralkyl, hydroxyalkyl, halo, haloalkyl, oxo, alkoxy, aryloxy, aralkoxy, alkoxyalkyl, alkylcarbonyl, alkoxycarbonyl, carboxyl, cyano, nitro, alkylsulfonyl, haloalkylsulfonyl, aryl, aralkyl, mercaptocarbonyl, alkylthio and alkylthiocarbonyl, and amino and amido radicals of the formula

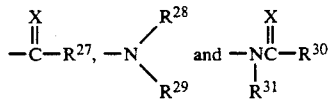

wherein X is oxygen atom or sulfur atom; wherein each of $R^{27}$ through $R^{31}$ is independently selected from hydrido, alkyl, cycloalkyl, cycloalkylalkyl, aralkyl, aryl, and $DR^{32}$ and

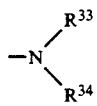

wherein D is selected from oxygen atom and sulfur atom, and $R^{32}$ is selected from hydrido, alkyl, cycloalkyl, cycloalkylalkyl, aralkyl and aryl; wherein each of $R^{27}$, $R^{28}$, $R^{29}$, $R^{30}$, $R^{31}$, $R^{33}$ and $R^{34}$ is independently selected from hydrido, alkyl, cycloalkyl, cyano, hydroxyalkyl, haloalkyl, cycloalkylalkyl, alkoxyalkyl, alkanoyl, alkoxycarbonyl, carboxyl, haloalkylsulfinyl, haloalkylsulfonyl, aralkyl and aryl;
or a tautomer thereof or a pharmaceutically-acceptable salt thereof.

A more preferred class of compounds consists of those compounds of Formula I wherein m is one;

wherein R¹ is selected from alkyl, hydroxyalkyl, haloalkyl, cycloalkyl, cycloalkylalkyl, aralkyl, aryl, aroyl, alkoxyalkyl, alkylcarbonyl, cycloalkylcarbonyl, cycloalkylalkylcarbonyl, aralkylcarbonyl, alkoxycarbonyl, alkenyl, cycloalkenyl, alkynyl, cycloalkynyl, alkylsulfonyl, aralkylsulfonyl and arylsulfonyl, and amido radicals of the formula

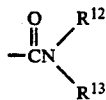

wherein each of R¹² and R¹³ is independently selected from hydrido, alkyl, cycloalkyl, cyano, amino, monoalkylamino, dialkylamino, hydroxyalkyl, cycloalkylalkyl, alkoxyalkyl, aralkyl and aryl;

wherein each of R⁰ and R² is independently selected from hydrido, alkyl, hydroxyalkyl, formyl, halo, haloalkyl, cycloalkyl, cycloalkylalkyl, cycloalkylhaloalkyl, cycloalkylcarbonyl, alkoxy, aralkyl, aralkylhaloalkyl, aryl, aroyl, aryloxy, aryloxyalkyl, aralkoxy, alkoxyalkyl, alkylcarbonyl, alkoxycarbonyl, alkenyl, cycloalkenyl, alkynyl, cycloalkynyl, cyano, nitro, carboxyl, carboxyalkyl, alkylcarbonyloxy, mercaptocarbonyl, alkoxycarbonyloxy, alkylcarbonyloxyalkyl, alkoxycarbonyloxyalkyl, aralkoxycarbonylalkyl, aralkylcarbonyloxyalkyl, alkylthio, cycloalkylthio, cycloalkylalkylthio, arylthio, aralkylthio, aralkylthiocarbonylthio, mercapto, alkylsulfinyl, alkylsulfonyl, aralkylsulfinyl, aralkylsulfonyl, arylsulfinyl, arylsulfonyl, phthalimido, phthalimidoalkyl, heteroaryl, heteroarylalkyl, cycloheteroalkyl, cycloheteroalkylalkyl and cycloheteroalklylcarbonylalkyl wherein each of said heteroaryl- and cycloheteroalkyl-containing groups has one or more hetero ring atoms selected from oxygen, sulfur and nitrogen atoms, and wherein each of R⁰ and R² may be further independently selected from amino and amido radicals of the formula

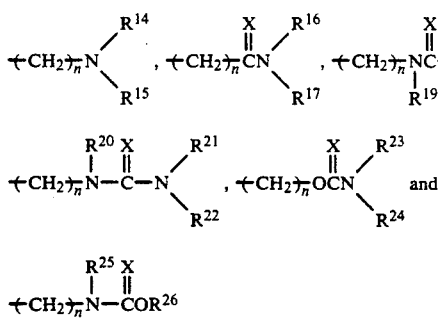

wherein X is selected from oxygen atom or sulfur atom;
wherein each n is a number independently selected from zero to six, inclusive;
wherein each of R¹⁴ through R²⁶ is independently selected from hydrido, alkyl, cycloalkyl, cyano, amino, monoalkylamino, dialkylamino, hydroxyalkyl, cycloalkylalkyl, alkoxyalkyl, aralkyl and aryl;
wherein each of R³ through R¹¹ is independently selected from hydrido, hydroxy, alkyl, hydroxyalkyl, halo, haloalkyl, cycloalkyl, alkoxy, aralkyl, aryl, aroyl, aryloxy, aralkoxy, alkoxyalkyl, alkylcarbonyl, alkoxycarbonyl, alkenyl, cycloalkenyl, alkynyl, cyano, nitro, carboxyl, alkylcarbonyloxy, mercaptocarbonyl, alkoxycarbonyloxy, alkylthio, arylthio, aralkylthio, mercapto, alkylsulfonyl, aralkylsulfonyl and arylsulfonyl, and amino and amido radicals of the formula

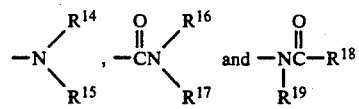

wherein each of R¹⁴, R¹⁵, R¹⁶, R¹⁷, R¹⁸ and R¹⁹ is independently selected from hydrido, alkyl, cycloalkyl, cyano, amino, monoalkylamino, dialkylamino, hydroxyalkyl, cycloalkylalkyl, alkoxyalkyl, aralkyl and aryl;

and wherein each of R⁰ and R³ through R¹¹ may be further independently selected from acidic moieties of the formula $$-Y_nA$$

wherein n is a number selected from zero through three, inclusive;
wherein A is selected from carboxylic acid and bioisosteres of carboxylic acid selected from

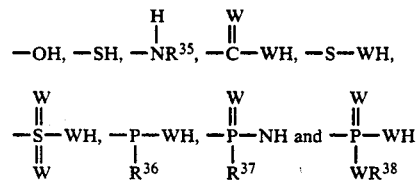

wherein each W is independently selected from oxygen atom, sulfur atom and NR³⁹; wherein each of R³⁵, R³⁶, R³⁷, R³⁸ and R³⁹ is independently selected from hydrido, alkyl, haloalkyl, haloalkylsulfonyl, haloalkylcarbonyl, cycloalkyl, cycloalkylalkyl, aryl and aralkyl; wherein each of R³⁵, R³⁶, R³⁷ and R³⁹ may be further independently selected from amino radical of the formula

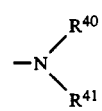

wherein each of R⁴⁰ and R⁴¹ is independently selected from hydrido, alkyl, cycloalkyl, hydroxyalkyl, haloalkyl, cycloalkylalkyl, alkoxyalkyl, aralkyl and aryl, and wherein R⁴⁰ and R⁴¹ taken together may form a heterocyclic group having five to seven ring members including the nitrogen atom of said amino radical, which heterocyclic group may further contain one or more hetero atoms as ring members selected from oxygen, nitrogen and sulfur atoms and which heterocyclic group may be saturated or partially unsaturated; wherein R⁴⁰ and R⁴¹ taken together may form an aromatic heterocyclic group having five ring members including the nitrogen atom of said amino radical and which aromatic heterocyclic group may further contain one or more hetero atoms as ring atoms selected from oxygen, nitrogen and sulfur atoms; wherein each of R³⁶ and R³⁷ may be further independently selected from hydroxy, alkoxy, alkylthio, aryloxy, arylthio, aralkylthio and aralkoxy; and the amide, ester and salt derivatives of said acidic groups;

wherein said bioisostere of carboxylic acid may be further selected from heterocyclic acidic groups consisting of heterocyclic rings of four to about nine ring members, which heterocyclic ring contains at least one hetero atom selected from oxygen, sulfur and nitrogen atoms, which heterocyclic ring may be saturated, fully unsaturated or partially unsaturated, and which heterocyclic ring may be attached at a single position selected from $R^3$ through $R^{11}$ or may be attached at any two adjacent positions selected from $R^3$ through $R^{11}$ so as to form a fused-ring system with one of the phenyl rings of Formula I; and the amide, ester and salt derivatives of said heterocyclic acidic groups;

wherein Y is a spacer group independently selected from one or more of alkyl, cycloalkyl, cycloalkylalkyl, alkenyl, aryl and aralkyl;

and wherein any of the foregoing $R^0$ through $R^{26}$ and $R^{35}$ through $R^{41}$, Y and A groups having a substitutable position may be substituted by one or more groups independently selected from hydroxy, alkyl, alkenyl, aralkyl, hydroxyalkyl, halo, oxo, haloalkyl, alkoxy, aryloxy, aralkoxy, alkoxyalkyl, alkylcarbonyl, alkoxycarbonyl, carboxyl, cyano, nitro, alkylsulfonyl, haloalkylsulfonyl, aryl, aralkyl, mercaptocarbonyl, alkylthio and alkylthiocarbonyl, and amino and amido radicals of the formula

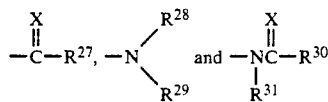

wherein X is selected from oxygen atom and sulfur atom; wherein $R^{27}$ is selected from hydrido, alkyl, cycloalkyl, cycloalkylalkyl, aralkyl, aryl and $DR^{32}$ and

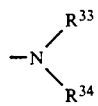

wherein D is selected from oxygen atom and sulfur atom; wherein $R^{32}$ is selected from hydrido, alkyl, cycloalkyl, cycloalkylalkyl, aralkyl and aryl;

wherein each of $R^{27}$, $R^{28}$, $R^{29}$, $R^{30}$, $R^{31}$, $R^{33}$ and $R^{34}$ is independently selected from hydrido, alkyl, cycloalkyl, cyano, hydroxyalkyl, haloalkyl, cycloalkylalkyl, alkoxyalkyl, alkanoyl, alkoxycarbonyl, carboxyl, haloalkylsulfinyl, haloalkylsulfonyl, aralkyl and aryl;

or a tautomer thereof or a pharmaceutically-acceptable salt thereof.

An even more preferred class of compounds consists of those compounds of Formula I wherein m is one; wherein $R^1$ is selected from alkyl, hydroxyalkyl, haloalkyl, cycloalkyl, cycloalkylalkyl, aralkyl, aryl, aroyl, alkoxyalkyl, alkylcarbonyl, cycloalkylcarbonyl, cycloalkylalkylcarbonyl, aralkylcarbonyl, alkenyl, cycloalkenyl, alkynyl, mercaptocarbonyl, alkylsulfonyl, aralkylsulfonyl, arylsulfonyl and amido radicals of the formula

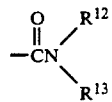

wherein each of $R^{12}$ and $R^{13}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;

wherein each of $R^0$ and $R^2$ is independently selected from hydrido, alkyl, hydroxyalkyl, formyl, halo, haloalkyl, cycloalkyl, cycloalkylalkyl, cycloalkylhaloalkyl, cycloalkylcarbonyl, alkoxy, aralkyl, aralkylhaloalkyl, aryl, aroyl, aryloxy, aryloxyalkyl, aralkoxy, alkoxyalkyl, alkylcarbonyl, alkoxycarbonyl, alkenyl, cycloalkenyl, alkynyl, cycloalkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptoalkyl, alkoxycarbonyloxy, alkylthio, cycloalkylthio, cycloalkylalkylthio, arylthio, aralkylthio, mercapto, alkylsulfinyl, alkylsulfonyl, aralkylsulfinyl, aralkylsulfonyl, arylsulfinyl, arylsulfonyl, phthalimido, phthalimidoalkyl, heteroaryl, heteroarylalkyl, cycloheteroalkyl, cycloheteroalkylalkyl and cycloheteroalkylcarbonylalkyl wherein each of said heteroaryl- and cycloheteroalkyl-containing groups has one or more hetero ring atoms selected from oxygen, sulfur and nitrogen atoms, and wherein each of $R^2$ through $R^{11}$ may be further independently selected from amino and amido radicals of the formula

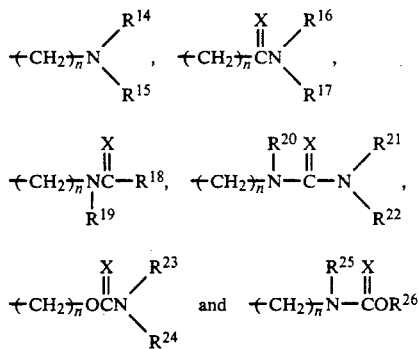

wherein X is selected from oxygen atom and sulfur atom;

wherein each n is a number independently selected from zero to six, inclusive;

wherein each of $R^{14}$ through $R^{26}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;

wherein each of $R^3$ through $R^{11}$ is independently selected from hydrido, hydroxy, alkyl, hydroxyalkyl, halo, haloalkyl, cycloalkyl, alkoxy, aralkyl, aryl, aroyl, aryloxy, aralkoxy, alkoxyalkyl, alkylcarbonyl, alkoxycarbonyl, alkenyl, cycloalkenyl, alkynyl, cyano, nitro, carboxyl, alkylthio, aralkylthio and mercapto;

and wherein each of $R^0$ and $R^3$ through $R^{11}$ may be further independently selected from acidic moieties of the formula $-Y_nA$ wherein n is a number selected from zero through three, inclusive; wherein A is selected from carboxylic acid and bioisosteres of carboxylic acid selected from

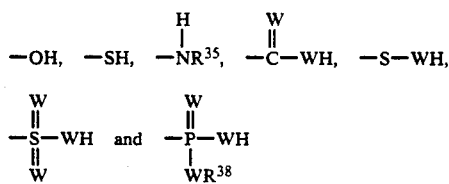

wherein each W is independently-selected from oxygen atom, sulfur atom and $NR^{39}$; wherein each of $R^{35}$, $R^{38}$ and $R^{39}$ is independently selected from hydrido, alkyl, haloalkyl, haloalkylsulfonyl, haloalkylcarbonyl, cycloalkyl, cycloalkylalkyl, aryl and aralkyl; wherein each of $R^{35}$ and $R^{39}$ may be further independently selected from amino radical of the formula

wherein each of $R^{40}$ and $R^{41}$ is independently selected from hydrido, alkyl, cycloalkyl, hydroxyalkyl, haloalkyl, cycloalkylalkyl, alkoxyalkyl, aralkyl and aryl, and wherein $R^{40}$ and $R^{41}$ taken together may form a heterocyclic group having five to seven ring members including the nitrogen atom of said amino radical, which heterocyclic group may further contain one or more hetero atoms as ring members selected from oxygen, nitrogen and sulfur atoms, and which heterocyclic group may be saturated or partially unsaturated; wherein $R^{40}$ and $R^{41}$ taken together may form an aromatic heterocyclic group having five ring members including the nitrogen atom of said amino radical and which aromatic heterocyclic group may further contain one or more hetero atoms as ring atoms selected from oxygen, nitrogen and sulfur atoms; and the amide, ester and salt derivatives of said acidic groups; wherein said bioisostere of carboxylic acid may be further selected from heterocyclic acidic groups consisting of heterocyclic rings of four to about nine ring members, which ring contains at least one hetero atom, selected from oxygen, sulfur and nitrogen atoms, which heterocyclic ring may be saturated, fully unsaturated or partially unsaturated, and which heterocyclic ring may be attached at a single position selected from $R^3$ through $R^{11}$ or may be attached at any two adjacent positions selected from $R^3$ through $R^{11}$ so as to form a fused-ring system with one of the phenyl rings of Formula I; and the amide, ester and salt derivatives of said heterocyclic acidic groups;

wherein Y is a spacer group independently selected from one or more of alkyl, cycloalkyl, cycloalkylalkyl, alkenyl, aryl and aralkyl;

wherein each of $R^0$ through $R^{26}$, $R^{35}$ and $R^{38}$ through $R^{41}$, Y and A independently may be substituted at any substitutable position with one or more groups selected from alkyl, hydroxy, halo, oxo, haloalkyl, alkoxycarbonyl, cyano, nitro, alkylsulfonyl, haloalkylsulfonyl, aryl, aralkyl, alkoxy, aryloxy and aralkoxy;

or a tautomer thereof or a pharmaceutically-acceptable salt thereof.

A highly preferred class of compounds within Formula I consists of those compounds wherein m is one; wherein $R^1$ is selected from alkyl, hydroxyalkyl, haloalkyl, cycloalkyl, cycloalkylalkyl, aralkyl, aryl, aroyl, alkoxyalkyl, alkylcarbonyl, cycloalkylcarbonyl, cycloalkylalkylcarbonyl, aralkylcarbonyl, alkenyl, alkynyl, alkylsulfonyl, aralkylsulfonyl, arylsulfonyl and amido radicals of the formula

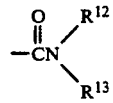

wherein each of $R^{12}$ and $R^{13}$ is independently selected from hydrido, alkyl, cycloalkyl, cyano, amino, hydroxyalkyl, alkoxyalkyl, phenalkyl and phenyl;

wherein each of $R^0$ and $R^2$ is independently selected from hydrido, alkyl, hydroxyalkyl, formyl, halo, haloalkyl, cycloalkyl, cycloalkylalkyl, cycloalkylhaloalkyl, cycloalkylcarbonyl, alkoxy, aralkyl, aralkylhaloalkyl, aryl, benzoyl, phenoxy, phenoxyalkyl, phenalkyloxy, phenylthio, phenalkylthio, aralkoxy, alkoxyalkyl, alkylcarbonyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptoalkyl, alkoxycarbonyloxy, alkylthio, cycloalkylthio, cycloalkylalkylthio, phthalimido, phthalimidoalkyl, heteroaryl, heteroarylalkyl, cycloheteroalkyl, cycloheteroalkylalkyl and cycloheteroalkylcarbonylalkyl wherein each of said heteroaryl- and cycloheteroalkyl-containing groups has one or more hetero ring atoms selected from oxygen, sulfur and nitrogen atoms, and wherein each of $R^0$ and $R^2$ through $R^{11}$ may be further independently selected from amino and amido radicals of the formula

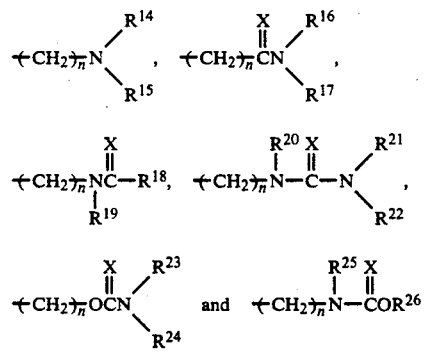

wherein X is selected from oxygen atom and sulfur atom;

wherein each n is a number independently selected from zero to six, inclusive;

wherein each of $R^{14}$ through $R^{26}$ is independently selected from hydrido, alkyl, cycloalkyl, cyano, amino, hydroxyalkyl, alkoxyalkyl, phenalkyl and phenyl;

wherein each of $R^3$ through $R^{11}$ is independently selected from hydrido, hydroxy, alkyl, hydroxyalkyl, halo, haloalkyl, cycloalkyl, alkoxy, phenalkyl, phenyl, benzoyl, phenoxy, phenalkyloxy, alkoxyalkyl, alkylcarbonyl, alkoxycarbonyl, alkenyl, cyano, nitro, carboxyl, alkylthio and mercapto;

and wherein each of $R^0$ and $R^3$ through $R^{11}$ may be further independently selected from acidic moieties of the formula $$-Y_nA$$

wherein n is a number selected from zero through two, inclusive; wherein A is selected from carboxylic acid and bioisosteres of carboxylic acid selected from

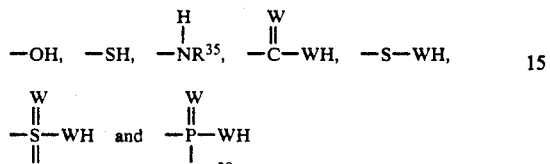

wherein each W is independently selected from oxygen atom, sulfur atom and $NR^{39}$; wherein each of $R^{35}$, $R^{38}$ and $R^{39}$ is independently selected from hydrido, alkyl, haloalkyl, haloalkylsulfonyl, haloalkylcarbonyl, cycloalkyl, phenyl and benzyl; wherein each of $R^{35}$ and $R^{39}$ may be further independently selected from amino radical of the formula

wherein each of $R^{40}$ and $R^{41}$ is independently selected from hydrido, alkyl, cycloalkyl, hydroxyalkyl, haloalkyl, alkoxyalkyl, benzyl and phenyl; and the amide, ester and salt derivatives of said acidic groups;

wherein said bioisostere of carboxylic acid may be further selected from heterocyclic acidic groups consisting of heterocyclic rings of four to about nine ring members, which ring contains at least one hetero atom, selected from oxygen, sulfur and nitrogen atoms, which heterocyclic ring may be saturated, fully unsaturated or partially unsaturated, and which heterocyclic ring may be attached at a single position selected from $R^3$ through $R^{11}$ or may be attached at any two adjacent positions selected from $R^3$ through $R^{11}$ so as to form a fused-ring system with one of the phenyl rings of Formula I; and the amide, ester and salt derivatives of said heterocyclic acidic groups;

wherein Y is a spacer group independently selected from one or more of alkyl, cycloalkyl, cycloalkylalkyl, alkenyl, phenyl, phenalkyl and aralkyl;

wherein each of $R^0$ through $R^{26}$, $R^{35}$ and $R^{38}$ through $R^{41}$, Y and A and independently may be substituted at any substitutable position with one or more groups selected from alkyl, cycloalkyl, cycloalkylalkyl, hydroxy, halo, oxo, haloalkyl, alkoxycarbonyl, cyano, nitro, alkylsulfonyl, haloalkylsulfonyl, aryl, aralkyl, alkoxy, aryloxy and aralkoxy;

or a tautomer thereof or a pharmaceutically-acceptable salt thereof.

An even more highly preferred class of compounds consists of those compounds of Formula I wherein m is one; wherein $R^1$ is selected from alkyl, hydroxyalkyl, haloalkyl, cycloalkyl, cycloalkylalkyl, aralkyl, aryl, benzoyl, alkoxyalkyl, alkylcarbonyl, alkoxycarbonyl, cycloalkylcarbonyl, cycloalkylalkylcarbonyl, aralkylcarbonyl, alkenyl and alkynyl;

where each of $R^0$ and $R^2$ is independently selected from hydrido, alkyl, aminoalkyl, hydroxyalkyl, formyl, halo, haloalkyl, cycloalkyl, cycloalkylalkyl, cycloalkylhaloalkyl, cycloalkylcarbonyl, alkoxy, aralkyl, aralkylhaloalkyl, aryl, benzoyl, phenoxy, phenoxyalkyl, phenalkyloxy, phenylthio, phenalkylthio, aralkoxy, alkoxyalkyl, acetyl, alkoxycarbonyl, alkenyl, cycloalkenyl, alkynyl, cyano, nitro, carboxyl, carboxyalkyl, alkylcarbonyl, alkylcarbonyloxy, mercaptoalkyl, mercaptocarbonyl, alkoxycarbonyloxy, alkylcarbonyloxyalkyl, alkoxycarbonylalkyl, aralkoxycarbonylalkyl, aralkylcarbonyloxyalkyl, phthalimido, phthalimidoalkyl, imidazoalkyl, tetrazole, tetrazolealkyl, alkylthio, cycloalkylthio, cycloalkylalkylthio, and amino and amido radicals of the formula

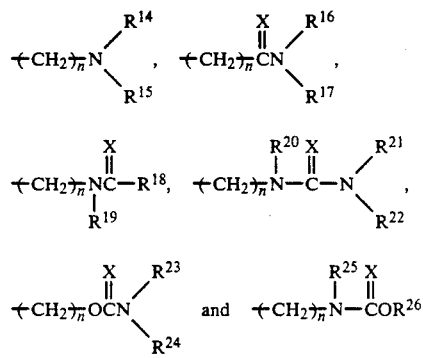

wherein X is selected from oxygen atom and sulfur atom;

wherein each n is a number independently selected from zero to six, inclusive;

wherein each of $R^{14}$ through $R^{26}$ is independently selected from hydrido, alkyl, cycloalkyl, cyano, amino, hydroxyalkyl, alkoxyalkyl, phenalkyl and phenyl;

wherein each of $R^3$ through $R^{11}$ is independently selected from hydrido, hydroxy, alkyl, hydroxyalkyl, halo, haloalkyl, alkoxy, phenyl, benzoyl, phenoxy, alkoxyalkyl, acetyl, alkoxycarbonyl, alkenyl, cyano, nitro, carboxyl, alkylthio and mercapto;

and wherein each of $R^0$ and $R^3$ through $R^{11}$ may be further independently selected from acidic moieties consisting of $CO_2H$, $CO_2CH_3$, SH, $CH_2SH$, $C_2H_4SH$, $PO_3H_2$, $NHSO_2CF_3$, $NHSO_2C_6F_5$, $SO_3H$, $CONHNH_2$, $CONHNHSO_2CF_3$, $CONHOCH_3$, $CONHOC_2H_5$, $CONHCF_3$, OH, $CH_2OH$, $C_2H_4OH$, $OPO_3H_2$, $OSO_3H$ ,

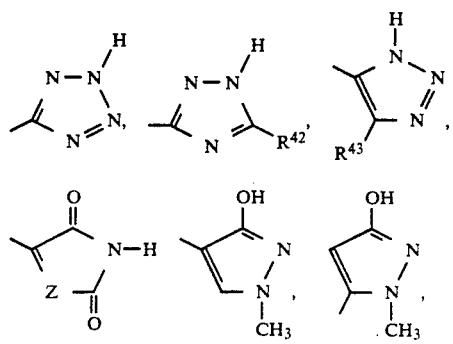

-continued

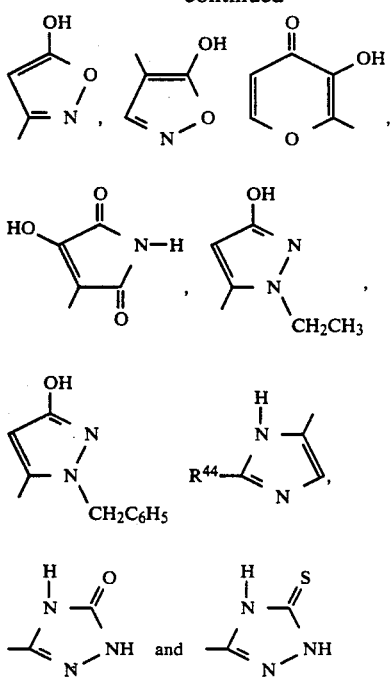

wherein each of R⁴², R⁴³ and R⁴⁴ is independently selected from H, Cl, CN, NO₂, CF₃, C₂F₅, C₃F₇, CHF₂, CH₂F, CO₂CH₃, CO₂C₂H₅, SO₂CH₃, SO₂CF₃ and SO₂C₆F₅; wherein Z is selected from O, S, NR⁴⁵ and CH₂; wherein R⁴⁵ is selected from hydrido, CH₃ and CH₂C₆H₅; and wherein said acidic moiety may be a heterocyclic acidic group attached at any two adjacent positions of R³ through R¹¹ so as to form a fused ring system with one of the phenyl rings of the biphenyl moiety of Formula I, said biphenyl fused ring system selected from

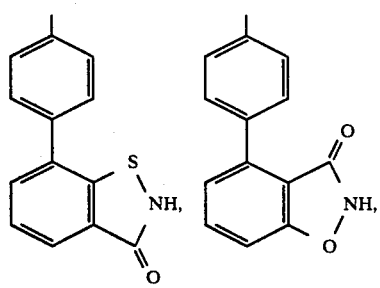

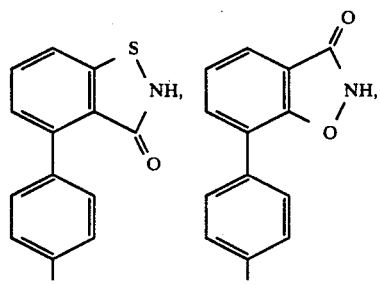

-continued

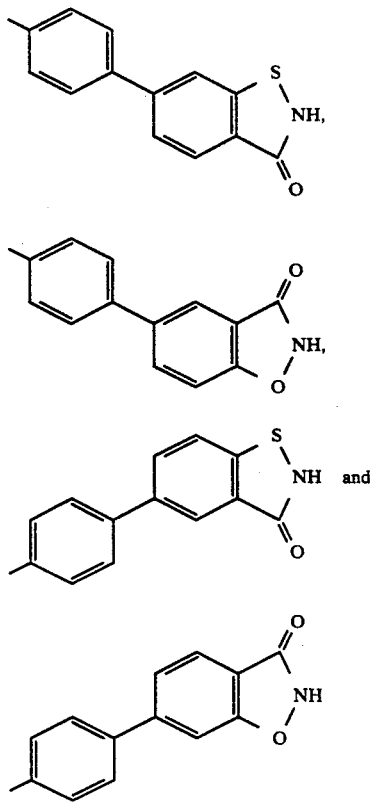

and the esters, amides and salts of said acidic moieties; or a tautomer thereof or a pharmaceutically-acceptable salt thereof.

A class of compounds of particular interest consists of those compounds of Formula I wherein m is one; wherein R¹ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, cyclohexylethyl, cyclohexanoyl, 1-oxo-2-cyclohexylethyl, benzoyl, 1-oxo-2-phenethyl, 1-oxoethyl, 1-oxopropyl, 1-oxobutyl, 1-oxopentyl, 2-butenyl, 3-butenyl, 2-butynyl, 3-butynyl and 2-hydroxybutyl; wherein R⁰ is selected from hydrido, C₄H₉(n), CH₃CH₂CH=CH, C₃H₇(n), SC₃H₇,

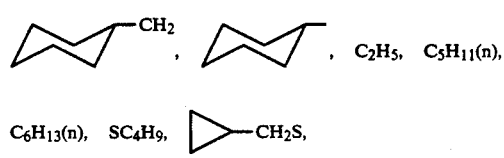

CH₃CH=CH, CH₃CH₂CH₂CH=CH—, amino, aminomethyl, aminoethyl, aminopropyl, CH₂OH, CH₂OCOCH₃, CH₂Cl, CH₂OCH₃, CH₂OCH(CH₃)₂, CHO,

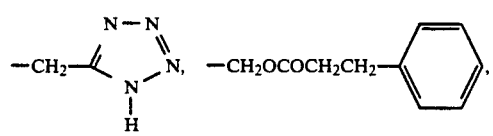

—CO₂CH₃, —CONH₂, —CONHCH₃, ·CON(CH₃)₂,

-continued

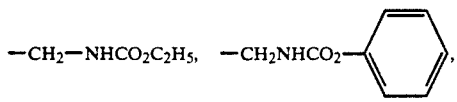

—CH₂NHCO₂CH₃, —CH₂NHCO₂C₃H₇, —CH₂NH-CO₂CH₂(CH₃)₂, —CH₂NHCO₂C₄H₉, CH₂NHCO₂-adamantyl, —CH₂NHCO₂—(1-napthyl), —CH₂NH-CONHCH₃, —CH₂NHCONHC₂H₅, —CH₂NH-CONHC₃H₇, —CH₂NHCONHC₄H₉, —CH₂NH-CONHCH(CH₃)₂, —CH₂NHCONH(1-napthyl), —CH₂NHCONH(1-adamantyl),

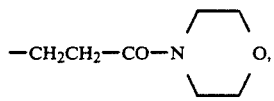

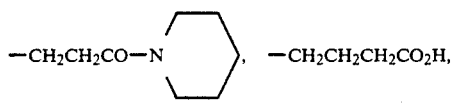

—CH₂CH₂F, —CH₂OCONHCH₃, —CH₂OCSNHCH₃,

—CH₂NHCSOC₃H₇, —CH₂CH₂CH₂F, —CH₂ONO₂,

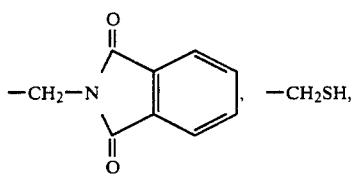

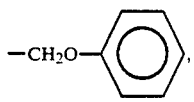

Cl, NO₂, CF₃, CH₂OH, Br, F, I, methyl, ethyl, n-propyl, isopropyl, n-butyl, sec-butyl, isobutyl, tert-butyl, n-pentyl, isopentyl, neopentyl, phenyl, cyclohexyl, cyclohexylmethyl, carboxyl, formyl, 1-oxoethyl, 1-oxopropyl, 1-oxobutyl, 1-oxopentyl, dimethoxymethyl, 1,1-dimethoxypropyl, 1,1-dimethoxypentyl, hydroxyalkyl, halo, 1-oxo-2-phenylethyl, 1-oxo-2-cyclohexylethyl, 1,1-difluoro-2-phenylethyl, monofluoromethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexylethyl, cyclohexanoyl, 1-butenyl, 2-butenyl, 3-butenyl, 1-butynyl, 2-butynyl, 3-butynyl, difluoromethyl, CO₂H, SH, PO₃H₂, SO₃H, CONHNH₂, CONHNHSO₂CF₃, OH,

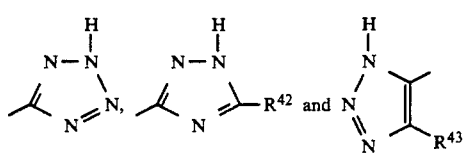

wherein each of R⁴² and R⁴³ is independently selected from chloro, cyano, nitro, trifluoromethyl, methoxycarbonyl and trifluoromethylsulfonyl; wherein R² is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, cyclohexylethyl, propylthio, butylthio, and hydroxyalkyl; wherein each of R³ through R¹¹ is hydrido with the proviso that at least one of R⁵, R⁶, R⁸ and R⁹ is an acidic group selected from CO₂H, SH, PO₃H₂, SO₃H, CONHNH₂, CONHNHSO₂CF₃, OH,

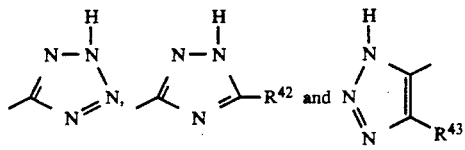

wherein each of R⁴² and R⁴³ is independently selected from chloro, cyano, nitro, trifluoromethyl, methoxycarbonyl and trifluoromethylsulfonyl;

or a tautomer thereof or a pharmaceutically-acceptable salt thereof.

A class of compounds of more particular interest consists of those compounds of Formula I wherein m is one; wherein R¹ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, cyclohexylethyl, cyclohexanoyl, 1-oxo-2-cyclohexylethyl, benzoyl, 1-oxo-2-phenethyl, 1-oxoethyl, 1-oxopropyl, 1-oxobutyl, 1-oxopentyl, 2-butenyl, 3-butenyl, 2-butynyl, 3-butynyl and 2-hydroxybutyl; wherein R⁰ is selected from hydrido, methyl, ethyl, n-propyl, isopropyl, n-butyl, sec-butyl, isobutyl, 4-methylbutyl, tert-butyl, n-pentyl, neopentyl, 1-oxoethyl, 1-oxopropyl, 1-oxobutyl, 1-oxopentyl 1-oxo-2-phenylethyl, 1-oxo-2-cyclohexylethyl, 1,1-difluoro-2-phenylethyl, 1,1-difluoro-2-cyclohexylethyl, 2-cyclohexylethyl, 1,1-difluoro-3-cyclohexylpropyl, fluoro, chloro, monofluoromethyl, difluoromethyl, trifluoromethyl, formyl, carboxyl, dimethoxymethyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexylethyl, cyclohexanoyl, 1-butenyl, 2-butenyl, 3-butenyl, 1-butynyl, 2-butynyl, 3-butynyl, propylthio, butylthio, CO₂H, SH, PO₃H₂, SO₃H, CONHNH₂, CONHNHSO₂CF₃, OH,

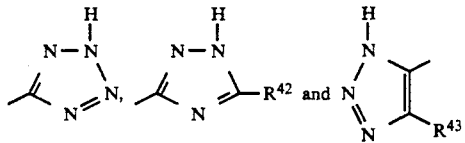

wherein each of R⁴² and R⁴³ is independently selected from chloro, cyano, nitro, trifluoromethyl, methoxycarbonyl and trifluoromethylsulfonyl; wherein R² is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, cyclohexylethyl, propylthio, butylthio, and hydroxyalkyl; wherein each of R³ through R¹¹ is hydrido with the proviso that at least one of R⁵, R⁶, R⁸ and R⁹ is an acidic group selected from CO₂H, SH, PO₃H₂, SO₃H, CONHNH₂, CONHNHSO₂CF₃, OH,

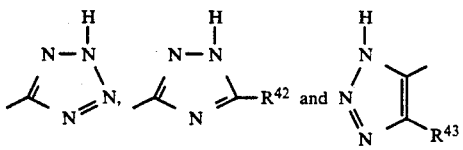

wherein each of $R^{42}$ and $R^{43}$ is independently selected from chloro, cyano, nitro, trifluoromethyl, methoxycarbonyl and trifluoromethylsulfonyl;

or a tautomer thereof or a pharmaceutically-acceptable salt thereof.

A class of compounds of even more particular interest consists of those compounds of Formula I wherein m is one; wherein $R^1$ is selected from methyl, ethyl, n-propyl, isopropyl, n-butyl, sec-butyl, isobutyl, tertbutyl, 4-methylbutyl, n-pentyl, neopentyl, phenyl, benzyl, phenethyl, cyclohexyl, cyclohexylmethyl, cyclohexylethyl cyclohexanoyl, 1-oxo-2-cyclohexylethyl, benzoyl, 1-oxo-2-phenethyl, 1-oxopropyl, 1-oxobutyl, 1-oxopentyl and 2-hydroxybutyl; wherein $R^0$ is selected from hydrido, methyl, ethyl, n-propyl, isopropyl, n-butyl, sec-butyl, isobutyl, 4-methylbutyl, n-pentyl, 1-oxo-2-phenylethyl, 1-oxo-2-cyclohexylethyl, fluoro, chloro, monofluoromethyl, difluoromethyl, trifluoromethyl, formyl, carboxyl, dimethoxymethyl, 1,1-difluoro-2-phenylethyl, 1,1-difluoro-2-cyclohexylethyl, 2-cyclohexylethyl, 1,1-difluoro-3-cyclohexylpropyl, dimethoxymethyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexylethyl, cyclohexanoyl, 1-butenyl, 2-butenyl, 3-butenyl, 1-butynyl, 2-butynyl, 3-butynyl, propylthio and butylthio; wherein $R^2$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, cyclohexylethyl, propylthio, butylthio, and hydroxyalkyl; wherein each of $R^3$, $R^4$, $R^6$, $R^7$, $R^8$, $R^{10}$ and $R^{11}$ is hydrido; wherein one of $R^5$ and $R^9$ is hydrido and the other of $R^5$ and $R^9$ is an acidic group selected from COOH, SH, PO$_3$H$_2$, SO$_3$H, CONHNH$_2$, CONHNHSO$_2$CF$_3$, OH,

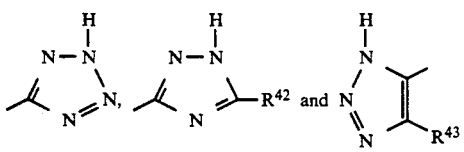

wherein each of $R^{42}$ and $R^{43}$ is independently selected from chloro, cyano, nitro, trifluoromethyl, methoxycarbonyl and trifluoromethylsulfonyl;

or a tautomer thereof or a pharmaceutically-acceptable salt thereof.

A class of compounds of even more particular interest consists of those compounds of Formula I wherein m is one; wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, cyclohexylethyl, cyclohexanoyl, 1-oxo-2-cyclohexylethyl, benzoyl, 1-oxo-2-phenethyl, 1-oxopropyl, 1-oxobutyl, 1-oxopentyl and 2-hydroxybutyl; wherein $R^0$ is selected from hydrido, methyl, fluoro, chloro, monofluoromethyl, difluoromethyl, trifluoromethyl, formyl, carboxyl and dimethoxymethyl; wherein $R^2$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, cyclohexylethyl, propylthio, butylthio, and hydroxyalkyl; wherein each of $R^3$, $R^4$, $R^6$, $R^7$, $R^8$, $R^{10}$ and $R^{11}$ is hydrido; with the proviso that at least one of $R^5$ and $R^9$ must be selected from COOH, SH, PO$_3$H$_2$, SO$_3$H, CONHNH$_2$, CONHNHSO$_2$CF$_3$, OH,

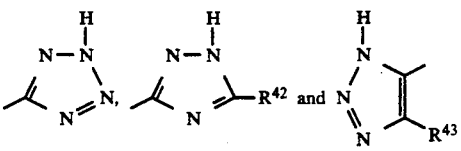

wherein each of $R^{42}$ and $R^{43}$ is independently selected from chloro, cyano, nitro, trifluoromethyl, methoxycarbonyl and trifluoromethylsulfonyl;

or a tautomer thereof or a pharmaceutically-acceptable salt thereof.

A class of compounds of even greater particular interest consists of those compounds of Formula I wherein m is one; wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, cyclohexylethyl cyclohexanoyl, 1-oxo-2-cyclohexylethyl, benzoyl, 1-oxo-2-phenethyl, 1-oxopropyl, 1-oxobutyl, 1-oxopentyl and 2-hydroxybutyl; wherein $R^0$ is selected from hydrido, methyl, fluoro, chloro, monofluoromethyl, difluoromethyl, trifluoromethyl, formyl, carboxyl and dimethoxymethyl; wherein $R^2$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, cyclohexylethyl, propylthio, butylthio, and hydroxyalkyl; wherein each of $R^3$, $R^4$, $R^6$, $R^7$, $R^8$, $R^{10}$ and $R^{11}$ is hydrido; wherein one of $R^5$ and $R^9$ is hydrido and the other of $R^5$ and $R^9$ is an acidic group selected from CO$_2$H and

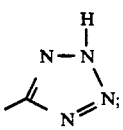

or a tautomer thereof or a pharmaceutically-acceptable salt thereof.

Within Formula I there is a sub-class of compounds of high interest as represented by Formula II:

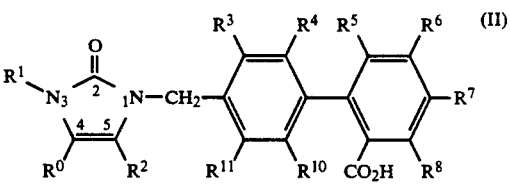

wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, cyclohexylethyl, cyclohexanoyl, 1-oxo-2-cyclohexylethyl, benzoyl, 1-oxo-2-phenethyl, 1-oxopropyl, 1-oxobutyl, 1-oxopentyl and 2-hydroxybutyl; wherein R0 is selected from hydrido, methyl, fluoro, chloro, monofluoromethyl, difluoromethyl, trifluoromethyl, formyl, carboxyl and dimethoxymethyl; wherein $R^2$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl and cyclohexylethyl; wherein each of $R^3$, $R^4$, $R^5$, $R^6$, $R^7$, $R^8$, $R^{10}$ and $R^{11}$ is hydrido; or a tautomer thereof or a pharmaceutically-acceptable salt thereof.

A family of specific compounds of particular interest within Formula II consists of compounds and pharmaceutically-acceptable salts-thereof as follows:

4'-[(3-ethyl-5-butyl-2,3-dihydro-2-oxo-1H-imidazol-1-yl)methyl][1,1'-biphenyl]-2-carboxylic acid;

4'-[(3-propyl-5-butyl-2,3-dihydro-2-oxo-1H-imidazol-1-yl)methyl][1,1'-biphenyl]-2-carboxylic acid;

4'-[(3-isopropyl-5-butyl-2,3-dihydro-2-oxo-1H-imidazol-1-yl)methyl][1,1'-biphenyl]-2-carboxylic acid;

4'-[(3,5-dibutyl-2,3-dihydro-2-oxo-1H-imidazol-1-yl)methyl][1,1'-biphenyl]-2-carboxylic acid;

4'-[(3-secbutyl-5-butyl-2,3-dihydro-2-oxo-1H-imidazol-1-yl)methyl][1,1'-biphenyl]-2-carboxylic acid;

4'-[(3-isobutyl-5-butyl-2,3-dihydro-2-oxo-1H-imidazol-1-yl)methyl][1,1'-biphenyl]-2-carboxylic acid;

4'-[(3-tertbutyl-5-butyl-2,3-dihydro-2-oxo-1H-imidazol-1-yl)methyl][1,1'-biphenyl]-2-carboxylic acid;

4'-[(3-pentyl-5-butyl-2,3-dihydro-2-oxo-1H-imidazol-1-yl)methyl][1,1'-biphenyl]-2-carboxylic acid;

4'-[(3-isopentyl-5-butyl-2,3-dihydro-2-oxo-1H-imidazol-1-yl)methyl][1,1'-biphenyl]-2-carboxylic acid;

4'-[(3-cyclohexyl-5-butyl-2,3-dihydro-2-oxo-1H-imidazol-1-yl)methyl][1,1'-biphenyl]-2-carboxylic acid;

4'-[(3-cyclohexylmethyl-5-butyl-2,3-dihydro-2-oxo-1H-imidazol-1-yl)methyl][1,1'-biphenyl]-2-carboxylic acid;

4'-[(3-(2-cyclohexylethyl)-5-butyl-2,3-dihydro-2-oxo-1H-imidazol-1-yl)methyl][1,1'-biphenyl]-2-carboxylic acid;

4'-[(3-cyclohexanoyl-5-butyl-2,3-dihydro-2-oxo-1H-imidazol-1-yl)methyl][1,1'-biphenyl]-2-carboxylic acid;

4'-[(3-(1-oxo-2-cyclohexylethyl)-5-butyl-2,3-dihydro-2-oxo-1H-imidazol-1-yl) methyl][1,1'-biphenyl]-2-carboxylic acid;

4'-[(3-phenyl-5-butyl-2,3-dihydro-2-oxo-1H-imidazol-1-yl)methyl][1,1'-biphenyl]-2-carboxylic acid;

4'-[(3-phenylmethyl-5-butyl-2,3-dihydro-2-oxo-1H-imidazol-1-yl)methyl][1,1'-biphenyl]-2-carboxylic acid;

4'-[(3-(2-phenylethyl)-5-butyl-2,3-dihydro-2-oxo-1H-imidazol-1-yl)methyl][1,1'-biphenyl]-2-carboxylic acid;

4'-[(3-benzoyl-5-butyl-2,3-dihydro-2-oxo-1H-imidazol-1-yl)methyl][1,1'-biphenyl]-2-carboxylic acid;

4'-[(3-(1-oxo-2-phenylethyl)-5-butyl-2,3-dihydro-2-oxo-1H-imidazol-1-yl) methyl][1,1'-biphenyl]-2-carboxylic acid;

4'-[(3-(1-oxopropyl)-5-butyl-2,3-dihydro-2-oxo-1H-imidazol-1-yl)methyl][1,1'-biphenyl]-2-carboxylic acid;

4'-[(3-(1-oxobutyl)-5-butyl-2,3-dihydro-2-oxo-1H-imidazol-1-yl)methyl][1,1'-biphenyl]-2-carboxylic acid;

4'-[(3-(1-oxopentyl)-5-butyl-2,3-dihydro-2-oxo-1H-imidazol-1-yl)methyl][1,1'-biphenyl]-2-carboxylic acid;

4'-[(3-ethyl-5-propyl-2,3-dihydro-2-oxo-1H-imidazol-1-yl)methyl][1,1'-biphenyl]-2-carboxylic acid;

4'-[(3,5-dipropyl-2,3-dihydro-2-oxo-1H-imidazol-1-yl)methyl][1,1'-biphenyl]-2-carboxylic acid;

4'-[(3-isopropyl-5-propyl-2,3-dihydro-2-oxo-1H-imidazol-1-yl)methyl][1,1'-biphenyl]-2-carboxylic acid;

4'-[(3-butyl-5-propyl-2,3-dihydro-2-oxo-1H-imidazol-1-yl)methyl][1,1'-biphenyl]-2-carboxylic acid;

4'-[(3-secbutyl-5-propyl-2,3-dihydro-2-oxo-1H-imidazol-1-yl)methyl][1,1'-biphenyl]-2-carboxylic acid;

4'-[(3-isobutyl-5-propyl-2,3-dihydro-2-oxo-1H-imidazol-1-yl)methyl][1,1'-biphenyl]-2-carboxylic acid;

4'-[(3-tertbutyl-5-propyl-2,3-dihydro-2-oxo-1H-imidazol-1-yl)methyl][1,1'-biphenyl]-2-carboxylic acid;

4'-[(3-pentyl-5-propyl-2,3-dihydro-2-oxo-1H-imidazol-1-yl)methyl][1,1'-biphenyl]-2-carboxylic acid;

4'-[(3-isopentyl-5-propyl-2,3-dihydro-2-oxo-1H-imidazol-1-yl)methyl][1,1'-biphenyl]-2-carboxylic acid;

4'-[(3-cyclohexyl-5-propyl-2,3-dihydro-2-oxo-1H-imidazol-1-yl)methyl][1,1'-biphenyl]-2-carboxylic acid;

4'-[(3-cyclohexylmethyl-5-propyl-2,3-dihydro-2-oxo-1H-imidazol-1-yl) methyl][1,1'-biphenyl]-2-carboxylic acid;

4'-[(3-(2-cyclohexylethyl)-5-propyl-2,3-dihydro-2-oxo-1H-imidazol-1-yl) methyl][1,1'-biphenyl]-2-carboxylic acid;

4'-[(3-cyclohexanoyl-5-propyl-2,3-dihydro-2-oxo-1H-imidazol-1-yl)methyl][1,1'-biphenyl]-2-carboxylic acid;

4'-[(3-(1-oxo-2-cyclohexylethyl)-5-propyl-2,3-dihydro-2-oxo-1H-imidazol-1-yl) methyl][1,1'-biphenyl]-2-carboxylic acid;

4'-[(3-phenyl-5-propyl-2,3-dihydro-2-oxo-1H-imidazol-1-yl)methyl][1,1'-biphenyl]-2-carboxylic acid;

4'-[(3-phenylmethyl-5-propyl-2,3-dihydro-2-oxo-1H-imidazol-1-yl)methyl][1,1'-biphenyl]-2-carboxylic acid;

4'-[(3-(2-phenylethyl)-5-propyl-2,3-dihydro-2-oxo-1H-imidazol-1-yl)methyl][1,1'-biphenyl]-2-carboxylic acid;

4'-[(3-benzoyl-5-propyl-2,3-dihydro-2-oxo-1H-imidazol-1-yl)methyl][1,1'-biphenyl]-2-carboxylic acid;

4'-[(3-(1-oxo-2-phenylethyl)-5-propyl-2,3-dihydro-2-oxo-1H-imidazol-1-yl) methyl][1,1'-biphenyl]-2-carboxylic acid;

4'-[(3-(1-oxobutyl)-5-propyl-2,3-dihydro-2-oxo-1H-imidazol-1-yl)methyl][1,1'-biphenyl]-2-carboxylic acid;

4'-[(3-(1-oxopentyl)-5-propyl-2,3-dihydro-2-oxo-1H-imidazol-1-yl)methyl][1,1'-biphenyl]-2-carboxylic acid;

4'-[(3,5-diethyl-2,3-dihydro-2-oxo-1H-imidazol-1-yl)methyl][1,1'-biphenyl]-2-carboxylic acid;

4'-[(3-propyl-5-ethyl-2,3-dihydro-2-oxo-1H-imidazol-1-yl)methyl][1,1'-biphenyl]-2-carboxylic acid;

4'-[(3-isopropyl-5-ethyl-2,3-dihydro-2-oxo-1H-imidazol-1-yl)methyl][1,1'-biphenyl]-2-carboxylic acid;

4'-[(3-butyl-5-ethyl-2,3-dihydro-2-oxo-1H-imidazol-1-yl)methyl][1,1'-biphenyl]-2-carboxylic acid;
4'-[(3-secbutyl-5-ethyl-2,3-dihydro-2-oxo-1H-imidazol-1-yl)methyl][1,1'-biphenyl]-2-carboxylic acid;
4'-[(3-isobutyl-5-ethyl-2,3-dihydro-2-oxo-1H-imidazol-1-yl)methyl][1,1'-biphenyl]-2-carboxylic acid;
4'-[(3-tertbutyl-5-ethyl-2,3-dihydro-2-oxo-1H-imidazol-1-yl)methyl][1,1'-biphenyl]-2-carboxylic acid;
4'-[(3-pentyl-5-ethyl-2,3-dihydro-2-oxo-1H-imidazol-1-yl)methyl][1,1'-biphenyl]-2-carboxylic acid;
4'-[(3-isopentyl-5-ethyl-2,3-dihydro-2-oxo-1H-imidazol-1-yl)methyl][1,1'-biphenyl]-2-carboxylic acid;
4'-[(3-cyclohexyl-5-ethyl-2,3-dihydro-2-oxo-1H-imidazol-1-yl)methyl][1,1'-biphenyl]-2-carboxylic acid;
4'-[(3-cyclohexylmethyl-5-ethyl-2,3-dihydro-2-oxo-1H-imidazol-1-yl)methyl][1,1'-biphenyl]-2-carboxylic acid;
4'-[(3-(2-cyclohexylethyl)-5-ethyl-2,3-dihydro-2-oxo-1H-imidazol-1-yl) methyl][1,1'-biphenyl]-2-carboxylic acid;
4'-[(3-cyclohexanoyl-5-ethyl-2,3-dihydro-2-oxo-1H-imidazol-1-yl)methyl][1,1'-biphenyl]-2-carboxylic acid;
4'-[(3-(1-oxo-2-cyclohexylethyl)-5-ethyl-2,3-dihydro-2-oxo-1H-imidazol-1-yl) methyl][1,1'-biphenyl]-2-carboxylic acid;
4'-[(3-phenyl-5-ethyl-2,3-dihydro-2-oxo-1H-imidazol-1-yl)methyl][1,1'-biphenyl]-2-carboxylic acid;
4'-[(3-phenylmethyl-5-ethyl-2,3-dihydro-2-oxo-1H-imidazol-1-yl)methyl][1,1'-biphenyl]-2-carboxylic acid;
4'-[(3-(2-phenylethyl)-5-ethyl-2,3-dihydro-2-oxo-1H-imidazol-1-yl)methyl][1,1'-biphenyl]-2-carboxylic acid;
4'-[(3-benzoyl-5-ethyl-2,3-dihydro-2-oxo-1H-imidazol-1-yl)methyl][1,1'-biphenyl]-2-carboxylic acid;
4'-[(3-(1-oxo-2-phenylethyl)-5-ethyl-2,3-dihydro-2-oxo-1H-imidazol-1-yl) methyl][1,1'-biphenyl]-2-carboxylic acid;
4'-[(3-(1-oxopropyl)-5-ethyl-2,3-dihydro-2-oxo-1H-imidazol-1-yl)methyl][1,1'-biphenyl]-2-carboxylic acid;
4'-[(3-(1-oxobutyl)-5-ethyl-2,3-dihydro-2-oxo-1H-imidazol-1-yl)methyl][1,1'-biphenyl]-2-carboxylic acid;
4'-[(3-(1-oxopentyl)-5-ethyl-2,3-dihydro-2-oxo-1H-imidazol-1-yl)methyl][1,1'-biphenyl]-2-carboxylic acid;
4'-[(3-ethyl-5-secbutyl-2,3-dihydro-2-oxo-1H-imidazol-1-yl)methyl][1,1'-biphenyl]-2-carboxylic acid;
4'-[(3-propyl-5-secbutyl-2,3-dihydro-2-oxo-1H-imidazol-1-yl)methyl][1,1'-biphenyl]-2-carboxylic acid;
4'-[(3-isopropyl-5-secbutyl-2,3-dihydro-2-oxo-1H-imidazol-1-yl)methyl][1,1'-biphenyl]-2-carboxylic acid;
4'-[(3-butyl-5-secbutyl-2,3-dihydro-2-oxo-1H-imidazol-1-yl)methyl][1,1'-biphenyl]-2-carboxylic acid;
4'-[(3,5-disecbutyl-2,3-dihydro-2-oxo-1H-imidazol-1-yl)methyl][1,1'-biphenyl]-2-carboxylic acid;
4'-[(3-isobutyl-5-secbutyl-2,3-dihydro-2-oxo-1H-imidazol-1-yl)methyl][1,1'-biphenyl]-2-carboxylic acid;
4'-[(3-tertbutyl-5-secbutyl-2,3-dihydro-2-oxo-1H-imidazol-1-yl)methyl][1,1'-biphenyl]-2-carboxylic acid;
4'-[(3-pentyl-5-secbutyl-2,3-dihydro-2-oxo-1H-imidazol-1-yl)methyl][1,1'-biphenyl]-2-carboxylic acid;
4'-[(3-isopentyl-5-secbutyl-2,3-dihydro-2-oxo-1H-imidazol-1-yl)methyl][1,1'-biphenyl]-2-carboxylic acid;
4'-[(3-cyclohexyl-5-secbutyl-2,3-dihydro-2-oxo-1H-imidazol-1-yl)methyl][1,1'-biphenyl]-2-carboxylic acid;
4'-[(3-cyclohexylmethyl-5-secbutyl-2,3-dihydro-2-oxo-1H-imidazol-1-yl) methyl][1,1'-biphenyl]-2-carboxylic acid;
4'-[(3-(2-cyclohexylethyl)-5-secbutyl-2,3-dihydro-2-oxo-1H-imidazol-1-yl) methyl][1,1'-biphenyl]-2-carboxylic acid;
4'-[(3-cyclohexanoyl-5-secbutyl-2,3-dihydro-2-oxo-1H-imidazol-1-yl)methyl][1,1'-biphenyl]-2-carboxylic acid;
4'-[(3-(1-oxo-2-cyclohexylethyl)-5-secbutyl-2,3-dihydro-2-oxo-1H-imidazol-1-yl) methyl][1,1'-biphenyl]-2-carboxylic acid;
4'-[(3-phenyl-5-secbutyl-2,3-dihydro-2-oxo-1H-imidazol-1-yl)methyl][1,1'-biphenyl]-2-carboxylic acid;
4'-[(3-phenylmethyl-5-secbutyl-2,3-dihydro-2-oxo-1H-imidazol-1-yl)methyl][1,1'-biphenyl]-2-carboxylic acid;
4'-[(3-(2-phenylethyl)-5-secbutyl-2,3-dihydro-2-oxo-1H-imidazol-1-yl) methyl][1,1'-biphenyl]-2-carboxylic acid;
4'-[(3-benzoyl-5-secbutyl-2,3-dihydro-2-oxo-1H-imidazol-1-yl)methyl][1,1'-biphenyl]-2-carboxylic acid;
4'-[(3-(1-oxo-2-phenylethyl)-5-secbutyl-2,3-dihydro-2-oxo-1H-imidazol-1-yl)methyl][1,1'-biphenyl]-2-carboxylic acid;
4'-[(3-(1-oxopropyl)-5-secbutyl-2,3-dihydro-2-oxo-1H-imidazol-yl)methyl][1,1'-biphenyl]-2-carboxylic acid;
4'-[(3-(1-oxobutyl)-5-secbutyl-2,3-dihydro-2-oxo-1H-imidazol-1-yl)methyl][1,1'-biphenyl]-2-carboxylic acid;
4'-[(3-(1-oxopentyl)-5-secbutyl-2,3-dihydro-2-oxo-1H-imidazol-1-yl)methyl][1,1'-biphenyl]-2-carboxylic acid;
4'-[(3-ethyl-5-isobutyl-2,3-dihydro-2-oxo-1H-imidazol-1-yl)methyl][1,1'-biphenyl]-2-carboxylic acid;
4'-[(3-propyl-5-isobutyl-2,3-dihydro-2-oxo-1H-imidazol-1-yl)methyl][1,1'-biphenyl]-2-carboxylic acid;
4'-[(3-isopropyl-5-isobutyl-2,3-dihydro-2-oxo-1H-imidazol-1-yl)methyl][1,1'-biphenyl]-2-carboxylic acid;
4'-[(3-butyl-5-isobutyl-2,3-dihydro-2-oxo-1H-imidazol-1-yl)methyl][1,1'-biphenyl]-2-carboxylic acid;
4'-[(3-secbutyl-5-isobutyl-2,3-dihydro-2-oxo-1H-imidazol-1-yl)methyl][1,1'-biphenyl]-2-carboxylic acid;
4'-[(3,5-diisobutyl-2,3-dihydro-2-oxo-1H-imidazol-1-yl)methyl][1,1'-biphenyl]-2-carboxylic acid;
4'-[(3-tertbutyl-5-isobutyl-2,3-dihydro-2-oxo-1H-imidazol-1-yl)methyl][1,1'-biphenyl]-2-carboxylic acid;
4'-[(3-pentyl-5-isobutyl-2,3-dihydro-2-oxo-1H-imidazol-1-yl)methyl][1,1'-biphenyl]-2-carboxylic acid;
4'-[(3-isopentyl-5-isobutyl-2,3-dihydro-2-oxo-1H-imidazol-1-yl)methyl][1,1'-biphenyl]-2-carboxylic acid;

4'-[(3-cyclohexyl-5-isobutyl-2,3-dihydro-2-oxo-1H-imidazol-1-yl)methyl][1,1'-biphenyl]-2-carboxylic acid;

4'-[(3-cyclohexylmethyl-5-isobutyl-2,3-dihydro-2-oxo-1H-imidazol-1-yl) methyl][1,1'-biphenyl]-2-carboxylic acid;

4'-[(3-(2-cyclohexylethyl)-5-isobutyl-2,3-dihydro-2-oxo-1H-imidazol-1-yl) methyl][1,1'-biphenyl]-2-carboxylic acid;

4'-[(3-cyclohexanoyl-5-isobutyl-2,3-dihydro-2-oxo-1H-imidazol-yl)methyl][1,1'-biphenyl]-2-carboxylic acid;

4'-[(3-(1-oxo-2-cyclohexylethyl)-5-isobutyl-2,3-dihydro-2-oxo-1H-imidazol-1-yl) methyl][1,1'-biphenyl]-2-carboxylic acid;

4'-[(3-phenyl-5-isobutyl-2,3-dihydro-2-oxo-1H-imidazol-1-yl)methyl][1,1'-biphenyl]-2-carboxylic acid;

4'-[(3-phenylmethyl-5-isobutyl-2,3-dihydro-2-oxo-1H-imidazol-1-yl)methyl][1,1'-biphenyl]-2-carboxylic acid;

4'-[(3-(2-phenylethyl)-5-isobutyl-2,3-dihydro-2-oxo-1H-imidazol-1-yl) methyl][1,1'-biphenyl]-2-carboxylic acid;

4'-[(3-benzoyl-5-isobutyl-2,3-dihydro-2-oxo-1H-imidazol-1-yl)methyl][1,1'-biphenyl]-2-carboxylic acid;

4'-[(3-(1-oxo-2-phenylethyl)-5-isobutyl-2,3-dihydro-2-oxo-1H-imidazol-1-yl) methyl][1,1'-biphenyl]-2-carboxylic acid;

4'-[(3-(1-oxopropyl)-5-isobutyl-2,3-dihydro-2-oxo-1H-imidazol-1-yl)methyl][1,1'-biphenyl]-2-carboxylic acid;

4'-[(3-(1-oxobutyl)-5-isobutyl-2,3-dihydro-2-oxo-1H-imidazol-1-yl)methyl][1,1'-biphenyl]-2-carboxylic acid;

4'-[(3-(1-oxopentyl)-5-isobutyl-2,3-dihydro-2-oxo-1H-imidazol-1-yl)methyl][1,1'-biphenyl]-2-carboxylic acid;

4'-[(3-ethyl-5-tertbutyl-2,3-dihydro-2-oxo-1H-imidazol-1-yl)methyl][1,1'-biphenyl]-2-carboxylic acid;

4'-[(3-propyl-5-tertbutyl-2,3-dihydro-2-oxo-1H-imidazol-1-yl)methyl][1,1'-biphenyl]-2-carboxylic acid;

4'-[(3-isopropyl-5-tertbutyl-2,3-dihydro-2-oxo-1H-imidazol-1-yl)methyl][1,1'-biphenyl]-2-carboxylic acid;

4'-[(3-butyl-5-tertbutyl-2,3-dihydro-2-oxo-1H-imidazol-1-yl)methyl][1,1'-biphenyl]-2-carboxylic acid;

4'-[(3-secbutyl-5-tertbutyl-2,3-dihydro-2-oxo-1H-imidazol-1-yl)methyl][1,1'-biphenyl]-2-carboxylic acid;

4'-[(3-isobutyl-5-tertbutyl-2,3-dihydro-2-oxo-1H-imidazol-1-yl)methyl][1,1'-biphenyl]-2-carboxylic acid;

4'-[(3-pentyl-5-tertbutyl-2,3-dihydro-2-oxo-1H-imidazol-1-yl)methyl][1,1'-biphenyl]-2-carboxylic acid;

4'-[(3-isopentyl-5-tertbutyl-2,3-dihydro-2-oxo-1H-imidazol-1-yl)methyl][1,1'-biphenyl]-2-carboxylic acid;

4'-[(3-cyclohexyl-5-tertbutyl-2,3-dihydro-2-oxo-1H-imidazol-1-yl)methyl][1,1'-biphenyl]-2-carboxylic acid;

4'-[(3-cyclohexylmethyl-5-tertbutyl-2,3-dihydro-2-oxo-1H-imidazol-1-yl) methyl][1,1'-biphenyl]-2-carboxylic acid;

4'-[(3-(2-cyclohexylethyl)-5-tertbutyl-2,3-dihydro-2-oxo-1H-imidazol-1-yl) methyl][1,1'-biphenyl]-2-carboxylic acid;

4'-[(3-cyclohexanoyl-5-tertbutyl-2,3-dihydro-2-oxo-1H-imidazol-1-yl) methyl][1,1'-biphenyl]-2-carboxylic acid;

4'-[(3-(1-oxo-2-cyclohexylethyl)-5-tertbutyl-2,3-dihydro-2-oxo-1H-imidazol-1-yl)methyl][1,1'-biphenyl]-2-carboxylic acid;

4'-[(3-phenyl-5-tertbutyl-2,3-dihydro-2-oxo-1H-imidazol-1-yl)methyl][1,1'-biphenyl]-2-carboxylic acid;

4'-[(3-phenylmethyl-5-tertbutyl-2,3-dihydro-2-oxo-1H-imidazol-1-yl)methyl][1,1'-biphenyl]-2-carboxylic acid;

4'-[(3-(2-phenylethyl)-5-tertbutyl-2,3-dihydro-2-oxo-1H-imidazol-1-yl)methyl ][1,1'-biphenyl]-2-carboxylic acid;

4'-[(3-benzoyl-5-tertbutyl-2,3-dihydro-2-oxo-1H-imidazol-1-yl)methyl][1,1'-biphenyl]-2-carboxylic acid;

4'-[(3-(1-oxo-2-phenylethyl)-5-tertbutyl-2,3-dihydro-2-oxo-1H-imidazol-1-yl) methyl][1,1'-biphenyl]-2-carboxylic acid;

4'-[(3-(1-oxopropyl)-5-tertbutyl-2,3-dihydro-2-oxo-1H-imidazol-1-yl) methyl][1,1'-biphenyl]-2-carboxylic acid;

4'-[(3-(1-oxobutyl)-5-tertbutyl-2,3-dihydro-2-oxo-1H-imidazol-1-yl)methyl][1,1'-biphenyl]-2-carboxylic acid;

4'-[(3-(1-oxopentyl)-5-tertbutyl-2,3-dihydro-2-oxo-1H-imidazol-1-yl) methyl][1,1'-biphenyl]-2-carboxylic acid;

4'-[(3-ethyl-5-pentyl-2,3-dihydro-2-oxo-1H-imidazol-1-yl)methyl][1,1'-biphenyl]-2-carboxylic acid;

4'-[(3-propyl-5-pentyl-2,3-dihydro-2-oxo-1H-imidazol-1-yl)methyl][1,1'-biphenyl]-2-carboxylic acid;

4'-[(3-isopropyl-5-pentyl-2,3-dihydro-2-oxo-1H-imidazol-1-yl)methyl][1,1'-biphenyl]-2-carboxylic acid;

4'-[(3-butyl-5-pentyl-2,3-dihydro-2-oxo-1H-imidazol-1-yl)methyl][1,1'-biphenyl]-2-carboxylic acid;

4'-[(3-secbutyl-5-pentyl-2,3-dihydro-2-oxo-1H-imidazol-1-yl)methyl][1,1'-biphenyl]-2-carboxylic acid;

4'-[(3-isobutyl-5-pentyl-2,3-dihydro-2-oxo-1H-imidazol-1-yl)methyl][1,1'-biphenyl]-2-carboxylic acid;

4'-[(3-tertbutyl-5-pentyl-2,3-dihydro-2-oxo-1H-imidazol-1-yl)methyl][1,1'-biphenyl]-2-carboxylic acid;

4'-[(3,5-dipentyl-2,3-dihydro-2-oxo-1H-imidazol-1-yl)methyl][1,1'-biphenyl]-2-carboxylic acid;

4'-[(3-isopentyl-5-pentyl-2,3-dihydro-2-oxo-1H-imidazol-1-yl)methyl][1,1'-biphenyl]-2-carboxylic acid;

4'-[(3-cyclohexyl-5-pentyl-2,3-dihydro-2-oxo-1H-imidazol-1-yl)methyl][1,1'-biphenyl]-2-carboxylic acid;

4'-[(3-cyclohexylmethyl-5-pentyl-2,3-dihydro-2-oxo-1H-imidazol-1-yl) methyl][1,1'-biphenyl]-2-carboxylic acid;

4'-[(3-(2-cyclohexylethyl)-5-pentyl-2,3-dihydro-2-oxo-1H-imidazol-1-yl) methyl][1,1'-biphenyl]-2-carboxylic acid;

4'-[(3-cyclohexanoyl-5-pentyl-2,3-dihydro-2-oxo-1H-imidazol-1-yl)methyl][1,1'-biphenyl]-2-carboxylic acid;

4'-[(3-(1-oxo-2-cyclohexylethyl)-5-pentyl-2,3-dihydro-2-oxo-1H-imidazol-1-yl) methyl][1,1'-biphenyl]-2-carboxylic acid;

4'-[(3-phenyl-5-pentyl-2,3-dihydro-2-oxo-1H-imidazol-1-yl)methyl][1,1'-biphenyl]-2-carboxylic acid;

4'-[(3-phenylmethyl-5-pentyl-2,3-dihydro-2-oxo-1H-imidazol-1-yl)methyl][1,1'-biphenyl]-2-carboxylic acid;

4'-[(3-(2-phenylethyl)-5-pentyl-2,3-dihydro-2-oxo-1H-imidazol-1-yl)methyl][1,1'-biphenyl]-2-carboxylic acid;

4'-[(3-benzoyl-5-pentyl-2,3-dihydro-2-oxo-1H-imidazol-1-yl)methyl][1,1'-biphenyl]-2-carboxylic acid;

4'-[(3-(1-oxopropyl)-5-pentyl-2,3-dihydro-2-oxo-1H-imidazol-1-yl)methyl][1,1'-biphenyl]-2-carboxylic acid;

4'-[(3-(1-oxobutyl)-5-pentyl-2,3-dihydro-2-oxo-1H-imidazol-1-yl)methyl][1,1'-biphenyl]-2-carboxylic acid;

4'-[(3-(1-oxopentyl)-5-pentyl-2,3-dihydro-2-oxo-1H-imidazol-1-yl)methyl][1,1'-biphenyl]-2-carboxylic acid;

4'-[(3-ethyl-5-isopentyl-2,3-dihydro-2-oxo-1H-imidazol-1-yl)methyl][1,1'-biphenyl]-2-carboxylic acid;

4'-[(3-propyl-5-isopentyl-2,3-dihydro-2-oxo-1H-imidazol-1-yl)methyl][1,1'-biphenyl]-2-carboxylic acid;

4'-[(3-isopropyl-5-isopentyl-2,3-dihydro-2-oxo-1H-imidazol-1-yl)methyl][1,1'-biphenyl]-2-carboxylic acid;

4'-[(3-butyl-5-isopentyl-2,3-dihydro-2-oxo-1H-imidazol-1-yl)methyl][1,1'-biphenyl]-2-carboxylic acid;

4'-[(3-secbutyl-5-isopentyl-2,3-dihydro-2-oxo-1H-imidazol-1-yl)methyl][1,1'-biphenyl]-2-carboxylic acid;

4'-[(3-isobutyl-5-isopentyl-2,3-dihydro-2-oxo-1H-imidazol-1-yl)methyl][1,1'-biphenyl]-2-carboxylic acid;

4'-[(3-tertbutyl-5-isopentyl-2,3-dihydro-2-oxo-1H-imidazol-1-yl)methyl][1,1'-biphenyl]-2-carboxylic acid;

4'-[(3-pentyl-5-isopentyl-2,3-dihydro-2-oxo-1H-imidazol-1-yl)methyl][1,1'-biphenyl]-2-carboxylic acid;

4'-[(3,5-diisopentyl-2,3-dihydro-2-oxo-1H-imidazol-1-yl)methyl][1,1'-biphenyl]-2-carboxylic acid;

4'-[(3-cyclohexyl-5-isopentyl-2,3-dihydro-2-oxo-1H-imidazol-1-yl)methyl][1,1'-biphenyl]-2-carboxylic acid;

4'-[(3-cyclohexylmethyl-5-isopentyl-2,3-dihydro-2-oxo-1H-imidazol-1-yl) methyl][1,1'-biphenyl]-2-carboxylic acid;

4'-[(3-(2-cyclohexylethyl)-5-isopentyl-2,3-dihydro-2-oxo-1H-imidazol-1-yl) methyl][1,1'-biphenyl]-2-carboxylic acid;

4'-[(3-cyclohexanoyl-5-isopentyl-2,3-dihydro-2-oxo-1H-imidazol-1-yl) methyl][1,1'-biphenyl]-2-carboxylic acid;

4'-[(3-(1-oxo-2-cyclohexylethyl)-5-isopentyl-2,3-dihydro-2-oxo-1H-imidazol-1-yl) methyl][1,1'-biphenyl]-2-carboxylic acid;

4'-[(3-phenyl-5-isopentyl-2,3-dihydro-2-oxo-1H-imidazol-1-yl)methyl][1,1'-biphenyl]-2-carboxylic acid;

4'-[(3-phenylmethyl-5-isopentyl-2,3-dihydro-2-oxo-1H-imidazol-1-yl)methyl][1,1'-biphenyl]-2-carboxylic acid;

4'-[(3-(2-phenylethyl)-5-isopentyl-2,3-dihydro-2-oxo-1H-imidazol-1-yl) methyl][1,1'-biphenyl]-2-carboxylic acid;

4'-[(3-benzoyl-5-isopentyl-2,3-dihydro-2-oxo-1H-imidazol-1-yl)methyl][1,1'-biphenyl]-2-carboxylic acid;

4'-[(3-(1-oxo-2-phenylethyl)-5-isopentyl-2,3-dihydro-2-oxo-1H-imidazol-1-yl) methyl][1,1'-biphenyl]-2-carboxylic acid;

4'-[(3-(1-oxopropyl)-5-isopentyl-2,3-dihydro-2-oxo-1H-imidazol-1-yl) methyl][1,1'-biphenyl]-2-carboxylic acid;

4'-[(3-(1-oxobutyl)-5-isopentyl-2,3-dihydro-2-oxo-1H-imidazol-1-yl)methyl][1,1'-biphenyl]-2-carboxylic acid;

4'-[(3-(1-oxopentyl)-5-isopentyl-2,3-dihydro-2-oxo-1H-imidazol-1-yl) methyl][1,1'-biphenyl]-2-carboxylic acid;

4'-[(3-ethyl-5-cyclohexyl-2,3-dihydro-2-oxo-1H-imidazol-1-yl)methyl][1,1'-biphenyl]-2-carboxylic acid;

4'-[(3-propyl-5-cyclohexyl-2,3-dihydro-2-oxo-1H-imidazol-1-yl)methyl][1,1'-biphenyl]-2-carboxylic acid;

4'-[(3-isopropyl-5-cyclohexyl-2,3-dihydro-2-oxo-1H-imidazol-1-yl)methyl][1,1'-biphenyl]-2-carboxylic acid;

4'-[(3-butyl-5-cyclohexyl-2,3-dihydro-2-oxo-1H-imidazol-1-yl)methyl][1,1'-biphenyl]-2-carboxylic acid;

4'-[(3-secbutyl-5-cyclohexyl-2,3-dihydro-2-oxo-1H-imidazol-1-yl)methyl][1,1'-biphenyl]-2-carboxylic acid;

4'-[(3-isobutyl-5-cyclohexyl-2,3-dihydro-2-oxo-1H-imidazol-1-yl)methyl][1,1'-biphenyl]-2-carboxylic acid;

4'-[(3-tertbutyl-5-cyclohexyl-2,3-dihydro-2-oxo-1H-imidazol-1-yl)methyl][1,1'-biphenyl]-2-carboxylic acid;

4'-[(3-pentyl-5-cyclohexyl-2,3-dihydro-2-oxo-1H-imidazol-1-yl)methyl][1,1'-biphenyl]-2-carboxylic acid;

4'-[(3-isopentyl-5-cyclohexyl-2,3-dihydro-2-oxo-1H-imidazol-1-yl)methyl][1,1'-biphenyl]-2-carboxylic acid;

4'-[(3-cyclohexyl-5-cyclohexyl-2,3-dihydro-2-oxo-1H-imidazol-1-yl)methyl][1,1'-biphenyl]-2-carboxylic acid;

4'-[(3-cyclohexylmethyl-5-cyclohexyl-2,3-dihydro-2-oxo-1H-imidazol-1-yl) methyl][1,1'-biphenyl]-2-carboxylic acid;

4'-[(3-(2-cyclohexylethyl)-5-cyclohexyl-2,3-dihydro-2-oxo-1H-imidazol-1-yl) methyl][1,1'-biphenyl]-2-carboxylic acid;

4'-[(3-cyclohexanoyl-5-cyclohexyl-2,3-dihydro-2-oxo-1H-1-imidazol-1-yl) methyl][1,1'-biphenyl]-2-carboxylic acid;

4'-[(3-(1-oxo-2-cyclohexylethyl)-5-cyclohexyl-2,3-dihydro-2-oxo-1H-imidazol-1-yl) methyl][1,1'-biphenyl]-2-carboxylic acid;

4'-[(3-phenyl-5-cyclohexyl-2,3-dihydro-2-oxo-1H-imidazol-1-yl)methyl][1,1'-biphenyl]-2-carboxylic acid;

4'-[(3-phenylmethyl-5-cyclohexyl-2,3-dihydro-2-oxo-1H-imidazol-1-yl) methyl][1,1'-biphenyl]-2-carboxylic acid;

4'-[(3-(2-phenylethyl)-5-cyclohexyl-2,3-dihydro-2-oxo-1H-imidazol-1-yl) methyl][1,1'-biphenyl]-2-carboxylic acid;

4'-[(3-benzoyl-5-cyclohexyl-2,3-dihydro-2-oxo-1H-imidazol-1-yl)methyl][1,1'-biphenyl]-2-carboxylic acid;

4'-[(3-(1-oxo-2-phenylethyl)-5-cyclohexyl-2,3-dihydro-2-oxo-1H-imidazol-1-yl) methyl][1,1'-biphenyl]-2-carboxylic acid;

4'-[(3-(1-oxopropyl)-5-cyclohexyl-2,3-dihydro-2-oxo-1H-imidazol-1-yl) methyl][1,1'-biphenyl]-2-carboxylic acid;

4'-[(3-(1-oxobutyl)-5-cyclohexyl-2,3-dihydro-2-oxo-1H-imidazol-1-yl) methyl][1,1'-biphenyl]-2-carboxylic acid;

4'-[(3-(1-oxopentyl)-5-cyclohexyl-2,3-dihydro-2-oxo-1H-imidazol-1-yl) methyl][1,1'-biphenyl]-2-carboxylic acid;

4'-[(3-ethyl-5-(2-butenyl)-2,3-dihydro-2-oxo-1H-imidazol-1-yl)methyl][1,1'-biphenyl]-2-carboxylic acid;

4'-[(3-propyl-5-(2-butenyl)-2,3-dihydro-2-oxo-1H-imidazol-1-yl)methyl][1,1'-biphenyl]-2-carboxylic acid;

4'-[(3-isopropyl-5-(2-butenyl)-2,3-dihydro-2-oxo-1H-imidazol-1-yl)methyl][1,1'-biphenyl]-2-carboxylic acid;

4'-[(3-butyl-5-(2-butenyl)-2,3-dihydro-2-oxo-1H-imidazol-1-yl)methyl][1,1'-biphenyl]-2-carboxylic acid;

4'-[(3-secbutyl-5-(2-butenyl)-2,3-dihydro-2-oxo-1H-imidazol-1-yl)methyl][1,1'-biphenyl]-2-carboxylic acid;

4'-[(3-isobutyl-5-(2-butenyl)-2,3-dihydro-2-oxo-1H-imidazol-1-yl)methyl][1,1'-biphenyl]-2-carboxylic acid;

4'-[(3-tertbutyl-5-(2-butenyl)-2,3-dihydro-2-oxo-1H-imidazol-1-yl)methyl][1,1'-biphenyl]-2-carboxylic acid;

4'-[(3-pentyl-5-(2-butenyl)-2,3-dihydro-2-oxo-1H-imidazol-1-yl)methyl][1,1'-biphenyl]-2-carboxylic acid;

4'-[(3-isopentyl-5-(2-butenyl)-2,3-dihydro-2-oxo-1H-imidazol-1-yl)methyl][1,1'-biphenyl]-2-carboxylic acid;

4'-[(3-cyclohexyl-5-(2-butenyl)-2,3-dihydro-2-oxo-1H-imidazol-1-yl)methyl][1,1'-biphenyl]-2-carboxylic acid;

4'-[(3-cyclohexylmethyl-5-(2-butenyl)-2,3-dihydro-2-oxo-1H-imidazol-1-yl) methyl][1,1'-biphenyl]-2-carboxylic acid;

4'-[(3-(2-cyclohexylethyl)-5-(2-butenyl)-2,3-dihydro-2-oxo-1H-imidazol-1-yl) methyl][1,1'-biphenyl]-2-carboxylic acid;

4'-[(3-cyclohexanoyl-5-(2-butenyl)-2,3-dihydro-2-oxo-1H-imidazol-1-yl) methyl][1,1'-biphenyl]-2-carboxylic acid;

4'-[(3-(1-oxo-2-cyclohexylethyl)-5-(2-butenyl)-2,3-dihydro-2-oxo-1H-imidazol-1-yl)methyl][1,1'-biphenyl]-2-carboxylic acid;

4'-[(3-phenyl-5-(2-butenyl)-2,3-dihydro-2-oxo-1H-imidazol-1-yl)methyl][1,1'-biphenyl]-2-carboxylic acid;

4'-[(3-phenylmethyl-5-(2-butenyl)-2,3-dihydro-2-oxo-1H-imidazol-1-yl) methyl][1,1'-biphenyl]-2-carboxylic acid;

4'-[(3-(2-phenylethyl)-5-(2-butenyl)-2,3-dihydro-2-oxo-1H-imidazol-1-yl) methyl][1,1'-biphenyl]-2-carboxylic acid;

4'-[(3-(1-oxopropyl)-5-(2-butenyl)-2,3-dihydro-2-oxo-1H-imidazol-1-yl) methyl][1,1'-biphenyl]-2-carboxylic acid;

4'-[(3-(1-oxobutyl)-5-(2-butenyl)-2,3-dihydro-2-oxo-1H-imidazol-1-yl) methyl][1,1'-biphenyl]-2-carboxylic acid;

4'-[(3-(1-oxopentyl)-5-(2-butenyl)-2,3-dihydro-2-oxo-1H-imidazol-1-yl) methyl][1,1'-biphenyl]-2-carboxylic acid;

4'-[(3-ethyl-5-(1-butenyl)-2,3-dihydro-2-oxo-1H-imidazol-1-yl)methyl][1,1'-biphenyl]-2-carboxylic acid;

4'-[(3-propyl-5-(1-butenyl)-2,3-dihydro-2-oxo-1H-imidazol-1-yl)methyl][1,1'-biphenyl]-2-carboxylic acid;

4'-[(3-isopropyl-5-(1-butenyl)-2,3-dihydro-2-oxo-1H-imidazol-1-yl)methyl][1,1'-biphenyl]-2-carboxylic acid;

4'-[(3-butyl-5-(1-butenyl)-2,3-dihydro-2-oxo-1H-imidazol-1-yl)methyl][1,1'-biphenyl]-2-carboxylic acid;

4'-[(3-secbutyl-5-(1-butenyl)-2,3-dihydro-2-oxo-1H-imidazol-1-yl)methyl][1,1'-biphenyl]-2-carboxylic acid;

4'-[(3-isobutyl-5-(1-butenyl)-2,3-dihydro-2-oxo-1H-imidazol-1-yl)methyl][1,1'-biphenyl]-2-carboxylic acid;

4'-[(3-tertbutyl-5-(1-butenyl)-2,3-dihydro-2-oxo-1H-imidazol-1-yl)methyl][1,1'-biphenyl]-2-carboxylic acid;

4'-[(3-pentyl-5-(1-butenyl)-2,3-dihydro-2-oxo-1H-imidazol-1-yl)methyl][1,1'-biphenyl]-2-carboxylic acid;

4'-[(3-isopentyl-5-(1-butenyl)-2,3-dihydro-2-oxo-1H-imidazol-1-yl)methyl][1,1'-biphenyl]-2-carboxylic acid;

4'-[(3-cyclohexyl-5-(1-butenyl)-2,3-dihydro-2-oxo-1H-imidazol-1-yl)methyl][1,1'-biphenyl]-2-carboxylic acid;

4'-[(3-cyclohexylmethyl-5-(1-butenyl)-2,3-dihydro-2-oxo-1H-imidazol-1-yl) methyl][1,1'-biphenyl]-2-carboxylic acid;

4'-[(3-(2-cyclohexylethyl)-5-(1-butenyl)-2,3-dihydro-2-oxo-1H-imidazol-1-yl) methyl][1,1'-biphenyl]-2-carboxylic acid;

4'-[(3-cyclohexanoyl-5-(1-butenyl)-2,3-dihydro-2-oxo-1H-imidazol-1-yl) methyl][1,1'-biphenyl]-2-carboxylic acid;

4'-[(3-(1-oxo-2-cyclohexylethyl)-5-(1-butenyl)-2,3-dihydro-2-oxo-1H-imidazol-1-yl)methyl][1,1'-biphenyl]-2-carboxylic acid;

4'-[(3-phenyl-5-(1-butenyl)-2,3-dihydro-2-oxo-1H-imidazol-1-yl)methyl][1,1'-biphenyl]-2-carboxylic acid;

4'-[(3-phenylmethyl-5-(1-butenyl)-2,3-dihydro-2-oxo-1H-imidazol-1-yl) methyl][1,1'-biphenyl]-2-carboxylic acid;

4'-[(3-(2-phenylethyl)-5-(1-butenyl)-2,3-dihydro-2-oxo-1H-imidazol-1-yl) methyl][1,1'-biphenyl]-2-carboxylic acid;

4'-[(3-(1-oxopropyl)-5-(1-butenyl)-2,3-dihydro-2-oxo-1H-imidazol-1-yl) methyl][1,1'-biphenyl]-2-carboxylic acid;

4'-[(3-(1-oxobutyl)-5-(1-butenyl)-2,3-dihydro-2-oxo-1H-imidazol-1-yl) methyl][1,1'-biphenyl]-2-carboxylic acid;

4'-[(3-(1-oxopentyl)-5-(1-butenyl)-2,3-dihydro-2-oxo-1H-imidazol-1-yl) methyl][1,1'-biphenyl]-2-carboxylic acid;

4'-[(3-ethyl-5-hexyl-2,3-dihydro-2-oxo-1H-imidazol-1-yl)methyl][1,1'-biphenyl]-2-carboxylic acid;

4'-[(3-propyl-5-hexyl-2,3-dihydro-2-oxo-1H-imidazol-1-yl)methyl][1,1'-biphenyl]-2-carboxylic acid;

4'-[(3-isopropyl-5-hexyl-2,3-dihydro-2-oxo-1H-imidazol-1-yl)methyl][1,1'-biphenyl]-2-carboxylic acid;

4'-[(3-butyl-5-hexyl-2,3-dihydro-2-oxo-1H-imidazol-1-yl)methyl][1,1'-biphenyl]-2-carboxylic acid;

4'-[(3-secbutyl-5-hexyl-2,3-dihydro-2-oxo-1H-imidazol-1-yl)methyl][1,1'-biphenyl]-2-carboxylic acid;

4'-[(3-isobutyl-5-hexyl-2,3-dihydro-2-oxo-1H-imidazol-1-yl)methyl][1,1'-biphenyl]-2-carboxylic acid;

4'-[(3-tertbutyl-5-hexyl-2,3-dihydro-2-oxo-1H-imidazol-1-yl)methyl][1,1'-biphenyl]-2-carboxylic acid;

4'-[(3-pentyl-5-hexyl-2,3-dihydro-2-oxo-1H-imidazol-1-yl)methyl][1,1'-biphenyl]-2-carboxylic acid;

4'-[(3-isopentyl-5-hexyl-2,3-dihydro-2-oxo-1H-imidazol-1-yl)methyl][1,1'-biphenyl]-2-carboxylic acid;

4'-[(3-cyclohexyl-5-hexyl-2,3-dihydro-2-oxo-1H-imidazol-1-yl)methyl][1,1'-biphenyl]-2-carboxylic acid;

4'-[(3-cyclohexylmethyl-5-hexyl-2,3-dihydro-2-oxo-1H-imidazol-1-yl)methyl][1,1'-biphenyl]-2-carboxylic acid;

4'-[(3-(2-cyclohexylethyl)-5-hexyl-2,3-dihydro-2-oxo-1H-imidazol-1-yl) methyl][1,1'-biphenyl]-2-carboxylic acid;

4'-[(3-cyclohexanoyl-5-hexyl-2,3-dihydro-2-oxo-1H-imidazol-1-yl)methyl][1,1'-biphenyl]-2-carboxylic acid;

4'-[(3-(1-oxo-2-cyclohexylethyl)-5-hexyl-2,3-dihydro-2-oxo-1H-imidazol-1-yl) methyl][1,1'-biphenyl]-2-carboxylic acid;

4'-[(3-phenyl-5-hexyl-2,3-dihydro-2-oxo-1H-imidazol-1-yl)methyl][1,1'-biphenyl]-2-carboxylic acid;

4'-[(3-phenylmethyl-5-hexyl-2,3-dihydro-2-oxo-1H-imidazol-1-yl)methyl][1,1'-biphenyl]-2-carboxylic acid;

4'-[(3-(2-phenylethyl)-5-hexyl-2,3-dihydro-2-oxo-1H-imidazol-1-yl)methyl][1,1'-biphenyl]-2-carboxylic acid;

4'-[(3-(1-oxopropyl)-5-hexyl-2,3-dihydro-2-oxo-1H-imidazol-1-yl)methyl][1,1'-biphenyl]-2-carboxylic acid;

4'-[(3-(1-oxobutyl)-5-hexyl-2,3-dihydro-2-oxo-1H-imidazol-1-yl)methyl][1,1'-biphenyl]-2-carboxylic acid;

4'-[(3-(1-oxopentyl)-5-hexyl-2,3-dihydro-2-oxo-1H-imidazol-1-yl)methyl][1,1'-biphenyl]-2-carboxylic acid;

4'-[(3-ethyl-5-(2-butynyl)-2,3-dihydro-2-oxo-1H-imidazol-1-yl)methyl][1,1'-biphenyl]-2-carboxylic acid;

4'-[(3-propyl-5-(2-butynyl)-2,3-dihydro-2-oxo-1H-imidazol-1-yl)methyl][1,1'-biphenyl]-2-carboxylic acid;

4'-[(3-isopropyl-5-(2-butynyl)-2,3-dihydro-2-oxo-1H-imidazol-1-yl)methyl][1,1'-biphenyl]-2-carboxylic acid;

4'-[(3-butyl-5-(2-butynyl)-2,3-dihydro-2-oxo-1H-imidazol-1-yl)methyl][1,1'-biphenyl]-2-carboxylic acid;

4'-[(3-secbutyl-5-(2-butynyl)-2,3-dihydro-2-oxo-1H-imidazol-1-yl)methyl][1,1'-biphenyl]-2-carboxylic acid;

4'-[(3-isobutyl-5-(2-butynyl)-2,3-dihydro-2-oxo-1H-imidazol-1-yl)methyl][1,1'-biphenyl]-2-carboxylic acid;

4'-[(3-tertbutyl-5-(2-butynyl)-2,3-dihydro-2-oxo-1H-imidazol-1-yl)methyl][1,1'-biphenyl]-2-carboxylic acid;

4'-[(3-pentyl-5-(2-butynyl)-2,3-dihydro-2-oxo-1H-imidazol-1-yl)methyl][1,1'-biphenyl]-2-carboxylic acid;

4'-[(3-isopentyl-5-(2-butynyl)-2,3-dihydro-2-oxo-1H-imidazol-1-yl)methyl][1,1'-biphenyl]-2-carboxylic acid;

4'-[(3-cyclohexyl-5-(2-butynyl)-2,3-dihydro-2-oxo-1H-imidazol-1-yl)methyl][1,1'-biphenyl]-2-carboxylic acid;

4'-[(3-cyclohexylmethyl-5-(2-butynyl)-2,3-dihydro-2-oxo-1H-imidazol-1-yl) methyl][1,1'-biphenyl]-2-carboxylic acid;

4'-[(3-(2-cyclohexylethyl)-5-(2-butynyl)-2,3-dihydro-2-oxo-1H-imidazol-1-yl) methyl][1,1'-biphenyl]-2-carboxylic acid;

4'-[(3-cyclohexanoyl-5-(2-butynyl)-2,3-dihydro-2-oxo-1H-imidazol-1-yl) methyl][1,1'-biphenyl]-2-carboxylic acid;

4'-[(3-(1-oxo-2-cyclohexylethyl)-5-(2-butynyl)-2,3-dihydro-2-oxo-1H-imidazol-1-yl)methyl][1,1'-biphenyl]-2-carboxylic acid;

4'-[(3-phenyl-5-(2-butynyl)-2,3-dihydro-2-oxo-1H-imidazol-1-yl)methyl][1,1'-biphenyl]-2-carboxylic acid;

4'-[(3-phenylmethyl-5-(2-butynyl)-2,3-dihydro-2-oxo-1H-imidazol-1-yl) methyl][1,1'-biphenyl]-2-carboxylic acid;

4'-[(3-(2-phenylethyl)-5-(2-butynyl)-2,3-dihydro-2-oxo-1H-imidazol-1-yl) methyl][1,1'-biphenyl]-2-carboxylic acid;

4'-[(3-(1-oxopropyl)-5-(2-butynyl-2,3-dihydro-2-oxo-1H-imidazol-1-yl) methyl][1,1'-biphenyl]-2-carboxylic acid;

4'-[(3-(1-oxobutyl)-5-(2-butynyl)-2,3-dihydro-2-oxo-1H-imidazol-1-yl) methyl][1,1'-biphenyl]-2-carboxylic acid;

4'-[(3-(1-oxopentyl)-5-(2-butynyl)-2,3-dihydro-2-oxo-1H-imidazol-1-yl) methyl][1,1'-biphenyl]-2-carboxylic acid;

4'-[(3-ethyl-5-(3-butynyl)-2,3-dihydro-2-oxo-1H-imidazol-1-yl)methyl][1,1'-biphenyl]-2-carboxylic acid;

4'-[(3-propyl-5-(3-butynyl)-2,3-dihydro-2-oxo-1H-imidazol-1-yl)methyl][1,1'-biphenyl]-2-carboxylic acid;

4'-[(3-isopropyl-5-(3-butynyl)-2,3-dihydro-2-oxo-1H-imidazol-1-yl)methyl][1,1'-biphenyl]-2-carboxylic acid;

4'-[(3-butyl-5-(3-butynyl)-2,3-dihydro-2-oxo-1H-imidazol-1-yl)methyl][1,1'-biphenyl]-2-carboxylic acid;

4'-[(3-secbutyl-5-(3-butynyl)-2,3-dihydro-2-oxo-1H-imidazol-1-yl)methyl][1,1'-biphenyl]-2-carboxylic acid;

4'-[(3-isobutyl-5-(3-butynyl)-2,3-dihydro-2-oxo-1H-imidazol-1-yl)methyl][1,1'-biphenyl]-2-carboxylic acid;

4'-[(3-tertbutyl-5-(3-butynyl)-2,3-dihydro-2-oxo-1H-imidazol-1-yl)methyl][1,1'-biphenyl]-2-carboxylic acid;

4'-[(3-pentyl-5-(3-butynyl)-2,3-dihydro-2-oxo-1H-imidazol-1-yl)methyl][1,1'-biphenyl]-2-carboxylic acid;

4'-[(3-isopentyl-5-(3-butynyl)-2,3-dihydro-2-oxo-1H-imidazol-1-yl)methyl][1,1'-biphenyl]-2-carboxylic acid;

4'-[(3-cyclohexyl-5-(3-butynyl)-2,3-dihydro-2-oxo-1H-imidazol-1-yl)methyl][1,1'-biphenyl]-2-carboxylic acid;

4'-[(3-cyclohexylmethyl-5-(3-butynyl)-2,3-dihydro-2-oxo-1H-imidazol-1-yl) methyl][1,1'-biphenyl]-2-carboxylic acid;

4'-[(3-(2-cyclohexylethyl)-5-(3-butynyl)-2,3-dihydro-2-oxo-1H-imidazol-1-yl) methyl][1,1'-biphenyl]-2-carboxylic acid;

4'-[(3-cyclohexanoyl-5-(3-butynyl)-2,3-dihydro-2-oxo-1H-imidazol-1-yl) methyl][1,1'-biphenyl]-2-carboxylic acid;

4'-[(3-(1-oxo-2-cyclohexylethyl)-5-(3-butynyl)-2,3-dihydro-2-oxo-1H-imidazol-1-yl)methyl][1,1'-biphenyl]-2-carboxylic acid;

4'-[(3-phenyl-5-(3-butynyl)-2,3-dihydro-2-oxo-1H-imidazol-1-yl)methyl][1,1'-biphenyl]-2-carboxylic acid;

4'-[(3-phenylmethyl-5-(3-butynyl)-2,3-dihydro-2-oxo-1H-imidazol-1-yl) methyl][1,1'-biphenyl]-2-carboxylic acid;

4'-[(3-(2-phenylethyl)-5-(3-butynyl)-2,3-dihydro-2-oxo-1H-imidazol-1-yl) methyl][1,1'-biphenyl]-2-carboxylic acid;

4'-[(3-(1-oxopropyl)-5-(3-butynyl)-2,3-dihydro-2-oxo-1H-imidazol-1-yl) methyl][1,1'-biphenyl]-2-carboxylic acid;

4'-[(3-(1-oxobutyl)-5-(3-butynyl)-2,3-dihydro-2-oxo-1H-imidazol-1-yl) methyl][1,1'-biphenyl]-2-carboxylic acid;

4'-[(3-(1-oxopentyl)-5-(3-butynyl)-2,3-dihydro-2-oxo-1H-imidazol-1-yl) methyl][1,1'-biphenyl]-2-carboxylic acid;

4'-[(3,5-di(2-butenyl)-2,3-dihydro-2-oxo-1H-imidazol-1-yl)methyl][1,1'-biphenyl]-2-carboxylic acid;

4'-[(3,5-di(3-butenyl)-2,3-dihydro-2-oxo-1H-imidazol-1-yl)methyl][1,1'-biphenyl]-2-carboxylic acid;

4'-[(3,5-dihexyl-2,3-dihydro-2-oxo-1H-imidazol-1-yl)methyl][1,1'-biphenyl]-2-carboxylic acid;

4'-[(3,5-di(2-butynyl)-2,3-dihydro-2-oxo-1H-imidazol-1-yl)methyl][1,1'-biphenyl]-2-carboxylic acid;

4'-[(3,5-di(3-butynyl)-2,3-dihydro-2-oxo-1H-imidazol-1-yl)methyl][1,1'-biphenyl]-2-carboxylic acid;

4'-[(3-ethyl-4-fluoro-5-butyl-2,3-dihydro-2-oxo-1H-imidazol-1-yl)methyl][1,1'-biphenyl]-2-carboxylic acid;

4'-[(3-propyl-4-fluoro-5-butyl-2,3-dihydro-2-oxo-1H-imidazol-1-yl)methyl][1,1'-biphenyl]-2-carboxylic acid;

4'-[(3-isopropyl-4-fluoro-5-butyl-2,3-dihydro-2-oxo-1H-imidazol-1-yl) methyl][1,1'-biphenyl]-2-carboxylic acid;

4'-[(3,5-dibutyl-4-fluoro-2,3-dihydro-2-oxo-1H-imidazol-1-yl)methyl][1,1'-biphenyl]-2-carboxylic acid;

4'-[(3-secbutyl-4-fluoro-5-butyl-2,3-dihydro-2-oxo-1H-imidazol-1-yl) methyl][1,1'-biphenyl]-2-carboxylic acid;

4'-[(3-isobutyl-4-fluoro-5-butyl-2,3-dihydro-2-oxo-1H-imidazol-1-yl)methyl][1,1'-biphenyl]-2-carboxylic acid;

4'-[(3-tertbutyl-4-fluoro-5-butyl-2,3-dihydro-2-oxo-1H-imidazol-1-yl)methyl][1,1'-biphenyl]-2-carboxylic acid;

4'-[(3-pentyl-4-fluoro-5-butyl-2,3-dihydro-2-oxo-1H-imidazol-1yl)methyl][1,1'-biphenyl]-2-carboxylic acid;

4'-[(3-isopentyl-4-fluoro-5-butyl-2,3-dihydro-2-oxo-1H-imidazol-1-yl)methyl][1,1'-biphenyl]-2-carboxylic acid;

4'-[(3-cyclohexyl-4-fluoro-5-butyl-2,3-dihydro-2-oxo-1H-imidazol-1-yl)methyl][1,1'-biphenyl]-2-carboxylic acid;

4'-[(3-cyclohexylmethyl-4-fluoro-5-butyl-2,3-dihydro-2-oxo-1H-imidazol-1-yl)methyl][1,1'-biphenyl]-2-carboxylic acid;

4'-[(3-(2-cyclohexylethyl)-4-fluoro-5-butyl-2,3-dihydro-2-oxo-1H-imidazol-1-yl)methyl][1,1'-biphenyl]-2-carboxylic acid;

4'-[(3-cyclohexanoyl-4-fluoro-5-butyl-2,3-dihydro-2-oxo-1H-imidazol-1-yl)methyl][1,1'-biphenyl]-2-carboxylic acid;

4'-[(3-(1-oxo-2-cyclohexylethyl)-4-fluoro-5-butyl-2,3-dihydro-2-oxo-1H-imidazol-1-yl)methyl][1,1'-biphenyl]-2-carboxylic acid;

4'-[(3-phenyl-4-fluoro-5-butyl-2,3-dihydro-2-oxo-1H-imidazol-1-yl)methyl][1,1'-biphenyl]-2-carboxylic acid;

4'-[(3-phenylmethyl-4-fluoro-5-butyl-2,3-dihydro-2-oxo-1H-imidazol-1-yl)methyl][1,1'-biphenyl]-2-carboxylic acid;

4'-[(3-(2-phenylethyl)-4-fluoro-5-butyl-2,3-dihydro-2-oxo-1H-imidazol-1-yl)methyl][1,1'-biphenyl]-2-carboxylic acid;

4'-[(3-benzoyl-4-fluoro-5-butyl-2,3-dihydro-2-oxo-1H-imidazol-1-yl)methyl][1,1'-biphenyl]-2-carboxylic acid;

4'-[(3-(1-oxo-2-phenylethyl)-4-fluoro-5-butyl-2,3-dihydro-2-oxo-1H-imidazol-1-yl)methyl][1,1'-biphenyl]-2-carboxylic acid;

4'-[(3-(1-oxopropyl)-4-fluoro-5-butyl-2,3-dihydro-2-oxo-1H-imidazol-1-yl)methyl][1,1'-biphenyl]-2-carboxylic acid;

4'-[(3-(1-oxobutyl)-4-fluoro-5-butyl-2,3-dihydro-2-oxo-1H-imidazol-1-yl)methyl][1,1'-biphenyl]-2-carboxylic acid;

4'-[(3-(1-oxopentyl)-4-fluoro-5-butyl-2,3-dihydro-2-oxo-1H-imidazol-1-yl)methyl][1,1'-biphenyl]-2-carboxylic acid;

4'-[(3-ethyl-4-chloro-5-butyl-2,3-dihydro-2-oxo-1H-imidazol-1-yl)methyl][1,1'-biphenyl]-2-carboxylic acid;

4'-[(3-propyl-4-chloro-5-butyl-2,3-dihydro-2-oxo-1H-imidazol-1-yl)methyl][1,1'-biphenyl]-2-carboxylic acid;

4'-[(3-isopropyl-4-chloro-5-butyl-2,3-dihydro-2-oxo-1H-imidazol-1-yl)methyl][1,1'-biphenyl]-2-carboxylic acid;

4'-[(3,5-dibutyl-4-chloro-2,3-dihydro-2-oxo-1H-imidazol-1-yl)methyl][1,1'-biphenyl]-2-carboxylic acid;

4'-[(3-secbutyl-4-chloro-5-butyl-2,3-dihydro-2-oxo-1H-imidazol-1-yl)methyl][1,1'-biphenyl]-2-carboxylic acid;

4'-[(3-isobutyl-4-chloro-5-butyl-2,3-dihydro-2-oxo-1H-imidazol-1-yl)methyl][1,1'-biphenyl]-2-carboxylic acid;

4'-[(3-tertbutyl-4-chloro-5-butyl-2,3-dihydro-2-oxo-1H-imidazol-1-yl)methyl][1,1'-biphenyl]-2-carboxylic acid;

4'-[(3-pentyl-4-chloro-5-butyl-2,3-dihydro-2-oxo-1H-imidazol-1-yl)methyl][1,1'-biphenyl]-2-carboxylic acid;

4'-[(3-isopentyl-4-chloro-5-butyl-2,3-dihydro-2-oxo-1H-imidazol-1-yl)methyl][1,1'-biphenyl]-2-carboxylic acid;

4'-[(3-cyclohexyl-4-chloro-5-butyl-2,3-dihydro-2-oxo-1H-imidazol-1-yl)methyl][1,1'-biphenyl]-2-carboxylic acid;

4'-[(3-cyclohexylmethyl-4-chloro-5-butyl-2,3-dihydro-2-oxo-1H-imidazol-1-yl)methyl][1,1'-biphenyl]-2-carboxylic acid;

4'-[(3-(2-cyclohexylethyl)-4-chloro-5-butyl-2,3-dihydro-2-oxo-1H-imidazol-1-yl)methyl][1,1'-biphenyl]-2-carboxylic acid;

4'-[(3-cyclohexanoyl-4-chloro-5-butyl-2,3-dihydro-2-oxo-1H-imidazol-1-yl)methyl][1,1'-biphenyl]-2-carboxylic acid;

4'-[(3-(1-oxo-2-cyclohexylethyl)-4-chloro-5-butyl-2,3-dihydro-2-oxo-1H-imidazol-1-yl)methyl][1,1'-biphenyl]-2-carboxylic acid;

4'-[(3-phenyl-4-chloro-5-butyl-2,3-dihydro-2-oxo-1H-imidazol-1-yl)methyl][1,1'-biphenyl]-2-carboxylic acid;

4'-[(3-phenylmethyl-4-chloro-5-butyl-2,3-dihydro-2-oxo-1H-imidazol-1-yl)methyl][1,1'-biphenyl]-2-carboxylic acid;

4'-[(3-(2-phenylethyl)-4-chloro-5-butyl-2,3-dihydro-2-oxo-1H-imidazol-1-yl)methyl][1,1'-biphenyl]-2-carboxylic acid;

4'-[(3-benzoyl-4-chloro-5-butyl-2,3-dihydro-2-oxo-1H-imidazol-1-yl)methyl][1,1'-biphenyl]-2-carboxylic acid;

4'-[(3-(1-oxo-2-phenylethyl)-4-chloro-5-butyl-2,3-dihydro-2-oxo-1H-imidazol-1-yl)methyl][1,1'-biphenyl]-2-carboxylic acid;

4'-[(3-(1-oxopropyl)-4-chloro-5-butyl-2,3-dihydro-2-oxo-1H-imidazol-1-yl)methyl][1,1'-biphenyl]-2-carboxylic acid;

4'-[(3-(1-oxobutyl)-4-chloro-5-butyl-2,3-dihydro-2-oxo-1H-imidazol-1-yl)methyl][1,1'-biphenyl]-2-carboxylic acid;

4'-[(3-(1-oxopentyl)-4-chloro-5-butyl-2,3-dihydro-2-oxo-1H-imidazol-1-yl)methyl][1,1'-biphenyl]-2-carboxylic acid;

4'-[(3-ethyl-4-formyl-5-butyl-2,3-dihydro-2-oxo-1H-imidazol-1-yl)methyl][1,1'-biphenyl]-2-carboxylic acid;

4'-[(3-propyl-4-formyl-5-butyl-2,3-dihydro-2-oxo-1H-imidazol-1-yl)methyl][1,1'-biphenyl]-2-carboxylic acid;

4'-[(3-isopropyl-4-formyl-5-butyl-2,3-dihydro-2-oxo-1H-imidazol-1-yl)methyl][1,1'-biphenyl]-2-carboxylic acid;

4'-[(3,5-dibutyl-4-formyl-2,3-dihydro-2-oxo-1H-imidazol-1-yl)methyl][1,1'-biphenyl]-2-carboxylic acid;

4'-[(3-secbutyl-4-formyl-5-butyl-2,3-dihydro-2-oxo-1H-imidazol-1-yl)methyl][1,1'-biphenyl]-2-carboxylic acid;

4'-[(3-isobutyl-4-formyl-5-butyl-2,3-dihydro-2-oxo-1H-imidazol-1-yl)methyl][1,1'-biphenyl]-2-carboxylic acid;

4'-[(3-tertbutyl-4-formyl-5-butyl-2,3-dihydro-2-oxo-1H-imidazol-1-yl)methyl][1,1'-biphenyl]-2-carboxylic acid;

4'-[(3-pentyl-4-formyl-5-butyl-2,3-dihydro-2-oxo-1H-imidazol-1-yl)methyl][1,1'-biphenyl]-2-carboxylic acid;

4'-[(3-isopentyl-4-formyl-5-butyl-2,3-dihydro-2-oxo-1H-imidazol-1-yl)methyl][1,1'-biphenyl]-2-carboxylic acid;

4'-[(3-cyclohexyl-4-formyl-5-butyl-2,3-dihydro-2-oxo-1H-imidazol-1-yl)methyl][1,1'-biphenyl]-2-carboxylic acid;

4'-[(3-cyclohexylmethyl-4-formyl-5-butyl-2,3-dihydro-2-oxo-1H-imidazol-1-yl)methyl][1,1'-biphenyl]-2-carboxylic acid;

4'-[(3-(2-cyclohexylethyl)-4-formyl-5-butyl-2,3-dihydro-2-oxo-1H-imidazol-1-yl)methyl][1,1'-biphenyl]-2-carboxylic acid;

4'-[(3-cyclohexanoyl-4-formyl-5-butyl-2,3-dihydro-2-oxo-1H-imidazol-1-yl)methyl][1,1'-biphenyl]-2-carboxylic acid;

4'-[(3-(1-oxo-2-cyclohexylethyl)-4-formyl-5-butyl-2,3-dihydro-2-oxo-1H-imidazol-1-yl)methyl][1,1'-biphenyl]-2-carboxylic acid;

4'-[(3-phenyl-4-formyl-5-butyl-2,3-dihydro-2-oxo-1H-imidazol-1-yl)methyl][1,1'-biphenyl]-2-carboxylic acid;

4'-[(3-phenylmethyl-4-formyl-5-butyl-2,3-dihydro-2-oxo-1H-imidazol-1-yl)methyl][1,1'-biphenyl]-2-carboxylic acid;

4'-[(3-(2-phenylethyl)-4-formyl-5-butyl-2,3-dihydro-2-oxo-1H-imidazol-1-yl)methyl][1,1'-biphenyl]-2-carboxylic acid;

4'-[(3-benzoyl-4-formyl-5-butyl-2,3-dihydro-2-oxo-1H-imidazol-1-yl)methyl][1,1'-biphenyl]-2-carboxylic acid;

4'-[(3-(1-oxo-2-phenylethyl)-4-formyl-5-butyl-2,3-dihydro-2-oxo-1H-imidazol-1-yl)methyl][1,1'-biphenyl]-2-carboxylic acid;

4'-[(3-(1-oxopropyl)-4-formyl-5-butyl-2,3-dihydro-2-oxo-1H-imidazol-1-yl)methyl][1,1'-biphenyl]-2-carboxylic acid;

4'-[(3-(1-oxobutyl)-4-formyl-5-butyl-2,3-dihydro-2-oxo-1H-imidazol-1-yl)methyl][1,1'-biphenyl]-2-carboxylic acid;

4'-[(3-(1-oxopentyl)-4-formyl-5-butyl-2,3-dihydro-2-oxo-1H-imidazol-1-yl)methyl][1,1'-biphenyl]-2-carboxylic acid;

4'-[(3-ethyl-4-dimethoxymethyl-5-butyl-2,3-dihydro-2-oxo-1H-imidazol-1-yl)methyl][1,1'-biphenyl]-2-carboxylic acid;

4'-[(3-propyl-4-dimethoxymethyl-5-butyl-2,3-dihydro-2-oxo-1H-imidazol-1-yl)methyl][1,1'-biphenyl]-2-carboxylic acid;

4'-[(3-isopropyl-4-dimethoxymethyl-5-butyl-2,3-dihydro-2-oxo-1H-imidazol-1-yl)methyl][1,1'-biphenyl]-2-carboxylic acid;

4'-[(3,5-dibutyl-4-dimethoxymethyl-2,3-dihydro-2-oxo-1H-imidazol-1-yl)methyl][1,1'-biphenyl]-2-carboxylic acid;

4'-[(3-secbutyl-4-dimethoxymethyl-5-butyl-2,3-dihydro-2-oxo-1H-imidazol-1-yl)methyl][1,1'-biphenyl]-2-carboxylic acid;

4'-[(3-isobutyl-4-dimethoxymethyl-5-butyl-2,3-dihydro-2-oxo-1H-imidazol-1-yl)methyl][1,1'-biphenyl]-2-carboxylic acid;

4'-[(3-tertbutyl-4-dimethoxymethyl-5-butyl-2,3-dihydro-2-oxo-1H-imidazol-1-yl)methyl][1,1'-biphenyl]-2-carboxylic acid;

4'-[(3-pentyl-4-dimethoxymethyl-5-butyl-2,3-dihydro-2-oxo-1H-imidazol-1-yl)methyl][1,1'-biphenyl]-2-carboxylic acid;

4'-[(3-isopentyl-4-dimethoxymethyl-5-butyl-2,3-dihydro-2-oxo-1H-imidazol-1-yl)methyl][1,1'-biphenyl]-2-carboxylic acid;

4'-[(3-cyclohexyl-4-dimethoxymethyl-5-butyl-2,3-dihydro-2-oxo-1H-imidazol-1-yl)methyl][1,1'-biphenyl]-2-carboxylic acid;

4'-[(3-cyclohexylmethyl-4-dimethoxymethyl-5-butyl-2,3-dihydro-2-oxo-1H-imidazol-1-yl)methyl][1,1'-biphenyl]-2-carboxylic acid;

4'-[(3-(2-cyclohexylethyl)-4-dimethoxymethyl-5-butyl-2,3-dihydro-2-oxo-1H-imidazol-1-yl)methyl][1,1'-biphenyl]-2-carboxylic acid;

4'-[(3-cyclohexanoyl-4-dimethoxymethyl-5-butyl-2,3-dihydro-2-oxo-1H-imidazol-1-yl)methyl][1,1'-biphenyl]-2-carboxylic acid;

4'-[(3-(1-oxo-2-cyclohexylethyl)-4-dimethoxymethyl-5-butyl-2,3-dihydro-2-oxo-1H-imidazol-1-yl)methyl][1,1'-biphenyl]-2-carboxylic acid;

4'-[(3-phenyl-4-dimethoxymethyl-5-butyl-2,3-dihydro-2-oxo-1H-imidazol-1-yl)methyl][1,1'-biphenyl]-2-carboxylic acid;

4'-[(3-phenylmethyl-4-dimethoxymethyl-5-butyl-2,3-dihydro-2-oxo-1H-imidazol-1-yl)methyl][1,1'-biphenyl]-2-carboxylic acid;

4'-[(3-(2-phenylethyl)-4-dimethoxymethyl-5-butyl-2,3-dihydro-2-oxo-1H-imidazol-1-yl)methyl][1,1'-biphenyl]-2-carboxylic acid;

4'-[(3-benzoyl-4-dimethoxymethyl-5-butyl-2,3-dihydro-2-oxo-1H-imidazol-1-yl)methyl][1,1'-biphenyl]-2-carboxylic acid;

4'-[(3-(1-oxo-2-phenylethyl)-4-dimethoxymethyl-5-butyl-2,3-dihydro-2-oxo-1H-imidazol-1-yl)methyl][1,1'-biphenyl]-2-carboxylic acid;

4'-[(3-(1-oxopropyl)-4-dimethoxymethyl-5-butyl-2,3-dihydro-2-oxo-1H-imidazol-1-yl)methyl][1,1'-biphenyl]-2-carboxylic acid;

4'-[(3-(1-oxobutyl)-4-dimethoxymethyl-5-butyl-2,3-dihydro-2-oxo-1H-imidazol-1-yl)methyl][1,1'-biphenyl]-2-carboxylic acid;

4'-[(3-(1-oxopentyl)-4-dimethoxymethyl-5-butyl-2,3-dihydro-2-oxo-1H-imidazol-1-yl)methyl][1,1'-biphenyl]-2-carboxylic acid;

4'-[(3-ethyl-4-methyl-5-butyl-2,3-dihydro-2-oxo-1H-imidazol-1-yl)methyl][1,1'-biphenyl]-2-carboxylic acid;

4'-[(3-propyl-4-methyl-5-butyl-2,3-dihydro-2-oxo-1H-imidazol-1-yl)methyl][1,1'-biphenyl]-2-carboxylic acid;

4'-[(3-isopropyl-4-methyl-5-butyl-2,3-dihydro-2-oxo-1H-imidazol-1-yl)methyl][1,1'-biphenyl]-2-carboxylic acid;

4'-[(3,5-dibutyl-4-methyl-2,3-dihydro-2-oxo-1H-imidazol-1-yl)methyl][1,1'-biphenyl]-2-carboxylic acid;

4'-[(3-secbutyl-4-methyl-5-butyl-2,3-dihydro-2-oxo-1H-imidazol-1-yl)methyl][1,1'-biphenyl]-2-carboxylic acid;

4'-[(3-isobutyl-4-methyl-5-butyl-2,3-dihydro-2-oxo-1H-imidazol-1-yl)methyl][1,1'-biphenyl]-2-carboxylic acid;

4'-[(3-tertbutyl-4-methyl-5-butyl-2,3-dihydro-2-oxo-1H-imidazol-1-yl)methyl][1,1'-biphenyl]-2-carboxylic acid;

4'-[(3-pentyl-4-methyl-5-butyl-2,3-dihydro-2-oxo-1H-imidazol-1-yl)methyl][1,1'-biphenyl]-2-carboxylic acid;

4'-[(3-isopentyl-4-methyl-5-butyl-2,3-dihydro-2-oxo-1H-imidazol-1-yl)methyl][1,1'-biphenyl]-2-carboxylic acid;

4'-[(3-cyclohexyl-4-methyl-5-butyl-2,3-dihydro-2-oxo-1H-imidazol-1-yl)methyl][1,1'-biphenyl]-2-carboxylic acid;

4'-[(3-cyclohexylmethyl-4-methyl-5-butyl-2,3-dihydro-2-oxo-1H-imidazol-1-yl)methyl][1,1'-biphenyl]-2-carboxylic acid;

4'-[(3-(2-cyclohexylethyl)-4-methyl-5-butyl-2,3-dihydro-2-oxo-1H-imidazol-1-yl)methyl][1,1'-biphenyl]-2-carboxylic acid;

4'-[(3-cyclohexanoyl-4-methyl-5-butyl-2,3-dihydro-2-oxo-1H-imidazol-1-yl)methyl][1,1'-biphenyl]-2-carboxylic acid;

4'-[(3-(1-oxo-2-cyclohexylethyl)-4-methyl-5-butyl-2,3-dihydro-2-oxo-1H-imidazol-1-yl)methyl][1,1'-biphenyl]-2-carboxylic acid;

4'-[(3-phenyl-4-methyl-5-butyl-2,3-dihydro-2-oxo-1H-imidazol-1-yl)methyl][1,1'-biphenyl]-2-carboxylic acid;

4'-[(3-phenylmethyl-4-methyl-5-butyl-2,3-dihydro-2-oxo-1H-imidazol-1-yl)methyl][1,1'-biphenyl]-2-carboxylic acid;

4'-[(3-(2-phenylethyl)-4-methyl-5-butyl-2,3-dihydro-2-oxo-1H-imidazol-1-yl)methyl][1,1'-biphenyl]-2-carboxylic acid;

4'-[(3-benzoyl-4-methyl-5-butyl-2,3-dihydro-2-oxo-1H-imidazol-1-yl)methyl][1,1'-biphenyl]-2-carboxylic acid;

4'-[(3-(1-oxo-2-phenylethyl)-4-methyl-5-butyl-2,3-dihydro-2-oxo-1H-imidazol-1-yl)methyl][1,1'-biphenyl]-2-carboxylic acid;

4'-[(3-(1,1-dimethoxypropyl)-4-methyl-5-butyl-2,3-dihydro-2-oxo-1H-imidazol-1-yl)methyl][1,1'-biphenyl]-2-carboxylic acid;

4'-[(3-(1-oxopropyl)-4-methyl-5-butyl-2,3-dihydro-2-oxo-1H-imidazol-1-yl)methyl][1,1'-biphenyl]-2-carboxylic acid;

4'-[(3-(1-oxobutyl)-4-methyl-5-butyl-2,3-dihydro-2-oxo-1H-imidazol-1-yl)methyl][1,1'-biphenyl]-2-carboxylic acid;

4'-[(3-(1-oxopentyl)-4-methyl-5-butyl-2,3-dihydro-2-oxo-1H-imidazol-1-yl)methyl][1,1'-biphenyl]-2-carboxylic acid;

4'-[(3-ethyl-4-fluoromethyl-5-butyl-2,3-dihydro-2-oxo-1H-imidazol-1-yl)methyl][1,1'-biphenyl]-2-carboxylic acid;

4'-[(3-propyl-4-fluoromethyl-5-butyl-2,3-dihydro-2-oxo-1H-imidazol-1-yl)methyl][1,1'-biphenyl]-2-carboxylic acid;

4'-[(3-isopropyl-4-fluoromethyl-5-butyl-2,3-dihydro-2-oxo-1H-imidazol-1-yl)methyl][1,1'-biphenyl]-2-carboxylic acid;

4'-[(3,5-dibutyl-4-fluoromethyl-2,3-dihydro-2-oxo-1H-imidazol-1-yl)methyl][1,1'-biphenyl]-2-carboxylic acid;

4'-[(3-secbutyl-4-fluoromethyl-5-butyl-2,3-dihydro-2-oxo-1H-imidazol-1-yl)methyl][1,1'-biphenyl]-2-carboxylic acid;

4'-[(3-isobutyl-4-fluoromethyl-5-butyl-2,3-dihydro-2-oxo-1H-imidazol-1-yl)methyl][1,1'-biphenyl]-2-carboxylic acid;

4'-[(3-tertbutyl-4-fluoromethyl-5-butyl-2,3-dihydro-2-oxo-1H-imidazol-1-yl)methyl][1,1'-biphenyl]-2-carboxylic acid;

4'-[(3-pentyl-4-fluoromethyl-5-butyl-2,3-dihydro-2-oxo-1H-imidazol-1-yl)methyl][1,1'-biphenyl]-2-carboxylic acid;

4'-[(3-isopentyl-4-fluoromethyl-5-butyl-2,3-dihydro-2-oxo-1H-imidazol-1-yl)methyl][1,1'-biphenyl]-2-carboxylic acid;

4'-[(3-cyclohexyl-4-fluoromethyl-5-butyl-2,3-dihydro-2-oxo-1H-imidazol-1-yl)methyl][1,1'-biphenyl]-2-carboxylic acid;

4'-[(3-cyclohexylmethyl-4-fluoromethyl-5-butyl-2,3-dihydro-2-oxo-1H-imidazol-1-yl)methyl][1,1'-biphenyl]-2-carboxylic acid;

4'-[(3-(2-cyclohexylethyl)-4-fluoromethyl-5-butyl-2,3-dihydro-2-oxo-1H-imidazol-1-yl)methyl][1,1'-biphenyl]-2-carboxylic acid;

4'-[(3-cyclohexanoyl-4-fluoromethyl-5-butyl-2,3-dihydro-2-oxo-1H-imidazol-1-yl)methyl][1,1'-biphenyl]-2-carboxylic acid;

4'-[(3-(1-oxo-2-cyclohexylethyl)-4-fluoromethyl-5-butyl-2,3-dihydro-2-oxo-1H-imidazol-1-yl)methyl][1,1'-biphenyl]-2-carboxylic acid;

4'-[(3-phenyl-4-fluoromethyl-5-butyl-2,3-dihydro-2-oxo-1H-imidazol-1-yl)methyl][1,1'-biphenyl]-2-carboxylic acid;

4'-[(3-phenylmethyl-4-fluoromethyl-5-butyl-2,3-dihydro-2-oxo-1H-imidazol-1-yl)methyl][1,1'-biphenyl]-2-carboxylic acid;

4'-[(3-(2-phenylethyl)-4-fluoromethyl-5-butyl-2,3-dihydro-2-oxo-1H-imidazol-1-yl)methyl][1,1'-biphenyl]-2-carboxylic acid;

4'-[(3-benzoyl-4-fluoromethyl-5-butyl-2,3-dihydro-2-oxo-1H-imidazol-1-yl)methyl][1,1'-biphenyl]-2-carboxylic acid;

4'-[(3-(1-oxo-2-phenylethyl)-4-fluoromethyl-5-butyl-2,3-dihydro-2-oxo-1H-imidazol-1-yl)methyl][1,1'-biphenyl]-2-carboxylic acid;

4'-[(3-(1-oxopropyl)-4-fluoromethyl-5-butyl-2,3-dihydro-2-oxo-1H-imidazol-1-yl)methyl][1,1'-biphenyl]-2-carboxylic acid;

4'-[(3-(1-oxobutyl)-4-fluoromethyl-5-butyl-2,3-dihydro-2-oxo-1H-imidazol-1-yl)methyl][1,1'-biphenyl]-2-carboxylic acid;

4'-[(3-(1-oxopentyl)-4-fluoromethyl-5-butyl-2,3-dihydro-2-oxo-1H-imidazol-1-yl)methyl][1,1'-biphenyl]-2-carboxylic acid;

4'-[(3-ethyl-4-difluoromethyl-5-butyl-2,3-dihydro-2-oxo-1H-imidazol-1-yl)methyl][1,1'-biphenyl]-2-carboxylic acid;

4'-[(3-propyl-4-difluoromethyl-5-butyl-2,3-dihydro-2-oxo-1H-imidazol-1-yl)methyl][1,1'-biphenyl]-2-carboxylic acid;

4'-[(3-isopropyl-4-difluoromethyl-5-butyl-2,3-dihydro-2-oxo-1H-imidazol-1-yl)methyl][1,1'-biphenyl]-2-carboxylic acid;

4'-[(3,5-dibutyl-4-difluoromethyl-2,3-dihydro-2-oxo-1H-imidazol-1-yl)methyl][1,1'-biphenyl]-2-carboxylic acid;

4'-[(3-secbutyl-4-difluoromethyl-5-butyl-2,3-dihydro-2-oxo-1H-imidazol-1-yl)methyl][1,1'-biphenyl]-2-carboxylic acid;

4'-[(3-isobutyl-4-difluoromethyl-5-butyl-2,3-dihydro-2-oxo-1H-imidazol-1-yl)methyl][1,1'-biphenyl]-2-carboxylic acid;

4'-[(3-tertbutyl-4-difluoromethyl-5-butyl-2,3-dihydro-2-oxo-1H-imidazol-1-yl)methyl][1,1'-biphenyl]-2-carboxylic acid;

4'-[(3-pentyl-4-difluoromethyl-5-butyl-2,3-dihydro-2-oxo-1H-imidazol-1-yl)methyl][1,1'-biphenyl]-2-carboxylic acid;

4'-[(3-isopentyl-4-difluoromethyl-5-butyl-2,3-dihydro-2-oxo-1H-imidazol-1-yl)methyl][1,1'-biphenyl]-2-carboxylic acid;

4'-[(3-cyclohexyl-4-difluoromethyl-5-butyl-2,3-dihydro-2-oxo-1H-imidazol-1-yl)methyl][1,1'-biphenyl]-2-carboxylic acid;

4'-[(3-cyclohexylmethyl-4-difluoromethyl-5-butyl-2,3-dihydro-2-oxo-1H-imidazol-1-yl)methyl][1,1'-biphenyl]-2-carboxylic acid;

4'-[(3-(2-cyclohexylethyl)-4-difluoromethyl-5-butyl-2,3-dihydro-2-oxo-1H-imidazol-1-yl)methyl][1,1'-biphenyl]-2-carboxylic acid;

4'-[(3-cyclohexanoyl-4-difluoromethyl-5-butyl-2,3-dihydro-2-oxo-1H-imidazol-1-yl)methyl][1,1'-biphenyl]-2-carboxylic acid;

4'-[(3-(1-oxo-2-cyclohexylethyl)-4-difluoromethyl-5-butyl-2,3-dihydro-2-oxo-1H-imidazol-1-yl)methyl][1,1'-biphenyl]-2-carboxylic acid;

4'-[(3-phenyl-4-difluoromethyl-5-butyl-2,3-dihydro-2-oxo-1H-imidazol-1-yl)methyl][1,1'-biphenyl]-2-carboxylic acid;

4'-[(3-phenylmethyl-4-difluoromethyl-5-butyl-2,3-dihydro-2-oxo-1H-imidazol-1-yl)methyl][1,1'-biphenyl]-2-carboxylic acid;

4'-[(3-(2-phenylethyl)-4-difluoromethyl-5-butyl-2,3-dihydro-2-oxo-1H-imidazol-1-yl)methyl][1,1'-biphenyl]-2-carboxylic acid;

4'-[(3-benzoyl-4-difluoromethyl-5-butyl-2,3-dihydro-2-oxo-1H-imidazol-1-yl)methyl][1,1'-biphenyl]-2-carboxylic acid;

4'-[(3-(1-oxo-2-phenylethyl)-4-difluoromethyl-5-butyl-2,3-dihydro-2-oxo-1H-imidazol-1-yl)methyl][1,1'-biphenyl]-2-carboxylic acid;

4'-[(3-(1-oxopropyl)-4-difluoromethyl-5-butyl-2,3-dihydro-2-oxo-1H-imidazol-1-yl)methyl][1,1'-biphenyl]-2-carboxylic acid;

4'-[(3-(1-oxobutyl)-4-difluoromethyl-5-butyl-2,3-dihydro-2-oxo-1H-imidazol-1-yl)methyl][1,1'-biphenyl]-2-carboxylic acid;

4'-[(3-(1-oxopentyl)-4-difluoromethyl-5-butyl-2,3-dihydro-2-oxo-1H-imidazol-1-yl)methyl][1,1'-biphenyl]-2-carboxylic acid;

4'-[(3-ethyl-4-trifluoromethyl-5-butyl-2,3-dihydro-2-oxo-1H-imidazol-1-yl)methyl][1,1'-biphenyl]-2-carboxylic acid;

4'-[(3-propyl-4-trifluoromethyl-5-butyl-2,3-dihydro-2-oxo-1H-imidazol-1-yl)methyl][1,1'-biphenyl]-2-carboxylic acid;

4'-[(3-isopropyl-4-trifluoromethyl-5-butyl-2,3-dihydro-2-oxo-1H-imidazol-1-yl)methyl][1,1'-biphenyl]-2-carboxylic acid;

4'-[(3,5-dibutyl-4-trifluoromethyl-2,3-dihydro-2-oxo-1H-imidazol-1-yl)methyl][1,1'-biphenyl]-2-carboxylic acid;

4'-[(3-secbutyl-4-trifluoromethyl-5-butyl-2,3-dihydro-2-oxo-1H-imidazol-1-yl)methyl][1,1'-biphenyl]-2-carboxylic acid;

4'-[(3-isobutyl-4-trifluoromethyl-5-butyl-2,3-dihydro-2-oxo-1H-imidazol-1-yl)methyl][1,1'-biphenyl]-2-carboxylic acid;

4'-[(3-tertbutyl-4-trifluoromethyl-5-butyl-2,3-dihydro-2-oxo-1H-imidazol-1-yl)methyl][1,1'-biphenyl]-2-carboxylic acid;

4'-[(3-pentyl-4-trifluoromethyl-5-butyl-2,3-dihydro-2-oxo-1H-imidazol-1-yl)methyl][1,1'-biphenyl]-2-carboxylic acid;

4'-[(3-isopentyl-4-trifluoromethyl-5-butyl-2,3-dihydro-2-oxo-1H-imidazol-1-yl)methyl][1,1'-biphenyl]-2-carboxylic acid;

4'-[(3-cyclohexyl-4-trifluoromethyl-5-butyl-2,3-dihydro-2-oxo-1H-imidazol-1-yl)methyl][1,1'-biphenyl]-2-carboxylic acid;

4'-[(3-cyclohexylmethyl-4-trifluoromethyl-5-butyl-2,3-dihydro-2-oxo-1H-imidazol-1-yl)methyl][1,1'-biphenyl]-2-carboxylic acid;

4'-[(3-(2-cyclohexylethyl)-4-trifluoromethyl-5-butyl-2,3-dihydro-2-oxo-1H-imidazol-1-yl)methyl][1,1'-biphenyl]-2-carboxylic acid;

4'-[(3-cyclohexanoyl-4-trifluoromethyl-5-butyl-2,3-dihydro-2-oxo-1H-imidazol-1-yl)methyl][1,1'-biphenyl]-2-carboxylic acid;

4'-[(3-(1-oxo-2-cyclohexylethyl))-4-trifluoromethyl-5-butyl-2,3-dihydro-2-oxo-1H-imidazol-1-yl)methyl][1,1'-biphenyl]-2-carboxylic acid;

4'-[(3-phenyl-4-trifluoromethyl-5-butyl-2,3-dihydro-2-oxo-1H-imidazol-1-yl)methyl][1,1'-biphenyl]-2-carboxylic acid;

4'-[(3-phenylmethyl-4-trifluoromethyl-5-butyl-2,3-dihydro-2-oxo-1H-imidazol-1-yl)methyl][1,1'-biphenyl]-2-carboxylic acid;

4'-[(3-(2-phenylethyl)-4-trifluoromethyl-5-butyl-2,3-dihydro-2-oxo-1H-imidazol-1-yl)methyl][1,1'-biphenyl]-2-carboxylic acid;

4'-[(3-benzoyl-4-trifluoromethyl-5-butyl-2,3-dihydro-2-oxo-1H-imidazol-1-yl)methyl][1,1'-biphenyl]-2-carboxylic acid;

4'-[(3-(1-oxo-2-phenylethyl)-4-trifluoromethyl-5-butyl-2,3-dihydro-2-oxo-1H-imidazol-1-yl)methyl][1,1'-biphenyl]-2-carboxylic acid;

4'-[(3-(1-oxopropyl)-4-trifluoromethyl-5-butyl-2,3-dihydro-2-oxo-1H-imidazol-1-yl)methyl][1,1'-biphenyl]-2-carboxylic acid;

4'-[(3-(1-oxobutyl)-4-trifluoromethyl-5-butyl-2,3-dihydro-2-oxo-1H-imidazol-1-yl)methyl][1,1'-biphenyl]-2-carboxylic acid;

4'-[(3-(1-oxopentyl)-4-trifluoromethyl-5-butyl-2,3-dihydro-2-oxo-1H-imidazol-1-yl)methyl][1,1'-biphenyl]-2-carboxylic acid;

4'-[(3-ethyl-4-fluoro-5-propyl-2,3-dihydro-2-oxo-1H-imidazol-1-yl)methyl][1,1'-biphenyl]-2-carboxylic acid;

4'-[(3,5-dipropyl-4-fluoro-2,3-dihydro-2-oxo-1H-imidazol-1-yl)methyl][1,1'-biphenyl]-2-carboxylic acid;

4'-[(3-isopropyl-4-fluoro-5-propyl-2,3-dihydro-2-oxo-1H-imidazol-1-yl)methyl][1,1'-biphenyl]-2-carboxylic acid;

4'-[(3-butyl-4-fluoro-5-propyl-2,3-dihydro-2-oxo-1H-imidazol-1-yl)methyl][1,1'-biphenyl]-2-carboxylic acid;

4'-[(3-secbutyl-4-fluoro-5-propyl-2,3-dihydro-2-oxo-1H-imidazol-1-yl)methyl][1,1'-biphenyl]-2-carboxylic acid;

4'-[(3-isobutyl-4-fluoro-5-propyl-2,3-dihydro-2-oxo-1H-imidazol-1-yl)methyl][1,1'-biphenyl]-2-carboxylic acid;

4'-[(3-tertbutyl-4-fluoro-5-propyl-2,3-dihydro-2-oxo-1H-imidazol-1-yl)methyl][1,1'-biphenyl]-2-carboxylic acid;

4'-[(3-pentyl-4-fluoro-5-propyl-2,3-dihydro-2-oxo-1H-imidazol-1-yl)methyl][1,1'-biphenyl]-2-carboxylic acid;

4'-[(3-isopentyl-4-fluoro-5-propyl-2,3-dihydro-2-oxo-1H-imidazol-1-yl)methyl][1,1'-biphenyl]-2-carboxylic acid;

4'-[(3-cyclohexyl-4-fluoro-5-propyl-2,3-dihydro-2-oxo-1H-imidazol-1-yl)methyl][1,1'-biphenyl]-2-carboxylic acid;

4', [(3-cyclohexmethyl-4-fluoro-5-propyl-2,3-dihydro-2-oxo-bH-imidazol-1-yl)methyl][1,1'-biphenyl]-2-carboxylic acid;

4'-[(3-(2-cyclohexylethyl)-4-fluoro-5-propyl-2,3-dihydro-2-oxo-1H-imidazol-1-yl)methyl][1,1'-biphenyl]-2-carboxylic acid;

4'-[(3-cyclohexanoyl-4-fluoro-5-propyl-2,3-dihydro-2-oxo-1H-imidazol-1-yl)methyl]['1,1'-biphenyl]-2-carboxylic acid;

4'-[(3-(1-oxo-2-cyclohexylethyl)-4-fluoro-5-propyl-2,3-dihydro-2-oxo-1H-imidazol-1-yl)methyl][1,1'-biphenyl]-2-carboxylic acid;

4'-[(3-phenyl-4-fluoro-5-propyl-2,3-dihydro-2-oxo-1H-imidazol-1-yl)methyl][1,1'-biphenyl]-2-carboxylic acid;

4'-[(3-phenylmethyl-4-fluoro-5-propyl-2,3-dihydro-2-oxo-1H-imidazol-1-yl)methyl][1,1'-biphenyl]-2-carboxylic acid;

4'[(3-(2phenylethyl)-4-fluoro-5-propyl-2,3-dihydro-2-oxo-1H-imidazol-1-yl)methyl][1,1'-biphenyl]-2-carboxylic acid;

4'-[(3-benzoyl-4-fluoro-5-propyl-2,3-dihydro-2-oxo-1H-imidazol-1-yl)methyl][1,1'-biphenyl]-2-carboxylic acid;

4'-[(3-(1-oxo-2-phenylethyl)-4-fluoro-5-propyl-2,3-dihydro-2-oxo-1H-imidazol-1-yl)methyl][1,1'-biphenyl]-2-carboxylic acid;

4'-[(3-(1-oxopropyl)-4-fluoro-5-propyl-2,3-dihydro-2-oxo-1H-imidazol-1-yl)methyl][1,1'-biphenyl]-2-carboxylic acid;

4'-[(3-(1-oxobutyl)-4-fluoro-5-propyl-2,3-dihydro-2-oxo-1H-imidazol-1-yl)methyl][1,1'-biphenyl]-2-carboxylic acid;

4'-[(3-(1-oxopentyl)-4-fluoro-5-propyl-2,3-dihydro-2-oxo-1H-imidazol-1-yl)methyl][1,1'-biphenyl]-2-carboxylic acid;

4'-[(3-ethyl-4-chloro-5-propyl-2,3-dihydro-2-oxo-1H-imidazol-1-yl)methyl][1,1'-biphenyl]-2-carboxylic acid;

4'-[(3,5-dipropyl-4-chloro-2,3-dihydro-2-oxo-1H-imidazol-1-yl)methyl][1,1'-biphenyl]-2-carboxylic acid;

4'-[(3-isopropyl-4-chloro-5-propyl-2,3-dihydro-2-oxo-1H-imidazol-1-yl)methyl][1,1'-biphenyl]-2-carboxylic acid;

4'-[(3-butyl-4-chloro-5-propyl-2,3-dihydro-2-oxo-1H-imidazol-1-yl)methyl][1,1'-biphenyl]-2-carboxylic acid;

4'-[(3-secbutyl-4-chloro-5-propyl-2,3-dihydro-2-oxo-1H-imidazol-1-yl)methyl][1,1'-biphenyl]-2-carboxylic acid;

4'-[(3-isobutyl-4-chloro-5-propyl-2,3-dihydro-2-oxo-1H-imidazol-1-yl)methyl][1,1'-biphenyl]-2-carboxylic acid;

4'-[(3-tertbutyl-4-chloro-5-propyl-2,3-dihydro-2-oxo-1H-imidazol-1-yl)methyl][1,1'-biphenyl]-2-carboxylic acid;

4'-[(3-pentyl-4-chloro-5-propyl-2,3-dihydro-2-oxo-1H-imidazol-1-yl)methyl][1,1'-biphenyl]-2-carboxylic acid;

4'-[(3-isopentyl-4-chloro-5-propyl-2,3-dihydro-2-oxo-1H-imidazol-1-yl)methyl][1,1'-biphenyl]-2-carboxylic acid;

4'-[(3-cyclohexyl-4-chloro-5-propyl-2,3-dihydro-2-oxo-1H-imidazol-1-yl)methyl][1,1'-biphenyl]-2-carboxylic acid;

4'-[(3-cyclohexylmethyl-4-chloro-5-propyl-2,3-dihydro-2-oxo-1H-imidazol-1-yl)methyl][1,1'-biphenyl]-2-carboxylic acid;

4'-[(3-(2-cyclohexylethyl)-4-chloro-5-propyl-2,3-dihydro-2-oxo-1H-imidazol-1-yl)methyl][1,1'-biphenyl]-2-carboxylic acid;

4'-[(3-cyclohexanoyl-4-chloro-5-propyl-2,3-dihydro-2-oxo-1H-imidazol-1-yl)methyl][1,1'-biphenyl]-2-carboxylic acid;

4'-[(3-(1-oxo-2-cyclohexylethyl)-4-chloro-5-propyl-2,3-dihydro-2-oxo-1H-imidazol-1-yl)methyl][1,1'-biphenyl]-2-carboxylic acid;

4'-[(3-phenyl-4-chloro-5-propyl-2,3-dihydro-2-oxo-1H-imidazol-1-yl)methyl][1,1'-biphenyl]-2-carboxylic acid;

4'-[(3-phenylmethyl-4-chloro-5-propyl-2,3-dihydro-2-oxo-1H-imidazol-1-yl)methyl][1,1'-biphenyl]-2-carboxylic acid;

4'-[(3-(2-phenylethyl)-4-chloro-5-propyl-2,3-dihydro-2-oxo-1H-imidazol-1-yl)methyl][1,1'-biphenyl]-2-carboxylic acid;

4'-[(3-benzoyl-4-chloro-5-propyl-2,3-dihydro-2-oxo-1H-imidazol-1-yl)methyl][1,1'-biphenyl]-2-carboxylic acid;

4'-[(3-(1-oxo-2-phenylethyl)-4-chloro-5-propyl-2,3-dihydro-2-oxo-1H-imidazol-1-yl)methyl][1,1'-biphenyl]-2-carboxylic acid;

4'-[(3-(1-oxopropyl)-4-chloro-5-propyl-2,3-dihydro-2-oxo-1H-imidazol-1-yl)methyl][1,1'-biphenyl]-2-carboxylic acid;

4'-[(3-(1-oxobutyl)-4-chloro-5-propyl-2,3-dihydro-2-oxo-1H-imidazol-1-yl)methyl][1,1'-biphenyl]-2-carboxylic acid;

4'-[(3-(1-oxopentyl)-4-chloro-5-propyl-2,3-dihydro-2-oxo-1H-imidazol-1-yl)methyl][1,1'-biphenyl]-2-carboxylic acid;

4'-[(3-ethyl-4-formyl-5-propyl-2,3-dihydro-2-oxo-1H-imidazol-1-yl)methyl][1,1'-biphenyl]-2-carboxylic acid;

4'-[(3,5-dipropyl-4-formyl-2,3-dihydro-2-oxo-1H-imidazol-1-yl)methyl][1,1'-biphenyl]-2-carboxylic acid;

4'-[(3-isopropyl-4-formyl-5-propyl-2,3-dihydro-2-oxo-1H-imidazol-1-yl)methyl][1,1'-biphenyl]-2-carboxylic acid;

4'-[(3-butyl-4-formyl-5-propyl-2,3-dihydro-2-oxo-1H-imidazol-1-yl)methyl][1,1'-biphenyl]-2-carboxylic acid;

4'-[(3-secbutyl-4-formyl-5-propyl-2,3-dihydro-2-oxo-1H-imidazol-1-yl)methyl][1,1'-biphenyl]-2-carboxylic acid;

4'-[(3-isobutyl-4-formyl-5-propyl-2,3-dihydro-2-oxo-1H-imidazol-1-yl)methyl][1,1'-biphenyl]-2-carboxylic acid;

4'-[(3-tertbutyl-4-formyl-5-propyl-2,3-dihydro-2-oxo-1H-imidazol-1-yl)methyl][1,1'-biphenyl]-2-carboxylic acid;

4'-[(3-pentyl-4-formyl-5-propyl-2,3-dihydro-2-oxo-1H-imidazol-1-yl)methyl][1,1'-biphenyl]-2-carboxylic acid;

4'-[(3-isopentyl-4-formyl-5-propyl-2,3-dihydro-2-oxo-1H-imidazol-1-yl)methyl][1,1'-biphenyl]-2-carboxylic acid;

4'-[(3-cyclohexyl-4-formyl-5-propyl-2,3-dihydro-2-oxo-1H-imidazol-1-yl)methyl][1,1'-biphenyl]-2-carboxylic acid;

4'-[(3-cyclohexylmethyl-4-formyl-5-propyl-2,3-dihydro-2-oxo-1H-imidazol-1-yl)methyl][1,1'-biphenyl]-2-carboxylic acid;

4'-[(3-(2-cyclohexylethyl)-4-formyl-5-propyl-2,3-dihydro-2-oxo-1H-imidazol-1-yl)methyl][1,1'-biphenyl]-2-carboxylic acid;

4'-[(3-cyclohexanoyl-4-formyl-5-propyl-2,3-dihydro-2-oxo-1H-imidazol-1-yl)methyl][1,1'-biphenyl]-2-carboxylic acid;

4'-[(3-(1-oxo-2-cyclohexylethyl)-4-formyl-5-propyl-2,3-dihydro-2-oxo-1H-imidazol-1-yl)methyl][1,1'-biphenyl]-2-carboxylic acid;

4'-[(3-phenyl-4-formyl-5-propyl-2,3-dihydro-2-oxo-1H-imidazol-1-yl)methyl][1,1'-biphenyl]-2-carboxylic acid;

4'-[(3-phenylmethyl-4-formyl-5-propyl-2,3-dihydro-2-oxo-1H-imidazol-1-yl)methyl][1,1'-biphenyl]-2-carboxylic acid;

4'-[(3-(2-phenylethyl)-4-formyl-5-propyl-2,3-dihydro-2-oxo-1H-imidazol-1-yl)methyl][1,1'-biphenyl]-2-carboxylic acid;

4'-[(3-benzoyl-4-formyl-5-propyl-2,3-dihydro-2-oxo-1H-imidazol-1-yl)methyl][1,1'-biphenyl]-2-carboxylic acid;

4'-[(3-(1-oxo-2-phenylethyl)-4-formyl-5-propyl-2,3-dihydro-2-oxo-1H-imidazol-1-yl)methyl][1,1'-biphenyl]-2-carboxylic acid;

4'-[(3-(1-oxopropyl)-4-formyl-5-propyl-2,3-dihydro-2-oxo-1H-imidazol-1-yl)methyl][1,1'-biphenyl]-2-carboxylic acid;

4'-[(3-(1-oxobutyl)-4-formyl-5-propyl-2,3-dihydro-2-oxo-1H-imidazol-1-yl)methyl][1,1'-biphenyl]-2-carboxylic acid;

4'-[(3-(1-oxopentyl)-4-formyl-5-propyl-2,3-dihydro-2-oxo-1H-imidazol-1-yl)methyl][1,1'-biphenyl]-2-carboxylic acid;

4'-[(3-ethyl-4-dimethoxymethyl-5-propyl-2,3-dihydro-2-oxo-1H-imidazol-1-yl)methyl][1,1'-biphenyl]-2-carboxylic acid;

4'-[(3,5-dipropyl-4-dimethoxymethyl-2,3-dihydro-2-oxo-1H-imidazol-1-yl)methyl][1,1'-biphenyl]-2-carboxylic acid;

4'-[(3-isopropyl-4-dimethoxymethyl-5-propyl-2,3-dihydro-2-oxo-1H-imidazol-1-yl)methyl][1,1'-biphenyl]-2-carboxylic acid;

4'-[(3-butyl-4-dimethoxymethyl-5-propyl-2,3-dihydro-2-oxo-1H-imidazol-1-yl)methyl][1,1'-biphenyl]-2-carboxylic acid;

4'-[(3-secbutyl-4-dimethoxymethyl-5-propyl-2,3-dihydro-2-oxo-1H-imidazol-1-yl)methyl][1,1'-biphenyl]-2-carboxylic acid;

4'-[(3-isobutyl-4-dimethoxymethyl-5-propyl-2,3-dihydro-2-oxo-1H-imidazol-1-yl)methyl][1,1'-biphenyl]-2-carboxylic acid;

4'-[(3-tertbutyl-4-dimethoxymethyl-5-propyl-2,3-dihydro-2-oxo-1H-imidazol-1-yl)methyl][1,1'-biphenyl]-2-carboxylic acid;

4'-[(3-pentyl-4-dimethoxymethyl-5-propyl-2,3-dihydro-2-oxo-1H-imidazol-1-yl)methyl][1,1'-biphenyl]-2-carboxylic acid;

4'-[(3-isopentyl-4-dimethoxymethyl-5-propyl-2,3-dihydro-2-oxo-1H-imidazol-1-yl)methyl][1,1'-biphenyl]-2-carboxylic acid;

4'-[(3-cyclohexyl-4-dimethoxymethyl-5-propyl-2,3-dihydro-2-oxo-1H-imidazol-1-yl)methyl][1,1'-biphenyl]-2-carboxylic acid;

4'-[(3-cyclohexylmethyl-4-dimethoxymethyl-5-propyl-2,3-dihydro-2-oxo-1H-imidazol-1-yl)methyl][1,1'-biphenyl]-2-carboxylic acid;

4'-[(3-(2-cyclohexylethyl)-4-dimethoxymethyl-5-propyl-2,3-dihydro-2-oxo-1H-imidazol-1-yl)methyl][1,1'-biphenyl]-2-carboxylic acid;

4'-[(3-cyclohexanoyl-4-dimethoxymethyl-5-propyl-2,3-dihydro-2-oxo-1H-imidazol-1-yl)methyl][1,1'-biphenyl]-2-carboxylic acid;

4'-[(3-(1-oxo-2-cyclohexylethyl)-4-dimethoxymethyl-5-propyl-2,3-dihydro-2-oxo-1H-imidazol-1-yl)methyl][1,1'-biphenyl]-2-carboxylic acid;

4'-[(3-phenyl-4-dimethoxymethyl-5-propyl-2,3-dihydro-2-oxo-1H-imidazol-1-yl)methyl][1,1'-biphenyl]-2-carboxylic acid;

4'-[(3-phenylmethyl-4-dimethoxymethyl-5-propyl-2,3-dihydro-2-oxo-1H-imidazol-1-yl)methyl][1,1'-biphenyl]-2-carboxylic acid;

4'-[(3-(2-phenylethyl)-4-dimethoxymethyl-5-propyl-2,3-dihydro-1-oxo-1H-imidazol-1-yl)methyl][1,1'-biphenyl]-2-carboxylic acid;

4'-[(3-benzoyl-4-dimethoxymethyl-5-propyl-2,3-dihydro-2-oxo-1H-imidazol-1-yl)methyl][1,1'-biphenyl]-2-carboxylic acid;

4'-[(3-(1-oxo-2-phenylethyl)-4-dimethoxymethyl-5-propyl-2,3-dihydro-2-oxo-1H-imidazol-1-yl)methyl][1,1'-biphenyl]-2-carboxylic acid;

4'-[(3-(1-oxopropyl)-4-dimethoxymethyl-5-propyl-2,3-dihydro-2-oxo-1H-imidazol-1-yl)methyl][1,1'-biphenyl]-2-carboxylic acid;

4'-[(3-(1-oxobutyl)-4-dimethoxymethyl-5-propyl-2,3-dihydro-2-oxo-1H-imidazol-1-yl)methyl][1,1'-biphenyl]-2-carboxylic acid;

4'-[(3-(1-oxopentyl)-4-dimethoxymethyl-5-propyl-2,3-dihydro-2-oxo-1H-imidazol-1-yl)methyl][1,1'-biphenyl]-2-carboxylic acid;

4'-[(3-ethyl-4-methyl-5-propyl-2,3-dihydro-2-oxo-1H-imidazol-1-yl)methyl][1,1'-biphenyl]-2-carboxylic acid;

4'-[(3,5-dipropyl-4-methyl-2,3-dihydro-2-oxo-1H-imidazol-1-yl)methyl][1,1'-biphenyl]-2-carboxylic acid;

4'-[(3-isopropyl-4-methyl-5-propyl-2,3-dihydro-2-oxo-1H-imidazol-1-yl)methyl][1,1'-biphenyl]-2-carboxylic acid;

4'-[(3-butyl-4-methyl-5-propyl-2,3-dihydro-2-oxo-1H-imidazol-1-yl)methyl][1,1'-biphenyl]-2-carboxylic acid;

4'-[(3-secbutyl-4-methyl-5-propyl-2,3-dihydro-2-oxo-1H-imidazol-1-yl)methyl][1,1'-biphenyl]-2-carboxylic acid;

4'-[(3-isobutyl-4-methyl-5-propyl-2,3-dihydro-2-oxo-1H-imidazol-1-yl)methyl][1,1'-biphenyl]-2-carboxylic acid;

4'-[(3-tertbutyl-4-methyl-5-propyl-2,3-dihydro-2-oxo-1H-imidazol-1-yl)methyl][1,1'-biphenyl]-2-carboxylic acid;

4'-[(3-pentyl-4-methyl-5-propyl-2,3-dihydro-2-oxo-1H-imidazol-1-yl)methyl][1,1'-biphenyl]-2-carboxylic acid;

4'-[(3-isopentyl-4-methyl-5-propyl-2,3-dihydro-2-oxo-1H-imidazol-1-yl)methyl][1,1'-biphenyl]-2-carboxylic acid;

4'-[(3-cyclohexyl-4-methyl-5-propyl-2,3-dihydro-2-oxo-1H-imidazol-1-yl)methyl][1,1'-biphenyl]-2-carboxylic acid;

4'-[(3-cyclohexylmethyl-4-methyl-5-propyl-2,3-dihydro-2-oxo-1H-imidazol-1-yl)methyl][1,1'-biphenyl]-2-carboxylic acid;

4'-[(3-(2-cyclohexylethyl)-4-methyl-5-propyl-2,3-dihydro-2-oxo-1H-imidazol-1-yl)methyl][1,1'-biphenyl]-2-carboxylic acid;

4'-[(3-cyclohexanoyl-4-methyl-5-propyl-2,3-dihydro-2-oxo-1H-imidazol-1-yl)methyl][1,1'-biphenyl]-2-carboxylic acid;

4'-[(3-(1-oxo-2-cyclohexylethyl)-4-methyl-5-propyl-2,3-dihydro-2-oxo-1H-imidazol-1-yl)methyl][1,1'-biphenyl]-2-carboxylic acid;

4'-[(3-phenyl-4-methyl-5-propyl-2,3-dihydro-2-oxo-1H-imidazol-1-yl)methyl][1,1'-biphenyl]-2-carboxylic acid;

4'-[(3-phenylmethyl-4-methyl-5-propyl-2,3-dihydro-2-oxo-1H-imidazol-1-yl)methyl][1,1'-biphenyl]-2-carboxylic acid;

4'-[(3-(2-phenylethyl)-4-methyl-5-propyl-2,3-dihydro-2-oxo-1H-imidazol-1-yl)methyl][1,1'-biphenyl]-2-carboxylic acid;

4'-[(3-benzoyl-4-methyl-5-propyl-2,3-dihydro-2-oxo-1H-imidazol-1-yl)methyl][1,1'-biphenyl]-2-carboxylic acid;

4'-[(3-(1-oxo-2-phenylethyl)-4-methyl-5-propyl-2,3-dihydro-2-oxo-1H-imidazol-1-yl)methyl][1,1'-biphenyl]-2-carboxylic acid;

4'-[(3-(1-oxopropyl)-4-methyl-5-propyl-2,3-dihydro-2-oxo-1H-imidazol-1-yl)methyl][1,1'-biphenyl]-2-carboxylic acid;

4'-[(3-(1-oxobutyl)-4-methyl-5-propyl-2,3-dihydro-2-oxo-1H-imidazol-1-yl)methyl][1,1'-biphenyl]-2-carboxylic acid;

4'-[(3-(1-oxopentyl)-4-methyl-5-propyl-2,3-dihydro-2-oxo-1H-imidazol-1-yl)methyl][1,1'-biphenyl]-2-carboxylic acid;

4'-[(3-ethyl-4-fluoromethyl-5-propyl-2,3-dihydro-2-oxo-1 H-imidazol-1-yl)methyl][1,1'-biphenyl]-2-carboxylic acid;

4'-[(3,5-dipropyl-4-fluoromethyl-2,3-dihydro-2-oxo-1H-imidazol-1-yl)methyl][1,1'-biphenyl]-2-carboxylic acid;

4'-[(3-isopropyl-4-fluoromethyl-5-propyl-2,3-dihydro-2-oxo-1H-imidazol-1-yl)methyl][1,1'-biphenyl]-2-carboxylic acid;

4'-[(3-butyl-4-fluoromethyl-5-propyl-2,3-dihydro-2-oxo-1H-imidazol-1-yl)methyl][1,1'-biphenyl]-2-carboxylic acid;

4'-[(3-secbutyl-4-fluoromethyl-5-propyl-2,3-dihydro-2-oxo-1H-imidazol-1-yl)methyl][1,1'-biphenyl]-2-carboxylic acid;

4'-[(3-isobutyl-4-fluoromethyl-5-propyl-2,3-dihydro-2-oxo-1H-imidazol-1-yl)methyl][1,1'-biphenyl]-2-carboxylic acid;

4'-[(3-tertbutyl-4-fluoromethyl-5-propyl-2,3-dihydro-2-oxo-1H-imidazol-1-yl)methyl][1,1'-biphenyl]-2-carboxylic acid;

4'-[(3-pentyl-4-fluoromethyl-5-propyl-2,3-dihydro-2-oxo-1H-imidazol-1-yl)methyl][1,1'-biphenyl]-2-carboxylic acid;

4'-[(3-isopentyl-4-fluoromethyl-5-propyl-2,3-dihydro-2-oxo-1H-imidazol-1-yl)methyl][1,1'-biphenyl]-2-carboxylic acid;

4'-[(3-cyclohexyl-4-fluoromethyl-5-propyl-2,3-dihydro-2-oxo-1H-imidazol-1-yl)methyl][1,1'-biphenyl]-2-carboxylic acid;

4'-[(3-cyclohexylmethyl-4-fluoromethyl-5-propyl-2,3-dihydro-2-oxo-1H-imidazol-1-yl)methyl][1,1'-biphenyl]-2-carboxylic acid;

4'-[(3-(2-cyclohexylethyl)-4-fluoromethyl-5-propyl-2,3-dihydro-2-oxo-1H-imidazol-1-yl)methyl][1,1'-biphenyl]-2-carboxylic acid;

4'-[(3-cyclohexanoyl-4-fluoromethyl-5-propyl-2,3-dihydro-2-oxo-1H-imidazol-1-yl)methyl][1,1'-biphenyl]-2-carboxylic acid;

4'-[(3-(1-oxo-2-cyclohexylethyl)-4-fluoromethyl-5-propyl-2,3-dihydro-2-oxo-1H-imidazol-1-yl)methyl][1,1'-biphenyl]-2-carboxylic acid;

4'-[(3-phenyl-4-fluoromethyl-5-propyl-2,3-dihydro-2-oxo-1H-imidazol-1-yl)methyl][1,1'-biphenyl]-2-carboxylic acid;

4'-[(3-phenylmethyl-4-fluoromethyl-5-propyl-2,3-dihydro-2-oxo-1H-imidazol-1-yl)methyl][1,1'-biphenyl]-2-carboxylic acid;

4'-[(3-(2-phenylethyl)-4-fluoromethyl-5-propyl-2,3-dihydro-2-oxo-1H-imidazol-1-yl)methyl][1,1'-biphenyl]-2-carboxylic acid;

4'-[(3-benzoyl-4-fluoromethyl-5-propyl-2,3-dihydro-2-oxo-1H-imidazol-1-yl)methyl][1,1'-biphenyl]-2-carboxylic acid;

4'-[(3-(1-oxo-2-phenylethyl)-4-fluoromethyl-5-propyl-2,3-dihydro-2-oxo-1H-imidazol-1-yl)methyl][1,1'-biphenyl]-2-carboxylic acid;

4'-[(3-(1-oxopropyl)-4-fluoromethyl-5-propyl-2,3-dihydro-2-oxo-1H-imidazol-1-yl)methyl][1,1'-biphenyl]-2-carboxylic acid;

4'-[(3-(1-oxobutyl)-4-fluoromethyl-5-propyl-2,3-dihydro-2-oxo-1H-imidazol-1-yl)methyl][1,1'-biphenyl]-2-carboxylic acid;

4'-[(3-(1-oxopentyl)-4-fluoromethyl-5-propyl-2,3-dihydro-2-oxo-1H-imidazol-1-yl)methyl][1,1'-biphenyl]-2-carboxylic acid;

4'-[(3-ethyl-4-difluoromethyl-5-propyl-2,3-dihydro-2-oxo-1H-imidazol-1-yl)methyl][1,1'-biphenyl]-2-carboxylic acid;

4'-[(3,5-dipropyl-4-difluoromethyl-2,3-dihydro-2-oxo-1H-imidazol-1-yl)methyl][1,1'-biphenyl]-2-carboxylic acid;

4'-[(3-isopropyl-4-difluoromethyl-5-propyl-2,3-dihydro-2-oxo-1H-imidazol-1-yl)methyl][1,1'-biphenyl]-2-carboxylic acid;

4'-[(3-butyl-4-difluoromethyl-5-propyl-2,3-dihydro-2-oxo-1H-imidazol-1-yl)methyl][1,1'-biphenyl]-2-carboxylic acid;

4'-[(3-secbutyl-4-difluoromethyl-5-propyl-2,3-dihydro-2-oxo-1H-imidazol-1-yl)methyl][1,1'-biphenyl]-2-carboxylic acid;

4'-[(3-isobutyl-4-difluoromethyl-5-propyl-2,3-dihydro-2-oxo-1H-imidazol-1-yl)methyl][1,1'-biphenyl]-2-carboxylic acid;

4'-[(3-tertbutyl-4-difluoromethyl-5-propyl-2,3-dihydro-2-oxo-1H-imidazol-1-yl)methyl][1,1'-biphenyl]-2-carboxylic acid;

4'-[(3-pentyl-4-difluoromethyl-5-propyl-2,3-dihydro-2-oxo-1H-imidazol-1-yl)methyl][1,1'-biphenyl]-2-carboxylic acid;

4'-[(3-isopentyl-4-difluoromethyl-5-propyl-2,3-dihydro-2-oxo-1H-imidazol-1-yl)methyl][1,1'-biphenyl]-2-carboxylic acid;

4'-[(3-cyclohexyl-4-difluoromethyl-5-propyl-2,3-dihydro-2-oxo-1H-imidazol-1-yl)methyl][1,1'-biphenyl]-2-carboxylic acid;

4'-[(3-cyclohexylmethyl-4-difluoromethyl-5-propyl-2,3-dihydro-2-oxo-1H-imidazol-1-yl)methyl][1,1'-biphenyl]-2-carboxylic acid;

4'-[(3-(2-cyclohexylethyl)-4-difluoromethyl-5-propyl-2,3-dihydro-2-oxo-1H-imidazol-1-yl)methyl][1,1'-biphenyl]-2-carboxylic acid;

4'-[(3-cyclohexanoyl-4-difluoromethyl-5-propyl-2,3-dihydro-2-oxo-1H-imidazol-1-yl)methyl][1,1'-biphenyl]-2-carboxylic acid;

4'-[(3-(1-oxo-2-cyclohexylethyl)-4-difluoromethyl-5-propyl-2,3-dihydro-2-oxo-1H-imidazol-1-yl)methyl][1,1'-biphenyl]-2-carboxylic acid;

4'-[(3-phenyl-4-difluoromethyl-5-propyl-2,3-dihydro-2-oxo-1H-imidazol-1-yl)methyl][1,1'-biphenyl]-2-carboxylic acid;

4'-[(3-phenylmethyl-4-difluoromethyl-5-propyl-2,3-dihydro-2-oxo-1H-imidazol-1-yl)methyl][1,1'-biphenyl]-2-carboxylic acid;

4'-[(3-(2-phenylethyl)-4-difluoromethyl-5-propyl-2,3-dihydro-2-oxo-1H-imidazol-1-yl)methyl][1,1'-biphenyl]-2-carboxylic acid;

4'-[(3-benzoyl-4-difluoromethyl-5-propyl-2,3-dihydro-2-oxo-1H-imidazol-1-yl)methyl][1,1'-biphenyl]-2-carboxylic acid;

4'-[(3-(1-oxo-2-phenylethyl)-4-difluoromethyl-5-propyl-2,3-dihydro-2-oxo-1H-imidazol-1-yl)methyl][1,1'-biphenyl]-2-carboxylic acid;

4'-[(3-(1-oxopropyl)-4-difluoromethyl-5-propyl-2,3-dihydro-2-oxo-1H-imidazol-1-yl)methyl][1,1'-biphenyl]-2-carboxylic acid;

4'-[(3-(1-oxobutyl)-4-difluoromethyl-5-propyl-2,3-dihydro-2-oxo-1H-imidazol-1-yl)methyl][1,1'-biphenyl]-2-carboxylic acid;

4'-[(3-(1-oxopentyl)-4-difluoromethyl-5-propyl-2,3-dihydro-2-oxo-1H-imidazol-1-yl)methyl][1,1'-biphenyl]-2-carboxylic acid;

4'-[(3-ethyl-4-trifluoromethyl-5-propyl-2,3-dihydro-2-oxo-1H-imidazol-1-yl)methyl][1,1'-biphenyl]-2-carboxylic acid;

4'-[(3,5-dipropyl-4-trifluoromethyl-2,3-dihydro-2-oxo-1H-imidazol-1-yl)methyl][1,1'-biphenyl]-2-carboxylic acid;

4'-[(3-isopropyl-4-trifluoromethyl-5-propyl-2,3-dihydro-2-oxo-1H-imidazol-1-yl)methyl][1,1'-biphenyl]-2-carboxylic acid;

4'-[(3-butyl-4-trifluoromethyl-5-propyl-2,3-dihydro-2-oxo-1H-imidazol-1-yl)methyl][1,1'-biphenyl]-2-carboxylic acid;

4'-[(3-secbutyl-4-trifluoromethyl-5-propyl-2,3-dihydro-2-oxo-1H-imidazol-1-yl)methyl][1,1'-biphenyl]-2-carboxylic acid;

4'-[(3-isobutyl-4-trifluoromethyl-5-propyl-2,3-dihydro-2-oxo-1H-imidazol-1-yl)methyl][1,1'-biphenyl]-2-carboxylic acid;

4'-[(3-tertbutyl-4-trifluoromethyl-5-propyl-2,3-dihydro-2-oxo-1H-imidazol-1-yl)methyl][1,1'-biphenyl]-2-carboxylic acid;

4'-[(3-pentyl-4-trifluoromethyl-5-propyl-2,3-dihydro-2-oxo-1H-imidazol-1-yl)methyl][1,1'-biphenyl]-2-carboxylic acid;

4'-[(3-isopentyl-4-trifluoromethyl-5-propyl-2,3-dihydro-2-oxo-1H-imidazol-1-yl)methyl][1,1'-biphenyl]-2-carboxylic acid;

4'-[(3-cyclohexyl-4-trifluoromethyl-5-propyl-2,3-dihydro-2-oxo-1H-imidazol-1-yl)methyl][1,1'-biphenyl]-2-carboxylic acid;

4'-[(3-cyclohexylmethyl-4-trifluoromethyl-5-propyl-2,3-dihydro-2-oxo-1H-imidazol-1-yl)methyl][1,1'-biphenyl]-2-carboxylic acid;

4'-[(3-(2-cyclohexylethyl)-4-trifluoromethyl-5-propyl-2,3-dihydro-2-oxo-1H-imidazol-1-yl)methyl][1,1'-biphenyl]-2-carboxylic acid;

4'-[(3-cyclohexanoyl-4-trifluoromethyl-5-propyl-2,3-dihydro-2-oxo-1H-imidazol-1-yl)methyl][1,1'-biphenyl]-2-carboxylic acid;

4'-[(3-(1-oxo-2-cyclohexylethyl)-4-trifluoromethyl-5-propyl-2,3-dihydro-2-oxo-1H-imidazol-1-yl)methyl][1,1'-biphenyl]-2-carboxylic acid;

4'-[(3-phenyl-4-trifluoromethyl-5-propyl-2,3-dihydro-2-oxo-1H-imidazol-1-yl)methyl][1,1'-biphenyl]-2-carboxylic acid;

4'-[(3-phenylmethyl-4-trifluoromethyl-5-propyl-2,3-dihydro-2-oxo-1H-imidazol-1-yl)methyl][1,1'-biphenyl]-2-carboxylic acid;

4'-[(3-(2-phenylethyl)-4-trifluoromethyl-5-propyl-2,3-dihydro-2-oxo-1H-imidazol-1-yl)methyl][1,1'-biphenyl]-2-carboxylic acid;

4'-[(3-benzoyl-4-trifluoromethyl-5-propyl-2,3-dihydro-2-oxo-1H-imidazol-1-yl)methyl][1,1'-biphenyl]-2-carboxylic acid;

4'-[(3-(1-oxo-2-phenylethyl)-4-trifluoromethyl-5-propyl-2,3-dihydro-2-oxo-1H-imidazol-1-yl)methyl][1,1'-biphenyl]-2-carboxylic acid;

4'-[(3-(1-oxopropyl)-4-trifluoromethyl-5-propyl-2,3-dihydro-2-oxo-1H-imidazol-1-yl)methyl][1,1'-biphenyl]-2-carboxylic acid;

4'-[(3-(1-oxobutyl)-4-trifluoromethyl-5-propyl-2,3-dihydro-2-oxo-1H-imidazol-1-yl)methyl][1,1'-biphenyl]-2-carboxylic acid;

4'-[(3-(1-oxopentyl)-4-trifluoromethyl-5-propyl-2,3-dihydro-2-oxo-1H-imidazol-1-yl)methyl][1,1'-biphenyl]-2-carboxylic acid;

4'-[(3-ethyl-4-fluoro-5-isopentyl-2,3-dihydro-2-oxo-1H-imidazol-1-yl)methyl][1,1'-biphenyl]-2-carboxylic acid;

4'-[(3-propyl-4-fluoro-5-isopentyl-2,3-dihydro-2-oxo-1H-imidazol-1-yl)methyl][1,1'-biphenyl]-2-carboxylic acid;

4'-[(3-isopropyl-4-fluoro-5-isopentyl-2,3-dihydro-2-oxo-1H-imidazol-1-yl)methyl][1,1'-biphenyl]-2-carboxylic acid;

4'-[(3-butyl-4-fluoro-5-isopentyl-2,3-dihydro-2-oxo-1H-imidazol-1-yl)methyl][1,1'-biphenyl]-2-carboxylic acid;

4'-[(3-secbutyl-4-fluoro-5-isopentyl-2,3-dihydro-2-oxo-1H-imidazol-1-yl)methyl][1,1'-biphenyl]-2-carboxylic acid;

4'-[(3-isobutyl-4-fluoro-5-isopentyl-2,3-dihydro-2-oxo-1H-imidazol-1-yl)methyl][1,1'-biphenyl]-2-carboxylic acid;

4'-[(3-tertbutyl-4-fluoro-5-isopentyl-2,3-dihydro-2-oxo-1H-imidazol-1-yl)methyl][1,1'-biphenyl]-2-carboxylic acid;

4'-[(3-pentyl-4-fluoro-5-isopentyl-2,3-dihydro-2-oxo-1H-imidazol-1-yl)methyl][1,1'-biphenyl]-2-carboxylic acid;

4'-[(3,5-diisopentyl-4-fluoro-2,3-dihydro-2-oxo-1H-imidazol-1-yl)methyl][1,1'-biphenyl]-2-carboxylic acid;

4'-[(3-cyclohexyl-4-fluoro-5-isopentyl-2,3-dihydro-2-oxo-1H-imidazol-1-yl)methyl][1,1'-biphenyl]-2-carboxylic acid;

4'-[(3-cyclohexylmethyl-4-fluoro-5-isopentyl-2,3-dihydro-2-oxo-1H-imidazol-1-yl)methyl][1,1'-biphenyl]-2-carboxylic acid;

4'-[(3-(2-cyclohexylethyl)-4-fluoro-5-isopentyl-2,3-dihydro-2-oxo-1H-imidazol-1-yl)methyl][1,1'-biphenyl]-2-carboxylic acid;

4'-[(3-cyclohexanoyl-4-fluoro-5-isopentyl-2,3-dihydro-2-oxo-1H-imidazol-1-yl)methyl][1,1'-biphenyl]-2-carboxylic acid;

4'-[(3-(1-oxo-2-cyclohexylethyl)-4-fluoro-5-isopentyl-2,3-dihydro-2-oxo-1H-imidazol-1-yl)methyl][1,1'-biphenyl]-2-carboxylic acid;

4'-[(3-phenyl-4-fluoro-5-isopentyl-2,3-dihydro-2-oxo-1H-imidazol-1-yl)methyl][1,1'-biphenyl]-2-carboxylic acid;

4'-[(3-phenylmethyl-4-fluoro-5-isopentyl-2,3-dihydro-2-oxo-1H-imidazol-1-yl)methyl][1,1'-biphenyl]-2-carboxylic acid;

4'-[(3-(2-phenylethyl)-4-fluoro-5-isopentyl-2,3-dihydro-2-oxo-1H-imidazol-1-yl)methyl][1,1'-biphenyl]-2-carboxylic acid;

4'-[(3-benzoyl-4-fluoro-5-isopentyl-2,3-dihydro-2-oxo-1H-imidazol-1-yl)methyl][1,1'-biphenyl]-2-carboxylic acid;

4'-[(3-(1-oxo-2-phenylethyl)-4-fluoro-5-isopentyl-2,3-dihydro-2-oxo-1H-imidazol-1-yl)methyl][1,1'-biphenyl]-2-carboxylic acid;

4'-[(3-(1-oxopropyl)-4-fluoro-5-isopentyl-2,3-dihydro-2-oxo-1H-imidazol-1-yl)methyl][1,1'-biphenyl]-2-carboxylic acid;

4'-[(3-(1-oxobutyl)-4-fluoro-5-isopentyl-2,3-dihydro-2-oxo-1H-imidazol-1-yl)methyl][1,1'-biphenyl]-2-carboxylic acid;

4'-[(3-(1-oxopentyl)-4-fluoro-5-isopentyl-2,3-dihydro-2-oxo-1H-imidazol-1-yl)methyl][1,1'-biphenyl]-2-carboxylic acid;

4'-[(3-ethyl-4-chloro-5-isopentyl-2,3-dihydro-2-oxo-1H-imidazol-1-yl)methyl][1,1'-biphenyl]-2-carboxylic acid;

4'-[(3-propyl-4-chloro-5-isopentyl-2,3-dihydro-2-oxo-1H-imidazol-1-yl)methyl][1,1'-biphenyl]-2-carboxylic acid;

4'-[(3-isopropyl-4-chloro-5-isopentyl-2,3-dihydro-2-oxo-1H-imidazol-1-yl)methyl][1,1'-biphenyl]-2-carboxylic acid;

4'-[(3-butyl-4-chloro-5-isopentyl-2,3-dihydro-2-oxo-1H-imidazol-1-yl)methyl][1,1'-biphenyl]-2-carboxylic acid;

4'-[(3-secbutyl-4-chloro-5-isopentyl-2,3-dihydro-2-oxo-1H-imidazol-1-yl)methyl][1,1'-biphenyl]-2-carboxylic acid;

4'-[(3-isobutyl-4-chloro-5-isopentyl-2,3-dihydro-2-oxo-1H-imidazol-1-yl)methyl][1,1'-biphenyl]-2-carboxylic acid;

4'-[(3-tertbutyl-4-chloro-5-isopentyl-2,3-dihydro-2-oxo-1H-imidazol-1-yl)methyl][1,1'-biphenyl]-2-carboxylic acid;

4'-[(3-pentyl-4-chloro-5-isopentyl-2,3-dihydro-2-oxo-1H-imidazol-1-yl)methyl][1,1'-biphenyl]-2-carboxylic acid;

4'-[(3,5-diisopentyl-4-chloro-2,3-dihydro-2-oxo-1H-imidazol-1-yl)methyl][1,1'-biphenyl]-2-carboxylic acid;

4'-[(3-cyclohexyl-4-chloro-5-isopentyl-2,3-dihydro-2-oxo-1H-imidazol-1-yl)methyl][1,1'-biphenyl]-2-carboxylic acid;

4'-[(3-cyclohexylmethyl-4-chloro-5-isopentyl-2,3-dihydro-2-oxo-1H-imidazol-1-yl)methyl][1,1'-biphenyl]-2-carboxylic acid;

4'-[(3-(2-cyclohexylethyl)-4-chloro-5-isopentyl-2,3-dihydro-2-oxo-1H-imidazol-1-yl)methyl][1,1'-biphenyl]-2-carboxylic acid;

4'-[(3-cyclohexanoyl-4-chloro-5-isopentyl-2,3-dihydro-2-oxo-1H-imidazol-1-yl)methyl][1,1'-biphenyl]-2-carboxylic acid;

4'-[(3-(1-oxo-2-cyclohexylethyl)-4-chloro-5-isopentyl-2,3-dihydro-2-oxo-1H-imidazol-1-yl)methyl][1,1'-biphenyl]-2-carboxylic acid;

4'-[(3-phenyl-4-chloro-5-isopentyl-2,3-dihydro-2-oxo-1H-imidazol-1-yl)methyl][1,1'-biphenyl]-2-carboxylic acid;

4'-[(3-phenylmethyl-4-chloro-5-isopentyl-2,3-dihydro-2-oxo-1H-imidazol-1-yl)methyl][1,1'-biphenyl]-2-carboxylic acid;

4'-[(3-(2-phenylethyl)-4-chloro-5-isopentyl-2,3-dihydro-2-oxo-1H-imidazol-1-yl)methyl][1,1'-biphenyl]-2-carboxylic acid;

4'-[(3-benzoyl-4-chloro-5-isopentyl-2,3-dihydro-2-oxo-1H-imidazol-1-yl)methyl][1,1'-biphenyl]-2-carboxylic acid;

4'-[(3-(1-oxo-2-phenylethyl)-4-chloro-5-isopentyl-2,3-dihydro-2-oxo-1H-imidazol-1-yl)methyl][1,1'-biphenyl]-2-carboxylic acid;

4'-[(3-(1-oxopropyl)-4-chloro-5-isopentyl-2,3-dihydro-2-oxo-1H-imidazol-1-yl)methyl][1,1'-biphenyl]-2-carboxylic acid;

4'-[(3-(1-oxobutyl)-4-chloro-5-isopentyl-2,3-dihydro-2-oxo-1H-imidazol-1-yl)methyl][1,1'-biphenyl]-2-carboxylic acid;

4'-[(3-(1-oxopentyl)-4-chloro-5-isopentyl-2,3-dihydro-2-oxo-1H-imidazol-1-yl)methyl][1,1'-biphenyl]-2-carboxylic acid;

4'-[(3-ethyl-4-formyl-5-isopentyl-2,3-dihydro-2-oxo-1H-imidazol-1-yl)methyl][1,1'-biphenyl]-2-carboxylic acid;

4'-[(3-propyl-4-formyl-5-isopentyl-2,3-dihydro-2-oxo-1H-imidazol-1-yl)methyl][1,1'-biphenyl]-2-carboxylic acid;

4'-[(3-isopropyl-4-formyl-5-isopentyl-2,3-dihydro-2-oxo-1H-imidazol-1-yl)methyl][1,1'-biphenyl]-2-carboxylic acid;

4'-[(3-butyl-4-formyl-5-isopentyl-2,3-dihydro-2-oxo-1H-imidazol-1-yl)methyl][1,1'-biphenyl]-2-carboxylic acid;

4'-[(3-secbutyl-4-formyl-5-isopentyl-2,3-dihydro-2-oxo-1H-imidazol-1-yl)methyl][1,1'-biphenyl]-2-carboxylic acid;

'-[(3-isobutyl-4-formyl-5-isopentyl-2,3-dihydro-2-oxo-1H-imidazol-1-yl)methyl][1,1'-biphenyl]-2-carboxylic acid;

4'-[(3-tertbutyl-4-formyl-5-isopentyl-2,3-dihydro-2-oxo-1H-imidazol-1-yl)methyl][1,1'-biphenyl]-2-carboxylic acid;

4'-[(3-pentyl-4-formyl-5-isopentyl-2,3-dihydro-2-oxo-1H-imidazol-1-yl)methyl][1,1'-biphenyl]-2-carboxylic acid;

4'-[(3,5-diisopentyl-4-formyl-2,3-dihydro-2-oxo-1H-imidazol-1-yl)methyl][1,1'-biphenyl]-2-carboxylic acid;

4'-[(3-cyclohexyl-4-formyl-5-isopentyl-2,3-dihydro-2-oxo-1H-imidazol-1-yl)methyl][1,1'-biphenyl]-2-carboxylic acid;

4'-[(3-cyclohexylmethyl-4-formyl-5-isopentyl-2,3-dihydro-2-oxo-1H-imidazol-1-yl)methyl][1,1'-biphenyl]-2-carboxylic acid;

4'-[(3-(2-cyclohexylethyl)-4-formyl-5-isopentyl-2,3-dihydro-2-oxo-1H-imidazol-1-yl)methyl][1,1'-biphenyl]-2-carboxylic acid;

4'-[(3-cyclohexanoyl-4-formyl-5-isopentyl-2,3-dihydro-2-oxo-1H-imidazol-1-yl)methyl][1,1'-biphenyl]-2-carboxylic acid;

4'-[(3-(1-oxo-2-cyclohexylethyl)-4-formyl-5-isopentyl-2,3-dihydro-2-oxo-1H-imidazol-1-yl)methyl][1,1'-biphenyl]-2-carboxylic acid;

4'-[(3-phenyl-4-formyl-5-isopentyl-2,3-dihydro-2-oxo-1H-imidazol-1-yl)methyl][1,1'-biphenyl]-2-carboxylic acid;

4'-[(3-phenylmethyl-4-formyl-5-isopentyl-2,3-dihydro-2-oxo-1H-imidazol-1-yl)methyl][1,1'-biphenyl]-2-carboxylic acid;

4'-[(3-(2-phenylethyl)-4-formyl-5-isopentyl-2,3-dihydro-2-oxo-1H-imidazol-1-yl)methyl][1,1'-biphenyl]-2-carboxylic acid;

4'-[(3-benzoyl-4-formyl-5-isopentyl-2,3-dihydro-2-oxo-1H-imidazol-1-yl)methyl][1,1'-biphenyl]-2-carboxylic acid;

4'-[(3-(1-oxo-2-phenylethyl)-4-formyl-5-isopentyl-2,3-dihydro-2-oxo-1H-imidazol-1-yl)methyl][1,1'-biphenyl]-2-carboxylic acid;

4'-[(3-(1-oxopropyl)-4-formyl-5-isopentyl-2,3-dihydro-2-oxo-1H-imidazol-1-yl)methyl][1,1'-biphenyl]-2-carboxylic acid;

4'-[(3-(1-oxobutyl)-4-formyl-5-isopentyl-2,3-dihydro-2-oxo-1H-imidazol-1-yl)methyl][1,1'-biphenyl]-2-carboxylic acid;

4'-[(3-(1-oxopentyl)-4-formyl-5-isopentyl-2,3-dihydro-2-oxo-1H-imidazol-1-yl)methyl][1,1'-biphenyl]-2-carboxylic acid;

4'-[(3-ethyl-4-dimethoxymethyl-5-isopentyl-2,3-dihydro-2-oxo-1H-imidazol-1-yl)methyl][1,1'-biphenyl]-2-carboxylic acid;

4'-[(3-propyl-4-dimethoxymethyl-5-isopentyl-2,3-dihydro-2-oxo-1H-imidazol-1-yl)methyl][1,1'-biphenyl]-2-carboxylic acid;

4'-[(3-isopropyl-4-dimethoxymethyl-5-isopentyl-2,3-dihydro-2-oxo-1H-imidazol-1-yl)methyl][1,1'-biphenyl]-2-carboxylic acid;

4'-[(3-butyl-4-dimethoxymethyl-5-isopentyl-2,3-dihydro-2-oxo-1H-imidazol-1-yl)methyl][1,1'-biphenyl]-2-carboxylic acid;

4'-[(3-secbutyl-4-dimethoxymethyl-5-isopentyl-2,3-dihydro-2-oxo-1H-imidazol-1-yl)methyl][1,1'-biphenyl]-2-carboxylic acid;

4'-[(3-isobutyl-4-dimethoxymethyl-5-isopentyl-2,3-dihydro-2-oxo-1H-imidazol-1-yl)methyl][1,1'-biphenyl]-2-carboxylic acid;

4'-[(3-tertbutyl-4-dimethoxymethyl-5-isopentyl-2,3-dihydro-2-oxo-1H-imidazol-1-yl)methyl][1,1'-biphenyl]-2-carboxylic acid;

4'-[(3-pentyl-4-dimethoxymethyl-5-isopentyl-2,3-dihydro-2-oxo-1H-imidazol-1-yl)methyl][1,1'-biphenyl]-2-carboxylic acid;

4'-[(3,5-diisopentyl-4-dimethoxymethyl-2,3-dihydro-2-oxo-1H-imidazol-1-yl)methyl][1,1'-biphenyl]-2-carboxylic acid;

4'-[(3-cyclohexyl-4-dimethoxymethyl-5-isopentyl-2,3-dihydro-2-oxo-1H-imidazol-1-yl)methyl][1,1'-biphenyl]-2-carboxylic acid;

4'-[(3-cyclohexylmethyl-4-dimethoxymethyl-5-isopentyl-2,3-dihydro-2-oxo-1H-imidazol-1-yl)methyl][1,1'-biphenyl]-2-carboxylic acid;

4'-[(3-(2-cyclohexylethyl)-4-dimethoxymethyl-5-isopentyl-2,3-dihydro-2-oxo-1H-imidazol-1-yl)methyl][1,1'-biphenyl]-2-carboxylic acid;

4'-[(3-cyclohexanoyl-4-dimethoxymethyl-5-isopentyl-2,3-dihydro-2-oxo-1H-imidazol-1-yl)methyl][1,1'-biphenyl]-2-carboxylic acid;

4'-[(3-(1-oxo-2-cyclohexylethyl)-4-dimethoxymethyl-5-isopentyl-2,3-dihydro-2-oxo-1H-imidazol-1-yl)methyl][1,1'-biphenyl]-2-carboxylic acid;

4'-[(3-phenyl-4-dimethoxymethyl-5-isopentyl-2,3-dihydro-2-oxo-1H-imidazol-1-yl)methyl][1,1'-biphenyl]-2-carboxylic acid;

4'-[(3-phenylmethyl-4-dimethoxymethyl-5-isopentyl-2,3-dihydro-2-oxo-1H-imidazol-1-yl)methyl][1,1'-biphenyl]-2-carboxylic acid;

4'-[(3-(2-phenylethyl)-4-dimethoxymethyl-5-isopentyl-2,3-dihydro-2-oxo-1H-imidazol-1-yl)methyl][1,1'-biphenyl]-2-carboxylic acid;

4'-[(3-benzoyl-4-dimethoxymethyl-5-isopentyl-2,3-dihydro-2-oxo-1H-imidazol-1-yl)methyl][1,1'-biphenyl]-2-carboxylic acid;

4'-[(3-(1-oxo-2-phenylethyl)-4-dimethoxymethyl-5-isopentyl-2,3-dihydro-2-oxo-1H-imidazol-1-yl)methyl][1,1'-biphenyl]-2-carboxylic acid;

4'-[(3-(1-oxopropyl)-4-dimethoxymethyl-5-isopentyl-2,3-dihydro-2-oxo-1H-imidazol-1-yl)methyl][1,1'-biphenyl]-2-carboxylic acid;

4'-[(3-(1-oxobutyl)-4-dimethoxymethyl-5-isopentyl-2,3-dihydro-2-oxo-1H-imidazol-1-yl)methyl][1,1'-biphenyl]-2-carboxylic acid;

4'-[(3-(1-oxopentyl)-4-dimethoxymethyl-5-isopentyl-2,3-dihydro-2-oxo-1H-imidazol-1-yl)methyl][1,1'-biphenyl]-2-carboxylic acid;

4'-[(3-ethyl-4-methyl-5-isopentyl-2,3-dihydro-2-oxo-1H-imidazol-1-yl)methyl][1,1'-biphenyl]-2-carboxylic acid;

4'-[(3-propyl-4-methyl-5-isopentyl-2,3-dihydro-2-oxo-1H-imidazol-1-yl)methyl][1,1'-biphenyl]-2-carboxylic acid;

4'-[(3-isopropyl-4-methyl-5-isopentyl-2,3-dihydro-2-oxo-1H-imidazol-1-yl)methyl][1,1'-biphenyl]-2-carboxylic acid;

4'-[(3-butyl-4-methyl-5-isopentyl-2,3-dihydro-2-oxo-1H-imidazol-1-yl)methyl][1,1'-biphenyl]-2-carboxylic acid;

4'-[(3-secbutyl-4-methyl-5-isopentyl-2,3-dihydro-2-oxo-1H-imidazol-1-yl)methyl][1,1'-biphenyl]-2-carboxylic acid;

4'-[(3-isobutyl-4-methyl-5-isopentyl-2,3-dihydro-2-oxo-1H-imidazol-1-yl)methyl][1,1'-biphenyl]-2-carboxylic acid;

4'-[(3-tertbutyl-4-methyl-5-isopentyl-2,3-dihydro-2-oxo-1H-imidazol-1-yl)methyl][1,1'-biphenyl]-2-carboxylic acid;

4'-[(3-pentyl-4-methyl-5-isopentyl-2,3-dihydro-2-oxo-1H-imidazol-1-yl)methyl][1,1'-biphenyl]-2-carboxylic acid;

4'-[(3,5-diisopentyl-4-methyl-2,3-dihydro-2-oxo-1H-imidazol-1-yl)methyl][1,1'-biphenyl]-2-carboxylic acid;

4'-[(3-cyclohexyl-4-methyl-5-isopentyl-2,3-dihydro-2-oxo-1H-imidazol-1-yl)methyl][1,1'-biphenyl]-2-carboxylic acid;

4'-[(3-cyclohexylmethyl-4-methyl-5-isopentyl-2,3-dihydro-2-oxo-1H-imidazol-1-yl)methyl][1,1'-biphenyl]-2-carboxylic acid;

4'-[(3-(2-cyclohexylethyl)-4-methyl-5-isopentyl-2,3-dihydro-2-oxo-1H-imidazol-1-yl)methyl][1,1'-biphenyl]-2-carboxylic acid;

4'-[(3-cyclohexanoyl-4-methyl-5-isopentyl-2,3-dihydro-2-oxo-1H-imidazol-1-yl)methyl][1,1'-biphenyl]-2-carboxylic acid;

4'-[(3-(1-oxo-2-cyclohexylethyl)-4-methyl-5-isopentyl-2,3-dihydro-2-oxo-1H-imidazol-1-yl)methyl][1,1'-biphenyl]-2-carboxylic acid;

4'-[(3-phenyl-4-methyl-5-isopentyl-2,3-dihydro-2-oxo-1H-imidazol-1-yl)methyl][1,1'-biphenyl]-2-carboxylic acid;

4'-[(3-phenylmethyl-4-methyl-5-isopentyl-2,3-dihydro-2-oxo-1H-imidazol-1-yl)methyl][1,1'-biphenyl]-2-carboxylic acid;

4'-[(3-(2-phenylethyl)-4-methyl-5-isopentyl-2,3-dihydro-2-oxo-1H-imidazol-1-yl)methyl][1,1'-biphenyl]-2-carboxylic acid;

4'-[(3-benzoyl-4-methyl-5-isopentyl-2,3-dihydro-2-oxo-1H-imidazol-1-yl)methyl][1,1'-biphenyl]-2-carboxylic acid;

4'-[(3-(1-oxo-2-phenylethyl)-4-methyl-5-isopentyl-2,3-dihydro-2-oxo-1H-imidazol-1-yl)methyl][1,1'-biphenyl]-2-carboxylic acid;

4'-[(3-(1-oxopropyl)-4-methyl-5-isopentyl-2,3-dihydro-2-oxo-1H-imidazol-1-yl)methyl][1,1'-biphenyl]-2-carboxylic acid;

4'-[(3-(1-oxobutyl)-4-methyl-5-isopentyl-2,3-dihydro-2-oxo-1H-imidazol-1-yl)methyl][1,1'-biphenyl]-2-carboxylic acid;

'-[(3-(1-oxopentyl)-4-methyl-5-isopentyl-2,3-dihydro-2-oxo-1H-imidazol-1-yl)methyl][1,1'-biphenyl]-2-carboxylic acid;

4'-[(3-ethyl-4-fluoromethyl-5-isopentyl-2,3-dihydro-2-oxo-1H-imidazol-1-yl)methyl][1,1'-biphenyl]-2-carboxylic acid;

4'-[(3-propyl-4-fluoromethyl-5-isopentyl-2,3-dihydro-2-oxo-1H-imidazol-1-yl)methyl][1,1'-biphenyl]-2-carboxylic acid;

4'-[(3-isopropyl-4-fluoromethyl-5-isopentyl-2,3-dihydro-2-oxo-1H-imidazol-1-yl)methyl][1,1'-biphenyl]-2-carboxylic acid;

4'-[(3-butyl-4-fluoromethyl-5-isopentyl-2,3-dihydro-2-oxo-1H-imidazol-1-yl)methyl][1,1'-biphenyl]-2-carboxylic acid;

4'-[(3-secbutyl-4-fluoromethyl-5-isopentyl-2,3-dihydro-2-oxo-1H-imidazol-1-yl)methyl][1,1'-biphenyl]-2-carboxylic acid;

4'-[(3-isobutyl-4-fluoromethyl-5-isopentyl-2,3-dihydro-2-oxo-1H-imidazol-1-yl)methyl][1,1'-biphenyl]-2-carboxylic acid;

4'-[(3-tertbutyl-4-fluoromethyl-5-isopentyl-2,3-dihydro-2-oxo-1H-imidazol-1-yl)methyl][1,1'-biphenyl]-2-carboxylic acid;

4'-[(3-pentyl-4-fluoromethyl-5-isopentyl-2,3-dihydro-2-oxo-1H-imidazol-1-yl)methyl][1,1'-biphenyl]-2-carboxylic acid;

4'-[(3,5-diisopentyl-4-fluoromethyl-2,3-dihydro-2-oxo-1H-imidazol-1-yl)methyl][1,1'-biphenyl]-2-carboxylic acid;

4'-[(3-cyclohexyl-4-fluoromethyl-5-isopentyl-2,3-dihydro-2-oxo-1H-imidazol-1-yl)methyl][1,1'-biphenyl]-2-carboxylic acid;

4'-[(3-cyclohexylmethyl-4-fluoromethyl-5-isopentyl-2,3-dihydro-2-oxo-1H-imidazol-1-yl)methyl][1,1'-biphenyl]-2-carboxylic acid;

4'-[(3-(2-cyclohexylethyl)-4-fluoromethyl-5-isopentyl-2,3-dihydro-2-oxo-1H-imidazol-1-yl)methyl][1,1'-biphenyl]-2-carboxylic acid;

4'-[(3-cyclohexanoyl-4-fluoromethyl-5-isopentyl-2,3-dihydro-2-oxo-1H-imidazol-1-yl)methyl][1,1'-biphenyl]-2-carboxylic acid;

4'-[(3-(1-oxo-2-cyclohexylethyl)- 4-fluoromethyl-5-isopentyl-2,3-dihydro-2-oxo-1H-imidazol-1-yl)methyl][1,1'-biphenyl]-2-carboxylic acid;

4'-[(3-phenyl-4-fluoromethyl-5-isopentyl-2,3-dihydro-2-oxo-1H-imidazol-1-yl)methyl][1,1'-biphenyl]-2-carboxylic acid;

4'-[(3-phenylmethyl-4-fluoromethyl-5-isopentyl-2,3-dihydro-2-oxo-1H-imidazol-1-yl)methyl][1,1'-biphenyl]-2-carboxylic acid;

4'-[(3-(2-phenylethyl)-4-fluoromethyl-5-isopentyl-2,3-dihydro-2-oxo-1H-imidazol-1-yl)methyl][1,1'-biphenyl]-2-carboxylic acid;

4'-[(3-benzoyl-4-fluoromethyl-5-isopentyl-2,3-dihydro-2-oxo-1H-imidazol-1-yl)methyl][1,1'-biphenyl]-2-carboxylic acid;

4'-[(3-(1-oxo-2-phenylethyl)-4-fluoromethyl-5-isopentyl-2,3-dihydro-2-oxo-1H-imidazol-1-yl)methyl][1,1'-biphenyl]-2-carboxylic acid;

4'-[(3-(1-oxopropyl)-4-fluoromethyl-5-isopentyl-2,3-dihydro-2-oxo-1H-imidazol-1-yl)methyl][1,1'-biphenyl]-2-carboxylic acid;

4'-[(3-(1-oxobutyl)-4-fluoromethyl-5-isopentyl-2,3-dihydro-2-oxo-1H-imidazol-1-yl)methyl][1,1'-biphenyl]-2-carboxylic acid;

4'-[(3-(1-oxopentyl)-4-fluoromethyl-5-isopentyl-2,3-dihydro-2-oxo-1H-imidazol-1-yl)methyl][1,1'-biphenyl]-2-carboxylic acid;

4'-[(3-ethyl-4-difluoromethyl-5-isopentyl-2,3-dihydro-2-oxo-1H-imidazol-1-yl)methyl][1,1'-biphenyl]-2-carboxylic acid;

4'-[(3-propyl-4-difluoromethyl-5-isopentyl-2,3-dihydro-2-oxo-1H-imidazol-1-yl)methyl][1,1'-biphenyl]-2-carboxylic acid;

4'-[(3-isopropyl-4-difluoromethyl-5-isopentyl-2,3-dihydro-2-oxo-1H-imidazol-1-yl)methyl][1,1'-biphenyl]-2-carboxylic acid;

4'-[(3-butyl-4-difluoromethyl-5-isopentyl-2,3-dihydro-2-oxo-1H-imidazol-1-yl)methyl][1,1'-biphenyl]-2-carboxylic acid;

4'-[(3-secbutyl-4-difluoromethyl-5-isopentyl-2,3-dihydro-2-oxo-1H-imidazol-1-yl)methyl][1,1'-biphenyl]-2-carboxylic acid;

4'-[(3-isobutyl-4-difluoromethyl-5-isopentyl-2,3-dihydro-2-oxo-1H-imidazol-1-yl)methyl][1,1'-biphenyl]-2-carboxylic acid;

4'-[(3-tertbutyl-4-difluoromethyl-5-isopentyl-2,3-dihydro-2-oxo-1H-imidazol-1-yl)methyl][1,1'-biphenyl]-2-carboxylic acid;

4'-[(3-pentyl-4-difluoromethyl-5-isopentyl-2,3-dihydro-2-oxo-1H-imidazol-1-yl)methyl][1,1'-biphenyl]-2-carboxylic acid;

4'-[(3,5-diisopentyl-4-difluoromethyl-2,3-dihydro-2-oxo-1H-imidazol-1-yl)methyl][1,1'-biphenyl]-2-carboxylic acid;

4'-[(3-cyclohexyl-4-difluoromethyl-5-isopentyl-2,3-dihydro-2-oxo-1H-imidazol-1-yl)methyl][1,1'-biphenyl]-2-carboxylic acid;

4'-[(3-cyclohexylmethyl-4-difluoromethyl-5-isopentyl-2,3-dihydro-2-oxo-1H-imidazol-1-yl)methyl][1,1'-biphenyl]-2-carboxylic acid;

4'-[(3-(2-cyclohexylethyl)-4-difluoromethyl-5-isopentyl-2,3-dihydro-2-oxo-1H-imidazol-1-yl)methyl][1,1'-biphenyl]-2-carboxylic acid;

4'-[(3-cyclohexanoyl-4-difluoromethyl-5-isopentyl-2,3-dihydro-2-oxo-1H-imidazol-1-yl)methyl][1,1'-biphenyl]-2-carboxylic acid;

4'-[(3-(1-oxo-2-cyclohexylethyl)-4-difluoromethyl-5-isopentyl-2,3-dihydro-2-oxo-1H-imidazol-1-yl)methyl][1,1'-biphenyl]-2-carboxylic acid;

4'-[(3-phenyl-4-difluoromethyl-5-isopentyl-2,3-dihydro-2-oxo-1H-imidazol-1-yl)methyl][1,1'-biphenyl]-2-carboxylic acid;

4'-[(3-phenylmethyl-4-difluoromethyl-5-isopentyl-2,3-dihydro-2-oxo-1H-imidazol-1-yl)methyl][1,1'-biphenyl]-2-carboxylic acid;

4'-[(3-(2-phenylethyl)-4-difluoromethyl-5-isopentyl-2,3-dihydro-2-oxo-1H-imidazol-1-yl)methyl][1,1'-biphenyl]-2-carboxylic acid;

4'-[(3-benzoyl-4-difluoromethyl-5-isopentyl-2,3-dihydro-2-oxo-1H-imidazol-1-yl)methyl][1,1'-biphenyl]-2-carboxylic acid;

4'-[(3-(1-oxo-2-phenylethyl)-4-difluoromethyl-5-isopentyl-2,3-dihydro-2-oxo-1H-imidazol-1-yl)methyl][1,1'-biphenyl]-2-carboxylic acid;

4'-[(3-(1-oxopropyl)-4-difluoromethyl-5-isopentyl-2,3-dihydro-2-oxo-1H-imidazol-1-yl)methyl][1,1'-biphenyl]-2-carboxylic acid;

4'-[(3-(1-oxobutyl)-4-difluoromethyl-5-isopentyl-2,3-dihydro-2-oxo-1H-imidazol-1-yl)methyl][1,1'-biphenyl]-2-carboxylic acid;

4'-[(3-(1-oxopentyl)-4-difluoromethyl-5-isopentyl-2,3-dihydro-2-oxo-1H-imidazol-1-yl)methyl][1,1'-biphenyl]-2-carboxylic acid;

4'-[(3-ethyl-4-trifluoromethyl-5-isopentyl-2,3-dihydro-2-oxo-1H-imidazol-1-yl)methyl][1,1'-biphenyl]-2-carboxylic acid;

4'-[(3-propyl-4-trifluoromethyl-5-isopentyl-2,3-dihydro-2-oxo-1H-imidazol-1-yl)methyl][1,1'-biphenyl]-2-carboxylic acid;

4'-[(3-isopropyl-4-trifluoromethyl-5-isopentyl-2,3-dihydro-2-oxo-1H-imidazol-1-yl)methyl][1,1'-biphenyl]-2-carboxylic acid;

4'-[(3-butyl-4-trifluoromethyl-5-isopentyl-2,3-dihydro-2-oxo-1H-imidazol-1-yl)methyl][1,1'-biphenyl]-2-carboxylic acid;

4'-[(3-secbutyl-4-trifluoromethyl-5-isopentyl-2,3-dihydro-2-oxo-1H-imidazol-1-yl)methyl][1,1'-biphenyl]-2-carboxylic acid;

4'-[(3-isobutyl-4-trifluoromethyl-5-isopentyl-2,3-dihydro-2-oxo-1H-imidazol-1-yl)methyl][1,1'-biphenyl]-2-carboxylic acid;

4'-[(3-tertbutyl-4-trifluoromethyl-5-isopentyl-2,3-dihydro-2-oxo-1H-imidazol-1-yl)methyl][1,1'-biphenyl]-2-carboxylic acid;

4'-[(3-pentyl-4-trifluoromethyl-5-isopentyl-2,3-dihydro-2-oxo-1H-imidazol-1-yl)methyl][1,1'-biphenyl]-2-carboxylic acid;

4'-[(3,5-diisopentyl-4-trifluoromethyl-2,3-dihydro-2-oxo-1H-imidazol-1-yl)methyl][1,1'-biphenyl]-2-carboxylic acid;

4'-[(3-cyclohexyl-4-trifluoromethyl-5-isopentyl-2,3-dihydro-2-oxo-1H-imidazol-1-yl)methyl][1,1'-biphenyl]-2-carboxylic acid;

4'-[(3-cyclohexylmethyl-4-trifluoromethyl-5-isopentyl-2,3-dihydro-2-oxo-1H-imidazol-1-yl)methyl][1,1'-biphenyl]-2-carboxylic acid;

4'-[(3-(2-cyclohexylethyl)-4-trifluoromethyl-5-isopentyl-2,3-dihydro-2-oxo-1H-imidazol-1-yl)methyl][1,1'-biphenyl]-2-carboxylic acid;

4'-[(3-cyclohexanoyl-4-trifluoromethyl-5-isopentyl-2,3-dihydro-2-oxo-1H-imidazol-1-yl)methyl][1,1'-biphenyl]-2-carboxylic acid;

4'-[(3-(1-oxo-2-cyclohexylethyl)-4-trifluoromethyl-5-isopentyl-2,3-dihydro-2-oxo-1H-imidazol-1-yl)methyl][1,1'-biphenyl]-2-carboxylic acid;

4'-[(3-phenyl-4-trifluoromethyl-5-isopentyl-2,3-dihydro-2-oxo-1H-imidazol-1-yl)methyl][1,1'-biphenyl]-2-carboxylic acid;

4'-[(3-phenylmethyl-4-trifluoromethyl-5-isopentyl-2,3-dihydro-2-oxo-1H-imidazol-1-yl)methyl][1,1'-biphenyl]-2-carboxylic acid;

4'-[(3-(2-phenylethyl)-4-trifluoromethyl-5-isopentyl-2,3-dihydro-2-oxo-1H-imidazol-1-yl)methyl][1,1'-biphenyl]-2-carboxylic acid;

4'-[(3-benzoyl-4-trifluoromethyl-5-isopentyl-2,3-dihydro-2-oxo-1H-imidazol-1-yl)methyl][1,1'-biphenyl]-2-carboxylic acid;

4'-[(3-(1-oxo-2-phenylethyl)-4-trifluoromethyl-5-isopentyl-2,3-dihydro-2-oxo-1H-imidazol-1-yl)methyl][1,1'-biphenyl]-2-carboxylic acid;

4'-[(3-(1-oxopropyl)-4-trifluoromethyl-5-isopentyl-2,3-dihydro-2-oxo-1H-imidazol-1-yl)methyl][1,1'-biphenyl]-2-carboxylic acid;

4'-[(3-(1-oxobutyl)-4-trifluoromethyl-5-isopentyl-2,3-dihydro-2-oxo-1H-imidazol-1-yl)methyl][1,1'-biphenyl]-2-carboxylic acid;

4'-[(3-(1-oxopentyl)-4-trifluoromethyl-5-isopentyl-2,3-dihydro-2-oxo-1H-imidazol-1-yl)methyl][1,1'-biphenyl]-2-carboxylic acid;

4'-[(3-ethyl-4-carboxy-5-butyl-2,3-dihydro-2-oxo-1H-imidazol-1-yl)methyl][1,1'-biphenyl]-2-carboxyic acid;

4'-[(3-propyl-4-carboxy-5-butyl-2,3-dihydro-2-oxo-1H-imidazol-1-yl)methyl][1,1'-biphenyl]-2-carboxyic acid;

4'-[(3-isopropyl-4-carboxy-5-butyl-2,3-dihydro-2-oxo-1H-imidazol-1-yl)methyl][1,1'-biphenyl]-2-carboxyic acid;

4'-[(3,5-dibutyl-4-carboxy-2,3-dihydro-2-oxo-1H-imidazol-1-yl)methyl][1,1'-biphenyl]-2-carboxyic acid;

4'-[(3-secbutyl-4-carboxy-5-butyl-2,3-dihydro-2-oxo-1H-imidazol-1-yl)methyl][1,1'-biphenyl]-2-carboxyic acid;

4'-[(3-isobutyl-4-carboxy-5-butyl-2,3-dihydro-2-oxo-1H-imidazol-1-yl)methyl][1,1'-biphenyl]-2-carboxyic acid;

4'-[(3-tertbutyl-4-carboxy-5-butyl-2,3-dihydro-2-oxo-1H-imidazol-1-yl)methyl][1,1'-biphenyl]-2-carboxyic acid;

4'-[(3-pentyl-4-carboxy-5-butyl-2,3-dihydro-2-oxo-1H-imidazol-1-yl)methyl][1,1'-biphenyl]-2-carboxyic acid;

4'-[(3-isopentyl-4-carboxy-5-butyl-2,3-dihydro-2-oxo-1H-imidazol-1-yl)methyl][1,1'-biphenyl]-2-carboxyic acid;

4'-[(3-cyclohexyl-4-carboxy-5-butyl-2,3-dihydro-2-oxo-1H-imidazol-1-yl)methyl][1,1'-biphenyl]-2-carboxyic acid;

4'-[(3-cyclohexylmethyl-4-carboxy-5-butyl-2,3-dihydro-2-oxo-1H-imidazol-1-yl)methyl][1,1'-biphenyl]-2-carboxyic acid;

4'-[(3-(2-cyclohexylethyl)-4-carboxy-5-butyl-2,3-dihydro-2-oxo-1H-imidazol-1-yl)methyl][1,1'-biphenyl]-2-carboxyic acid;

4'-[(3-cyclohexanoyl-4-carboxy-5-butyl-2,3-dihydro-2-oxo-1H-imidazol-1-yl)methyl][1,1'-biphenyl]-2-carboxyic acid;

4'-[(3-(1-oxo-2-cyclohexylethyl)-4-carboxy-5-butyl-2,3-dihydro-2-oxo-1H-imidazol-1-yl)methyl][1,1'-biphenyl]-2-carboxyic acid;

4'-[(3-phenyl-4-carboxy-5-butyl-2,3-dihydro-2-oxo-1H-imidazol-1-yl)methyl][1,1'-biphenyl]-2-carboxyic acid;

4'-[(3-phenylmethyl-4-carboxy-5-butyl-2,3-dihydro-2-oxo-1H-imidazol-1-yl)methyl][1,1'-biphenyl]-2-carboxyic acid;

4'-[(3-(2-phenylethyl)-4-carboxy-5-butyl-2,3-dihydro-2-oxo-1H-imidazol-1-yl)methyl][1,1'-biphenyl]-2-carboxyic acid;

4'-[(3-benzoyl-4-carboxy-5-butyl-2,3-dihydro-2-oxo-1H-imidazol-1-yl)methyl][1,1'-biphenyl]-2-carboxyic acid;

4'-[(3-(1-oxo-2-phenylethyl)-4-carboxy-5-butyl-2,3-dihydro-2-oxo-1H-imidazol-1-yl)methyl][1,1'-biphenyl]-2-carboxyic acid;

4'-[(3-(1-oxopropyl)-4-carboxy-5-butyl-2,3-dihydro-2-oxo-1H-imidazol-1-yl)methyl][1,1'-biphenyl]-2-carboxyic acid;

4'-[(3-(1-oxobutyl)-4-carboxy-5-butyl-2,3-dihydro-2-oxo-1H-imidazol-1-yl)methyl][1,1'-biphenyl]-2-carboxyic acid;

4'-[(3-(1-oxopentyl)-4-carboxy-5-butyl-2,3-dihydro-2-oxo-1H-imidazol-1-yl)methyl][1,1'-biphenyl]-2-carboxyic acid;

4'-[(3-ethyl-4-carboxy-5-propyl-2,3-dihydro-2-oxo-1H-imidazol-1-yl)methyl][1,1'-biphenyl]-2-carboxyic acid;

4'-[(3,5-dipropyl-4-carboxy-2,3-dihydro-2-oxo-1H-imidazol-1-yl)methyl][1,1'-biphenyl]-2-carboxyic acid;

4'-[(3-isopropyl-4-carboxy-5-propyl-2,3-dihydro-2-oxo-1H-imidazol-1-yl)methyl][1,1'-biphenyl]-2-carboxyic acid;

4'-[(3-butyl-4-carboxy-5-propyl-2,3-dihydro-2-oxo-1H-imidazol-1-yl)methyl][1,1'-biphenyl]-2-carboxyic acid;

4'-[(3-secbutyl-4-carboxy-5-propyl-2,3-dihydro-2-oxo-1H-imidazol-1-yl)methyl][1,1'-biphenyl]-2-carboxyic acid;

4'-[(3-isobutyl-4-carboxy-5-propyl-2,3-dihydro-2-oxo-1H-imidazol-1-yl)methyl][1,1'-biphenyl]-2-carboxyic acid;

4'-[(3-tertbutyl-4-carboxy-5-propyl-2,3-dihydro-2-oxo-1H-imidazol-1-yl)methyl][1,1'-biphenyl]-2-carboxyic acid;

4'-[(3-pentyl-4-carboxy-5-propyl-2,3-dihydro-2-oxo-1H-imidazol-1-yl)methyl][1,1'-biphenyl]-2-carboxyic acid;

4'-[(3-isopentyl-4-carboxy-5-propyl-2,3-dihydro-2-oxo-1H-imidazol-1-yl)methyl][1,1'-biphenyl]-2-carboxyic acid;

4'-[(3-cyclohexyl-4-carboxy-5-propyl-2,3-dihydro-2-oxo-1H-imidazol-1-yl)methyl][1,1'-biphenyl]-2-carboxyic acid;

4'-[(3-cyclohexylmethyl-4-carboxy-5-propyl-2,3-dihydro-2-oxo-1H-imidazol-1-yl)methyl][1,1'-biphenyl]-2-carboxyic acid;

4'-[(3-(2-cyclohexylethyl)-4-carboxy-5-propyl-2,3-dihydro-2-oxo-1H-imidazol-1-yl)methyl][1,1'-biphenyl]-2-carboxyic acid;

4'-[(3-cyclohexanoyl-4-carboxy-5-propyl-2,3-dihydro-2-oxo-1H-imidazol-1-yl)methyl][1,1'-biphenyl]-2-carboxyic acid;

4'-[(3-(1-oxo-2-cyclohexylethyl)-4-carboxy-5-propyl-2,3-dihydro-2-oxo-1H-imidazol-1-yl)methyl][1,1'-biphenyl]-2-carboxyic acid;

4'-[(3-phenyl-4-carboxy-5-propyl-2,3-dihydro-2-oxo-1H-imidazol-1-yl)methyl][1,1'-biphenyl]-2-carboxyic acid;

4'-[(3-phenylmethyl-4-carboxy-5-propyl-2,3-dihydro-2-oxo-1H-imidazol-1-yl)methyl][1,1'-biphenyl]-2-carboxyic acid;

4'-[(3-(2-phenylethyl)-4-carboxy-5-propyl-2,3-dihydro-2-oxo-1H-imidazol-1-yl)methyl][1,1'-biphenyl]-2-carboxyic acid;

4'-[(3-benzoyl-4-carboxy-5-propyl-2,3-dihydro-2-oxo-1H-imidazol-1-yl)methyl][1,1'-biphenyl]-2-carboxyic acid;

4'-[(3-(1-oxo-2-phenylethyl)-4-carboxy-5-propyl-2,3-dihydro-2-oxo-1H-imidazol-1-yl)methyl][1,1'-biphenyl]-2-carboxyic acid;

4'-[(3-(1-oxopropyl)-4-carboxy-5-propyl-2,3-dihydro-2-oxo-1H-imidazol-1-yl)methyl][1,1'-biphenyl]-2-carboxyic acid;

4'-[(3-(1-oxobutyl)-4-carboxy-5-propyl-2,3-dihydro-2-oxo-1H-imidazol-1-yl)methyl][1,1'-biphenyl]-2-carboxyic acid;

4'-[(3-(1-oxopentyl)-4-carboxy-5-propyl-2,3-dihydro-2-oxo-1H-imidazol-1-yl)methyl][1,1'-biphenyl]-2-carboxyic acid;

4'-[(3-ethyl-4-carboxy-5-isopentyl-2,3-dihydro-2-oxo-1H-imidazol-1-yl)methyl][1,1'-biphenyl]-2-carboxyic acid;

4'-[(3-propyl-4-carboxy-5-isopentyl-2,3-dihydro-2-oxo-1H-imidazol-1-yl)methyl][1,1'-biphenyl]-2-carboxyic acid;

4'-[(3-isopropyl-4-carboxy-5-isopentyl-2,3-dihydro-2-oxo-1H-imidazol-1-yl)methyl][1,1'-biphenyl]-2-carboxyic acid;

4'-[(3-butyl-4-carboxy-5-isopentyl-2,3-dihydro-2-oxo-1H-imidazol-1-yl)methyl][1,1'-biphenyl]-2-carboxyic acid;

4'-[(3-secbutyl-4-carboxy-5-isopentyl-2,3-dihydro-2-oxo-1H-imidazol-1-yl)methyl][1,1'-biphenyl]-2-carboxyic acid;

4'-[(3-isobutyl-4-carboxy-5-isopentyl-2,3-dihydro-2-oxo-1H-imidazol-1-yl)methyl][1,1'-biphenyl]-2-carboxyic acid;

4'-[(3-tertbutyl-4-carboxy-5-isopentyl-2,3-dihydro-2-oxo-1H-imidazol-1-yl)methyl][1,1'-biphenyl]-2-carboxyic acid;

4'-[(3-pentyl-4-carboxy-5-isopentyl-2,3-dihydro-2-oxo-1H-imidazol-1-yl)methyl][1,1'-biphenyl]-2-carboxyic acid;

4'-[(3,5-diisopentyl-4-carboxy-2,3-dihydro-2-oxo-1H-imidazol-1-yl)methyl][1,1'-biphenyl]-2-carboxyic acid;

4'-[(3-cyclohexyl-4-carboxy-5-isopentyl-2,3-dihydro-2-oxo-1H-imidazol-1-yl)methyl][1,1'-biphenyl]-2-carboxyic acid;

4'-[(3-cyclohexylmethyl-4-carboxy-5-isopentyl-2,3-dihydro-2-oxo-1H-imidazol-1-yl)methyl][1,1'-biphenyl]-2-carboxyic acid;

4'-[(3-(2-cyclohexylethyl)-4-carboxy-5-isopentyl-2,3-dihydro-2-oxo-1H-imidazol-1-yl)methyl][1,1'-biphenyl]-2-carboxyic acid;

4'-[(3-cyclohexanoyl-4-carboxy-5-isopentyl-2,3-dihydro-2-oxo-1H-imidazol-1-yl)methyl][1,1'-biphenyl]-2-carboxyic acid;

4'-[(3-(1-oxo-2-cyclohexylethyl)-4-carboxy-5-isopentyl-2,3-dihydro-2-oxo-1H-imidazol-1-yl)methyl][1,1'-biphenyl]-2-carboxyic acid;

4'-[(3-phenyl-4-carboxy-5-isopentyl-2,3-dihydro-2-oxo-1H-imidazol-1-yl)methyl][1,1'-biphenyl]-2-carboxyic acid;

4'-[(3-phenylmethyl-4-carboxy-5-isopentyl-2,3-dihydro-2-oxo-1H-imidazol-1-yl)methyl][1,1'-biphenyl]-2-carboxyic acid;

4'-[(3-(2-phenylethyl)-4-carboxy-5-isopentyl-2,3-dihydro-2-oxo-1H-imidazol-1-yl)methyl][1,1'-biphenyl]-2-carboxyic acid;

4'-[(3-benzoyl-4-carboxy-5-isopentyl-2,3-dihydro-2-oxo-1H-imidazol-1-yl)methyl][1,1'-biphenyl]-2-carboxyic acid;

4'-[(3-(1-oxo-2-phenylethyl)-4-carboxy-5-isopentyl-2,3-dihydro-2-oxo-1H-imidazol-1-yl)methyl][1,1'-biphenyl]-2-carboxyic acid;

4'-[(3-(1-oxopropyl)-4-carboxy-5-isopentyl-2,3-dihydro-2-oxo-1H-imidazol-1-yl)methyl][1,1'-biphenyl]-2-carboxyic acid;

4'-[(3-(1-oxobutyl)-4-carboxy-5-isopentyl-2,3-dihydro-2-oxo-1H-imidazol-1-yl)methyl][1,1'-biphenyl]-2-carboxyic acid; and 4'-[(3-(1-oxopentyl)-4-carboxy-5-isopentyl-2,3-dihydro-2-oxo-1H-imidazol-1-yl)methyl][1,1'-biphenyl]-2-carboxyic acid.

A family of specific compounds of more particular interest within Formula II consists of compounds and pharmaceutically-acceptable-salts thereof as follows:

4'-[(3-propyl-5-butyl-2,3-dihydro-2-oxo-1H-imidazol-1-yl)methyl][1,1'-biphenyl]-2-carboxylic acid;

4'-[(3,5-dibutyl-2,3-dihydro-2-oxo-1H-imidazol-1-yl)methyl][1,1'-biphenyl]-2-carboxylic acid;

4'-[(3-pentyl-5-butyl-2,3-dihydro-2-oxo-1H-imidazol-1-yl)methyl][1,1'-biphenyl]-2-carboxylic acid;

4'-[(3-isopentyl-5-butyl-2,3-dihydro-2-oxo-1H-imidazol-1-yl)methyl][1,1'-biphenyl]-2-carboxylic acid;

4'-[(3-cyclohexyl-5-butyl-2,3-dihydro-2-oxo-1H-imidazol-1-yl)methyl][1,1'-biphenyl]-2-carboxylic acid;

4'-[(3-phenylmethyl-5-butyl-2,3-dihydro-2-oxo-1H-imidazol-1-yl)methyl][1,1'-biphenyl]-2-carboxylic acid;

4'-[(3-(2-phenylethyl)-5-butyl-2,3-dihydro-2-oxo-1H-imidazol-1-yl)methyl][1,1'-biphenyl]-2-carboxylic acid;

4'-[(3,5-dipropyl-2,3-dihydro-2-oxo-1H-imidazol-1-yl)methyl][1,1'-biphenyl]-2-carboxylic acid;

4'-[(3-butyl-5-propyl-2,3-dihydro-2-oxo-1H-imidazol-1-yl)methyl][1,1'-biphenyl]-2-carboxylic acid;

4'-[(3-phenylmethyl-5-propyl-2,3-dihydro-2-oxo-1H-imidazol-1-yl)methyl][1,1'-biphenyl]-2-carboxylic acid;

4'-[(3-(2-phenylethyl)-5-propyl-2,3-dihydro-2-oxo-1H-imidazol-1-yl)methyl][1,1'-biphenyl]-2-carboxylic acid;

4'-[(3-butyl-5-ethyl-2,3-dihydro-2-oxo-1H-imidazol-1-yl)methyl][1,1'-biphenyl]-2-carboxylic acid;

4'-[(3-butyl-5-secbutyl-2,3-dihydro-2-oxo-1H-imidazol-1-yl)methyl][1,1'-biphenyl]-2-carboxylic acid;

4'-[(3-butyl-5-isobutyl-2,3-dihydro-2-oxo-1H-imidazol-1-yl)methyl][1,1'-biphenyl]-2-carboxylic acid;

4'-[(3-butyl-5-tertbutyl-2,3-dihydro-2-oxo-1H-imidazol-1-yl)methyl][1,1'-biphenyl]-2-carboxylic acid;

4'-[(3-butyl-5-pentyl-2,3-dihydro-2-oxo-1H-imidazol-1-yl)methyl][1,1'-biphenyl]-2-carboxylic acid;

4'-[(3-butyl-5-isopentyl-2,3-dihydro-2-oxo-1H-imidazol-1-yl)methyl][1,1'-biphenyl]-2-carboxylic acid;

4'-[(3-butyl-5-cyclohexyl-2,3-dihydro-2-oxo-1H-imidazol-1-yl)methyl][1,1'-biphenyl]-2-carboxylic acid;

4'-[(3-butyl-5-(2-butenyl)-2,3-dihydro-2-oxo-1H-imidazol-1-yl)methyl][1,1'-biphenyl]-2-carboxylic acid;

4'-[(3-butyl-5-(3-butenyl)-2,3-dihydro-2-oxo-1H-imidazol-1-yl)methyl][1,1'-biphenyl]-2-carboxylic acid;

4'-[(3-butyl-5-hexyl-2,3-dihydro-2-oxo-1H-imidazol-1-yl)methyl][1,1'-biphenyl]-2-carboxylic acid;

4'-[(3-butyl-5-(2-butynyl)-2,3-dihydro-2-oxo-1H-imidazol-1-yl)methyl][1,1'-biphenyl]-2-carboxylic acid;

4'-[(3-butyl-5-(3-butynyl)-2,3-dihydro-2-oxo-1H-imidazol-1-yl)methyl][1,1'-biphenyl]-2-carboxylic acid;

4'-[(3,5-dibutyl-4-fluoro-2,3-dihydro-2-oxo-1H-imidazol-1-yl)methyl][1,1'-biphenyl]-2-carboxylic acid;

4'-[(3,5-dibutyl-4-chloro-2,3-dihydro-2-oxo-1H-imidazol-1-yl)methyl][1,1'-biphenyl]-2-carboxylic acid;

4'-[(3,5-dibutyl-4-formyl-2,3-dihydro-2-oxo-1H-imidazol-1-yl)methyl][1,1'-biphenyl]-2-carboxylic acid;

4'-[(3,5-dibutyl-4-dimethoxymethyl-2,3-dihydro-2-oxo-1H-imidazol-1-yl)methyl][1,1'-biphenyl]-2-carboxylic acid;

4'-[(3,5-dibutyl-4-methyl-2,3-dihydro-2-oxo-1H-imidazol-1-yl)methyl][1,1'-biphenyl]-2-carboxylic acid;

4'-[(3,5-dibutyl-4-fluoromethyl-2,3-dihydro-2-oxo-1H-imidazol-1-yl)methyl][1,1'-biphenyl]-2-carboxylic acid;

4'-[(3,5-dibutyl-4-difluoromethyl-2,3-dihydro-2-oxo-1H-imidazol-1-yl)methyl][1,1'-biphenyl]-2-carboxylic acid;

4'-[(3,5-dibutyl-4-trifluoromethyl-2,3-dihydro-2-oxo-1H-imidazol-1-yl)methyl][1,1'-biphenyl]-2-carboxylic acid;

4'-[(3-butyl-4-fluoro-5-propyl-2,3-dihydro-2-oxo-1H-imidazol-1-yl)methyl][1,1'-biphenyl]-2-carboxylic acid;

4'-[(3-butyl-4-chloro-5-propyl-2,3-dihydro-2-oxo-1H-imidazol-1-yl)methyl][1,1'-biphenyl]-2-carboxylic acid;

4'-[(3-butyl-4-formyl-5-propyl-2,3-dihydro-2-oxo-1H-imidazol-1-yl)methyl][1,1'-biphenyl]-2-carboxylic acid;

4'-[(3-butyl-4-dimethoxymethyl-5-propyl-2,3-dihydro-2-oxo-1H-imidazol-1-yl)methyl][1,1'-biphenyl]-2-carboxylic acid;

4'-[(3-butyl-4-methyl-5-propyl-2,3-dihydro-2-oxo-1H-imidazol-1-yl)methyl][1,1'-biphenyl]-2-carboxylic acid;

4'-[(3-butyl-4-fluoromethyl-5-propyl-2,3-dihydro-2-oxo-1H-imidazol-1-yl)methyl][1,1'-biphenyl]-2-carboxylic acid;

4'-[(3-butyl-4-difluoromethyl-5-propyl-2,3-dihydro-2-oxo-1H-imidazol-1-yl)methyl][1,1'-biphenyl]-2-carboxylic acid;

4'-[(3-butyl-4-trifluoromethyl-5-propyl-2,3-dihydro-2-oxo-1H-imidazol-1-yl)methyl][1,1'-biphenyl]-2-carboxylic acid;

4'-[(3-butyl-4-fluoro-5-isopentyl-2,3-dihydro-2-oxo-1H-imidazol-1-yl)methyl][1,1'-biphenyl]-2-carboxylic acid;

4'-[(3-butyl-4-chloro-5-isopentyl-2,3-dihydro-2-oxo-1H-imidazol-1-yl)methyl][1,1'-biphenyl]-2-carboxylic acid;

4'-[(3-butyl-4-formyl-5-isopentyl-2,3-dihydro-2-oxo-1H-imidazol-1-yl)methyl][1,1'-biphenyl]-2-carboxylic acid;

4'-[(3-butyl-4-dimethoxymethyl-5-isopentyl-2,3-dihydro-2-oxo-1H-imidazol-1-yl)methyl][1,1'-biphenyl]-2-carboxylic acid;

4'-[(3-butyl-4-methyl-5-isopentyl-2,3-dihydro-2-oxo-1H-imidazol-1-yl)methyl][1,1,'-biphenyl]-2-carboxylic acid;

4'-[(3-butyl-4-fluoromethyl-5-isopentyl-2,3-dihydro-2-oxo-1H-imidazol-1-yl)methyl][1,1'-biphenyl]-2-carboxylic acid;

4'-[(3-butyl-4-difluoromethyl-5-isopentyl-2,3-dihydro-2-oxo-1H-imidazol-1-yl)methyl][1,1'-biphenyl]-2-carboxylic acid;

4'-[(3-butyl-4-trifluoromethyl-5-isopentyl-2,3-dihydro-2-oxo-1H-imidazol-1-yl)methyl][1,1'-biphenyl]-2-carboxylic acid;

4'-[(3-propyl-4-carboxy-5-butyl-2,3-dihydro-2-oxo-1H-imidazol-1-yl)methyl][1,1'-biphenyl]-2-carboxyic acid;

4'-[(3,5-dibutyl-4-carboxy-2,3-dihydro-2-oxo-1H-imidazol-1-yl)methyl][1,1'-biphenyl]-2-carboxyic acid;

4'-[(3,5-dipropyl-4-carboxy-2,3-dihydro-2-oxo-1H-imidazol-1-yl)methyl][1,1'-biphenyl]-2-carboxyic acid;

4'-[(3-butyl-4-carboxy-5-propyl-2,3-dihydro-2-oxo-1H-imidazol-1-yl)methyl][1,1'-biphenyl]-2-carboxyic acid;

4'-[(3-butyl-4-carboxy-5-isopentyl-2,3-dihydro-2-oxo-1H-imidazol-1-yl)methyl][1,1'-biphenyl]-2-carboxyic acid; and
4'-[(3,5-diisopentyl-4-carboxy-2,3-dihydro-2-oxo-1H-imidazol-1-yl)methyl][1,1'-biphenyl]-2-carboxyic acid.

Within Formula I there is another sub-class of compounds of high interest as represented by Formula III:

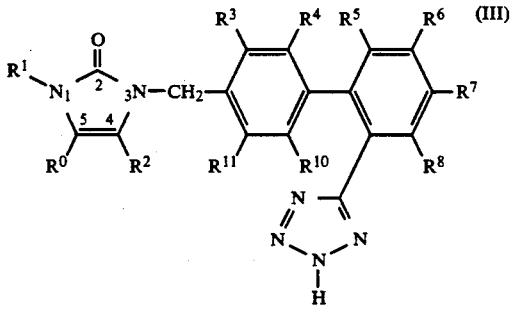

wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, cyclohexylethyl, cyclohexanoyl, 1-oxo-2-cyclohexylethyl, benzoyl, 1-oxo-2-phenethyl, 1-oxopropyl, 1-oxobutyl, 1-oxopentyl and 2-hydroxybutyl; wherein $R^0$ is selected from hydrido, methyl, fluoro, chloro, monofluoromethyl, difluoromethyl, trifluoromethyl, formyl, carboxyl and dimethoxymethyl; wherein $R^2$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl and cyclohexylethyl; wherein each of $R^3$, $R^4$, $R^5$, $R^6$, $R^7$, $R^8$, $R^{10}$ and $R^{11}$ is hydrido; or a tautomer thereof or a pharmaceutically-acceptable salt thereof.

A family of specific compounds of particular interest within Formula III consists of compounds and pharmaceutically-acceptable salts thereof as follows:

1-ethyl-4-butyl-1,3-dihydro-3-[2'-(1H-tetrazol-5-yl)[1,1'-biphenyl]-4-ylmethyl]-2H-imidazol-2-one;
1-propyl-4-butyl-1,3-dihydro-3-[2'-(1H-tetrazol-5-yl)[1,1'-biphenyl]-4-ylmethyl]-2H-imidazol-2-one;
1-isopropyl-4-butyl-1,3-dihydro-3-[2'-(1H-tetrazol-5-yl)[1,1'-biphenyl]-4-ylmethyl]-2H-imidazol-2-one;
1,4dibutyl-1,3-dihydro-3-[2'-(1H-tetrazol-5-yl)[1,1'-biphenyl]-4-ylmethyl]-2H-imidazol-2-one;
1-secbutyl-4-butyl-1,3-dihydro-3-[2'-(1H-tetrazol-5-yl)[1,1'-biphenyl]-4-ylmethyl]-2H-imidazol-2-one;
1-isobutyl-4-butyl-1,3-dihydro-3-[2'-(1H-tetrazol-5-yl)[1,1'-biphenyl]-4-ylmethyl]-2H-imidazol-2-one;
1-tertbutyl-4-butyl-1,3-dihydro-3-[2'-(1H-tetrazol-5-yl)[1,1'-biphenyl]-4-ylmethyl]-2H-imidazol-2-one;
1-pentyl-4-butyl-1,3-dihydro-3-[2'-(1H-tetrazol-5-yl)[1,1'-biphenyl]-4-ylmethyl]-2H-imidazol-2-one;
1-isopentyl-4-butyl-1,3-dihydro-3-[2'-(1H-tetrazol-5-yl)[1,1'-biphenyl]-4-ylmethyl]-2H-imidazol-2-one;
1-cyclohexyl-4-butyl-1,3-dihydro-3-[2'-(1H-tetrazol-5-yl)[1,1'-biphenyl]-4-ylmethyl]-2H-imidazol-2-one;
1-cyclohexylmethyl-4-butyl-1,3-dihydro-3-[2'-(1H-tetrazol-5-yl)[1,1'-biphenyl]-4-ylmethyl]-2H-imidazol-2-one;
1-(2-cyclohexylethyl)-4-butyl-1,3-dihydro-3-[2'-(1H-tetrazol-5-yl)[1,1'-biphenyl]-4-ylmethyl]-2H-imidazol-2-one;
1-cyclohexanoyl-4-butyl-1,3-dihydro-3-[2'-(1H-tetrazol-5-yl)[1,1'-biphenyl]-4-ylmethyl]-2H-imidazol-2-one;
1-(1-oxo-2-cyclohexylethyl)-4-butyl-1,3-dihydro-3-[2'-(1H-tetrazol-5-yl)[1,1'-biphenyl]-4-ylmethyl]-2H-imidazol-2-one;
1-phenyl-4 butyl-1,3-dihydro-3-[2'-(1H-tetrazol-5-yl)[1,1'-biphenyl]-4-ylmethyl]-2H-imidazol-2-one;
1-phenylmethyl-4-butyl-1,3-dihydro-3-[2'-(1H-tetrazol-5-yl)[1,1'-biphenyl]-4-ylmethyl]-2H-imidazol-2-one;
1-(2-phenylethyl)-4-butyl-1,3-dihydro-3-[2'-(1H-tetrazol-5-yl)[1,1'-biphenyl]-4-ylmethyl]-2H-imidazol-2-one;
1-benzoyl-4-butyl-1,3-dihydro-3-[2'-(1H-tetrazol-5-yl)[1,1'-biphenyl]-4-ylmethyl]-2H-imidazol-2-one;
1-(1-oxo-2-phenylethyl)-4-butyl-1,3-dihydro-3-[2'-(1H-tetrazol-5-yl)[1,1'-biphenyl]-4-ylmethyl]-2H-imidazol-2-one;
1-(1-oxopropyl)-4-butyl-1,3-dihydro-3-[2'-(1H-tetrazol-5-yl)[1,1'-biphenyl]-4-ylmethyl]-2H-imidazol-2-one;
1-(1-oxobutyl)-4-butyl-1,3-dihydro-3-[2'-(1H-tetrazol-5-yl)[1,1'-biphenyl]-4-ylmethyl]-2H-imidazol-2-one;
1-(1-oxopentyl)-4-butyl-1,3-dihydro-3-[2'-(1H-tetrazol-5-yl)[1,1'-biphenyl]-4-ylmethyl]-2H-imidazol-2-one;
1-ethyl-4-propyl-1,3-dihydro-3-[2'-(1H-tetrazol-5-yl)[1,1'-biphenyl]-4-ylmethyl]-2H-imidazol-2-one;
1-4-dipropyl-1,3-dihydro-3-[2'-(1H-tetrazol-5-yl)[1,1'-biphenyl]-4-ylmethyl]-2H-imidazol-2-one;
1-isopropyl-4-propyl-1,3-dihydro-3-[2'-(1H-tetrazol-5-yl)[1,1'-biphenyl]-4-ylmethyl]-2H-imidazol-2-one;
1-butyl-4-propyl-1,3-dihydro-3-[2'-(1H-tetrazol-5-yl)[1,1'-biphenyl]-4-ylmethyl]-2H-imidazol-2-one;
1-secbutyl-4-propyl-1,3-dihydro-3-[2'-(1H-tetrazol-5-yl)[1,1'-biphenyl]-4-ylmethyl]-2H-imidazol-2-one;
1-isobutyl-4-propyl-1,3-dihydro-3-[2'-(1H-tetrazol-5-yl)[1,1'-biphenyl]-4-ylmethyl]-2H-imidazol-2-one;
1-tertbutyl-4-propyl-1,3-dihydro-3-[2'-(1H-tetrazol-5-yl)[1,1'-biphenyl]-4-ylmethyl]-2H-imidazol-2-one;
1-pentyl-4-propyl-1,3-dihydro-3-[2'-(1H-tetrazol-5-yl)[1,1'-biphenyl]-4-ylmethyl]-2H-imidazol-2-one;
1-isopentyl-4-propyl-1,3-dihydro-3-[2'-(1H-tetrazol-5-yl)[1,1'-biphenyl]-4-ylmethyl]-2H-imidazol-2-one;
1-cyclohexyl-4-propyl-1,3-dihydro-3-[2'-(1H-tetrazol-5-yl)[1,1'-biphenyl]-4-ylmethyl]-2H-imidazol-2-one;
1-cyclohexylmethyl-4-propyl-1,3-dihydro-3-[2'-(1H-tetrazol-5yl)[1,1,'-biphenyl]-4-ylmethyl]-2H-imidazol-2-one;
1-(2-cyclohexylethyl)-4-propyl-1,3-dihydro-3-[2'-(1H-tetrazol-5-yl)[1,1'-biphenyl]-4-ylmethyl]-2H-imidazol-2-one;
1-cyclohexanoyl-4-propyl-1,3-dihydro-3-[2'-(1H-tetrazol-5-yl)[1,1'-biphenyl]-4-ylmethyl]-2H-imidazol-2-one;
1-(1-oxo-2-cyclohexylethyl)-4-propyl-1,3-dihydro-3-[2'-(1H-tetrazol-5-yl)[1,1'-biphenyl]-4-ylmethyl]-2H-imidazol-2-one;
1-phenyl-4-propyl-1,3-dihydro-3-[2'-(1H-tetrazol-5-yl)[1,1'-biphenyl]-4-ylmethyl]-2H-imidazol-2-one;
1-phenylmethyl-4-propyl-1,3-dihydro-3-[2'-(1H-tetrazol-5-yl)[1,1'-biphenyl]-4-ylmethyl]-2H-imidazol-2-one;
1-(2-phenylethyl)-4-propyl-1,3-dihydro-3-[2'-(1H-tetrazol-5-yl)[1,1'-biphenyl]-4-ylmethyl]-2H-imidazol-2-one;
1-benzoyl-4-propyl-1,3-dihydro-3-[2'-(1H-tetrazol-5-yl)[1,1'-biphenyl]-4-ylmethyl]-2H-imidazol-2-one;

1-(1-oxo-2-phenylethyl)-4-propyl-1,3-dihydro-3-[2'-(1H-tetrazol-5-yl)[1,1'-biphenyl]-4-ylmethyl]-2H-imidazol-2-one;

1-(1-oxopropyl)-4-propyl-1,3-dihydro-3-[2'-(1H-tetrazol-5-yl)[1,1'-biphenyl]-4-ylmethyl]-2H-imidazol-2-one;

1-(1-oxobutyl)-4-propyl-1,3-dihydro-3-[2'-(1H-tetrazol-5-yl)[1,1'-biphenyl]-4-ylmethyl]-2H-imidazol-2-one;

1-(1-oxopentyl)-4-propyl-1,3-dihydro-3-[2'-(1H-tetrazol-5-yl)[1,1'-biphenyl]-4-ylmethyl]-2H-imidazol-2-one;

1,4-diethyl-1,3-dihydro-3-[2'-(1H-tetrazol-5-yl)[1,1'-biphenyl]-4-ylmethyl]-2H-imidazol-2-one;

1-propyl-4-ethyl-1,3-dihydro-3-[2'-(1H-tetrazol-5-yl)[1,1'-biphenyl]-4-ylmethyl]-2H-imidazol-2-one;

1-isopropyl-4-ethyl-1,3-dihydro-3-[2'-(1H-tetrazol-5-yl)[1,1'-biphenyl]-4-ylmethyl]-2H-imidazol-2-one;

1-butyl-4-ethyl-1,3-dihydro-3-[2'-(1H-tetrazol-5-yl)[1,1'-biphenyl]-4-ylmethyl]-2H-imidazol-2-one;

1-secbutyl-4-ethyl-1,3-dihydro-3-[2'-(1H-tetrazol-5-yl[-1,1'biphenyl]-4-ylmethyl]2H-imidazol-2-one;

1-isobutyl-4-ethyl-1,3-dihydro-3-[2'-(1H-tetrazol-5-yl)[1,1'-biphenyl]-4-ylmethyl]-2H-imidazol-2-one;

1-tertbutyl-4-ethyl-1,3-dihydro-3-[2'-(1H-tetrazol-5-yl)[1,1'-biphenyl]-4-ylmethyl]-2H-imidazol-2-one;

1-pentyl-4-ethyl-1,3-dihydro-3-[2'-(1H-tetrazol-5-yl)[1,1'-biphenyl]-4-ylmethyl]-2H-imidazol-2-one;

1-isopentyl-4ethyl-1,3-dihydro-3-[2'-(1H-tetrazol-5-yl)[1,1'-biphenyl]-4-ylmethyl]-2H-imidazol-2-one;

1-cyclohexyl-4-ethyl-1,3-dihydro-3-[2'-(1H-tetrazol-5-yl)[1,1'-biphenyl]-4-ylmethyl]-2H-imidazol-2-one;

1-cyclohexylmethyl-4-ethyl-1,3-dihydro-3-[2'-(1H-tetrazol-5-yl)[1,1'-biphenyl]-4-ylmethyl]-2H-imidazol-2-one;

1-(2-cyclohexylethyl)-4-ethyl-1,3-dihydro-3-[2'-(1H-tetrazol-5-yl)[1,1'-biphenyl]-4-ylmethyl]-2H-imidazol-2-one;

1-cyclohexanoyl-4-ethyl-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-ethyl-1,3-dihydro-3-[2'-(1H-tetrazol-5-yl)[1 1'-biphenyl]-4-ylmethyl]-2H-imidazol-2-one;

1-phenyl-4-ethyl-1,3-dihydro-3-[2'-(1H-tetrazol-5-yl)[1,1'-biphenyl]-4-ylmethyl]-2H-imidazol-2-one;

1-phenylmethyl-4-ethyl-1,3-dihydro-3-[2'-(1H-tetrazol-5-yl)[1,1,-biphenyl]-4-ylmethyl]-2H-imidazol-2-one;

1-(2-phenylethyl)-4-ethyl-1,3-dihydro-3-[2'-(1H-tetrazol-5-yl)[1,1'-biphenyl]-4-ylmethyl]-2H-imidazol-2-one;

1-benzoyl-4-ethyl-1,3-dihydro-3-[2'-(1H-tetrazol-5-yl)[1,1'-biphenyl]-4-ylmethyl]-2H-imidazol-2-one;

1-(1-oxo-2-phenylethyl)-4-ethyl-1,3-dihydro-3-[2'-(1H-tetrazol-5-yl)[1,1'-biphenyl]-4-ylmethyl]-2H-imidazol-2-one;

1-(1-oxopropyl)-4-ethyl-1,3-dihydro-3-[2'-(1H-tetrazol-5-yl)[1,1'-biphenyl]-4-ylmethyl]-2H-imidazol-2-one;

1-(1-oxobutyl)-4-ethyl-1,3-dihydro-3-[2'-(1H-tetrazol-5-yl)[1,1'-biphenyl]-4-ylmethyl]-2H-imidazol-2-one;

1-(1-oxopentyl)-4-ethyl-1,3-dihydro-3-[2'-(1H-tetrazol-5-yl)[1,1'-biphenyl]-4-ylmethyl]-2H-imidazol-2-one;

1-ethyl-4-secbutyl-1,3-dihydro-3-[2'-(1H-tetrazol-5-yl)[1,1'-biphenyl]-4-ylmethyl]-2H-imidazol-2-one;

1-propyl-4-secbutyl-1,3-dihydro-3-[2'-(1H-tetrazol-5-yl)[1,1'-biphenyl]-4-ylmethyl]-2H-imidazol-2-one;

1-isopropyl-4-secbutyl-1,3-dihydro-3-[2'-(1H-tetrazol-5-yl)[1,1'-biphenyl]-4-ylmethyl]-2H-imidazol-2-one;

1-butyl-4-secbutyl-1,3-dihydro-3-[2'-(1H-tetrazol-5-yl)[1,1'-biphenyl]-4-ylmethyl]-2H-imidazol-2-one;

1,4-disecbutyl-1,3-dihydro-3-[2'-(1H-tetrazol-5-yl)[1,1'-biphenyl]-4-ylmethyl]-2H-imidazol-2-one;

1-isobutyl-4-secbutyl-1,3-dihydro-3-[2'-(1H-tetrazol-5-yl)[1,1'-biphenyl]-4-ylmethyl]-2H-imidazol-2-one;

1-tertbutyl-4-secbutyl-1,3-dihydro-3-[2'-(1H-tetrazol-5-yl)[1,1'-biphenyl]-4-ylmethyl]-2H-imidazol-2-one;

1-pentyl-4-secbutyl-1,3-dihydro-3-[2'-(1H-tetrazol-5-yl)[1,1'-biphenyl]-4-ylmethyl]-2H-imidazol-2-one;

1-isopentyl-4-secbutyl-1,3-dihydro-3-[2'-(1H-tetrazol-5-yl)[1,1'-biphenyl]-4-ylmethyl]-2H-imidazol-2-one;

1-cyclohexyl-4-secbutyl-1,3-dihydro-3-[2'-(1H-tetrazol-5-yl)[1,1'-biphenyl]-4-ylmethyl]-2H-imidazol-2-one;

1-cyclohexylmethyl-4-secbutyl-1,3-dihydro-3-[2'-(1H-tetrazol-5-yl)[1,1'-biphenyl]-4-ylmethyl]-2H-imidazol-2-one;

1-(2-cyclohexylethyl)-4-secbutyl-1,3-dihydro-3-[2'-(1H-tetrazol-5-yl)[1,1'-biphenyl]-4-ylmethyl]-2H-imidazol-2-one;

1-cyclohexanoyl-4-secbutyl-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-secbutyl-1,3-dihydro-3-[2'-(1H-tetrazol-5-yl)[1,1'-biphenyl]-4-ylmethyl]-2H-imidazol-2-one;

1-phenyl-4-secbutyl-1,3-dihydro-3-[2'-(1H-tetrazol-5-yl)[1,1'-biphenyl]-4-ylmethyl]-2H-imidazol-2-one;

1-phenylmethyl-4-secbutyl-1,3-dihydro-3-[2'-(1H-tetrazol-5-yl)[1,1'-biphenyl]-4-ylmethyl]-2H-imidazol-2-one;

1-(2-phenylethyl)-4-secbutyl-1,3-dihydro-3-[2'-(1H-tetrazol-5-yl)[1,1'-biphenyl]-4-ylmethyl]-2H-imidazol-2-one;

1-benzoyl-4-secbutyl-1,3-dihydro-3-[2'-(1H-tetrazol-5-yl)[1,1'-biphenyl]-4-ylmethyl]-2H-imidazol-2-one;

1-(1-oxo-2-phenylethyl)-4-secbutyl-1,3-dihydro-3-[2'-(1H-tetrazol-5-yl)[1,1'-biphenyl]-4-ylmethyl]-2H-imidazol-2-one;

1-(1-oxopropyl)-4-secbutyl-1,3-dihydro-3-[2'-(1H-tetrazol-5-yl)[1,1'-biphenyl]-4-ylmethyl]-2H-imidazol-2-one;

1-(1-oxobutyl)-4-secbutyl-1,3-dihydro-3-[2'-(1H-tetrazol-5-yl)[1,1'-biphenyl]-4-ylmethyl]-2H-imidazol-2-one;

1-(1-oxopentyl)-4-secbutyl-1,3-dihydro-3-[2'-(1H-tetrazol-5-yl)[1,1'-biphenyl]-4-ylmethyl]-2H-imidazol-2-one;

1-ethyl-4-isobutyl-1,3-dihydro-3-[2'-(1H-tetrazol-5-yl)[1,1'-biphenyl]-4-ylmethyl]-2H-imidazol-2-one;

1-propyl-4-isobutyl-1,3-dihydro-3-[2'-(1H-tetrazol-5-yl)[1,1'-biphenyl]-4-ylmethyl]-2H-imidazol-2-one;

1-isopropyl-4-isobutyl-1,3-dihydro-3-[2'-(1H-tetrazol-5-yl)[1,1'-biphenyl]-4-ylmethyl]-2H-imidazol-2-one;

1-butyl-4-isobutyl-1,3-dihydro-3-[2'-(1H-tetrazol-5-yl)[1,1'-biphenyl]-4-ylmethyl]-2H-imidazol-2-one;

1-isopropyl-4-isobutyl-1,3-dihydro-3-[2'-(1H-tetrazol-5-yl)[1,1'-biphenyl]-4-ylmethyl]-2H-imidazol-2-one;

1,4-diisobutyl-1,3-dihydro-3-[2'-(1H-tetrazol-5-yl)[1,1'-biphenyl]-4-ylmethyl]-2H-imidazol-2-one;

1-tertbutyl-4-isobutyl-1,3-dihydro-3-[2'-(1H-tetrazol-5-yl)[1,1'-biphenyl]-4-ylmethyl]-2H-imidazol-2-one;

1-pentyl-4-isobutyl-1,3-dihydro-3-[2'-(1H-tetrazol-5-yl)[1,1'-biphenyl]-4-ylmethyl]-2H-imidazol-2-one;

1-isopentyl-4-isobutyl-1,3-dihydro-3-[2'-(1H-tetrazol-5-yl)[1,1'-biphenyl]-4-ylmethyl]-2H-imidazol-2-one;

1-cyclohexyl-4-isobutyl-1,3-dihydro-3-[2'-(1H-tetrazol-5-yl)[1,1'-biphenyl]-4-ylmethyl]-2H-imidazol-2-one;

1-cyclohexylmethyl-4-isobutyl-1,3-dihydro-3-[2'-(1H-tetrazol-5-yl)[1,1'-biphenyl]-4-ylmethyl]-2H-imidazol-2-one;
1-(2-cyclohexylethyl)-4-isobutyl-1,3-dihydro-3-[2'-(1H-tetrazol-5-yl)[1,1'-biphenyl]-4-ylmethyl]-2H-imidazol-2-one;
1-cyclohexanoyl-4-isobutyl-1,3-dihydro-3-[2'-(1H-tetrazol-5-yl)[1,1'-biphenyl]-4-ylmethyl]-2H-imidazol-2-one;
1-(1-oxo-2-cyclohexylethyl)-4-isobutyl-1,3-dihydro-3-[2'-(1H-tetrazol-5-yl)[1,1'-biphenyl]-4-ylmethyl]-2H-imidazol-2-one;
1-phenyl-4-isobutyl-1,3-dihydro-3-[2'-(1H-tetrazol-5-yl)[1,1'-biphenyl]-4-ylmethyl]-2H-imidazol-2-one;
1-phenylmethyl-4-isobutyl-1,3-dihydro-3-[2'-(1H-tetrazol-5-yl)[1,1'-biphenyl]-4-ylmethyl]-2H-imidazol-2-one;
1-(2-phenylethyl)-4-isobutyl-1,3dihydro-3-[2'-(1H-tetrazol-5-yl)[1,1'-biphenyl]-4-ylmethyl]-2H-imidazol-2-one;
1-benzoyl-4-isobutyl-1,3-dihydro-3-[2'-(1H-tetrazol-5-yl)[1,1'-biphenyl]-4-ylmethyl]-2H-imidazol-2-one;
1-(1-oxo-2-phenylethyl)-4-isobutyl-1,3-dihydro-3-[2'-(1H-tetrazol-5-yl)[1,1'-biphenyl]-4-ylmethyl]-2H-imidazol-2-one;
1-(1-oxopropyl)-4-isobutyl-1,3-dihydro-3-[2'-(1H-tetrazol-5-yl)[1,1'-biphenyl]-4-ylmethyl]-2H-imidazol-2-one;
1-(1-oxobutyl)-4-isobutyl-1,3-dihydro-3-[2'-(1H-tetrazol-5-yl)[1,1'-biphenyl]-4-ylmethyl]-2H-imidazol-2-one;
1-(1-oxopentyl)-4-isobutyl-1,3-dihydro-3-[2'-(1H-tetrazol-5-yl)[1,1'-biphenyl]-4-ylmethyl]-2H-imidazol-2-one;
1-ethyl-4-tertbutyl-1,3-dihydro-3-[2'-(1H-tetrazol-5-yl)[1,1'-biphenyl]-4-ylmethyl]-2H-imidazol-2-one;
1-propyl-4-tertbutyl-1,3-dihydro-3-[2'-(1H-tetrazol-5-yl)[1,1'-biphenyl]-4-ylmethyl]-2H-imidazol-2-one;
1-isopropyl-4-tertbutyl-1,3-dihydro-3-[2'-(1H-tetrazol-5-yl)[1,1'-biphenyl]-4-ylmethyl]-2H-imidazol-2-one;
1-butyl-4-tertbutyl-1,3-dihydro-3-[2'-(1H-tetrazol-5-yl)[1,1'-biphenyl]-4-ylmethyl]-2H-imidazol-2-one;
1-secbutyl-4-tertbutyl-1,3-dihydro-3-[2'-(1H-tetrazol-5-yl)[1,1'-biphenyl]-4-ylmethyl]-2H-imidazol-2-one;
1-isobutyl-4-tertbutyl-1,3-dihydro-3-[2'-(1H-tetrazol-5-yl)[1,1'-biphenyl]-4-ylmethyl]-2H-imidazol-2-one;
1,4-ditertbutyl-1,3-dihydro-3-[2'-(1H-tetrazol-5-yl)[1,1'-biphenyl]-4-ylmethyl]-2H-imidazol-2-one;
1-pentyl-4-tertbutyl-1,3-dihydro-3-[2'-(1H-tetrazol-5-yl)[1,1'-biphenyl]-4-ylmethyl]-2H-imidazol-2-one;
1-isopentyl-4-tertbutyl-1,3-dihydro-3-[2'-(1H-tetrazol-5-yl)[1,1'-biphenyl]-4-ylmethyl]-2H-imidazol-2-one;
1-cyclohexyl-4-tertbutyl-1,3-dihydro-3-[2'-(1H-tetrazol-5-yl)[1,1'-biphenyl]-4-ylmethyl]-2H-imidazol-2-one;
1-cyclohexylmethyl-4-tertbutyl-1,3-dihydro-3-[2'-(1H-tetrazol-5-yl)[1,1'-biphenyl]-4-ylmethyl]-2H-imidazol-2-one;
1-(2-cyclohexylethyl)-4-tertbutyl-1,3-dihydro-3-[2'-(1H-tetrazol-5-yl)[1,1'-biphenyl]-4-ylmethyl]-2H-imidazol-2-one;
1-cyclohexanoyl-4-tertbutyl-1,3-dihydro-3-[2'-(1H-tetrazol-5-yl)[1,1'-biphenyl]-4-ylmethyl]-2H-imidazol-2-one;
1-(1-oxo-2-cyclohexylethyl)-4-tertbutyl-1,3-dihydro-3-[2'-(1H-tetrazol-5-yl)[1,1'-biphenyl]-4-ylmethyl]-2H-imidazol-2-one;
1-phenyl-4-tertbutyl-1,3-dihydro-3-[2'-(1H-tetrazol-5-yl)[1,1'-biphenyl]-4-ylmethyl]-2H-imidazol-2-one;
1-phenylmethyl-4-tertbutyl-1,3-dihydro-3-[2'-(1H-tetrazol-5-yl)[1,1'-biphenyl]-4-ylmethyl]-2H-imidazol-2-one;
1-(2-phenylethyl)-4-tertbutyl-1,3-dihydro-3-[2'-(1H-tetrazol-5-yl)[1,1'-biphenyl]-4-ylmethyl]-2H-imidazol-2-one;
1-benzoyl-4-tertbutyl-1,3-dihydro-3-[2'-(1H-tetrazol-5-yl)[1,1'-biphenyl]-4-ylmethyl]-2H-imidazol-2-one;
1-(1-oxo-2-phenylethyl)-4-tertbutyl-1,3-dihydro-3-[2'-(1H-tetrazol-5-yl)[1,1'-biphenyl]-4-ylmethyl]-2H-imidazol-2-one;
1-(1-oxopropyl)-4-tertbutyl-1,3-dihydro-3-[2'-(1H-tetrazol-5-yl)[1,1'-biphenyl]-4-ylmethyl]-2H-imidazol-2-one;
1-(1-oxobutyl)-4-tertbutyl-1,3-dihydro-3-[2'-(1H-tetrazol-5-yl)[1,1'-biphenyl]-4-ylmethyl]-2H-imidazol-2-one;
1-(1-oxopentyl)-4-tertbutyl-1,3-dihydro-3-[2'-(1H-tetrazol-5-yl)[1,1'-biphenyl]-4-ylmethyl]-2H-imidazol-2-one;
1-ethyl-4-pentyl-1,3-dihydro-3-[2'-(1H-tetrazol-5-yl)[1,1'-biphenyl]-4-ylmethyl]-2H-imidazol-2-one;
1-propyl-4-pentyl-1,3-dihydro-3-[2'-(1H-tetrazol-5-yl)[1,1'-biphenyl]-4-ylmethyl]-2H-imidazol-2-one;
1-isopropyl-4-pentyl-1,3-dihydro-3-[2'-(1H-tetrazol-5-yl)[1,1'-biphenyl]-4-ylmethyl]-2H-imidazol-2-one;
1-butyl-4-pentyl-1,3-dihydro-3-[2'-(1H-tetrazol-5-yl)[1,1'-biphenyl]-4-ylmethyl]-2H-imidazol-2-one;
1-secbutyl-4-pentyl-1,3-dihydro-3-[2'-(1H-tetrazol-5-yl)[1,1'-biphenyl]-4-ylmethyl]-2H-imidazol-2-one;
1-isobutyl-4-pentyl-1,3-dihydro-3-[2'-(1H-tetrazol-5-yl)[1,1'-biphenyl]-4-ylmethyl]-2H-imidazol-2-one;
1-tertbutyl-4-pentyl-1,3-dihydro-3-[2'-(1H-tetrazol-5-yl)[1,1'-biphenyl]-4-ylmethyl]-2H-imidazol-2-one;
1,4-dipentyl-1,3-dihydro-3-[2'-(1H-tetrazol-5-yl)[1,1'-biphenyl]-4-ylmethyl]-2H-imidazol-2-one;
1-isopentyl-4-pentyl-1,3-dihydro-3-[2'-(1H-tetrazol-5-yl)[1,1'-biphenyl]-4-ylmethyl]-2H-imidazol-2-one;
1-cyclohexyl-4-pentyl-1,3-dihydro-3-[2'-(1H-tetrazol-5-yl)[1,1'-biphenyl]-4-ylmethyl]-2H-imidazol-2-one;
1-cyclohexylmethyl-4-pentyl-1,3-dihydro-3-[2'-(1H-tetrazol-5-yl)[1,1'-biphenyl]-4-ylmethyl]-2H-imidazol-2-one;
1-(2-cyclohexylethyl)-4-pentyl-1,3-dihydro-3-[2'-(1H-tetrazol-5-yl)[1,1'-biphenyl]-4-ylmethyl]-2H-imidazol-2-one;
1-cyclohexanoyl-4-pentyl-1,3-dihydro-3-[2'-(1H-tetrazol-5-yl)[1,1'-biphenyl]-4-ylmethyl]-2H-imidazol-2-one;
1-(1-oxo-2-cyclohexylethyl)-4-pentyl-1,3-dihydro-3-[2'-(1H-tetrazol-5-yl)[1,1'-biphenyl]-4-ylmethyl]-2H-imidazol-2-one;
1-phenyl-4-pentyl-1,3-dihydro-3-[2'-(1H-tetrazol-5-yl)[1,1'-biphenyl]-4-ylmethyl]-2H-imidazol-2-one;
1-phenylmethyl-4-pentyl-1,3-dihydro-3-[2'-(1H-tetrazol-5-yl)[1,1'-biphenyl]-4-ylmethyl]-2H-imidazol-2-one;
1-(2-phenylethyl)-4-pentyl-1,3-dihydro-3-[2'-(1H-tetrazol-5-yl)[1,1'-biphenyl]-4-ylmethyl]-2H-imidazol-2-one;
1-benzoyl-4-pentyl-1,3-dihydro-3-[2'-(1H-tetrazol-5-yl)[1,1'-biphenyl]-4-ylmethyl]-2H-imidazol-2-one;
1-(1-oxo-2-phenylethyl)-4-pentyl-1,3-dihydro-3-[2'-(1H-tetrazol-5-yl)[1,1'-biphenyl]-4-ylmethyl]-2H-imidazol-2-one;
1-(1-oxopropyl)-4-pentyl-1,3-dihydro-3-[2'-(1H-tetrazol-5-yl)[1,1'-biphenyl]-4-ylmethyl]-2H-imidazol-2-one;

1-(1-oxobutyl)-4-pentyl-1,3-dihydro-3-[2'-(1H-tetrazol-5-yl)[1,1'-biphenyl]-4-ylmethyl]-2H-imidazol-2-one;

1-(1-oxopentyl)-4-pentyl-1,3-dihydro-3-[2'-(1H-tetrazol-5-yl)[1,1'-biphenyl]-4-ylmethyl]-2H-imidazol-2-one;

1-ethyl-4-isopentyl-1,3-dihydro-3-[2'-(1H-tetrazol-5-yl)[1,1'-biphenyl]-4-ylmethyl]-2H-imidazol-2-one;

1-propyl-4-isopentyl-1,3-dihydro-3-[2'-(1H-tetrazol-5-yl)[1,1'-biphenyl]-4-ylmethyl]-2H-imidazol-2-one;

1-isopropyl-4-isopentyl-1,3-dihydro-3-[2'-(1H-tetrazol-5-yl)[1,1'-biphenyl]-4-ylmethyl]-2H-imidazol-2-one;

1-butyl-4-isopentyl-1,3-dihydro-3-[2'-(1H-tetrazol-5-yl)[1,1'-biphenyl]-4-ylmethyl]-2H-imidazol-2-one;

1-secbutyl-4-isopentyl-1,3-dihydro-3-[2'-(1H-tetrazol-5-yl)[1,1'-biphenyl]-4-ylmethyl]-2H-imidazol-2-one;

1-isobutyl-4-isopentyl-1,3-dihydro-3-[2'-(1H-tetrazol-5-yl)[1,1'-biphenyl]-4-ylmethyl]-2H-imidazol-2-one;

1-tertbutyl-4-isopentyl-1,3-dihydro-3-[2'-(1H-tetrazol-5-yl)[1,1'-biphenyl]-4-ylmethyl]-2H-imidazol-2-one;

1-pentyl-4-isopentyl-1,3-dihydro-3-[2'-(1H-tetrazol-5-yl)[1,1'-biphenyl]-4-ylmethyl]-2H-imidazol-2-one;

1,4-diisopentyl-1,3-dihydro-3-[2'-(1H-tetrazol-5-yl)[1,1'-biphenyl]-4-ylmethyl]-2H-imidazol-2-one;

1-cyclohexyl-4-isopentyl-1,3-dihydro-3-[2'-(1H-tetrazol-5-yl)[1,1'-biphenyl]-4-ylmethyl]-2H-imidazol-2-one;

1-cyclohexylmethyl-4-isopentyl-1,3-dihydro-3-[2'-(1H-tetrazol-5-yl)[1,1'-biphenyl]-4-ylmethyl]-2H-imidazol-2-one;

1-(2-cyclohexylethyl)-4-isopentyl-1,3-dihydro-3-[2'-(1H-tetrazol-5-yl)[1,1'-biphenyl]-4-ylmethyl]-2H-imidazol-2-one;

1-cyclohexanoyl-4-isopentyl-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-isopentyl-1,3-dihydro-3-[2'-(1H-tetrazol-5-yl)[1,1'-biphenyl]-4-ylmethyl]-2H-imidazol-2-one;

1-phenyl-4-isopentyl-1,3-dihydro-3-[2'-(1H-tetrazol-5-yl)[1,1'-biphenyl]-4-ylmethyl]2H-imidazol-2-one;

1-phenylmethyl-4-isopentyl-1,3-dihydro-3-[2'-(1H-tetrazol-5-yl)[1,1'-biphenyl]-4-ylmethyl]-2H-imidazol-2-one;

1-(2-phenylethyl)-4-isopentyl -1,3-dihydro-3-[2'-(1H-tetrazol-5yl([1,1'-biphenyl]-4-ylmethyl]-2H-imidazol-2-one;

1-benzoyl-4-isopentyl-1,3-dihydro-3-[2'-(1H-tetrazol-5-yl)[1,1'-biphenyl]-4-ylmethyl]-2H-imidazol-2-one;

1(1-oxo-2-phenylethyl)-4-isopentyl-1,3-dihydro-3-[2'-(1H-tetrazol-5-yl)[1,1'-biphenyl]-4-ylmethyl]-2H-imidazol-2-one;

1-(1-oxopropyl)-4-isopentyl-1,3-dihydro-3-[2'-(1H-tetrazol-5-yl)[1,1'-biphenyl]-4-ylmethyl]-2H-imidazol-2-one;

1-(1-oxobutyl)-4-isopentyl-1,3-dihydro-3-[2'-(1H-tetrazol-5-yl)[1,1'-biphenyl]-4-ylmethyl]-2H-imidazol-2-one;

1-(1-oxopentyl)-4-isopentyl-1,3-dihydro-3-[2'-(1H-tetrazol-5-yl)[1,1'-biphenyl]-4-ylmethyl]-2H-imidazol-2-one;

1-ethyl-4-cyclohexyl-1,3-dihydro-3-[2'-(1H-tetrazol-5-yl)[1,1'-biphenyl]-4-ylmethyl]-2H-imidazol-2-one;

1-propyl-4-cyclohexyl-1,3-dihydro-3-[2'-(1H-tetrazol-5-yl)[1,1'-biphenyl]-4-ylmethyl]-2H-imidazol-2-one;

1-isopropyl-4-cyclohexyl-1,3-dihydro-3-[2'-(1H-tetrazol-5-yl)[1,1'-biphenyl]-4-ylmethyl]-2H-imidazol-2-one;

1-butyl-4-cyclohexyl-1,3-dihydro-3-[2'-(1H-tetrazol-5-yl)[1,1'-biphenyl]-4-ylmethyl]-2H-imidazol-2-one;

1-secbutyl-4-cyclohexyl-1,3-dihydro-3-[2'-(1H-tetrazol-5-yl)[1,1'-biphenyl]-4-ylmethyl]-2H-imidazol-2-one;

1-isobutyl-4-cyclohexyl-1,3-dihydro-3-[2'-(1H-tetrazol-5-yl)[1,1'-biphenyl]-4-ylmethyl]-2H-imidazol-2-one;

1-tertbutyl-4-cyclohexyl-1,3-dihydro-3-[2'-(1H-tetrazol-5-yl)[1,1'-biphenyl]-4-ylmethyl]-2H-imidazol-2-one;

1-pentyl-4-cyclohexyl-1,3-dihydro-3-[2'-(1H-tetrazol-5-yl)[1,1'-biphenyl]-4-ylmethyl]-2H-imidazol-2-one;

1-isopentyl-4-cyclohexyl-1,3-dihydro-3-[2'-(1H-tetrazol-5-yl)[1,1'-biphenyl]-4-ylmethyl]-2H-imidazol-2-one;

1,4-dicyclohexyl-1,3-dihydro-3-[2'-(1H-tetrazol-5-yl)[1,1'-biphenyl]-4-ylmethyl]-2H-imidazol-2-one;

1-cyclohexylmethyl-4-cyclohexyl-1,3-dihydro-3-[2'-(1H-tetrazol-5-yl)[1,1'-biphenyl]-4-ylmethyl]-2H-imidazol-2-one;

1-(2-cyclohexylethyl)-4-cyclohexyl-1,3-dihydro-3-[2'-(1H-tetrazol-5-yl)[1,1'-biphenyl]-4-ylmethyl]-2H-imidazol-2-one;

1-cyclohexanoyl-4-cyclohexyl-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-cyclohexyl-1,3-dihydro-3-[2'-(1H-tetrazol-5-yl)[1,1'-biphenyl]-4-ylmethyl]-2H-imidazol-2- one;

1-phenyl-4-cyclohexyl-1,3-dihydro-3-[2'-(1H-tetrazol-5-yl)[1,1'-biphenyl]-4-ylmethyl]-2H-imidazol-2-one;

1-phenylmethyl-4-cyclohexyl-1,3-dihydro-3-[2'-(1H-tetrazol-5-yl)[1,1'-biphenyl]-4-ylmethyl]-2H-imidazol-2-one;

1-(2-phenylethyl)-4-cyclohexyl-1,3-dihydro-3-[2'-(1H-tetrazol-5-yl)[1,1'-biphenyl]-4-ylmethyl]-2H-imidazol-2-one;

1-benzoyl-4-cyclohexyl-1,3-dihydro-3-[2'-(1H-tetrazol-5-yl)[1,1'-biphenyl]-4-ylmethyl]-2H-imidazol-2-one;

1-(1-oxo-2-phenylethyl)-4-cyclohexyl-1,3-dihydro-3-[2'-(1H-tetrazol-5-yl)[1,1'-biphenyl]-4-ylmethyl]-2H-imidazol-2-one;

1-(1-oxopropyl)-4-cyclohexyl-1,3-dihydro-3-[2'-(1H-tetrazol-5-yl)[1,1'-biphenyl]-4-ylmethyl]-2H-imidazol-2-one;

1-(1-oxobutyl)-4-cyclohexyl-1,3-dihydro-3-[2'-(1H-tetrazol-5-yl)[1,1'-biphenyl]-4-ylmethyl]-2H-imidazol-2-one;

1-(1-oxopentyl)-4-cyclohexyl-1,3-dihydro-3-[2'-(1H-tetrazol-5-yl)[1,1'-biphenyl]-4-ylmethyl]-2H-imidazol-2-one;

1-ethyl-4-(1-butenyl)-1,3-dihydro-3-[2'-(1H-tetrazol-5-yl)[1,1'-biphenyl]-4-ylmethyl]-2H-imidazol-2-one;

1-propyl-4-(1-butenyl)-1,3-dihydro-3-[2'-(1H-tetrazol-5-yl)[1,1'-biphenyl]-4-ylmethyl]-2H-imidazol-2-one;

1-isopropyl-4-(1-butenyl)-1,3-dihydro-3-[2'-(1H-tetrazol-5-yl)[1,1'-biphenyl]-4-ylmethyl]-2H-imidazol-2-one;

1-butyl-4-(1-butenyl)-1,3-dihydro-3-[2'-(1H-tetrazol-5-yl)[1,1'-biphenyl]-4-ylmethyl]-2H-imidazol-2-one;

1-secbutyl-4-(1-butenyl)-1,3-dihydro-3-[2'-(1H-tetrazol-5-yl)[1,1'-biphenyl]-4-ylmethyl]-2H-imidazol-2-one;

1-isobutyl-4-(1-butenyl)-1,3-dihydro-3-[2'-(1H-tetrazol-5-yl)[1,1'-biphenyl]-4-ylmethyl]-2H-imidazol-2-one;

1-tertbutyl-4-(1-butenyl)-1,3-dihydro-3-[2'-(1H-tetrazol-5-yl)[1,1'-biphenyl]-4-ylmethyl]-2H-imidazol-2-one;

1-pentyl-4-(1-butenyl)-1,3-dihydro-3-[2'-(1H-tetrazol-5-yl)[1,1'-biphenyl]-4-ylmethyl]-2H-imidazol-2-one;

1-isopentyl-4-(1-butenyl)-1,3-dihydro-3-[2'-(1H-tetrazol-5-yl)[1,1'-biphenyl]-4-ylmethyl]-2H-imidazol-2-one;

1-cyclohexyl-4-(1-butenyl)-1,3-dihydro-3-[2'-(1H-tetrazol-5-yl)[1,1'-biphenyl]-4-ylmethyl]-2H-imidazol-2-one;

1-cyclohexylmethyl-4-(1-butenyl)-1,3-dihydro-3-[2'-(1H-tetrazol-5-yl)[1,1'-biphenyl]-4-ylmethyl]-2H-imidazol-2-one;

1-(2-cyclohexylethyl)-4-(1-butenyl)-1,3-dihydro-3-[2'-(1H-tetrazol-5-yl)[1,1'-biphenyl]-4-ylmethyl]-2H-imidazol-2-one;

1-cyclohexanoyl-4-(1-butenyl)-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-(1-butenyl)-1,3-dihydro-3-[2'-(1H-tetrazol-5-yl)[1,1'-biphenyl]-4-ylmethyl]-2H-imidazol-2-one;

1-phenyl-4-(1-butenyl)-1,3-dihydro-3-[2'-(1H-tetrazol-5-yl)[1,1'-biphenyl]-4-ylmethyl]-2H-imidazol-2-one;

1-phenylmethyl-4-(1-butenyl)-1,3-dihydro-3-[2'-(1H-tetrazol-5-yl)[1,1'-biphenyl]-4-ylmethyl]-2H-imidazol-2-one;

1-(2-phenylethyl)-4-(1-butenyl)-1,3-dihydro-3-[2'-(1H-tetrazol-5-yl)[1,1'-biphenyl]-4-ylmethyl]-2H-imidazol-2-one;

1-(1-oxopropyl)-4-(1-butenyl)-1,3-dihydro-3-[2'-(1H-tetrazol-5-yl)[1,1'-biphenyl]-4-ylmethyl]-2H-imidazol-2-one;

1-(1-oxobutyl)-4-(1-butenyl)-1,3-dihydro-3-[2'-(1H-tetrazol-5-yl)[1,1'-biphenyl]-4-ylmethyl]-2H-imidazol-2-one;

1-(1-oxopentyl)-4-(1-butenyl)-1,3-dihydro-3-[2'-(1H-tetrazol-5-yl)[1,1'-biphenyl]-4-ylmethyl]-2H-imidazol-2-one;

1-ethyl-4-(2-butenyl)-1,3-dihydro-3-[2'-(1H-tetrazol-5-yl)[1,1'-biphenyl]-4-ylmethyl]-2H-imidazol-2-one;

1-propyl-4-(2-butenyl)-1,3-dihydro-3-[2'-(1H-tetrazol-5-yl)[1,1'-biphenyl]-4-ylmethyl]-2H-imidazol-2-one;

1-isopropyl-4-(2-butenyl)-1,3-dihydro-3-[2'-(1H-tetrazol-5-yl)[1,1'-biphenyl]-4-ylmethyl]-2H-imidazol-2-one;

1-butyl-4-(2-butenyl)-1,3-dihydro-3-[2'-(1H-tetrazol-5-yl)[1,1'-biphenyl]-4-ylmethyl]-2H-imidazol-2-one;

1-secbutyl-4-(2-butenyl)-1,3-dihydro-3-[2'-(1H-tetrazol-5-yl)[1,1'-biphenyl]-4-ylmethyl]-2H-imidazol-2-one;

1-isobutyl-4-(2-butenyl)-1,3-dihydro-3-[2'-(1H-tetrazol-5-yl)[1,1'-biphenyl]-4-ylmethyl]-2H-imidazol-2-one;

1-tertbutyl-4-(2-butenyl)-1,3-dihydro-3-[2'-(1H-tetrazol-5-yl)[1,1'-biphenyl]-4-ylmethyl]-2H-imidazol-2-one;

1-pentyl-4-(2-butenyl)-1,3-dihydro-3-[2'-(1H-tetrazol-5-yl)[1,1'-biphenyl]-4-ylmethyl]-2H-imidazol-2-one;

1-isopentyl-4-(2-butenyl)-1,3-dihydro-3-[2'-(1H-tetrazol-5-yl)[1,1'-biphenyl]-4-ylmethyl]-2H-imidazol-2-one;

1-cyclohexyl-4-(2-butenyl)-1,3-dihydro-3-[2'-(1H-tetrazol-5-yl)[1,1'-biphenyl]-4-ylmethyl]-2H-imidazol-2-one;

1-cyclohexylmethyl-4-(2-butenyl)-1,3-dihydro-3-[2'-(1H-tetrazol-5-yl)[1,1'-biphenyl]-4-ylmethyl]-2H-imidazol-2-one;

1-(2-cyclohexylethyl)-4-(2-butenyl)-1,3-dihydro-3-[2'-(1H-tetrazol-5-yl)[1,1'-biphenyl]-4-ylmethyl]-2H-imidazol-2-one;

1-cyclohexanoyl-4-(2-butenyl)-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-(2-butenyl)-1,3-dihydro-3-[2'-(1H-tetrazol-5-yl)[1,1'-biphenyl]-4-ylmethyl]-2H-imidazol-2-one;

1-phenyl-4-(2-butenyl)-1,3-dihydro-3-[2'-(1H-tetrazol-5-yl)[1,1'-biphenyl]-4-ylmethyl]-2H-imidazol-2-one;

1-phenylmethyl-4-(2-butenyl)-1,3-dihydro-3-[2'-(1H-tetrazol-5-yl)[1,1'-biphenyl]-4-ylmethyl]-2H-imidazol-2-one;

1-(2-phenylethyl)-4-(2-butenyl)-1,3-dihydro-3-[2'-(1H-tetrazol-5-yl)[1,1'-biphenyl]-4-ylmethyl]-2H-imidazol-2-one;

1-(1-oxopropyl)-4-(2-butenyl)-1,3-dihydro-3-[2'-(1H-tetrazol-5-yl)[1,1'-biphenyl]-4-ylmethyl]-2H-imidazol-2-one;

1-(1-oxobutyl)-4-(2-butenyl)-1,3-dihydro-3-[2'-(1H-tetrazol-5-yl)[1,1'-biphenyl]-4-ylmethyl]-2H-imidazol-2-one;

1-(1-oxopentyl)-4-(2-butenyl)-1,3-dihydro-3-[2'-(1H-tetrazol-5-yl)[1,1'-biphenyl]-4-ylmethyl]-2H-imidazol-2-one;

1-ethyl-4-(3-butenyl)-1,3-dihydro-3-[2'-(1H-tetrazol-5-yl)[1,1'-biphenyl]-4-ylmethyl]-2H-imidazol-2-one;

1-propyl-4-(3-butenyl)-1,3-dihydro-3-[2'-(1H-tetrazol-5-yl)[1,1'-biphenyl]-4-ylmethyl]-2H-imidazol-2-one;

1-isopropyl-4-(3-butenyl)-1,3-dihydro-3-[2'-(1H-tetrazol-5-yl)[1,1'-biphenyl]-4-ylmethyl]-2H-imidazol-2-one;

1-butyl-4-(3-butenyl)-1,3-dihydro-3-[2'-(1H-tetrazol-5-yl)[1,1'-biphenyl]-4-ylmethyl]-2H-imidazol-2-one;

1-secbutyl-4-(3-butenyl)-1,3-dihydro-3-[2'-(1H-tetrazol-5-yl)[1,1'-biphenyl]-4-ylmethyl]-2H-imidazol-2-one;

1-isobutyl-4-(3-butenyl)-1,3-dihydro-3-[2'-(1H-tetrazol-5-yl)[1,1'-biphenyl]-4-ylmethyl]-2H-imidazol-2-one;

1-tertbutyl-4-(3-butenyl)-1,3-dihydro-3-[2'-(1H-tetrazol-5-yl)[1,1'-biphenyl]-4-ylmethyl]-2H-imidazol-2-one;

1-pentyl-4-(3-butenyl)-1,3-dihydro-3-[2'-(1H-tetrazol-5-yl)[1,1'-biphenyl]-4-ylmethyl]-2H-imidazol-2-one;

1-isopentyl-4-(3-butenyl)-1,3-dihydro-3-[2'-(1H-tetrazol-5-yl)[1,1'-biphenyl]-4-ylmethyl]-2H-imidazol-2-one;

1-cyclohexyl-4-(3-butenyl)-1,3-dihydro-3-[2'-(1H-tetrazol-5-yl)[1,1'-biphenyl]-4-ylmethyl]-2H-imidazol-2-one;

1-cyclohexylmethyl-4-(3-butenyl)-1,3-dihydro-3-[2'-(1H-tetrazol-5-yl)[1,1'-biphenyl]-4-ylmethyl]-2H-imidazol-2-one;

1-(2-cyclohexylethyl)-4-(3-butenyl)-1,3-dihydro-3-[2'-(1H-tetrazol-5-yl)[1,1'-biphenyl]-4-ylmethyl]-2H-imidazol-2-one;

1-cyclohexanoyl-4-(3-butenyl)-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-(3-butenyl)-1,3-dihydro-3-[2'-(1H-tetrazol-5-yl)[1,1'-biphenyl]-4-ylmethyl]-2H-imidazol-2-one;

1-phenyl-4-(3-butenyl)-1,3-dihydro-3-[2'-(1H-tetrazol-5-yl)[1,1'-biphenyl]-4-ylmethyl]-2H-imidazol-2-one;

1-phenylmethyl-4-(3-butenyl)-1,3-dihydro-3-[2'-(1H-tetrazol-5-yl)[1,1'-biphenyl]-4-ylmethyl]-2H-imidazol-2-one;

1-(2-phenylethyl)-4-(3-butenyl)-1,3-dihydro-3-[2'-(1H-tetrazol-5-yl)[1,1'-biphenyl]-4-ylmethyl]-2H-imidazol-2-one;

1-benzoyl-4-(3-butenyl)-1,3-dihydro-3-[2'-(1H-tetrazol-5-yl)[1,1'-biphenyl]-4-ylmethyl]-2H-imidazol-2-one;

1-(1-oxo-2-phenylethyl)-4-(3-butenyl)-1,3-dihydro-3-[2'-(1H-tetrazol-5-yl)[1,1'-biphenyl]-4-ylmethyl]-2H-imidazol-2-one;

1-(1-oxopropyl)-4-(3-butenyl)-1,3-dihydro-3-[2'-(1H-tetrazol-5-yl)[1,1'-biphenyl]-4-ylmethyl]-2H-imidazol-2-one;

1-(1-oxobutyl)-4-(3-butenyl)-1,3-dihydro-3-[2'-(1H-tetrazol-5-yl)[1,1'-biphenyl]-4-ylmethyl]-2H-imidazol-2-one;

1-(1-oxopentyl)-4-(3-butenyl)-1,3-dihydro-3-[2'-(1H-tetrazol-5-yl)[1,1'-biphenyl]-4-ylmethyl]-2H-imidazol-2-one;

1-ethyl-4-hexyl-1,3-dihydro-3-[2'-(1H-tetrazol-5-yl)[1,1'-biphenyl]-4-ylmethyl]-2H-imidazol-2-one;

1-propyl-4-hexyl-1,3-dihydro-3-[2'-(1H-tetrazol-5-yl)[1,1'-biphenyl]-4-ylmethyl]-2H-imidazol-2-one;

1-butyl-4-hexyl-1,3-dihydro-3-[2'-(1H-tetrazol-5-yl)[1,1'-biphenyl]-4-ylmethyl]-2H-imidazol-2-one;

1-secbutyl-4-hexyl-1,3-dihydro-3-[2'-(1H-tetrazol-5-yl)[1,1'-biphenyl]-4-ylmethyl]-2H-imidazol-2-one;

1-isobutyl-4-hexyl-1,3-dihydro-3-[2'-(1H-tetrazol-5-yl)[1,1'-biphenyl]-4-ylmethyl]-2H-imidaxol-2-one;

1-tertbutyl-4-hexyl-1,3-dihydro-3-[2'-(1H-tetrazol-5-yl)[1,1'-biphenyl]-4-ylmethyl]-2H-imidazol-2-one;

1-pentyl-4-hexyl-1,3-dihydro-3-[2'-(1H-tetrazol-5-yl)[1,1'-biphenyl]-4-ylmethyl]-2H-imidazol-2-one;

1-isopentyl-4-hexyl-1,3-dihydro-3-[2'-(1H-tetrazol-5-yl)[1,1'-biphenyl]-4-ylmethyl]-2H-imidazol-2-one;

1-cyclohexyl-4-hexyl-1,3-dihydro-3-[2'-(1H-tetrazol-5-yl)[1,1'-biphenyl]-4-ylmethyl]-2H-imidazol-2-one;

1-cyclohexylmethyl-4-hexyl-1,3-dihydro-3-[2'-(1H-tetrazol-5-yl)[1,1'-biphenyl]-4-ylmethyl]-2H-imidazol-2-one;

1-(2-cyclohexylethyl)-4-hexyl-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-hexyl-1,3-dihydro-3-[2'-(1H-tetrazol-5-yl)[1,1'-biphenyl]-4-ylmethyl]-2H-imidazol-2-one;

1-phenyl-4-hexyl-1,3-dihydro-3-[2'-(1H-tetrazol-5-yl)[1,1'-biphenyl]-4-ylmethyl]-2H-imidazol-2-one;

1-phenylmethyl-4-hexyl-1,3-dihydro-3-[2'-(1H-tetrazol-5-yl)[1,1'-biphenyl]-4-ylmethyl]-2H-imidazol-2-one;

1-(2-phenylethyl)-4-hexyl-1,3-dihydro-3-[2'-(1H-tetrazol-5-yl)[1,1'-biphenyl]-4-ylmethyl]-2H-imidazol-2-one;

1-benzoyl-4-hexyl-1,3-dihydro-3-[2'-(1H-tetrazol-5-yl)[1,1'-biphenyl]-4-ylmethyl]-2H-imidazol-2-one;

1-(1-oxo-2-phenylethyl)-4-hexyl-1,3-dihydro-3-[2'-(1H-tetrazol-5-yl)[1,1'-biphenyl]-4-ylmethyl]-2H-imidazol-2-one;

1-(1-oxopropyl)-4-hexyl-1,3-dihydro-3-[2'-(1H-tetrazol-5-yl)[1,1'-biphenyl]-4-ylmethyl]-2H-imidazol-2-one;

1-(1-oxobutyl)-4-hexyl-1,3-dihydro-3-[2'-(1H-tetrazol-5-yl)[1,1'-biphenyl]-4-ylmethyl]-2H-imidazol-2-one;

1-(1-oxopentyl)-4-hexyl-1,3-dihydro-3-[2'-(1H-tetrazol-5-yl)[1,1'-biphenyl]-4-ylmethyl]-2H-imidazol-2-one;

1-ethyl-4-(2-butynyl)-1,3-dihydro-3-[2'-(1H-tetrazol-5-yl)[1,1'-biphenyl]-4-ylmethyl]-2H-imidazol-2-one;

1-propyl-4-(2-butynyl)-1,3-dihydro-3-[2'-(1H-tetrazol-5-yl)[1,1'-biphenyl]-4-ylmethyl]-2H-imidazol-2-one;

1-butyl-4-(2-butynyl)-1,3-dihydro-3-[2'-(1H-tetrazol-5-yl)[1,1'-biphenyl]-4-ylmethyl]-2H-imidazol-2-one;

1-secbutyl-4-(2-butynyl)-1,3-dihydro-3-[2'-(1H-tetrazol-5-yl)[1,1'-biphenyl]-4-ylmethyl]-2H-imidazol-2-one;

1-isobutyl-4-(2-butynyl)-1,3-dihydro-3-[2'-(1H-tetrazol-5-yl)[1,1'-biphenyl]-4-ylmethyl]-2H-imidazol-2-one;

1-tertbutyl-4-(2-butynyl)-1,3-dihydro-3-[2'-(1H-tetrazol-5-yl)[1,1'-biphenyl]-4-ylmethyl]-2H-imidazol-2-one;

1-pentyl-4-(2-butynyl)-1,3-dihydro-3-[2'-(1H-tetrazol-5-yl)[1,1'-biphenyl]-4-ylmethyl]-2H-imidazol-2-one;

1-isopentyl-4-(2-butynyl)-1,3-dihydro-3-[2'-(1H-tetrazol-5-yl)[1,1'-biphenyl]-4-ylmethyl]-2H-imidazol-2-one;

1-cyclohexyl-4-(2-butynyl)-1,3-dihydro-3-[2'-(1H-tetrazol-5-yl)[1,1'-biphenyl]-4-ylmethyl]-2H-imidazol-2-one;

1-cyclohexylmethyl-4-(2-butynyl)-1,3-dihydro-3-[2'-(1H-tetrazol-5-yl)[1,1'-biphenyl]-4-ylmethyl]-2H-imidazol-2-one;

1-(2-cyclohexylethyl)-4-(2-butynyl)-1,3-dihydro-3-[2'-(1H-tetrazol-5-yl)[1,1'-biphenyl]-4-ylmethyl]-2H-imidazol-2-one;

1-cyclohexanoyl-4-(2-butynyl)-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-(2-butynyl)-1,3-dihydro-3-[2'-(1H-tetrazol-5-yl)[1,1'-biphenyl]-4-ylmethyl]-2H-imidazol-2-one;

1-phenyl-4-(2-butynyl)-1,3-dihydro-3-[2'-(1H-tetrazol-5-yl)[1,1'-biphenyl]-4-ylmethyl]-2H-imidazol-2-one;

1-phenylmethyl-4-(2-butynyl)-1,3-dihydro-3-[2'-(1H-tetrazol-5-yl)[1,1'-biphenyl]-4-ylmethyl]-2H-imidazol-2-one;

1-(2-phenylethyl)-4-(2-butynyl)-1,3-dihydro-3-[2'-(1H-tetrazol-5-yl)[1,1'-biphenyl]-4-ylmethyl]-2H-imidazol-2-one;

1-benzoyl-4-(2-butynyl)-1,3-dihydro-3-[2'-(1H-tetrazol-5-yl)[1,1'-biphenyl]-4-ylmethyl]-2H-imidazol-2-one;

1-(1-oxo-2-phenylethyl)-4-(2-butynyl)-1,3-dihydro-3-[2'-(1H-tetrazol-5-yl)[1,1'-biphenyl]-4-ylmethyl]-2H-imidazol-2-one;

1-(1-oxopropyl)-4-(2-butynyl)-1,3-dihydro-3-[2'-(1H-tetrazol-5-yl)[1,1'-biphenyl]-4-ylmethyl]-2H-imidazol-2-one;

1-(1-oxobutyl)-4-(2-butynyl)-1,3-dihydro-3-[2'-(1H-tetrazol-5-yl)[1,1'-biphenyl]-4-ylmethyl]-2H-imidazol-2-one;

1-(1-oxopentyl)-4-(2-butynyl)-1,3-dihydro-3-[2'-(1H-tetrazol-5-yl)[1,1'-biphenyl]-4-ylmethyl]-2H-imidazol-2-one;

1-ethyl-4-(3-butynyl)-1,3-dihydro-3-[2'-(1H-tetrazol-5-yl)[1,1'-biphenyl]-4-ylmethyl]-2H-imidazol-2-one;

1-propyl-4-(3-butynyl)-1,3-dihydro-3-[2'-(1H-tetrazol-5-yl)[1,1'-biphenyl]-4-ylmethyl]-2H-imidazol-2-one;

1-isopropyl-4-(3-butynyl)-1,3-dihydro-3-[2'-(1H-tetrazol-5-yl)[1,1'-biphenyl]-4-ylmethyl]-2H-imidazol-2-one;

1-butyl-4-(3-butynyl)-1,3-dihydro-3-[2'-(1H-tetrazol-5-yl)[1,1'-biphenyl]-4-ylmethyl]-2H-imidazol-2-one;

1-secbutyl-4-(3-butynyl)-1,3-dihydro-3-[2'-(1H-tetrazol-5-yl)[1,1'-biphenyl]-4-ylmethyl]-2H-imidazol-2-one;

1-isobutyl-4-(3-butynyl)-1,3-dihydro-3-[2'-(1H-tetrazol-5-yl)[1,1'-biphenyl]-4-ylmethyl]-2H-imidazol-2-one;

1-tertbutyl-4-(3-butynyl)-1,3-dihydro-3-[2'-(1H-tetrazol-5-yl)[1,1'-biphenyl]-4-ylmethyl]-2H-imidazol-2-one;

1-isopentyl-4-(3-butynyl)-1,3-dihydro-3-[2'-(1H-tetrazol-5-yl)[1,1'-biphenyl]-4-ylmethyl]-2H-imidazol-2-one;

1-pentyl-4-(3-butynyl)-1,3-dihydro-3-[2'-(1H-tetrazol-5-yl)[1,1'-biphenyl]-4-ylmethyl]-2H-imidazol-2-one;

1-cyclohexyl-4-(3-butynyl)-1,3-dihydro-3-[2'-(1H-tetrazol-5-yl)[1,1'-biphenyl]-4-ylmethyl]-2H-imidazol-2-one;

1-cyclohexylmethyl-4-(3-butynyl)-1,3-dihydro-3-[2'-(1H-tetrazol-5-yl)[1,1'-biphenyl]-4-ylmethyl]-2H-imidazol-2-one;

1-(2-cyclohexylethyl)-4-(3-butynyl)-1,3-dihydro-3-[2'-(1H-tetrazol-5-yl)[1,1'-biphenyl]-4-ylmethyl]-2H-imidazol-2-one;

1-cyclohexanoyl-4-(3-butynyl)-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-(3-butynyl)-1,3-dihydro-3-[2'-(1H-tetrazol-5-yl)[1,1'-biphenyl]-4-ylmethyl]-2H-imidazol-2-one;

1-phenyl-4-(3-butynyl)-1,3-dihydro-3-[2'-(1H-tetrazol-5-yl)[1,1'-biphenyl]-4-ylmethyl]-2H-imidazol-2-one;

1-phenylmethyl-4-(3-butynyl)-1,3-dihydro-3-[2'-(1H-tetrazol-5-yl)[1,1'-biphenyl]-4-ylmethyl]-2H-imidazol-2-one;

1-(2-phenylethyl)-4-(3-butynyl)-1,3-dihydro-3-[2'-(1H-tetrazol-5-yl)[1,1'-biphenyl]-4-ylmethyl]-2H-imidazol-2-one;

1-benzoyl-4-(3-butynyl)-1,3-dihydro-3-[2'-(1H-tetrazol-5-yl)[1,1'-biphenyl]-4-ylmethyl]-2H-imidazol-2-one;

1-(1-oxo-2-phenylethyl)-4-(3-butynyl)-1,3-dihydro-3-[2'-(1H-tetrazol-5-yl)[1,1'-biphenyl]-4-ylmethyl]-2H-imidazol-2-one;

1-(1-oxopropyl)-4-(3-butynyl)-1,3-dihydro-3-[2'-(1H-tetrazol-5-yl)[1,1'-biphenyl]-4-ylmethyl]-2H-imidazol-2-one;

1-(1-oxobutyl)-4-(3-butynyl)-1,3-dihydro-3-[2'-(1H-tetrazol-5-yl)[1,1'-biphenyl]-4-ylmethyl]-2H-imidazol-2-one;

1-(1-oxopentyl)-4-(3-butynyl)-1,3-dihydro-3-[2'-(1H-tetrazol-5-yl)[1,1'-biphenyl]-4-ylmethyl]-2H-imidazol-2-one;

1,4-di(2-butenyl)-1,3-dihydro-3-[2'-(1H-tetrazol-5-yl)[1,1'-biphenyl]-4-ylmethyl]-2H-imidazol-2-one;

1,4-di(3-butenyl)-1,3-dihydro-3-[2'-(1H-tetrazol-5-yl)[1,1'-biphenyl]-4-ylmethyl]-2H-imidazol-2-one;

1,4-dihexyl-1,3-dihydro-3-[2'-(1H-tetrazol-5-yl)[1,1'-biphenyl]-4-ylmethyl]-2H-imidazol-2-one;

1,4-di(2-butynyl)-1,3-dihydro-3-[2'-(1H-tetrazol-5-yl)[1,1'-biphenyl]-4-ylmethyl]-2H-imidazol-2-one;

1,4-di(3-butynyl)-1,3-dihydro-3-[2'-(1H-tetrazol-5-yl)[1,1'-biphenyl]-4-ylmethyl]-2H-imidazol-2-one;

1-ethyl-4-butyl-5-fluoro-1,3-dihydro-3-[2'-(1H-tetrazol-5-yl)[1,1'-biphenyl]-4-ylmethyl]-2H-imidazol-2-one;

1-propyl-4-butyl-5-fluoro-1,3-dihydro-3-[2'-(1H-tetrazol-5-yl)[1,1'-biphenyl]-4-ylmethyl]-2H-imidazol-2-one;

1-isopropyl-4-butyl-5-fluoro-1,3-dihydro-3-[2'-(1H-tetrazol-5-yl)[1,1'-biphenyl]-4-ylmethyl]-2H-imidazol-2-one;

1,4-dibutyl-5-fluoro-1,3-dihydro-3-[2'-(1H-tetrazol-5-yl)[1,1'-biphenyl]-4-ylmethyl]-2H-imidazol-2-one;

1-secbutyl-4-butyl-5-fluoro-1,3-dihydro-3-[2'-(1H-tetrazol-5-yl)[1,1'-biphenyl]-4-ylmethyl]-2H-imidazol-2-one;

1-isobutyl-4-butyl-5-fluoro-1,3-dihydro-3-[2'-(1H-tetrazol-5-yl)[1,1'-biphenyl]-4-ylmethyl]-2H-imidazol-2-one;

1-tertbutyl-4-butyl-5-fluoro-1,3-dihydro-3-[2'-(1H-tetrazol-5-yl)[1,1'-biphenyl]-4-ylmethyl]-2H-imidazol-2-one;

1-pentyl-4-butyl-5-fluoro-1,3-dihydro-3-[2'-(1H-tetrazol-5-yl)[1,1'-biphenyl]-4-ylmethyl]-2H-imidazol-2-one;

1-isopentyl-4-butyl-5-fluoro-1,3-dihydro-3-[2'-(1H-tetrazol-5-yl)[1,1'-biphenyl]-4-ylmethyl]-2H-imidazol-2-one;

1-cyclohexyl-4-butyl-5-fluoro-1,3-dihydro-3-[2'-(1H-tetrazol-5-yl)[1,1'-biphenyl]-4-ylmethyl]-2H-imidazol-2-one;

1-cyclohexylmethyl-4-butyl-5-fluoro-1,3-dihydro-3-[2'-(1H-tetrazol-5-yl)[1,1'-biphenyl]-4-ylmethyl]-2H-imidazol-2-one;

1-(2-cyclohexylethyl)-4-butyl-5-fluoro-1,3-dihydro-3-[2'-(1H-tetrazol-5-yl)[1,1'-biphenyl]-4-ylmethyl]-2H-imidazol-2-one;

1-cyclohexanoyl-4-butyl-5-fluoro-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-butyl-5-fluoro-1,3-dihydro-3-[2'-(1H-tetrazol-5-yl)[1,1'-biphenyl]-4-ylmethyl]-2H-imidazol-2-one;

1-phenyl-4-butyl-5-fluoro-1,3-dihydro-3-[2'-(1H-tetrazol-5-yl)[1,1'-biphenyl]-4-ylmethyl]-2H-imidazol-2-one;

1-phenylmethyl-4-butyl-5-fluoro-1,3-dihydro-3-[2'-(1H-tetrazol-5-yl)[1,1'-biphenyl]-4-ylmethyl]-2H-imidazol-2-one;

1-(2-phenylethyl)-4-butyl-5-fluoro-1,3-dihydro-3-[2'-(1H-tetrazol-5-yl)[1,1'-biphenyl]-4-ylmethyl]-2H-imidazol-2-one;

1-benzoyl-4-butyl-5-fluoro-1,3-dihydro-3-[2'-(1H-tetrazol-5-yl)[1,1'-biphenyl]-4-ylmethyl]-2H-imidazol-2-one;

1-(1-oxo-2-phenylethyl)-4-butyl-5-fluoro-1,3-dihydro-3-[2'-(1H-tetrazol-5-yl)[1,1'-biphenyl]-4-ylmethyl]-2H-imidazol-2-one;

1-(1-oxopropyl)-4-butyl-5-fluoro-1,3-dihydro-3-[2'-(1H-tetrazol-5-yl)[1,1'-biphenyl]-4-ylmethyl]-2H-imidazol-2-one;

1-(1-oxobutyl)-4-butyl-5-fluoro-1,3-dihydro-3-[2'-(1H-tetrazol-5-yl)[1,1'-biphenyl]-4-ylmethyl]-2H-imidazol-2-one;

1-(1-oxopentyl)-4-butyl-5-fluoro-1,3-dihydro-3-[2'-(1H-tetrazol-5-yl)[1,1'-biphenyl]-4-ylmethyl]-2H-imidazol-2-one;

1-ethyl-4-butyl-5-chloro-1,3-dihydro-3-[2'-(1H-tetrazol-5-yl)[1,1'-biphenyl]-4-ylmethyl]-2H-imidazol-2-one;

1-propyl-4-butyl-5-chloro-1,3-dihydro-3-[2'-(1H-tetrazol-5-yl)[1,1'-biphenyl]-4-ylmethyl]-2H-imidazol-2-one;

1-isopropyl-4-butyl-5-chloro-1,3-dihydro-3-[2'-(1H-tetrazol-5-yl)[1,1'-biphenyl]-4-ylmethyl]-2H-imidazol-2-one;

1,4-dibutyl-5-chloro-1,3-dihydro-3-[2'-(1H-tetrazol-5-yl)[1,1'-biphenyl]-4-ylmethyl]-2H-imidazol-2-one;

1-secbutyl-4-butyl-5-chloro-1,3-dihydro-3-[2'-(1H-tetrazol-5-yl)[1,1'-biphenyl]-4-ylmethyl]-2H-imidazol-2-one;

1-isobutyl-4-butyl-5-chloro-1,3-dihydro-3-[2'-(1H-tetrazol-5-yl)[1,1'-biphenyl]-4-ylmethyl]-2H-imidazol-2-one;

1-tertbutyl-4-butyl-5-chloro-1,3-dihydro-3-[2'-(1H-tetrazol-5-yl)[1,1'-biphenyl]-4-ylmethyl]-2H-imidazol-2-one;

1-pentyl-4-butyl-5-chloro-1,3-dihydro-3-[2'-(1H-tetrazol-5-yl)[1,1'-biphenyl]-4-ylmethyl]-2H-imidazol-2-one;

1-isopentyl-4-butyl-5-chloro-1,3-dihydro-3-[2'-(1H-tetrazol-5-yl)[1,1'-biphenyl]-4-ylmethyl]-2H-imidazol-2-one;

1-cyclohexyl-4-butyl-5-chloro-1,3-dihydro-3-[2'-(1H-tetrazol-5-yl)[1,1'-biphenyl]-4-ylmethyl]-2H-imidazol-2-one;

1-cyclohexylmethyl-4-butyl-5-chloro-1,3-dihydro-3-[2'-(1H-tetrazol-5-yl)[1,1'-biphenyl]-4-ylmethyl]-2H-imidazol-2-one;

1-(2-cyclohexylethyl)-4-butyl-5-chloro-1,3-dihydro-3-[2'-(1H-tetrazol-5-yl)[1,1'-biphenyl]-4-ylmethyl]-2H-imidazol-2-one;

1-cyclohexanoyl-4-butyl-5-chloro-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-butyl-5-chloro-1,3-dihydro-3-[2'-(1H-tetrazol-5-yl)[1,1'-biphenyl]-4-ylmethyl]-2H-imidazol-2-one;

1-phenyl-4-butyl-5-chloro-1,3-dihydro-3-[2'-(1H-tetrazol-5-yl)[1,1'-biphenyl]-4-ylmethyl]-2H-imidazol-2-one;

1-phenylmethyl-4-butyl-5-chloro-1,3-dihydro-3-[2'-(1H-tetrazol-5-yl)[1,1'-biphenyl]-4-ylmethyl]-2H-imidazol-2-one;

1-(2-phenylethyl)-4-butyl-5-chloro-1,3-dihydro-3-[2'-(1H-tetrazol-5-yl)[1,1'-biphenyl]-4-ylmethyl]-2H-imidazol-2-one;

1-benzoyl-4-butyl-5-chloro-1,3-dihydro-3-[2'-(1H-tetrazol-5-yl)[1,1'-biphenyl]-4-ylmethyl]-2H-imidazol-2-one;

1-(1-oxo-2-phenylethyl)-4-butyl-5-chloro-1,3-dihydro-3-[2'-(1H-tetrazol-5-yl)[1,1'-biphenyl]-4-ylmethyl]-2H-imidazol-2-one;

1-(1-oxopropyl)-4-butyl-5-chloro-1,3-dihydro-3-[2'-(1H-tetrazol-5-yl)[1,1'-biphenyl]-4-ylmethyl]-2H-imidazol-2-one;

1-(1-oxobutyl)-4-butyl-5-chloro-1,3-dihydro-3-[2'-(1H-tetrazol-5-yl)[1,1'-biphenyl]-4-ylmethyl]-2H-imidazol-2-one;

1-(1-oxopentyl)-4-butyl-5-chloro-1,3-dihydro-3-[2'-(1H-tetrazol-5-yl)[1,1'-biphenyl]-4-ylmethyl]-2H-imidazol-2-one;

1-ethyl-4-butyl-5-formyl-1,3-dihydro-3-[2'-(1H-tetrazol-5-yl)[1,1'-biphenyl]-4-ylmethyl]-2H-imidazol-2-one;

1-propyl-4-butyl-5-formyl-1,3-dihydro-3-[2'-(1H-tetrazol-5-yl)[1,1'-biphenyl]-4-ylmethyl]-2H-imidazol-2-one;

1-isopropyl-4-butyl-5-formyl-1,3-dihydro-3-[2'-(1H-tetrazol-5-yl)[1,1'-biphenyl]-4-ylmethyl]-2H-imidazol-2-one;

1,4-dibutyl-5-formyl-1,3-dihydro-3-[2'-(1H-tetrazol-5-yl)[1,1'-biphenyl]-4-ylmethyl]-2H-imidazol-2-one;

1-secbutyl-4-butyl-5-formyl-1,3-dihydro-3-[2'-(1H-tetrazol-5-yl)[1,1'-biphenyl]-4-ylmethyl]-2H-imidazol-2-one;

1-isobutyl-4-butyl-5-formyl-1,3-dihydro-3-[2'-(1H-tetrazol-5-yl)[1,1'-biphenyl]-4-ylmethyl]-2H-imidazol-2-one;

1-tertbutyl-4-butyl-5-formyl-1,3-dihydro-3-[2'-(1H-tetrazol-5-yl)[1,1'-biphenyl]-4-ylmethyl]-2H-imidazol-2-one;

1-pentyl-4-butyl-5-formyl-1,3-dihydro-3-[2'-(1H-tetrazol-5-yl)[1,1'-biphenyl]-4-ylmethyl]-2H-imidazol-2-one;

1-isopentyl-4-butyl-5-formyl-1,3-dihydro-3-[2'-(1H-tetrazol-5-yl)[1,1'-biphenyl]-4-ylmethyl]-2H-imidazol-2-one;

1-cyclohexyl-4-butyl-5-formyl-1,3-dihydro-3-[2'-(1H-tetrazol-5-yl)[1,1'-biphenyl]-4-ylmethyl]-2H-imidazol-2-one;

1-cyclohexylmethyl-4-butyl-5-formyl-1,3-dihydro-3-[2'-(1H-tetrazol-5-yl)[1,1'-biphenyl]-4-ylmethyl]-2H-imidazol-2-one;

1-(2-cyclohexylethyl)-4-butyl-5-formyl-1,3-dihydro-3-[2'-(1H-tetrazol-5-yl)[1,1'-biphenyl]-4-ylmethyl]-2H-imidazol-2-one;

1-cyclohexanoyl-4-butyl-5-formyl-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-butyl-5-formyl-1,3-dihydro-3-[2'-(1H-tetrazol-5-yl)[1,1'-biphenyl]-4-ylmethyl]-2H-imidazol-2-one;

1-phenyl-4-butyl-5-formyl-1,3-dihydro-3-[2'-(1H-tetrazol-5-yl)[1,1'-biphenyl]-4-ylmethyl]-2H-imidazol-2-one;

1-phenylmethyl-4-butyl-5-formyl-1,3-dihydro-3-[2'-(1H-tetrazol-5-yl)[1,1'-biphenyl]-4-ylmethyl]-2H-imidazol-2-one;

1-(2-phenylethyl)-4-butyl-5-formyl-1,3-dihydro-3-[2'-(1H-tetrazol-5-yl)[1,1'-biphenyl]-4-ylmethyl]-2H-imidazol-2-one;

1-benzoyl-4-butyl-5-formyl-1,3-dihydro-3-[2'-(1H-tetrazol-5-yl)[1,1'-biphenyl]-4-ylmethyl]-2H-imidazol-2-one;

1-(1-oxo-2-phenylethyl)-4-butyl-5-formyl-1,3-dihydro-3-[2'-(1H-tetrazol-5-yl)[1,1'-biphenyl]-4-ylmethyl]-2H-imidazol-2-one;

1-(1-oxopropyl)-4-butyl-5-formyl-1,3-dihydro-3-[2'-(1H-tetrazol-5-yl)[1,1'-biphenyl]-4-ylmethyl]-2H-imidazol-2-one;

1-(1-oxobutyl)-4-butyl-5-formyl-1,3-dihydro-3-[2'-(1H-tetrazol-5-yl)[1,1'-biphenyl]-4-ylmethyl]-2H-imidazol-2-one;

1-(1-oxopentyl)-4-butyl-5-formyl-1,3-dihydro-3-[2'-(1H-tetrazol-5-yl)[1,1'-biphenyl]-4-ylmethyl]-2H-imidazol-2-one;

1-ethyl-4-butyl-5-dimethoxymethyl-1,3-dihydro-3-[2'-(1H-tetrazol-5-yl)[1,1'-biphenyl]-4-ylmethyl]-2H-imidazol-2-one;

1-propyl-4-butyl-5-dimethoxymethyl-1,3-dihydro-3-[2'-(1H-tetrazol-5-yl)[1,1'-biphenyl]-4-ylmethyl]-2H-imidazol-2-one;

1-isopropyl-4-butyl-5-dimethoxymethyl-1,3-dihydro-3-[2'-(1H-tetrazol-5-yl)[1,1'-biphenyl]-4-ylmethyl]-2H-imidazol-2-one;

1,4-dibutyl-5-dimethoxymethyl-1,3-dihydro-3-[2'-(1H-tetrazol-5-yl)[1,1'-biphenyl]-4-ylmethyl]-2H-imidazol-2-one;

1-secbutyl-4-butyl-5-dimethoxymethyl-1,3-dihydro-3-[2'-(1H-tetrazol-5-yl)[1,1'-biphenyl]-4-ylmethyl]-2H-imidazol-2-one;

1-isobutyl-4-butyl-5-dimethoxymethyl-1,3-dihydro-3-[2'-(1H-tetrazol-5-yl)[1,1'-biphenyl]-4-ylmethyl]-2H-imidazol-2-one;

1-tertbutyl-4-butyl-5-dimethoxymethyl-1,3-dihydro-3-[2'-(1H-tetrazol-5-yl)[1,1'-biphenyl]-4-ylmethyl]-2H-imidazol-2-one;

1-pentyl-4-butyl-5-dimethoxymethyl-1,3-dihydro-3-[2'-(1H-tetrazol-5-yl)[1,1'-biphenyl]-4-ylmethyl]-2H-imidazol-2-one;

1-isopentyl-4-butyl-5-dimethoxymethyl-1,3-dihydro-3-[2'-(1H-tetrazol-5-yl)[1,1'-biphenyl]-4-ylmethyl]-2H-imidazol-2-one;

1-cyclohexyl-4-butyl-5-dimethoxymethyl-1,3-dihydro-3-[2'-(1H-tetrazol-5-yl)[1,1'-biphenyl]-4-ylmethyl]-2H-imidazol-2-one;

1-cyclohexylmethyl-4-butyl-5-dimethoxymethyl-1,3-dihydro-3-[2'-(1H-tetrazol-5-yl)[1,1'-biphenyl]-4-ylmethyl]-2H-imidazol-2-one;

1-(2-cyclohexylethyl)-4-butyl-5-dimethoxymethyl-1,3-dihydro-3-[2'-(1H-tetrazol-5-yl)[1,1'-biphenyl]-4-ylmethyl]-2H-imidazol-2-one;

1-cyclohexanoyl-4-butyl-5-dimethoxymethyl-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-butyl-5-dimethoxymethyl-1,3-dihydro-3-[2'-(1H-tetrazol-5-yl)[1,1'-biphenyl]-4-ylmethyl]-2H-imidazol-2-one;

1-phenyl-4-butyl-5-dimethoxymethyl-1,3-dihydro-3-[2'-(1H-tetrazol-5-yl)[1,1'-biphenyl]-4-ylmethyl]-2H-imidazol-2-one;

1-phenylmethyl-4-butyl-5-dimethoxymethyl-1,3-dihydro-3-[2'-(1H-tetrazol-5-yl)[1,1'-biphenyl]-4-ylmethyl]-2H-imidazol-2-one;

1-(2-phenylethyl)-4-butyl-5-dimethoxymethyl-1,3-dihydro-3-[2'-(1H-tetrazol-5-yl)[1,1'-biphenyl]-4-ylmethyl]-2H-imidazol-2-one;

1-benzoyl-4-butyl-5-dimethoxymethyl-1,3-dihydro-3-[2'-(1H-tetrazol-5-yl)[1,1'-biphenyl]-4-ylmethyl]-2H-imidazol-2-one;

1-(1-oxo-2-phenylethyl)-4-butyl-5-dimethoxymethyl-1,3-dihydro-3-[2'-(1H-tetrazol-5-yl)[1,1'-biphenyl]-4-ylmethyl]-2H-imidazol-2-one;

1-(1-oxopropyl)-4-butyl-5-dimethoxymethyl-1,3-dihydro-3-[2'-(1H-tetrazol-5-yl)[1,1'-biphenyl]-4-ylmethyl]-2H-imidazol-2-one;

1-(1-oxobutyl)-4-butyl-5-dimethoxymethyl-1,3-dihydro-3-[2'-(1H-tetrazol-5-yl)[1,1'-biphenyl]-4-ylmethyl]-2H-imidazol-2-one;

1-(1-oxopentyl)-4-butyl-5-dimethoxymethyl-1,3-dihydro-3-[2'-(1H-tetrazol-5-yl)[1,1'-biphenyl]-4-ylmethyl]-2H-imidazol-2-one;

1-ethyl-4-butyl-5-methyl-1,3-dihydro-3-[2'-(1H-tetrazol-5-yl)[1,1'-biphenyl]-4-ylmethyl]-2H-imidazol-2-one;

1-propyl-4-butyl-5-methyl-1,3-dihydro-3-[2'-(1H-tetrazol-5-yl)[1,1'-biphenyl]-4-ylmethyl]-2H-imidazol-2-one;

1-isopropyl-4-butyl-5-methyl-1,3-dihydro-3-[2'-(1H-tetrazol-5-yl)[1,1'-biphenyl]-4-ylmethyl]-2H-imidazol-2-one;

1,4-dibutyl-5-methyl-1,3-dihydro-3-[2'-(1H-tetrazol-5-yl)[1,1'-biphenyl]-4-ylmethyl]-2H-imidazol-2-one;

1-secbutyl-4-butyl-5-methyl-1,3-dihydro-3-[2'-(1H-tetrazol-5-yl)[1,1'-biphenyl]-4-ylmethyl]-2H-imidazol-2-one;

1-isobutyl-4-butyl-5-methyl-1,3-dihydro-3-[2'-(1H-tetrazol-5-yl)[1,1'-biphenyl]-4-ylmethyl]-2H-imidazol-2-one;

1-tertbutyl-4-butyl-5-methyl-1,3-dihydro-3-[2'-(1H-tetrazol-5-yl)[1,1'-biphenyl]-4-ylmethyl]-2H-imidazol-2-one;

1-pentyl-4-butyl-5-methyl-1,3-dihydro-3-[2'-(1H-tetrazol-5-yl)[1,1'-biphenyl]-4-ylmethyl]-2H-imidazol-2-one;

1-isopentyl-4-butyl-5-methyl-1,3-dihydro-3-[2'-(1H-tetrazol-5-yl)[1,1'-biphenyl]-4-ylmethyl]-2H-imidazol-2-one;

1-cyclohexyl-4-butyl-5-methyl-1,3-dihydro-3-[2'-(1H-tetrazol-5-yl)[1,1'-biphenyl]-4-ylmethyl]-2H-imidazol-2-one;

1-cyclohexylmethyl-4-butyl-5-methyl-1,3-dihydro-3-[2'-(1H-tetrazol-5-yl)[1,1'-biphenyl]-4-ylmethyl]-2H-imidazol-2-one;

1-(2-cyclohexylethyl)-4-butyl-5-methyl-1,3-dihydro-3-[2'-(1H-tetrazol-5-yl)[1,1'-biphenyl]-4-ylmethyl]-2H-imidazol-2-one;

1-cyclohexanoyl-4-butyl-5-methyl-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-butyl-5-methyl-1,3-dihydro-3-[2'-(1H-tetrazol-5-yl)[1,1'-biphenyl]-4-ylmethyl]-2H-imidazol-2-one;

1-phenyl-4-butyl-5-methyl-1,3-dihydro-3-[2'-(1H-tetrazol-5-yl)[1,1'-biphenyl]-4-ylmethyl]-2H-imidazol-2-one;

1-phenylmethyl-4-butyl-5-methyl-1,3-dihydro-3-[2'-(1H-tetrazol-5-yl)[1,1'-biphenyl]-4-ylmethyl]-2H-imidazol-2-one;

1-(2-phenylethyl)-4-butyl-5-methyl-1,3-dihydro-3-[2'-(1H-tetrazol-5-yl)[1,1'-biphenyl]-4-ylmethyl]-2H-imidazol-2-one;

1-benzoyl-4-butyl-5-methyl-1,3-dihydro-3-[2'-(1H-tetrazol-5-yl)[1,1'-biphenyl]-4-ylmethyl]-2H-imidazol-2-one;

1-(1-oxo-2-phenylethyl)-4-butyl-5-methyl-1,3-dihydro-3-[2'-(1H-tetrazol-5yl)[1,1'-biphenyl]-4-ylmethyl]-2H-imidazol-2-one;

1-(1-oxopropyl)-4-butyl-5-methyl-1,3-dihydro-3-[2'-(1H-tetrazol-5-yl)[1,1'-biphenyl]-4-ylmethyl]-2H-imidazol-2-one;

1-(1-oxobutyl)-4-butyl-5-methyl-1,3-dihydro-3-[2'-(1H-tetrazol-5-yl)[1,1'-biphenyl]-4-ylmethyl]-2H-imidazol-2-one;

1-(1-oxopentyl)-4-butyl-5-methyl-1,3-dihydro-3-[2'-(1H-tetrazol-5-yl)[1,1'-biphenyl]-4-ylmethyl]-2H-imidazol-2-one;

1-ethyl-4-butyl-5-fluoromethyl-1,3-dihydro-3-[2'-(1H-tetrazol-5-yl)[1,1'-biphenyl]-4-ylmethyl]-2H-imidazol-2-one;

1-propyl-4-butyl-5-fluoromethyl-1,3-dihydro-3-[2'-(1H-tetrazol-5-yl)[1,1'-biphenyl]-4-ylmethyl]-2H-imidazol-2-one;

1-isopropyl-4-butyl-5-fluoromethyl-1,3-dihydro-3-[2'-(1H-tetrazol-5-yl)[1,1'-biphenyl]-4-ylmethyl]-2H-imidazol-2-one;

1,4-dibutyl-5-fluoromethyl-1,3-dihydro-3-[2'-(1H-tetrazol-5-yl)[1,1'-biphenyl]-4-ylmethyl]-2H-imidazol-2-one;

1-secbutyl-4-butyl-5-fluoromethyl-1,3-dihydro-3-[2'-(1H-tetrazol-5-yl)[1,1'-biphenyl]-4-ylmethyl]-2H-imidazol-2-one;

1-isobutyl-4-butyl-5-fluoromethyl-1,3-dihydro-3-[2'-(1H-tetrazol-5-yl)[1,1'-biphenyl]-4-ylmethyl]-2H-imidazol-2-one;

1-tertbutyl-4-butyl-5-fluoromethyl-1,3-dihydro-3-[2'-(1H-tetrazol-5-yl)[1,1'-biphenyl]-4-ylmethyl]-2H-imidazol-2-one;

1-pentyl-4-butyl-5-fluoromethyl-1,3-dihydro-3-[2'-(1H-tetrazol-5-yl)[1,1'-biphenyl]-4-ylmethyl]-2H-imidazol-2-one;

1-isopentyl-4-butyl-5-fluoromethyl-1,3-dihydro-3-[2'-(1H-tetrazol-5-yl)[1,1'-biphenyl]-4-ylmethyl]-2H-imidazol-2-one;

1-cyclohexyl-4-butyl-5-fluoromethyl-1,3-dihydro-3-[2'-(1H-tetrazol-5-yl)[1,1'-biphenyl]-4-ylmethyl]-2H-imidazol-2-one;

1-cyclohexylmethyl-4-butyl-5-fluoromethyl-1,3-dihydro-3-[2'-(1H-tetrazol-5-yl)[1,1'-biphenyl]-4-ylmethyl]-2H-imidazol-2-one;

1-(2-cyclohexylethyl)-4-butyl-5-fluoromethyl-1,3-dihydro-3-[2'-(1H-tetrazol-5-yl)[1,1'-biphenyl]-4-ylmethyl]-2H-imidazol-2-one;

1-cyclohexanoyl-4-butyl-5-fluoromethyl-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-butyl-5-fluoromethyl-1,3-dihydro-3-[2'-(1H-tetrazol-5-yl)[1,1'-biphenyl]-4-ylmethyl]-2H-imidazol-2-one;

1-phenyl-4-butyl-5-fluoromethyl-1,3-dihydro-3-[2'-(1H-tetrazol-5-yl)[1,1'-biphenyl]-4-ylmethyl]-2H-imidazol-2-one;

1-phenylmethyl-4-butyl-5-fluoromethyl-1,3-dihydro-3-[2'-(1H-tetrazol-5-yl)[1,1'-biphenyl]-4-ylmethyl]-2H-imidazol-2-one;

1-(2 phenylethyl)-4-butyl-5-fluoromethyl-1,3-dihydro-3-[2'-(1H-tetrazol-5-yl)[1,1'-biphenyl]-4-ylmethyl]-2H-imidazol-2-one;

1-benzoyl-4-butyl-5-fluoromethyl-1,3-dihydro-3-[2'-(1H-tetrazol-5-yl)[1,1'-biphenyl]-4-ylmethyl]-2H-imidazol-2-one;

1-(1-oxo-2-phenylethyl)-4-butyl-5-fluoromethyl-1,3-dihydro-3-[2'-(1H-tetrazol-5-yl)[1,1'-biphenyl]-4-ylmethyl]-2H-imidazol-2-one;

1-(1-oxopropyl)-4-butyl-5-fluoromethyl-1,3-dihydro-3-[2'-(1H-tetrazol-5-yl)[1,1'-biphenyl]-4-ylmethyl]-2H-imidazol-2-one;

1-(1-oxobutyl)-4-butyl-5-fluoromethyl-1,3-dihydro-3-[2'-(1H-tetrazol-5-yl)[1,1'-biphenyl]-4-ylmethyl]-2H-imidazol-2-one;

1-(1-oxopentyl)-4-butyl-5-fluoromethyl-1,3-dihydro-3-[2'-(1H-tetrazol-5-yl)[1,1'-biphenyl]-4-ylmethyl]-2H-imidazol-2-one;

1-ethyl-4-butyl-5-difluoromethyl-1,3-dihydro-3-[2'-(1H-tetrazol-5-yl)[1,1'-biphenyl]-4-ylmethyl]-2H-imidazol-2-one;

1-propyl-4-butyl-5-difluoromethyl-1,3-dihydro-3-[2'-(1H-tetrazol-5-yl)[1,1'-biphenyl]-4-ylmethyl]-2H-imidazol-2-one;

1-isopropyl-4-butyl-5-difluoromethyl-1,3-dihydro-3-[2'-(1H-tetrazol-5-yl)[1,1'-biphenyl]-4-ylmethyl]-2H-imidazol-2-one;

1,4-dibutyl-5-difluoromethyl-1,3-dihydro-3-[2'-(1H-tetrazol-5-yl)[1,1'-biphenyl]-4-ylmethyl]-2H-imidazol-2-one;

1-secbutyl-4-butyl-5-difluoromethyl-1,3-dihydro-3-[2'-(1H-tetrazol-5-yl)[1,1'-biphenyl]-4-ylmethyl]-2H-imidazol-2-one;

1-isobutyl-4-butyl-5-difluoromethyl-1,3-dihydro-3-[2'-(1H-tetrazol-5-yl)[1,1'-biphenyl]-4-ylmethyl]-2H-imidazol-2-one;

1-tertbutyl-4-butyl-5-difluoromethyl-1,3-dihydro-3-[2'-(1H-tetrazol-5-yl)[1,1'-biphenyl]-4-ylmethyl]-2H-imidazol-2-one;

1-pentyl-4-butyl-5-difluoromethyl-1,3-dihydro-3-[2'-(1H-tetrazol-5-yl)[1,1'-biphenyl]-4-ylmethyl]-2H-imidazol-2-one;

1-isopentyl-4-butyl-5-difluoromethyl-1,3-dihydro-3-[2'-(1H-tetrazol-5-yl)[1,1'-biphenyl]-4-ylmethyl]-2H-imidazol-2-one;

1-cyclohexyl-4-butyl-5-difluoromethyl-1,3-dihydro-3-[2'-(1H-tetrazol-5-yl)[1,1'-biphenyl]-4-ylmethyl]-2H-imidazol-2-one;

1-cyclohexylmethyl-4-butyl-5-difluoromethyl-1,3-dihydro-3-[2'-(1H-tetrazol-5-yl)[1,1'-biphenyl]-4-ylmethyl]-2H-imidazol-2-one;

1-(2-cyclohexylethyl)-4-butyl-5-difluoromethyl-1,3-dihydro-3-[2'-(1H-tetrazol-5-yl)[1,1'-biphenyl]-4-ylmethyl]-2H-imidazol-2-one;

1-cyclohexanoyl-4-butyl-5-difluoromethyl-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-butyl-5-difluoromethyl-1,3-dihydro-3-[2'-(1H-tetrazol-5-yl)[1,1'-biphenyl]-4-ylmethyl]-2H-imidazol-2-one;

1-phenyl-4-butyl-5-difluoromethyl-1,3-dihydro-3-[2'-(1H-tetrazol-5-yl)[1,1'-biphenyl]-4-ylmethyl]-2H-imidazol-2-one;

1-phenylmethyl-4-butyl-5-difluoromethyl-1,3-dihydro-3-[2'-(1H-tetrazol-5-yl)[1,1'-biphenyl]-4-ylmethyl]-2H-imidazol-2-one;

1-(2-phenylethyl)-4-butyl-5-difluoromethyl-1,3-dihydro-3-[2'-(1H-tetrazol-5-yl)[1,1'-biphenyl]-4-ylmethyl]-2H-imidazol-2-one;

1-benzoyl-4-butyl-5-difluoromethyl-1,3-dihydro-3-[2'-(1H-tetrazol-5-yl)[1,1'-biphenyl]-4-ylmethyl]-2H-imidazol-2-one;

1-(1-oxo-2-phenylethyl)-4-butyl-5-difluoromethyl-1,3-dihydro-3-[2'-(1H-tetrazol-5-yl)[1,1'-biphenyl]-4-ylmethyl]-2H-imidazol-2-one;

1-(1-oxopropyl)-4-butyl-5-difluoromethyl-1,3-dihydro-3-[2'-(1H-tetrazol-5-yl)[1,1'-biphenyl]-4-ylmethyl]-2H-imidazol-2-one;

1-(1-oxobutyl)-4-butyl-5-difluoromethyl-1,3-dihydro-3-[2'-(1H-tetrazol-5-yl)[1,1'-biphenyl]-4-ylmethyl]-2H-imidazol-2-one;

1-(1-oxopentyl)-4-butyl-5-difluoromethyl-1,3-dihydro-3-[2'-(1H-tetrazol-5-yl)[1,1'-biphenyl]-4-ylmethyl]-2H-imidazol-2-one;

1-ethyl-4-butyl-5-trifluoromethyl-1,3-dihydro-3-[2'-(1H-tetrazol-5-yl)[1,1'-biphenyl]-4-ylmethyl]-2H-imidazol-2-one;

1-propyl-4-butyl-5-trifluoromethyl-1,3-dihydro-3-[2'-(1H-tetrazol-5-yl)[1,1'-biphenyl]-4-ylmethyl]-2H-imidazol-2-one;

1-isopropyl-4-butyl-5-trifluoromethyl-1,3-dihydro-3-[2'-(1H-tetrazol-5-yl)[1,1'-biphenyl]-4-ylmethyl]-2H-imidazol-2-one;

1,4-dibutyl-5-trifluoromethyl-1,3-dihydro-3-[2'-(1H-tetrazol-5-yl)[1,1'-biphenyl]-4-ylmethyl]-2H-imidazol-2-one;

1-secbutyl-4-butyl-5-trifluoromethyl-1,3-dihydro-3-[2'-(1H-tetrazol-5-yl)[1,1'-biphenyl]-4-ylmethyl]-2H-imidazol-2-one;

1-isobutyl-4-butyl-5-trifluoromethyl-1,3-dihydro-3-[2'-(1H-tetrazol-5-yl)[1,1'-biphenyl]-4-ylmethyl]-2H-imidazol-2-one;

1-tertbutyl-4-butyl-5-trifluoromethyl-1,3-dihydro-3-[2'-(1H-tetrazol-5-yl)[1,1'-biphenyl]-4-ylmethyl]-2H-imidazol-2-one;

1-pentyl-4-butyl-5-trifluoromethyl-1,3-dihydro-3-[2'-(1H-tetrazol-5-yl)[1,1'-biphenyl]-4-ylmethyl]-2H-imidazol-2-one;

1-isopentyl-4-butyl-5-trifluoromethyl-1,3-dihydro-3-[2'-(1H-tetrazol-5-yl)[1,1'-biphenyl]-4-ylmethyl]-2H-imidazol-2-one;

1-cyclohexyl-4-butyl-5-trifluoromethyl-1,3-dihydro-3-[2'-(1H-tetrazol-5-yl)[1,1'-biphenyl]-4-ylmethyl]-2H-imidazol-2-one;

1-cyclohexylmethyl-4-butyl-5-trifluoromethyl-1,3-dihydro-3-[2'-(1H-tetrazol-5-yl)[1,1'-biphenyl]-4-ylmethyl]-2H-imidazol-2-one;

1-(2-cyclohexylethyl)-4-butyl-5-trifluoromethyl-1,3-dihydro-3-[2'-(1H-tetrazol-5-yl)[1,1'-biphenyl]-4-ylmethyl]-2H-imidazol-2-one;

1-cyclohexanoyl-4-butyl-5-trifluoromethyl-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-butyl-5-trifluoromethyl-1,3-dihydro-3-[2'-(1H-tetrazol-5-yl)[1,1'-biphenyl]-4-ylmethyl]-2H-imidazol-2-one;

1-phenyl-4-butyl-5-trifluoromethyl-1,3-dihydro-3-[2'-(1H-tetrazol-5-yl)[1,1'-biphenyl]-4-ylmethyl]-2H-imidazol-2-one;

1-phenylmethyl-4-butyl-5-trifluoromethyl-1,3-dihydro-3-[2'-(1H-tetrazol-5-yl)[1,1'-biphenyl]-4-ylmethyl]-2H-imidazol-2-one;

1-(2-phenylethyl)-4-butyl-5-trifluoromethyl-1,3-dihydro-3-[2'-(1H-tetrazol-5-yl)[1,1'-biphenyl]-4-ylmethyl]-2H-imidazol-2-one;

1-benzoyl-4-butyl-5-trifluoromethyl-1,3-dihydro-3-[2'-(1H-tetrazol-5-yl)[1,1'-biphenyl]-4-ylmethyl]-2H-imidazol-2-one;

1-(1-oxo-2-phenylethyl)-4-butyl-5-trifluoromethyl-1,3-dihydro-3-[2'-(1H-tetrazol-5-yl)[1,1'-biphenyl]-4-ylmethyl]-2H-imidazol-2-one;

1-(1-oxopropyl)-4-butyl-5-trifluoromethyl-1,3-dihydro-3-[2'-(1H-tetrazol-5-yl)[1,1'-biphenyl]-4-ylmethyl]-2H-imidazol-2-one;

1-(1-oxobutyl)-4-butyl-5-trifluoromethyl-1,3-dihydro-3-[2'-(1H-tetrazol-5-yl)[1,1'-biphenyl]-4-ylmethyl]-2H-imidazol-2-one;

1-(1-oxopentyl)-4-butyl-5-trifluoromethyl-1,3-dihydro-3-[2'-(1H-tetrazol-5-yl)[1,1'-biphenyl]-4-ylmethyl]-2H-imidazol-2-one;

1-ethyl-4-propyl-5-fluoro-1,3-dihydro-3-[2'-(1H-tetrazol-5-yl)[1,1'-biphenyl]-4-ylmethyl]-2H-imidazol-2-one;

1,4-dipropyl-5-fluoro-1,3-dihydro-3-[2'-(1H-tetrazol-5-yl)[1,1'-biphenyl]-4-ylmethyl]-2H-imidazol-2-one;

1-isopropyl-4-propyl-5-fluoro-1,3-dihydro-3-[2'-(1H-tetrazol-5-yl)[1,1'-biphenyl]-4-ylmethyl]-2H-imidazol-2-one;

1-butyl-4-propyl-5-fluoro-1,3-dihydro-3-[2'-(1H-tetrazol-5-yl)[1,1'-biphenyl]-4-ylmethyl]-2H-imidazol-2-one;

1-secbutyl-4-propyl-5-fluoro-1,3-dihydro-3-[2'-(1H-tetrazol-5-yl)[1,1'-biphenyl]-4-ylmethyl]-2H-imidazol-2-one;

1-isobutyl-4-propyl-5-fluoro-1,3-dihydro-3-[2'-(1H-tetrazol-5-yl)[1,1'-biphenyl]-4-ylmethyl]-2H-imidazol-2-one;

1-tertbutyl-4-propyl-5-fluoro-1,3-dihydro-3-[2'-(1H-tetrazol-5-yl)[1,1'-biphenyl]-4-ylmethyl]-2H-imidazol-2-one;

1-pentyl-4-propyl-5-fluoro-1,3-dihydro-3-[2'-(1H-tetrazol-5-yl)[1,1'-biphenyl]-4-ylmethyl]-2H-imidazol-2-one;

1-isopentyl-4-propyl-5-fluoro-1,3-dihydro-3-[2'-(1H-tetrazol-5-yl)[1,1'-biphenyl]-4-ylmethyl]-2H-imidazol-2-one;

1-cyclohexyl-4-propyl-5-fluoro-1,3-dihydro-3-[2'-(1H-tetrazol-5-yl)[1,1'-biphenyl]-4-ylmethyl]-2H-imidazol-2-one;

1-cyclohexylmethyl-4-propyl-5-fluoro-1,3-dihydro-3-[2'-(1H-tetrazol-5-yl)[1,1'-biphenyl]-4-ylmethyl]-2H-imidazol-2-one;

1-(2-cyclohexylethyl)-4-propyl-5-fluoro-1,3-dihydro-3-[2'-(1H-tetrazol-5-yl)[1,1'-biphenyl]-4-ylmethyl]-2H-imidazol-2-one;

1-cyclohexanoyl-4-propyl-5-fluoro-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-propyl-5-fluoro-1,3-dihydro-3-[2'-(1H-tetrazol-5-yl)[1,1'-biphenyl]-4-ylmethyl]-2H-imidazol-2-one;

1-phenyl-4-propyl-5-fluoro-1,3-dihydro-3-[2'-(1H-tetrazol-5-yl)[1,1'-biphenyl]-4-ylmethyl]-2H-imidazol-2-one;

1-phenylmethyl-4-propyl-5-fluoro-1,3-dihydro-3-[2'-(1H-tetrazol-5-yl)[1,1'-biphenyl]-4-ylmethyl]-2H-imidazol-2-one;

1-(2-phenylethyl)-4-propyl-5-fluoro-1,3-dihydro-3-[2'-(1H-tetrazol-5-yl)[1,1'-biphenyl]-4-ylmethyl]-2H-imidazol-2-one;

1-benzoyl-4-propyl-5-fluoro-1,3-dihydro-3-[2'-(1H-tetrazol-5-yl)[1,1'-biphenyl]-4-ylmethyl]-2H-imidazol-2-one;

1-(1-oxo-2-phenylethyl)-4-propyl-5-fluoro-1,3-dihydro-3-[2'-(1H-tetrazol-5-yl)[1,1'-biphenyl]-4-ylmethyl]-2H-imidazol-2-one;

1-(1-oxopropyl)-4-propyl-5-fluoro-1,3-dihydro-3-[2'-(1H-tetrazol-5-yl)[1,1'-biphenyl]-4-ylmethyl]-2H-imidazol-2-one;

1-(1-oxobutyl)-4-propyl-5-fluoro-1,3-dihydro-3-[2'-(1H-tetrazol-5-yl)[1,1'-biphenyl]-4-ylmethyl]-2H-imidazol-2-one;

1-(1-oxopentyl)-4-propyl-5-fluoro-1,3-dihydro-3-[2'-(1H-tetrazol-5-yl)[1,1'-biphenyl]-4-ylmethyl]-2H-imidazol-2-one;

1-ethyl-4-propyl-5-chloro-1,3-dihydro-3-[2'-(1H-tetrazol-5-yl)[1,1'-biphenyl]-4-ylmethyl]-2H-imidazol-2-one;

1,4-dipropyl-5-chloro-1,3-dihydro-3-[2'-(1H-tetrazol-5-yl)[1,1'-biphenyl]-4-ylmethyl]-2H-imidazol-2-one;

1-isopropyl-4-propyl-5-chloro-1,3-dihydro-3-[2'-(1H-tetrazol-5-yl)[1,1'-biphenyl]-4-ylmethyl]-2H-imidazol-2-one;

1-butyl-4-propyl-5-chloro-1,3-dihydro-3-[2'-(1H-tetrazol-5-yl)[1,1'-biphenyl]-4-ylmethyl]-2H-imidazol-2-one;

1-secbutyl-4-propyl-5-chloro-1,3-dihydro-3-[2'-(1H-tetrazol-5-yl)[1,1'-biphenyl]-4-ylmethyl]-2H-imidazol-2-one;

1-isobutyl-4-propyl-5-chloro-1,3-dihydro-3-[2'-(1H-tetrazol-5-yl)[1,1'-biphenyl]-4-ylmethyl]-2H-imidazol-2-one;

1-tertbutyl-4-propyl-5-chloro-1,3-dihydro-3-[2'-(1H-tetrazol-5-yl)[1,1'-biphenyl]-4-ylmethyl]-2H-imidazol-2-one;

1-pentyl-4-propyl-5-chloro-1,3-dihydro-3-[2'-(1H-tetrazol-5-yl)[1,1'-biphenyl]-4-ylmethyl]-2H-imidazol-2-one;

1-isopentyl-4-propyl-5-chloro-1,3-dihydro-3-[2'-(1H-tetrazol-5-yl)[1,1'-biphenyl]-4-ylmethyl]-2H-imidazol-2-one;

1-cyclohexyl-4-propyl-5-chloro-1,3-dihydro-3-[2'-(1H-tetrazol-5-yl)[1,1'-biphenyl]-4-ylmethyl]-2H-imidazol-2-one;

1-cyclohexylmethyl-4-propyl-5-chloro-1,3-dihydro-3-[2'-(1H-tetrazol-5-yl)[1,1'-biphenyl]-4-ylmethyl]-2H-imidazol-2-one;

1-(2-cyclohexylethyl)-4-propyl-5-chloro-1,3-dihydro-3-[2'-(1H-tetrazol-5-yl)[1,1'-biphenyl]-4-ylmethyl]-2H-imidazol-2-one;

1-cyclohexanoyl-4-propyl-5-chloro-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-propyl-5-chloro-1,3-dihydro-3-[2'-(1H-tetrazol-5-yl)[1,1'-biphenyl]-4-ylmethyl]-2H-imidazol-2-one;

1-phenyl-4-propyl-5-chloro-1,3-dihydro-3-[2'-(1H-tetrazol-5-yl)[1,1'-biphenyl]-4-ylmethyl]-2H-imidazol-2-one;

1-phenylmethyl-4-propyl-5-chloro-1,3-dihydro-3-[2'-(1H-tetrazol-5-yl)[1,1'-biphenyl]-4-ylmethyl]-2H-imidazol-2-one;

1-(2-phenylethyl)-4-propyl-5-chloro-1,3-dihydro-3-[2'-(1H-tetrazol-5-yl)[1,1'-biphenyl]-4-ylmethyl]-2H-imidazol-2-one;

1-benzoyl-4-propyl-5-chloro-1,3-dihydro-3-[2'-(1H-tetrazol-5-yl)[1,1'-biphenyl]-4-ylmethyl]-2H-imidazol-2-one;

1-(1-oxo-2-phenylethyl)-4-propyl-5-chloro-1,3-dihydro-3-[2'-(1H-tetrazol-5-yl)[1,1'-biphenyl]-4-ylmethyl]-2H-imidazol-2-one;

1-(1-oxopropyl)-4-propyl-5-chloro-1,3-dihydro-3-[2'-(1H-tetrazol-5-yl)[1,1'-biphenyl]-4-ylmethyl]-2H-imidazol-2-one;

1-(1-oxobutyl)-4-propyl-5-chloro-1,3-dihydro-3-[2'-(1H-tetrazol-5-yl)[1,1'-biphenyl]-4-ylmethyl]-2H-imidazol-2-one;

1-(1-oxopentyl)-4-propyl-5-chloro-1,3-dihydro-3-[2'-(1H-tetrazol-5-yl)[1,1'-biphenyl]-4-ylmethyl]-2H-imidazol-2-one;

1-ethyl-4-propyl-5-formyl-1,3-dihydro-3-[2'-(1H-tetrazol-5-yl)[1,1'-biphenyl]-4-ylmethyl]-2H-imidazol-2-one;

1,4-dipropyl-5-formyl-1,3-dihydro-3-2'-(1H-tetrazol-5-yl)[1,1'-biphenyl]-4-ylmethyl]-2H-imidazol-2-one;

1-isopropyl-4-propyl-5-formyl-1,3-dihydro-3-[2'-(1H-tetrazol-5-yl)[1,1'-biphenyl]-4-ylmethyl]-2H-imidazol-2-one;

1-butyl-4-propyl-5-formyl-1,3-dihydro-3-[2'-(1H-tetrazol-5-yl)[1,1'-biphenyl]-4-ylmethyl]-2H-imidazol-2-one;

1-secbutyl-4-propyl-5-formyl-1,3-dihydro-3-[2'-(1H-tetrazol-5-yl)[1,1'-biphenyl]-4-ylmethyl]-2H-imidazol-2-one;

1-isobutyl-4-propyl-5-formyl-1,3-dihydro-3-[2'-(1H-tetrazol-5-yl)[1,1'-biphenyl]-4-ylmethyl]-2H-imidazol-2-one;

1-tertbutyl-4-propyl-5-formyl-1,3-dihydro-3-[2'-(1H-tetrazol-5-yl)[1,1'-biphenyl]-4-ylmethyl]-2H-imidazol-2-one;

1-pentyl-4-propyl-5-formyl-1,3-dihydro-3-[2'-(1H-tetrazol-5-yl)[1,1'-biphenyl]-4-ylmethyl]-2H-imidazol-2-one;

1-isopentyl-4-propyl-5-formyl-1,3-dihydro-3-[2'-(1H-tetrazol-5-yl)[1,1'-biphenyl]-4-ylmethyl]-2H-imidazol-2-one;

1-cyclohexyl-4-propyl-5-formyl-1,3-dihydro-3-[2'-(1H-tetrazol-5-yl)[1,1'-biphenyl]-4-ylmethyl]-2H-imidazol-2-one;

1-cyclohexylmethyl-4-propyl-5-formyl-1,3-dihydro-3-[2'-(1H-tetrazol-5-yl)[1,1'-biphenyl]-4-ylmethyl]-2H-imidazol-2-one;

1-(2-cyclohexylethyl)-4-propyl-5-formyl-1,3-dihydro-3-[2'-(1H-tetrazol-5-yl)[1,1'-biphenyl]-4-ylmethyl]-2H-imidazol-2-one;

1-cyclohexanoyl-4-propyl-5-formyl-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-propyl-5-formyl-1,3-dihydro-3-[2'-(1H-tetrazol-5-yl)[1,1'-biphenyl]-4-ylmethyl]-2H-imidazol-2-one;

1-phenyl-4-propyl-5-formyl-1,3-dihydro-3-[2'-(1H-tetrazol-5-yl)[1,1'-biphenyl]-4-ylmethyl]-2H-imidazol-2-one;

1-phenylmethyl-4-propyl-5-formyl-1,3-dihydro-3-[2'-(1H-tetrazol-5-yl)[1,1'-biphenyl]-4-ylmethyl]-2H-imidazol-2-one;

1-(2-phenylethyl)-4-propyl-5-formyl-1,3-dihydro-3-[2'-(1H-tetrazol-5-yl)[1,1'-biphenyl]-4-ylmethyl]-2H-imidazol-2-one;

1-benzoyl-4-propyl-5-formyl-1,3-dihydro-3-[2'-(1H-tetrazol-5-yl)[1,1'-biphenyl]-4-ylmethyl]-2H-imidazol-2-one;

1-(1-oxo-2-phenylethyl)-4-propyl-5-formyl-1,3-dihydro-3-[2'-(1H-tetrazol-5-yl)[1,1'-biphenyl]-4-ylmethyl]-2H-imidazol-2-one;

1-(1-oxopropyl)-4-propyl-5-formyl-1,3-dihydro-3-[2'-(1H-tetrazol-5-yl)[1,1'-biphenyl]-4-ylmethyl]-2H-imidazol-2-one;

1-(1-oxobutyl)-4-propyl-5-formyl-1,3-dihydro-3-[2'-(1H-tetrazol-5-yl)[1,1'-biphenyl]-4-ylmethyl]-2H-imidazol-2-one;

1-(1-oxopentyl)-4-propyl-5-formyl-1,3-dihydro-3-[2'-(1H-tetrazol-5-yl)[1,1'-biphenyl]-4-ylmethyl]-2H-imidazol-2-one;

1-ethyl-4-propyl-5-dimethoxymethyl-1,3-dihydro-3-[2'-(1H-tetrazol-5-yl)[1,1'-biphenyl]-4-ylmethyl]-2H-imidazol-2-one;

1,4-dipropyl-5-dimethoxymethyl-1,3-dihydro-3-[2'-(1H-tetrazol-5-yl)[1,1'-biphenyl]-4-ylmethyl]-2H-imidazol-2-one;

1-isopropyl-4-propyl-5-dimethoxymethyl-1,3-dihydro-3-[2'-(1H-tetrazol-5-yl)[1,1'-biphenyl]-4-ylmethyl]-2H-imidazol-2-one;

1-butyl-4-propyl-5-dimethoxymethyl-1,3-dihydro-3-[2'-(1H-tetrazol-5-yl)[1,1'-biphenyl]-4-ylmethyl]-2H-imidazol-2-one;

1-secbutyl-4-propyl-5-dimethoxymethyl-1,3-dihydro-3-[2'-(1H-tetrazol-5-yl)[1,1'-biphenyl]-4-ylmethyl]-2H-imidazol-2-one;

1-isobutyl-4-propyl-5-dimethoxymethyl-1,3-dihydro-3-[2'-(1H-tetrazol-5-yl)[1,1'-biphenyl]-4-ylmethyl]-2H-imidazol-2-one;

1-tertbutyl-4-propyl-5-dimethoxymethyl-1,3-dihydro-3-[2'-(1H-tetrazol-5-yl)[1,1'-biphenyl]-4-ylmethyl]-2H-imidazol-2-one;

1-pentyl-4-propyl-5-dimethoxymethyl-1,3-dihydro-3-[2'-(1H-tetrazol-5-yl)[1,1'-biphenyl]-4-ylmethyl]-2H-imidazol-2-one;

1-isopentyl-4-propyl-5-dimethoxymethyl-1,3-dihydro-3-[2'-(1H-tetrazol-5-yl)[1,1'-biphenyl]-4-ylmethyl]-2H-imidazol-2-one;

1-cyclohexyl-4-propyl-5-dimethoxymethyl-1,3-dihydro-3-[2'-(1H-tetrazol-5-yl)[1,1'-biphenyl]-4-ylmethyl]-2H-imidazol-2-one;

1-cyclohexylmethyl-4-propyl-5-dimethoxymethyl-1,3-dihydro-3-[2'-(1H-tetrazol-5-yl)[1,1'-biphenyl]-4-ylmethyl]-2H-imidazol-2-one;

1-(2-cyclohexylethyl)-4-propyl-5-dimethoxymethyl-1,3-dihydro-3-[2'-(1H-tetrazol-5-yl)[1,1'-biphenyl]-4-ylmethyl]-2H-imidazol-2-one;

1-cyclohexanoyl-4-propyl-5-dimethoxymethyl-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-propyl-5-dimethoxymethyl-1,3-dihydro-3-[2'-(1H-tetrazol-5-yl)[1,1'-biphenyl]-4-ylmethyl]-2H-imidazol-2-one;

1-phenyl-4-propyl-5-dimethoxymethyl-1,3-dihydro-3-[2'-(1H-tetrazol-5-yl)[1,1'-biphenyl]-4-ylmethyl]-2H-imidazol-2-one;

1-phenylmethyl-4-propyl-5-dimethoxymethyl-1,3-dihydro-3-[2'-(1H-tetrazol-5-yl)[1,1'-biphenyl]-4-ylmethyl]-2H-imidazol-2-one;

1-(2-phenylethyl)-4-propyl-5-dimethoxymethyl-1,3-dihydro-3-[2'-(1H-tetrazol-5-yl)[1,1'-biphenyl]-4-ylmethyl]-2H-imidazol-2-one;

1-benzoyl-4-propyl-5-dimethoxymethyl-1,3-dihydro-3-[2'-(1H-tetrazol-5-yl)[1,1'-biphenyl]-4-ylmethyl]-2H-imidazol-2-one;

1-(1-oxo-2-phenylethyl)-4-propyl-5-dimethoxymethyl-1,3-dihydro-3-[2'-(1H-tetrazol-5-yl)[1,1'-biphenyl]-4-ylmethyl]-2H-imidazol-2-one;

1-(1-oxopropyl)-4-propyl-5-dimethoxymethyl-1,3-dihydro-3-[2'-(1H-tetrazol-5-yl)[1,1'-biphenyl]-4-ylmethyl]-2H-imidazol-2-one;

1-(1-oxobutyl)-4-propyl-5-dimethoxymethyl-1,3-dihydro-3-2'-1H-tetrazol-5-yl)1,1 -biphenyl]-4-ylmethyl]-2H-imidazol-2-one;

1-(1-oxopentyl)-4-propyl-5-dimethoxymethyl-1,3-dihydro-3-[2'-(1H-tetrazol-5-yl)[1,1'-biphenyl]-4-ylmethyl]2H-imidazol-2-one;

1-ethyl-4-propyl-5-methyl-1,3-dihydro-3-2'-(1H-tetrazol-5-yl)1,1 -biphenyl]-4-ylmethyl]-2H-imidazol-2-one;

1,4-dipropyl-5-methyl-1,3-dihydro-3-[2'-(1H-tetrazol-5-yl)[1,1'-biphenyl]-4-ylmethyl]2H-imidazol-2-one;

1-isopropyl-4-propyl-5-methyl-1,3-dihydro-3-[2'-(1H-tetrazol-5-yl)[1,1 -biphenyl]-4-ylmethyl]-2H-imidazol-2-one;

1-butyl-4-propyl-5-methyl-1,3-dihydro-3-[2'-(1H-tetrazol-5-yl)[1,1 -biphenyl]-4-ylmethyl]-2H-imidazol-2-one;

1-secbutyl-4-propyl-5-methyl-1,3-dihydro-3-[2'-(1H-tetrazol-5-yl)[1,1'-biphenyl]-4-ylmethyl]-2H-imidazol-2-one;

1-isobutyl-4-propyl-5-methyl-1,3-dihydro-3-[2'-(1H-tetrazol-5-yl)[1,1'-biphenyl]-4-ylmethyl]-2H-imidazol-2-one;

1-tertbutyl-4-propyl-5-methyl-1,3-dihydro-3-[2'-(1H-tetrazol-5-yl)[1,1'-biphenyl]-4-ylmethyl]-2H-imidazol-2-one;

1-pentyl-4-propyl-5-methyl-1,3-dihydro-3-[2'-(1H-tetrazol-5-yl)[1,1'-biphenyl]-4-ylmethyl]-2H-imidazol-2-one;

1-isopentyl-4-propyl-5-methyl-1,3-dihydro-3-[2'-(1H-tetrazol-5-yl)[1,1'-biphenyl]-4-ylmethyl]-2H-imidazol-2-one;

1-cyclohexyl-4-propyl-5-methyl-1,3-dihydro-3-[2'-(1H-tetrazol-5-yl)[1,1'-biphenyl]-4-ylmethyl]-2H-imidazol-2-one;

1-cyclohexylmethyl-4-propyl-5-methyl-1,3-dihydro-3-[2'-(1H-tetrazol-5-yl)[1,1'-biphenyl]-4-ylmethyl]-2H-imidazol-2-one;

1-(2-cyclohexylethyl)-4-propyl-5-methyl-1,3-dihydro-3-[2'-(1H-tetrazol-5-yl)[1,1'-biphenyl]-4-ylmethyl]-2H-imidazol-2-one;

1-cyclohexanoyl-4-propyl-5-methyl-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-propyl-5-methyl-1,3-dihydro-3-[2'-(1H-tetrazol-5-yl)[1,1'-biphenyl]-4-ylmethyl]-2H-imidazol-2-one;

1-phenyl-4-propyl-5-methyl-1,3-dihydro-3-[2'-(1H-tetrazol-5-yl)[1,1'-biphenyl]-4-ylmethyl]-2H-imidazol-2-one;

1-phenylmethyl-4-propyl-5-methyl-1,3-dihydro-3-[2'-(1H-tetrazol-5-yl)[1,1'-biphenyl]-4-ylmethyl]-2H-imidazol-2-one;

1-(2-phenylethyl)-4-propyl-5-methyl-1,3-dihydro-3-[2'-(1H-tetrazol-5-yl)[1,1'-biphenyl]-4-ylmethyl]-2H-imidazol-2-one;

1-benzoyl-4-propyl-5-methyl-1,3-dihydro-3-[2'-(1H-tetrazol-5-yl)[1,1'-biphenyl]-4-ylmethyl]-2H-imidazol-2-one;

1-(1-oxo-2-phenylethyl)-4-propyl-5-methyl-1,3-dihydro-3-[2'-(1H-tetrazol-5-yl)[1,1'-biphenyl]-4-ylmethyl]-2H-imidazol-2-one;

1-(1-oxopropyl)-4-propyl-5-methyl-1,3-dihydro-3-[2'-(1H-tetrazol-5-yl)[1,1'-biphenyl]-4-ylmethyl]-2H-imidazol-2-one;

1-(1-oxobutyl)-4-propyl-5-methyl-1,3-dihydro-3-[2'-(1H-tetrazol-5-yl)[1,1'-biphenyl]-4-ylmethyl]-2H-imidazol-2-one;

1-(1-oxopentyl)-4-propyl-5-methyl-1,3-dihydro-3-[2'-(1H-tetrazol-5-yl)[1,1'-biphenyl]-4-ylmethyl]-2H-imidazol-2-one;

1-ethyl-4-propyl-5-fluoromethyl-1,3-dihydro-3-[2'-(1H-tetrazol-5-yl)[1,1'-biphenyl]-4-ylmethyl]-2H-imidazol-2-one;

1,4-dipropyl-5-fluoromethyl-1,3-dihydro-3-[2'-(1H-tetrazol-5-yl)[1,1'-biphenyl]-4-ylmethyl]-2H-imidazol-2-one;

1-isopropyl-4-propyl-5-fluoromethyl-1,3-dihydro-3-[2'-(1H-tetrazol-5-yl)[1,1'-biphenyl]-4-ylmethyl]-2H-imidazol-2-one;

1-butyl-4-propyl-5-fluoromethyl-1,3-dihydro-3-[2'-(1H-tetrazol-5-yl)[1,1'-biphenyl]-4-ylmethyl]-2H-imidazol-2-one;

1-secbutyl-4-propyl-5-fluoromethyl-1,3-dihydro-3-[2'-(1H- tetrazol-5-yl)[1,1'-biphenyl]-4-ylmethyl]-2H-imidazol-2-one;

1-isobutyl-4-propyl-5-fluoromethyl-1,3-dihydro-3-[2'-(1H-tetrazol-5-yl)[1,1'-biphenyl]-4-ylmethyl]-2H-imidazol-2-one;

1-tertbutyl-4-propyl-5-fluoromethyl-1,3-dihydro-3-[2'-(1H-tetrazol-5-yl)[1,1'-biphenyl]-4-ylmethyl]-2H-imidazol-2-one;

1-pentyl-4-propyl-5-fluoromethyl-1,3-dihydro-3-[2'-(1H-tetrazol-5-yl)[1,1'-biphenyl]-4-ylmethyl]-2H-imidazol-2-one;

1-isopentyl-4-propyl-5-fluoromethyl-1,3-dihydro-3-[2'-(1H-tetrazol-5-yl)[1,1'-biphenyl]-4-ylmethyl]-2H-imidazol-2-one;

1-cyclohexyl-4-propyl-5-fluoromethyl-1,3-dihydro-3-[2'-(1H-tetrazol-5-yl)[1,1'-biphenyl]-4-ylmethyl]-2H-imidazol-2-one;

1-cyclohexylmethyl-4-propyl-5-fluoromethyl-1,3-dihydro-3-[2'-(1H-tetrazol-5-yl)[1,1'-biphenyl]-4-ylmethyl]-2H-imidazol-2-one;

1-(2-cyclohexylethyl)-4-propyl-5-fluoromethyl-1,3-dihydro-3-[2'-(1H-tetrazol-5-yl)[1,1'-biphenyl]-4-ylmethyl]-2H-imidazol-2-one;

1-cyclohexanoyl-4-propyl-5-fluoromethyl-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-propyl-5-fluoromethyl-1,3-dihydro-3-[2'-(1H-tetrazol-5-yl)[1,1'-biphenyl]-4-ylmethyl]-2H-imidazol-2-one;

1 phenyl-4-propyl-5-fluoromethyl-1,3-dihydro-3-[2'-(1H-tetrazol-5-yl)[1,1'-biphenyl]-4-ylmethyl]-2H-imidazol-2-one;

1-phenylmethyl-4-propyl-5-fluoromethyl-1,3-dihydro-3-[2'-(1H-tetrazol-5-yl)[1,1'-biphenyl]-4-ylmethyl]-2H-imidazol-2-one;

1-(2-phenylethyl)-4-propyl-5-fluoromethyl-1,3-dihydro-3-[2'-(1H-tetrazol-5-yl)[1,1'-biphenyl]-4-ylmethyl]-2H-imidazol-2-one;

1-benzoyl-4-propyl-5-fluoromethyl-1,3-dihydro-3-[2'-(1H-tetrazol-5-yl)[1,1'-biphenyl]-4-ylmethyl]-2H-imidazol-2-one;

1-(1-oxo-2-phenylethyl)-4-propyl-5-fluoromethyl-1,3-dihydro-3-[2'-(1H-tetrazol-5-yl)[1,1'-biphenyl]-4-ylmethyl]-2H-imidazol-2-one;

1-(1-oxopropyl)-4-propyl-5-fluoromethyl-1,3-dihydro-3-[2'-(1H-tetrazol-5-yl)[1,1'-biphenyl]-4-ylmethyl]-2H-imidazol-2-one;

1-(1-oxobutyl)-4-propyl-5-fluoromethyl-1,3-dihydro-3-[2'-(1H-tetrazol-5-yl)[1,1'-biphenyl]-4-ylmethyl]-2H-imidazol-2-one;

1-(1-oxopentyl)-4-propyl-5-fluoromethyl-1,3-dihydro-3-[2'-(1H-tetrazol-5-yl)[1,1'-biphenyl]-4-ylmethyl]-2H-imidazol-2-one;

1-ethyl-4-propyl-5-difluoromethyl-1,3-dihydro-3-[2'-(1H-tetrazol-5-yl)[1,1'-biphenyl]-4-ylmethyl]-2H-imidazol-2-one;

1,4-dipropyl-5-difluoromethyl-1,3-dihydro-3-[2'-(1H-tetrazol-5-yl)[1,1'-biphenyl]-4-ylmethyl]-2H-imidazol-2-one;

1-isopropyl-4-propyl-5-difluoromethyl-1,3-dihydro-3-[2'-(1H-tetrazol-5-yl)[1,1'-biphenyl]-4-ylmethyl]-2H-imidazol-2-one;

1-butyl-4-propyl-5-difluoromethyl-1,3-dihydro-3-[2'-(1H-tetrazol-5-yl)[1,1'-biphenyl]-4-ylmethyl]-2H-imidazol-2-one;

1-secbutyl-4-propyl-5-difluoromethyl-1,3-dihydro-3-[2'-(1H-tetrazol-5-yl)[1,1'-biphenyl]-4-ylmethyl]-2H-imidazol-2-one;

1-isobutyl-4-propyl-5-difluoromethyl-1,3-dihydro-3-[2'-(1H-tetrazol-5-yl)[1,1'-biphenyl]-4-ylmethyl]-2H-imidazol-2-one;

1-tertbutyl-4-propyl-5-difluoromethyl-1,3-dihydro-3-[2'-(1H-tetrazol-5-yl)[1,1'-biphenyl]-4-ylmethyl]-2H-imidazol-2-one;

1 pentyl-4-propyl-5-difluoromethyl-1,3-dihydro-3-[2'-(1H-tetrazol-5-yl)[1,1'-biphenyl]-4-ylmethyl]-2H-imidazol-2-one;

1-isopentyl-4-propyl-5-difluoromethyl-1,3-dihydro-3-[2'-(1H-tetrazol-5-yl)[1,1'-biphenyl]-4-ylmethyl]-2H-imidazol-2-one;

1-cyclohexyl-4-propyl-5-difluoromethyl-1,3-dihydro-3-[2'-(1H-tetrazol-5-yl)[1,1'-biphenyl]-4-ylmethyl]-2H-imidazol-2-one;

1-cyclohexylmethyl-4-propyl-5-difluoromethyl-1,3-dihydro-3-[2'-(1H-tetrazol-5-yl)[1,1'-biphenyl]-4-ylmethyl]-2H-imidazol-2-one;

1-(2-cyclohexylethyl)-4-propyl-5-difluoromethyl-1,3-dihydro-3-[2'-(1H-tetrazol-5-yl)[1,1'-biphenyl]-4-ylmethyl]-2H-imidazol-2-one;

1-cyclohexanoyl-4-propyl-5-difluoromethyl-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-propyl-5-difluoromethyl-1,3-dihydro-3-[2'-(1H-tetrazol-5-yl)[1,1'-biphenyl]-4-ylmethyl]-2H-imidazol-2-one;

1-phenyl-4-propyl-5-difluoromethyl-1,3-dihydro-3-[2'-(1H-tetrazol-5-yl)[1,1'-biphenyl]-4-ylmethyl]-2H-imidazol-2-one;

1-phenylmethyl-4-propyl-5-difluoromethyl-1,3-dihydro-3-[2'-(1H-tetrazol-5-yl)[1,1'-biphenyl]-4-ylmethyl]-2H-imidazol-2-one;

1-(2-phenylethyl)-4-propyl-5-difluoromethyl-1,3-dihydro-3-[2'-(1H-tetrazol-5-yl)[1,1'-biphenyl]-4-ylmethyl]-2H-imidazol-2-one;

1-benzoyl-4-propyl-5-difluoromethyl-1,3-dihydro-3-[2'-(1H-tetrazol-5-yl)[1,1'-biphenyl]-4-ylmethyl]-2H-imidazol-2-one;

1-(1-oxo-2-phenylethyl)-4-propyl-5-difluoromethyl-1,3-dihydro-3-[2'-(1H-tetrazol-5-yl)[1,1'-biphenyl]-4-ylmethyl]-2H-imidazol-2-one;

1-(1-oxopropyl)-4-propyl-5-difluoromethyl-1,3-dihydro-3-[2'-(1H-tetrazol-5-yl)[1,1'-biphenyl]-4-ylmethyl]-2H-imidazol-2-one;

1-(1-oxobutyl)-4-propyl-5-difluoromethyl-1,3-dihydro-3-[2'-(1H-tetrazol-5-yl)[1,1'-biphenyl]-4-ylmethyl]-2H-imidazol-2-one;

1-(1-oxopentyl)-4-propyl-5-difluoromethyl-1,3-dihydro-3-[2'-(1H-tetrazol-5-yl)[1,1'-biphenyl]-4-ylmethyl]-2H-imidazol-2-one;

1-ethyl-4-propyl-5-trifluoromethyl-1,3-dihydro-3-[2'-(1H-tetrazol-5-yl)[1,1'-biphenyl]-4-ylmethyl]-2H-imidazol-2-one;

1,4-dipropyl-5-trifluoromethyl-1,3-dihydro-3-[2'-(1H-tetrazol-5-yl)[1,1'-biphenyl]-4-ylmethyl]-2H-imidazol-2-one;

1-isopropyl-4-propyl-5-trifluoromethyl-1,3-dihydro-3-[2'-(1H-tetrazol-5-yl)[1,1'-biphenyl]-4-ylmethyl]-2H-imidazol-2-one;

1-butyl-4-propyl-5-trifluoromethyl-1,3-dihydro-3-[2'-(1H-tetrazol-5-yl)[1,1'-biphenyl]-4-ylmethyl]-2H-imidazol-2-one;

1-secbutyl-4-propyl-5-trifluoromethyl-1,3-dihydro-3-[2'-(1H-tetrazol-5-yl)[1,1'-biphenyl]-4-ylmethyl]-2H-imidazol-2-one;

1-isobutyl-4-propyl-5-trifluoromethyl-1,3-dihydro-3-[2'-(1H-tetrazol-5-yl)[1,1'-biphenyl]-4-ylmethyl]-2H-imidazol-2-one;

1-tertbutyl-4-propyl-5-trifluoromethyl-1,3-dihydro-3-[2'-(1H-tetrazol-5-yl)[1,1'-biphenyl]-4-ylmethyl]-2H-imidazol-2-one;

1-pentyl-4-propyl-5-trifluoromethyl-1,3-dihydro-3-[2'-(1H-tetrazol-5-yl)[1,1'-biphenyl]-4-ylmethyl]-2H-imidazol-2-one;

1-isopentyl-4-propyl-5-trifluoromethyl-1,3-dihydro-3-[2'-(1H-tetrazol-5-yl)[1,1'-biphenyl]-4-ylmethyl]-2H-imidazol-2-one;

1-cyclohexyl-4-propyl-5-trifluoromethyl-1,3-dihydro-3-[2'-(1H-tetrazol-5-yl)[1,1'-biphenyl]-4-ylmethyl]-2H-imidazol-2-one;

1-cyclohexylmethyl-4-propyl-5-trifluoromethyl-1,3-dihydro-3-[2'-(1H-tetrazol-5-yl)[1,1'-biphenyl]-4-ylmethyl]-2H-imidazol-2-one;

1-(2-cyclohexylethyl)-4-propyl-5-trifluoromethyl-1,3-dihydro-3-[2'-(1H-tetrazol-5-yl)[1,1'-biphenyl]-4-ylmethyl]-2H-imidazol-2-one;

1-cyclohexanoyl-4-propyl-5-trifluoromethyl-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-propyl-5-trifluoromethyl-1,3-dihydro-3-[2'-(1H-tetrazol-5-yl)[1,1'-biphenyl]-4-ylmethyl]-2H-imidazol-2-one;

1-4-propyl-5-trifluoromethyl-1,3-dihydro-3-[2'-(1H-tetrazol-5-yl)[1,1'-biphenyl]-4-ylmethyl]-2H-imidazol-2-one;

1-phenylmethyl-4-propyl-5-trifluoromethyl-1,3-dihydro-3-[2'-(1H-tetrazol-5-yl)[1,1'-biphenyl]-4-ylmethyl]-2H-imidazol-2-one;

1-(2-phenylethyl)-4-propyl-5-trifluoromethyl-1,3-dihydro-3-[2'-(1H-tetrazol-5-yl)[1,1'-biphenyl]-4-ylmethyl]-2H-imidazol-2-one;

1-benzoyl-4-propyl-5-trifluoromethyl-1,3-dihydro-3-[2'-(1H-tetrazol-5-yl)[1,1'-biphenyl]-4-ylmethyl]-2H-imidazol-2-one;

1-(1-oxo-2-phenylethyl)-4-propyl-5-trifluoromethyl-1,3-dihydro-3-[2'-(1H-tetrazol-5-yl)[1,1'-biphenyl]-4-ylmethyl]-2H-imidazol-2-one;

1-(1-oxopropyl)-4-propyl-5-trifluoromethyl-1,3-dihydro-3-[2'-(1H-tetrazol-5-yl)[1,1'-biphenyl]-4-ylmethyl]-2H-imidazol-2-one;

1-(1-oxobutyl)-4-propyl-5-trifluoromethyl-1,3-dihydro-3-[2'-(1H-tetrazol-5-yl)[1,1'-biphenyl]-4-ylmethyl]-2H-imidazol-2-one;

1-(1-oxopentyl)-4-propyl-5-trifluoromethyl-1,3-dihydro-3-[2'-(1H-tetrazol-5-yl)[1,1'-biphenyl]-4-ylmethyl]-2H-imidazol-2-one;

1-ethyl-4-isopentyl-5-fluoro-1,3-dihydro-3-[2'-(1H-tetrazol-5-yl)[1,1'-biphenyl]-4-ylmethyl]-2H-imidazol-2-one;

1,4-dipropyl-5-fluoro-1,3-dihydro-3-[2'-(1H-tetrazol-5-yl)[1,1'-biphenyl]-4-ylmethyl]-2H-imidazol-2-one;

1-isopropyl-4-isopentyl-5-fluoro-1,3-dihydro-3-[2'-(1H-tetrazol-5-yl)[1,1'-biphenyl]-4-ylmethyl]-2H-imidazol-2-one;

1-butyl-4-isopentyl-5-fluoro-1,3-dihydro-3-[2'-(1H-tetrazol-5-yl)[1,1'-biphenyl]-4-ylmethyl]-2H-imidazol-2-one;

1-secbutyl-4-isopentyl-5-fluoro-1,3-dihydro-3-[2'-(1H-tetrazol-5-yl)[1,1'-biphenyl]-4-ylmethyl]-2H-imidazol-2-one;

1-isobutyl-4-isopentyl-5-fluoro-1,3-dihydro-3-[2'-(1H-tetrazol-5-yl)[1,1'-biphenyl]-4-ylmethyl]-2H-imidazol-2-one;

1-tertbutyl-4-isopentyl-5-fluoro-1,3-dihydro-3-[2'-(1H-tetrazol-5-yl)[1,1'-biphenyl]-4-ylmethyl]-2H-imidazol-2-one;

1-pentyl-4-isopentyl-5-fluoro-1,3-dihydro-3-[2'-(1H-tetrazol-5-yl)[1,1'-biphenyl]-4-ylmethyl]-2H-imidazol-2-one;

1,4-diisopentyl-5-fluoro-1,3-dihydro-3-[2'-(1H-tetrazol-5-yl)[1,1'-biphenyl]-4-ylmethyl]-2H-imidazol-2-one;

1-cyclohexyl-4-isopentyl-5-fluoro-1,3-dihydro-3-[2'-(1H-tetrazol-5-yl)[1,1'-biphenyl]-4-ylmethyl]-2H-imidazol-2-one;

1-cyclohexylmethyl-4-isopentyl-5-fluoro-1,3-dihydro-3-[2'-(1H-tetrazol-5-yl)[1,1'-biphenyl]-4-ylmethyl]-2H-imidazol-2-one;

1-(2-cyclohexylethyl)-4-isopentyl-5-fluoro-1,3-dihydro-3-[2'-(1H-tetrazol-5-yl)[1,1'-biphenyl]-4-ylmethyl]-2H-imidazol-2-one;

1-cyclohexanoyl-4-isopentyl-5-fluoro-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-isopentyl-5-fluoro-1,3-dihydro-3-[2'-(1H-tetrazol-5-yl)[1,1'-biphenyl]-4-ylmethyl]-2H-imidazol-2-one;

1-phenyl-4-isopentyl-5-fluoro-1,3-dihydro-3-[2'-(1H-tetrazol-5-yl)[1,1'-biphenyl]-4-ylmethyl]-2H-imidazol-2-one;

1-phenylmethyl-4-isopentyl-5-fluoro-1,3-dihydro-3-[2'-(1H-tetrazol-5-yl)[1,1'-biphenyl]-4-ylmethyl]-2H-imidazol-2-one;

1-(2-phenylethyl)-4-isopentyl-5-fluoro-1,3-dihydro-3-[2'-(1H-tetrazol-5-yl)[1,1'-biphenyl]-4-ylmethyl]-2H-imidazol-2-one;

1-benzoyl-4-isopentyl-5-fluoro-1,3-dihydro-3-[2'-(1H-tetrazol-5-yl)[1,1'-biphenyl]-4-ylmethyl]-2H-imidazol-2-one; 1-(1-oxo-2-phenylethyl)-4-isopentyl-5-fluoro-1,3-dihydro-3-[2'-(1H-tetrazol-5-yl)[1,1'-biphenyl]-4-ylmethyl]-2H-imidazol-2-one;

1-(1-oxopropyl)-4-isopentyl-5-fluoro-1,3-dihydro-3-[2'-(1H-tetrazol-5-yl)[1,1'-biphenyl]-4-ylmethyl]-2H-imidazol-2-one;

1-(1-oxobutyl)-4-isopentyl-5-fluoro-1,3-dihydro-3-[2'-(1H-tetrazol-5-yl)[1,1'-biphenyl]-4-ylmethyl]-2H-imidazol-2-one;

1-(1-oxopentyl)-4-isopentyl-5-fluoro-1,3-dihydro-3-[2'-(1H-tetrazol-5-yl)[1,1'-biphenyl]-4-ylmethyl]-2H-imidazol-2-one;

1-ethyl-4-isopentyl-5-chloro-1,3-dihydro-3-[2'-(1H-tetrazol-5-yl)[1,1'-biphenyl]-4-ylmethyl]-2H-imidazol-2-one;

1-propyl-4-isopentyl-5-chloro-1,3-dihydro-3-[2'-(1H-tetrazol-5-yl)[1,1'-biphenyl]-4-ylmethyl]-2H-imidazol-2-one;

1-isopropyl-4-isopentyl-5-chloro-1,3-dihydro-3-[2'-(1H-tetrazol-5-yl)[1,1'-biphenyl]-4-ylmethyl]-2H-imidazol-2-one;

1-butyl-4-isopentyl-5-chloro-1,3-dihydro-3-[2'-(1H-tetrazol-5-yl)[1,1'-biphenyl]-4-ylmethyl]-2H-imidazol-2-one;

1-secbutyl-4-isopentyl-5-chloro-1,3-dihydro-3-[2'-(1H-tetrazol-5-yl)[1,1'-biphenyl]-4-ylmethyl]-2H-imidazol-2-one;

1-isobutyl-4-isopentyl-5-chloro-1,3-dihydro-3-[2'-(1H-tetrazol-5-yl)[1,1'-biphenyl]-4-ylmethyl]-2H-imidazol-2-one;

1-tertbutyl-4-isopentyl-5-chloro-1,3-dihydro-3-[2'-(1H-tetrazol-5-yl)[1,1'-biphenyl]-4-ylmethyl]-2H-imidazol-2-one;

1-pentyl-4-isopentyl-5-chloro-1,3-dihydro-3-[2'-(1H-tetrazol-5-yl)[1,1'-biphenyl]-4-ylmethyl]-2H-imidazol-2-one;

1,4-diisopentyl-5-chloro-1,3-dihydro-3-[2'-(1H-tetrazol-5-yl)[1,1'-biphenyl]-4-ylmethyl]-2H-imidazol-2-one;

1-cyclohexyl-4-isopentyl-5-chloro-1,3-dihydro-3-[2'-(1H-tetrazol-5-yl)[1,1'-biphenyl]-4-ylmethyl]-2H-imidazol-2-one;

1-cyclohexylmethyl-4-isopentyl-5-chloro-1,3-dihydro-3-[2'-(1H-tetrazol-5-yl)[1,1'-biphenyl]-4-ylmethyl]-2H-imidazol-2-one;

1-(2-cyclohexylethyl)-4-isopentyl-5-chloro-1,3-dihydro-3-[2'-(1H-tetrazol-5-yl)[1,1'-biphenyl]-4-ylmethyl]-2H-imidazol-2-one;

1-cyclohexanoyl-4-isopentyl-5-chloro-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-isopentyl-5-chloro-1,3-dihydro-30[2'-(1H-tetrazol-5-yl)[1,1'-biphenyl]-4-ylmethyl]-2H-imidazol-2-one;

1-phenyl-4-isopentyl-5-chloro-1,3-dihydro-3-[2'-(1H-tetrazol-5-yl)[1,1'-biphenyl]-4-ylmethyl]-2H-imidazol-2-one;

1-phenylmethyl-4-isopentyl-5-chloro-1,3-dihydro-3-[2'-(1H-tetrazol-5-yl)[1,1'-biphenyl]-4-ylmethyl]-2H-imidazol-2-one;

1-(2-phenylethyl)-4-isopentyl-5-chloro-1,3-dihydro-3-[2'-(1H-tetrazol-5-yl)[1,1'-biphenyl]-4-ylmethyl]-2H-imidazol-2-one;

1-benzoyl-4-isopentyl-5-chloro-1, -dihydro-3-[2'-(1H-tetrazol-5-yl)[1,1'-biphenyl]-4-ylmethyl]-2H-imidazol-2-one;

1-(1-oxo-2-phenylethyl)-4-isopentyl-5-chloro-1,3-dihydro-3-[2'-(1H-tetrazol-5-yl)[1,1'-biphenyl]-4-ylmethyl]-2H-imidazol-2-one;

1-(1-oxopropyl)-4-isopentyl-5-chloro-1,3-dihydro-3-[2'-(1H-tetrazol-5-yl)[1,1'-biphenyl]-4-ylmethyl]-2H-imidazol-2-one;

1-(1-oxobutyl)-4-isopentyl-5-chloro-1,3-dihydro-3-[2'-(1H-tetrazol-5-yl)[1,1'-biphenyl]-4-ylmethyl]-2H-imidazol-2-one;

1-(1-oxopentyl)-4-isopentyl-5-chloro-1,3-dihydro-3-[2'-(1H-tetrazol-5-yl)[1,1'-biphenyl]-4-ylmethyl]-2H-imidazol-2-one;

1-ethyl-4-isopentyl-5-formyl-1,3-dihydro-3-[2'-(1H-tetrazol-5-yl)[1,1'-biphenyl]-4-ylmethyl]-2H-imidazol-2-one;

1-propyl-4-isopentyl-5-formyl-1,3-dihydro-3-[2'-(1H-tetrazol-5-yl)[1,1'-biphenyl]-4-ylmethyl]-2H-imidazol-2-one;

1-isopropyl-4-isopentyl-5-formyl-1,3-dihydro-3-[2'-(1H-tetrazol-5-yl)[1,1'-biphenyl]-4-ylmethyl]-2H-imidazol-2-one;

1-butyl-4-isopentyl-5-formyl-1,3-dihydro-3-[2'-(1H-tetrazol-5-yl)[1,1'-biphenyl]-4-ylmethyl]-2H-imidazol-2-one;

1-secbutyl-4-isopentyl-5-formyl-1,3-dihydro-3-[2'-(1H-tetrazol-5-yl)[1,1'-biphenyl]-4-ylmethyl]-2H-imidazol-2-one;

1-isobutyl-4-isopentyl-5-formyl-1,3-dihydro-3-[2'-(1H-tetrazol-5-yl)[1,1'-biphenyl]-4-ylmethyl]-2H-imidazol-2-one;

1-tertbutyl-4-isopentyl-5-formyl-1,3-dihydro-3-[2'-(1H-tetrazol-5-yl)[1,1'-biphenyl]-4-ylmethyl]-2H-imidazol-2-one;

1-pentyl-4-isopentyl-5-formyl-1,3-dihydro-3-[2'-(1H-tetrazol-5-yl)[1,1'-biphenyl]-4-ylmethyl]-2H-imidazol-2-one;

1,4-diisopentyl-5-formyl-1,3-dihydro-3-[2'-(1H-tetrazol-5-yl)[1,1'-biphenyl]-4-ylmethyl]-2H-imidazol-2-one;

1-cyclohexyl-4-isopentyl-5-formyl-1,3-dihydro-3-[2'-(1H-tetrazol-5-yl)[1,1'-biphenyl]-4-ylmethyl]-2H-imidazol-2-one;

1-cyclohexylmethyl-4-isopentyl-5-formyl-1,3-dihydro-3-[2'-(1H-tetrazol-5-yl)[1,1'-biphenyl]-4-ylmethyl]-2H-imidazol-2-one;

1-(2-cyclohexylethyl)-4-isopentyl-5-formyl-1,3-dihydro-3-[2'-(1H-tetrazol-5-yl)[1,1'-biphenyl]-4-ylmethyl]-2H-imidazol-2-one;

1-cyclohexanoyl-4-isopentyl-5-formyl-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-isopentyl-5-formyl-1,3-dihydro-3-[2'-(1H-tetrazol-5-yl)[1,1'-biphenyl]-4-ylmethyl]-2H-imidazol-2-one;

1-phenyl-4-isopentyl-5-formyl-1,3-dihydro-3-[2'-(1H-tetrazol-5-yl)[1,1'-biphenyl]-4-ylmethyl]-2H-imidazol-2-one;

1-phenylmethyl-4-isopentyl-5-formyl-1,3-dihydro-3-[2'-(1H-tetrazol-5-yl)[1,1'-biphenyl]-4-ylmethyl]-2H-imidazol-2-one;

1-(2-phenylethyl)-4-isopentyl-5-formyl-1,3-dihydro-3-[2'-(1H-tetrazol-5-yl)[1,1'-biphenyl]-4-ylmethyl]-2H-imidazol-2-one;

1-benzoyl-4-isopentyl-5-formyl-1,3-dihydro-3-[2'-(1H-tetrazol-5-yl)[1,1'-biphenyl]-4-ylmethyl]-2H-imidazol-2-one;

1-(1-oxo-2-phenylethyl)-4-isopentyl-5-formyl-1,3-dihydro-3-[2'-(1H-tetrazol-5-yl)[1,1'-biphenyl]-4-ylmethyl]-2H-imidazol-2-one;

1-(1-oxopropyl)-4-isopentyl-5-formyl-1,3-dihydro-3-[2'-(1H-tetrazol-5-yl)[1,1'-biphenyl]-4-ylmethyl]-2H-imidazol-2-one;

1-(1-oxobutyl)-4-isopentyl-5-formyl-1,3-dihydro-3-[2'-(1H-tetrazol-5-yl)[1,1'-biphenyl]-4-ylmethyl]-2H-imidazol-2-one;

1-(1-oxopentyl)-4-isopentyl-5-formyl-1,3-dihydro-3-[2'-(1H-tetrazol-5-yl)[1,1'-biphenyl]-4-ylmethyl]-2H-imidazol-2-one;

1-ethyl-4-isopentyl-5-dimethoxymethyl-1,3-dihydro-3-[2'-(1H-tetrazol-5-yl)[1,1'-biphenyl]-4-ylmethyl]-2H-imidazol-2-one;

1-propyl-4-isopentyl-5-dimethoxymethyl-1,3-dihydro-3-[2'-(1H-tetrazol-5-yl)[1,1'-biphenyl]-4-ylmethyl]-2H-imidazol-2-one;

1-isopropyl-4-isopentyl-5-dimethoxymethyl-1,3-dihydro-3-[2'-(1H-tetrazol-5-yl)[1,1'-biphenyl]-4-ylmethyl]-2H-imidazol-2-one;

1-butyl-4-isopentyl-5-dimethoxymethyl-1,3-dihydro-3-[2'-(1H-tetrazol-5-yl)[1,1'-biphenyl]-4-ylmethyl]-2H-imidazol-2-one;

1-secbutyl-4-isopentyl-5-dimethoxymethyl-1,3-dihydro-3-[2'-(1H-tetrazol-5-yl)[1,1'-biphenyl]-4-ylmethyl]-2H-imidazol-2-one;

1-isobutyl-4-isopentyl-5-dimethoxymethyl-1,3-dihydro-3-[2'-(1H-tetrazol-5-yl)[1,1'-biphenyl]-4-ylmethyl]-2H-imidazol-2-one;

1-tertbutyl-4-isopentyl-5-dimethoxymethyl-1,3-dihydro-3-[2'-(1H-tetrazol-5-yl)[1,1'-biphenyl]-4-ylmethyl]-2H-imidazol-2-one;

1-pentyl-4-isopentyl-5-dimethoxymethyl-1,3-dihydro-3-[2'-(1H-tetrazol-5-yl)[1,1'-biphenyl]-4-ylmethyl]-2H-imidazol-2-one;

1,4-diisopentyl-5-dimethoxymethyl-1,3-dihydro-3-[2'-(1H-tetrazol-5-yl)[1,1'-biphenyl]-4-ylmethyl]-2H-imidazol-2-one;

1-cyclohexyl-4-isopentyl-5-dimethoxymethyl-1,3-dihydro-3-[2'-(1H-tetrazol-5-yl)[1,1'-biphenyl]-4-ylmethyl]-2H-imidazol-2-one;

1-cyclohexylmethyl-4-isopentyl-5-dimethoxymethyl-1,3-dihydro-3-[2'-(1H-tetrazol-5-yl)[1,1'-biphenyl]-4-ylmethyl]-2H-imidazol-2-one;

1-(2-cyclohexylethyl)-4-isopentyl-5-dimethoxymethyl-1,3-dihydro-3-[2'-(1H-tetrazol-5-yl)[1,1'-biphenyl]-4-ylmethyl]-2H-imidazol-2-one;

1-cyclohexanoyl-4-isopentyl-5-dimethoxymethyl-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-isopentyl-5-dimethoxymethyl-1,3-dihydro-3-[2'-(1H-tetrazol-5-yl)[1,1'-biphenyl]-4-ylmethyl]-2H-imidazol-2-one;

1-phenyl-4-isopentyl-5-dimethoxymethyl-1,3-dihydro-3-[2'-(1H-tetrazol-5-yl)[1,1'-biphenyl]-4-ylmethyl]-2H-imidazol-2-one;

1-phenylmethyl-4-isopentyl-5-dimethoxymethyl-1,3-dihydro-3-[2'-(1H-tetrazol-5-yl)[1,1'-biphenyl]-4-ylmethyl]-2H-imidazol-2-one 1-(2-phenylethyl)-4-isopentyl-5-dimethoxymethyl-1,3-dihydro-3-[2'-(1H-tetrazol-5-yl)[1,1'-biphenyl]-4-ylmethyl]-2H-imidazol-2-one;

1-benzoyl-4-isopentyl-5-dimethoxymethyl-1,3-dihydro-3-[2'-(1H-tetrazol-5-yl)[1,1'-biphenyl]-4-ylmethyl]-2H-imidazol-2-one;

1-(1-oxo-2-phenylethyl)-4-isopentyl-5-dimethoxymethyl-1,3-dihydro-3-[2'-(1H-tetrazol-5-yl)[1,1'-biphenyl]-4-ylmethyl]-2H-imidazol-2-one;
1-(1-oxopropyl)-4-isopentyl-5-dimethoxymethyl-1,3-dihydro-3-[2'-(1H-tetrazol-5-yl)[1,1'-biphenyl]-4-ylmethyl]-2H-imidazol-2-one;
1-(1-oxobutyl)-4-isopentyl-5-dimethoxymethyl-1,3-dihydro-3-[2'-(1H-tetrazol-5-yl)[1,1'-biphenyl]-4-ylmethyl]-2H-imidazol-2-one;
1-(1-oxopentyl)-4-isopentyl-5-dimethoxymethyl-1,3-dihydro-3-[2'-(1H-tetrazol-5-yl)[1,1'-biphenyl]-4-ylmethyl]-2H-imidazol-2-one;
1-ethyl-4-isopentyl-5-methyl-1,3-dihydro-3-[2'-(1H-tetrazol-5-yl)[1,1'-biphenyl]-4-ylmethyl]-2H-imidazol-2-one;
1-propyl-4-isopentyl-5-methyl-1,3-dihydro-3-[2'-(1H-tetrazol-5-yl)[1,1'-biphenyl]-4-ylmethyl]-2H-imidazol-2-one;
1-isopropyl-4-isopentyl-5-methyl-1,3-dihydro-3-[2'-(1H-tetrazol-5-yl)[1,1'-biphenyl]-4-ylmethyl]-2H-imidazol-2-one;
1-butyl-4-isopentyl-5-methyl-1,3-dihydro-3-[2'-(1H-tetrazol-5-yl)[1,1'-biphenyl]-4-ylmethyl]-2H-imidazol-2-one;
1-secbutyl-4-isopentyl-5-methyl-1,3-dihydro-3-[2'-(1H-tetrazol-5-yl)[1,1'-biphenyl]-4-ylmethyl]-2H-imidazol-2-one;
1-isobutyl-4-isopentyl-5-methyl-1,3-dihydro-3-[2'-(1H-tetrazol-5-yl)[1,1'-biphenyl]-4-ylmethyl]-2H-imidazol-2-one;
1-tertbutyl-4-isopentyl-5-methyl-1,3-dihydro-3-[2'-(1H-tetrazol-5-yl)[1,1'-biphenyl]-4-ylmethyl]-2H-imidazol-2-one;
1-pentyl-4-isopentyl-5-methyl-1,3-dihydro-3-[2'-(1H-tetrazol-5-yl)[1,1'-biphenyl]-4-ylmethyl]-2H-imidazol-2-one;
1,4-diisopentyl-5-methyl-1,3-dihydro-3-[2'-(1H-tetrazol-5-yl)[1,1'-biphenyl]-4-ylmethyl]-2H-imidazol-2-one;
5-yl)[1,1'-biphenyl]-4-ylmethyl]-2H-imidazol-2-one;
1-cyclohexyl-4-isopentyl-5-methyl-1,3-dihydro-3-[2'-(1H-tetrazol-5-yl)[1,1'-biphenyl]-4-ylmethyl]-2H-imidazol-2-one;
1-cyclohexylmethyl-4-isopentyl-5-methyl-1,3-dihydro-3-[2'-(1H-tetrazol-5-yl)[1,1'-biphenyl]-4-ylmethyl]-2H-imidazol-2-one;
1-(2-cyclohexylethyl)-4-isopentyl-5-methyl-1,3-dihydro-3-[2'-(1H-tetrazol-5-yl)[1,1'-biphenyl]-4-ylmethyl]-2H-imidazol-2-one;
1-cyclohexanoyl-4-isopentyl-5-methyl-1,3-dihydro-3-[2'-(1H-tetrazol-5-yl)[1,1'-biphenyl]-4-ylmethyl]-2H-imidazol-2-one;
1-(1-oxo-2-cyclohexylethyl)-4-isopentyl-5-methyl-1,3-dihydro-3-[2'-(1H-tetrazol-5-yl)[1,1'-biphenyl]-4-ylmethyl]-2H-imidazol-2-one;
1-phenyl-4-isopentyl-5-methyl-1,3-dihydro-3-[2'-(1H-tetrazol-5-yl)[1,1'-biphenyl]-4-ylmethyl]-2H-imidazol-2-one;
1-phenylmethyl-4-isopentyl-5-methyl-1,3-dihydro-3-[2'-(1H-tetrazol-5-yl)[1,1'-biphenyl]-4-ylmethyl]-2H-imidazol-2-one;
1-(2-phenylethyl)-4-isopentyl-5-methyl-1,3-dihydro-3-[2'-(1H-tetrazol-5-yl)[1,1'-biphenyl]-4-ylmethyl]-2H-imidazol-2-one;
1-benzoyl-4-isopentyl-5-methyl-1,3-dihydro-3-[2'-(1H-tetrazol-5-yl)[1,1'-biphenyl]-4-ylmethyl]-2H-imidazol-2-one;
1-(1-oxo-2-phenylethyl)-4-isopentyl-5-methyl-1,3-dihydro-3-[2'-(1H-tetrazol-5-yl)[1,1'-biphenyl]-4-ylmethyl]-2H-imidazol-2-one;
1-(1-oxopropyl)-4-isopentyl-5-methyl-1,3-dihydro-3-[2'-(1H-tetrazol-5-yl)[1,1'-biphenyl]-4-ylmethyl]-2H-imidazol-2-one;
1-(1-oxobutyl)-4-isopentyl-5-methyl-1,3-dihydro-3-[2'-(1H-tetrazol-5-yl)[1,1'-biphenyl]-4-ylmethyl]-2H-imidazol-2-one;
1-(1-oxopentyl)-4-isopentyl-5-methyl-1,3-dihydro-3-[2'-(1H-tetrazol-5-yl)[1,1'-biphenyl]-4-ylmethyl]-2H-imidazol-2-one;
1-ethyl-4-isopentyl-5-fluoromethyl-1,3-dihydro-3-[2'-(1H-tetrazol-5-yl)[1,1'-biphenyl]-4-ylmethyl]-2H-imidazol-2-one;
1-propyl-4-isopentyl-5-fluoromethyl-1,3-dihydro-3-[2'-(1H-tetrazol-5-yl)[1,1'-biphenyl]-4-ylmethyl]-2H-imidazol-2-one;
1-isopropyl-4-isopentyl-5-fluoromethyl-1,3-dihydro-3-[2'-(1H-tetrazol-5-yl)[1,1'-biphenyl]-4-ylmethyl]-2H-imidazol-2-one;
1-butyl-4-isopentyl-5-fluoromethyl-1,3-dihydro-3-[2'-(1H-tetrazol-5-yl)[1,1'-biphenyl]-4-ylmethyl]-2H-imidazol-2-one;
1-secbutyl-4-isopentyl-5-fluoromethyl-1,3-dihydro-3-[2'-(1H-tetrazol-5-yl)[1,1'-biphenyl]-4-ylmethyl]-2H-imidazol-2-one;
1-isobutyl-4-isopentyl-5-fluoromethyl-1,3-dihydro-3-[2'-(1H-tetrazol-5-yl)[1,1'-biphenyl]-4-ylmethyl]-2H-imidazol-2-one;
1-tertbutyl-4-isopentyl-5-fluoromethyl-1,3-dihydro-3-[2'-(1H-tetrazol-5-yl)[1,1'-biphenyl]-4-ylmethyl]-2H-imidazol-2-one;
1-pentyl-4-isopentyl-5-fluoromethyl-1,3-dihydro-3-[2'-(1H-tetrazol-5-yl)[1,1'-biphenyl]-4-ylmethyl]-2H-imidazol-2-one;
1,4-diisopentyl-5-fluoromethyl-1,3-dihydro-3-[2'-(1H-tetrazol-5-yl)[1,1'-biphenyl]-4-ylmethyl]-2H-imidazol-2-one;
1-cyclohexyl-4-isopentyl-5-fluoromethyl-1,3-dihydro-3-[2'-(1H-tetrazol-5-yl)[1,1'-biphenyl]-4-ylmethyl]-2H-imidazol-2-one;
1-cyclohexylmethyl-4-isopentyl-5-fluoromethyl-1,3-dihydro-3-[2'-(1H-tetrazol-5-yl)[1,1'-biphenyll-4-ylmethyl]-2H-imidazol-2-one;
1-(2-cyclohexylethyl)-4-isopentyl-5-fluoromethyl-1,3-dihydro-3-[2'-(1H-tetrazol-5-yl)[1,1'-biphenyl]-4-ylmethyl]-2H-imidazol-2-one;
1-cyclohexanoyl-4-isopentyl-5-fluoromethyl-1,3-dihydro-3-[2'-(1H-tetrazol-5-yl)[1,1'-biphenyl]-4-ylmethyl]-2H-imidazol-2-one;
1-(1-oxo-2-cyclohexylethyl)-4-isopentyl-5-fluoromethyl-1,3-dihydro-3-[2'-(1H-tetrazol-5-yl)[1,1'-biphenyl]-4-ylmethyl]-2H-imidazol-2-one;
1-phenyl-4-isopentyl-5-fluoromethyl-1,3-dihydro-3-[2'-(1H-tetrazol-5-yl)[1,1'-biphenyl]-4-ylmethyl]-2H-imidazol-2-one;
1-phenylmethyl-4-isopentyl-5-fluoromethyl-1,3-dihydro-3-[2'-(1H-tetrazol-5-yl)[1,1'-biphenyl]-4-ylmethyl]-2H-imidazol-2-one;
1-(2-phenylethyl)-4-isopentyl-5-fluoromethyl-1,3-dihydro-3-[2'-(1H-tetrazol-5-yl)[1,1'-biphenyl]-4-ylmethyl]-2H-imidazol -2-one;
1-benzoyl-4-isopentyl-5-fluoromethyl-1,3-dihydro-3-[2'-(1H -tetrazol-5-yl)[1,1'-biphenyl]-4-ylmethyl]-2H-imidazol-2-one;

1-(1-oxo-2-phenylethyl)-4-isopentyl-5-fluoromethyl-1,3-dihydro-3-[2'-(1H-tetrazol-5-yl)[1,1'-biphenyl]-4-ylmethyl]-2H-imidazol-2-one;

1-(1-oxopropyl)-4-isopentyl-5-fluoromethyl-1,3-dihydro-3-[2'-(1H-tetrazol-5-yl)[1,1'-biphenyl]-4-ylmethyl]-2H-imidazol-2-one;

1-(1-oxobutyl)-4-isopentyl-5-fluoromethyl-1,3-dihydro-3-[2'-(1H-tetrazol-5-yl)[1,1'-biphenyl]-4-ylmethyl]-2H-imidazol-2-one;

1-(1-oxopentyl)-4-isopentyl-5-fluoromethyl-1,3-dihydro-3-[2'-(1H-tetrazol-5-yl)[1,1'-biphenyl]-4-ylmethyl]-2H-imidazol-2-one;

1-ethyl-4-isopentyl-5-difluoromethyl-1,3-dihydro-3-[2'-(1H-tetrazol-5-yl)[1,1'-biphenyl]-4-ylmethyl]-2H-imidazol-2-one;

1-propyl-4-isopentyl-5-difluoromethyl-1,3-dihydro-3-[2'-(1H-tetrazol-5-yl)[1,1'-biphenyl]-4-ylmethyl]-2H-imidazol-2-one;

1-isopropyl-4-isopentyl-5-difluoromethyl-1,3-dihydro-3-[2'-(1H-tetrazol-5-yl)[1,1'-biphenyl]-4-ylmethyl]-2H-imidazol-2-one;

1-butyl-4-isopentyl-5-difluoromethyl-1,3-dihydro-3-[2'-(1H-tetrazol-5-yl)[1,1'-biphenyl]-4-ylmethyl]-2H-imidazol-2-one;

1-secbutyl-4-isopentyl-5-difluoromethyl-1,3-dihydro-3-[2'-(1H-tetrazol-5-yl)[1,1'-biphenyl]-4-ylmethyl]-2H-imidazol-2-one;

1-isobutyl-4-isopentyl-5-difluoromethyl-1,3-dihydro-3-[2'-(1H-tetrazol-5-yl)[1,1'-biphenyl]-4-ylmethyl]-2H-imidazol-2-one;

1-tertbutyl-4-isopentyl-5-difluoromethyl-1,3-dihydro-3-[2'-(1H-tetrazol-5-yl)[1,1'-biphenyl]-4-ylmethyl]-2H-imidazol-2-one;

1-pentyl-4-isopentyl-5-difluoromethyl-1,3-dihydro-3-[2'-(1H-tetrazol-5-yl)[1,1'-biphenyl]-4-ylmethyl]-2H-imidazol-2-one;

1,4-diisopentyl-5-difluoromethyl-1,3-dihydro-3-[2'-(1H-tetrazol-5-yl)[1,1'-biphenyl]-4-ylmethyl]-2H-imidazol-2-one;

1-cyclohexyl-4-isopentyl-5-difluoromethyl-1,3-dihydro-3-[2'-(1H-tetrazol-5-yl)[1,1'-biphenyl]-4-ylmethyl]-2H-imidazol-2-one;

1-cyclohexylmethyl-4-isopentyl-5-difluoromethyl-1,3-dihydro-3-[2'-(1H-tetrazol-5-yl)[1,1'-biphenyl]-4-ylmethyl]-2H-imidazol-2-one;

1-(2-cyclohexylethyl)-4-isopentyl-5-difluoromethyl-1,3-dihydro-3-[2'-(1H-tetrazol-5-yl)[1,1'-biphenyl]-4-ylmethyl]-2H-imidazol-2-one;

1-cyclohexanoyl-4-isopentyl-5-difluoromethyl-1,3-dihydry-3-[2'-(1H-tetrazol-5-yl)[1,1'-biphenyl]-4-ylmethyl]-2H-imidazol-2-one;

1-(1-oxo-2-cyclohexylethyl)-4-isopentyl-5-difluoromethyl-1,3-dihydro-3-[2'-(1H-tetrazol-5-yl)[1,1'-biphenyl]-4-ylmethyl]-2H-imidazol-2-one;

1-phenyl-4-isopentyl-5-difluoromethyl-1,3-dihydro-3-[2'-(1H-tetrazol-5-yl)[1,1'-biphenyl]-4-ylmethyl]-2H-imidazol-2-one;

1-phenylmethyl-4-isopentyl-5-difluoromethyl-1,3-dihydro-3-[2'-(1H-tetrazol-5-yl)[1,1'-biphenyl]-4-ylmethyl]-2H-imidazol-2-one;

1-(2 phenylethyl)-4-isopentyl-5-difluoromethyl-1,3-dihydro-3-[2'-(1H-tetrazol-5-yl)[1,1'-biphenyl]-4-ylmethyl]-2H-imidazol-2-one;

1-benzoyl-4-isopentyl-5-difluoromethyl-1,3-dihydro-3-[2'-(1H-tetrazol-5-yl)[1,1'-biphenyl]-4-ylmethyl]-2H-imidazol-2-one;

1-(1-oxo-2-phenylethyl)-4-isopentyl-5-difluoromethyl-1,3-dihydro-3-[2'-(1H-tetrazol-5-yl)[1,1'-biphenyl]-4-ylmethyl]-2H-imidazol-2-one;

1-(1-oxopropyl)-4-isopentyl-5-difluoromethyl-1,3-dihydro-3-[2'-(1H-tetrazol-5-yl)[1,1'-biphenyl]-4-ylmethyl]-2H-imidazol-2-one;

1-(1-oxobutyl)-4-isopentyl-5-difluoromethyl-1,3-dihydro-3-[2'-(1H-tetrazol-5-yl)[1,1'-biphenyl]-4-ylmethyl]-2H-imidazol-2-one;

1-(1-oxopentyl)-4-isopentyl-5-difluoromethyl-1,3-dihydro-3-[2'-(1H-tetrazol-5-yl)[1,1'-biphenyl]-4-ylmethyl]-2H-imidazol-2-one;

1-ethyl-4-isopentyl-5-trifluoromethyl-1,3-dihydro-3-[2'-(1H-tetrazol-5-yl)[1,1'-biphenyl]-4-ylmethyl]-2H-imidazol-2-one;

1-propyl-4-isopentyl-5-trifluoromethyl-1,3-dihydro-3-[2'-(1H-tetrazol-5-yl)[1,1'-biphenyl]-4-ylmethyl]-2H-imidazol-2-one;

1-isopropyl-4-isopentyl-5-trifluoromethyl-1,3-dihydro-3-[2'-(1H-tetrazol-5-yl)[1,1'-biphenyl]-4-ylmethyl]-2H-imidazol-2-one;

1-butyl-4-isopentyl-5-trifluoromethyl-1,3-dihydro-3-[2'-(1H-tetrazol-5-yl)[1,1'-biphenyl]-4-ylmethyl]-2H-imidazol-2-one;

1-secbutyl-4-isopentyl-5-trifluoromethyl-1,3-dihydro-3-[2'-(1H-tetrazol-5-yl)[1,1'-biphenyl]-4-ylmethyl]-2H-imidazol-2-one;

1-isobutyl-4-isopentyl-5-trifluoromethyl-1,3-dihydro-3-[2'-(1H-tetrazol-5-yl)[1,1'-biphenyl]-4-ylmethyl]-2H-imidazol-2-one;

1-tertbutyl-4-isopentyl-5-trifluoromethyl-1,3-dihydro-3-[2'-(1H-tetrazol-5-yl)[1,1'-biphenyl]-4-ylmethyl]-2H-imidazol-2-one;

1-pentyl-4-isopentyl-5-trifluoromethyl-1,3-dihydro-3-[2'-(1H-tetrazol-5-yl)[1,1'-biphenyl]-4-ylmethyl]-2H-imidazol-2-one;

1,4-diisopentyl-5-trifluoromethyl-1,3-dihydro-3-[2'-(1H-tetrazol-5-yl)[1,1'-biphenyl]-4-ylmethyl]-2H-imidazol-2-one;

1-cyclohexyl-4-isopentyl-5-trifluoromethyl-1,3-dihydro-3-[2'-(1H-tetrazol-5-yl)[1,1'-biphenyl]-4-ylmethyl]-2H-imidazol-2-one;

1-cyclohexylmethyl-4-isopentyl-5-trifluoromethyl-1,3-dihydro-3-[2'-(1H-tetrazol-5-yl)[1,1'-biphenyl]-4-ylmethyl]-2H-imidazol-2-one;

1-(2-cyclohexylethyl)-4-isopentyl-5-trifluoromethyl-1,3-dihydro-3-[2'-(1H-tetrazol-5-yl)[1,1'-biphenyl]-4-ylmethyl]-2H-imidazol-2-one;

1-cyclohexanoyl-4-isopentyl-5-trifluoromethyl-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-isopentyl-5-trifluoromethyl-1,3-dihydro-3-[2'-(1H-tetrazol-5-yl)[1,1'-biphenyl]-4-ylmethyl]-2H-imidazol-2-one;

1-phenyl-4-isopentyl-5-trifluoromethyl-1,3-dihydro-3-[2'-(1H-tetrazol-5-yl)[1,1'-biphenyl]-4-ylmethyl]-2H-imidazol-2-one;

1-phenylmethyl-4-isopentyl-5-trifluoromethyl-1,3-dihydro-3-[2'-(1H-tetrazol-5-yl)[1,1'-biphenyl]-4-ylmethyl]-2H-imidazol-2-one;

1-(2-phenylethyl)-4-isopentyl-5-trifluoromethyl-1,3-dihydro-3-[2'-(1H-tetrazol-5-yl)[1,1'-biphenyl]-4-ylmethyl]-2H-imidazol-2-one;

1-benzoyl-4-isopentyl-5-trifluoromethyl-1,3-dihydro-3-[2'-(1H-tetrazol-5-yl)[1,1'-biphenyl]-4-ylmethyl]-2H-imidazol-2-one;

1-(1-oxo-2-phenylethyl)-4-isopentyl-5-trifluoromethyl-1,3-dihydro-3-[2'-(1H-tetrazol-5-yl)[1,1'-biphenyl]-4-ylmethyl]-b 2H-imidazol-2-one;

1-(1-oxopropyl)-4-isopentyl-5-trifluoromethyl-1,3-dihydro-3-[2'-(1H-tetrazol-5-yl)[1,1'-biphenyl]-4-ylmethyl]-2H-imidazol-2-one;

1-(1-oxobutyl)-4-isopentyl-5-trifluoromethyl-1,3-dihydro-3-[2'-(1H-tetrazol-5-yl)[1,1'-biphenyl]-4-ylmethyl]-2H-imidazol-2-one;

1-(1-oxopentyl)-4-isopentyl-5-trifluoromethyl-1,3-dihydro-3-[2'-(1H-tetrazol-5-yl)[1,1'-biphenyl]-4-ylmethyl]-2H-imidazol-2-one;

1-ethyl-4-butyl-5-carboxy-1,3-dihydro-3-[2'-(1H-tetrazol-5-yl)[1,1'-biphenyl]-4-ylmethyl]-2H-imidazol-2-one;

1-propyl-4-butyl-5-carboxy-1,3-dihydro-3-[2'-(1H-tetrazol-5-yl)[1,1'-biphenyl]-4-ylmethyl]-2H-imidazol-2-one;

1-isopropyl-4-butyl-5-carboxy-1,3-dihydro-3-[2'-(1H-tetrazol-5-yl)[1,1'-biphenyl]-4-ylmethyl]-2H-imidazol-2-one;

1,4-dibutyl-5-carboxy-1,3-dihydro-3-[2'-(1H-tetrazol-5-yl)[1,1'-biphenyl]-4-ylmethyl]-2H-imidazol-2-one;

1-secbutyl-4-butyl-5-carboxy-1,3-dihydro-3-[2'-(1H-tetrazol-5-yl)[1,1'-biphenyl]-4-ylmethyl]-2H-imidazol-2-one;

1-isobutyl-4-butyl-5-carboxy-1,3-dihydro-3-[2'-(1H-tetrazol-5-yl)[1,1'-biphenyl]-4-ylmethyl]-2H-imidazol-2-one;

1-tertbutyl-4-butyl-5-carboxy-1,3-dihydro-3-[2'-(1H-tetrazol-5-yl)[1,1'-biphenyl]-4-ylmethyl]-2H-imidazol-2-one;

1-pentyl-4-butyl-5-carboxy-1,3-dihydro-3-[2'-(1H-tetrazol-5-yl)[1,1'-biphenyl]-4-ylmethyl]-2H-imidazol-2-one;

1-isopentyl-4-butyl-5-carboxy-1,3-dihydro-3-[2'-(1H-tetrazol-5-yl)[1,1'-biphenyl]-4-ylmethyl]-2H-imidazol-2-one;

1-cyclohexyl-4-butyl-5-carboxy-1,3-dihydro-3-[2'-(1H-tetrazol-5-yl)[1,1'-biphenyl]-4-ylmethyl]-2H-imidazol-2-one;

1-cyclohexylmethyl-4-butyl-5-carboxy-1,3-dihydro-3-[2'-(1H-tetrazol-5-yl)[1,1'-biphenyl]-4-ylmethyl]-2H-imidazol-2-one;

1-(2-cyclohexylethyl)-4-butyl-5-carboxy-1,3-dihydro-3-[2'-(1H-tetrazol-5-yl)[1,1'-biphenyl]-4-ylmethyl]-2H-imidazol-2-one;

1-cyclohexanoyl-4-butyl-5-carboxy-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-butyl-5-carboxy-1,3-dihydro-3-[2'-(1H-tetrazol-5-yl)[1,1'-biphenyl]-4-ylmethyl]-2H-imidazol-2-one;

1-phenyl-4-butyl-5-carboxy-1,3-dihydro-3-[2'-(1H-tetrazol-5-yl)[1,1'-biphenyl]-4-ylmethyl]-2H-imidazol-2-one;

1-phenylmethyl-4-butyl-5-carboxy-1,3-dihydro-3-[2'-(1H-tetrazol-5-yl)[1,1'-biphenyl]-4-ylmethyl]-2H-imidazol-2-one;

1-(2-phenylethyl)-4-butyl-5-carboxy-1,3-dihydro-3-[2'-(1H-tetrazol-5-yl)[1,1'-biphenyl]-4-ylmethyl]-2H-imidazol-2-one;

1-benzoyl-4-butyl-5-carboxy-1,3-dihydro-3-[2'-(1H-tetrazol-5-yl)[1,1'-biphenyl]-4-ylmethyl]-2H-imidazol-2-one;

1-(1-oxo-2-phenylethyl)-4-butyl-5-carboxy-1,3-dihydro-3-[2'-(1H-tetrazol-5-yl)[1,1'-biphenyl]-4-ylmethyl]-2H-imidazol-2-one;

1-(1-oxopropyl)-4-butyl-5-carboxy-1,3-dihydro-3-[2'-(1H-tetrazol-5-yl)[1,1'-biphenyl]-4-ylmethyl]-2H-imidazol-2-one;

1-(1-oxobutyl)-4-butyl-5-carboxy-1,3-dihydro-3-[2'-(1H-tetrazol-5-yl)[1,1'-biphenyl]-4-ylmethyl]-2H-imidazol-2-one;

1-(1-oxopentyl)-4-butyl-5-carboxy-1,3-dihydro-3-[2'-(1H-tetrazol-5-yl)[1,1'-biphenyl]-4-ylmethyl]-2H-imidazol-2-one;

1-ethyl-4-propyl-5-carboxy-1,3-dihydro-3-[2'-(1H-tetrazol-5-yl)[1,1'-biphenyl]-4-ylmethyl]-2H-imidazol-2-one;

1,4-dipropyl-5-carboxy-1,3-dihydro-3-[2'-(1H-tetrazol-5-yl)[1,1'-biphenyl]-4-ylmethyl]-2H-imidazol-2-one;

1-isopropyl-4-propyl-5-carboxy-1,3-dihydro-3-[2'-(1H-tetrazol-5-yl)[1,1'-biphenyl]-4-ylmethyl]-2H-imidazol-2-one;

1-butyl-4-propyl-5-carboxy-1,3-dihydro-3-[2'-(1H-tetrazol-5-yl)[1,1'-biphenyl]-4-ylmethyl]-2H-imidazol-2-one;

1-secbutyl-4-propyl-5-carboxy-1,3-dihydro-3-[2'-(1H-tetrazol-5-yl)[1,1'-biphenyl]-4-ylmethyl]-2H-imidazol-2-one;

1-isobutyl-4-propyl-5-carboxy-1,3-dihydro-3-[2'-(1H-tetrazol-5-yl)[1,1'-biphenyl]-4-ylmethyl]-2H-imidazol-2-one;

1-tertbutyl-4-propyl-5-carboxy-1,3-dihydro-3-[2'-(1H-tetrazol-5-yl)[1,1'-biphenyl]-4-ylmethyl]-2H-imidazol-2-one;

1-pentyl-4-propyl-5-carboxy-1,3-dihydro-3-[2'-(1H-tetrazol-5-yl)[1,1'-biphenyl]-4-ylmethyl]-2H-imidazol-2-one;

1-isopentyl-4-propyl-5-carboxy-1,3-dihydro-3-[2'-(1H-tetrazol-5-yl)[1,1'-biphenyl]-4-ylmethyl]-2H-imidazol-2-one;

1-cyclohexyl-4-propyl-5-carboxy-1,3-dihydro-3-[2'-(1H-tetrazol-5-yl)[1,1'-biphenyl]-4-ylmethyl]-2H-imidazol-2-one;

1-cyclohexylmethyl-4-propyl-5-carboxy-1,3-dihydro-3-[2'-(1H-tetrazol-5-yl)[1,1'-biphenyl]-4-ylmethyl]-2H-imidazol-2-one;

1-(2-cyclohexylethyl)-4-propyl-5-carboxy-1,3-dihydro-3-[2'-(1H-tetrazol-5-yl)[1,1'-biphenyl]-4-ylmethyl]-2H-imidazol-2-one;

1-cyclohexanoyl-4-propyl-5-carboxy-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-propyl-5-carboxy-1,3-dihydro-3-[2'-(1H-tetrazol-5-yl)[1,1'-biphenyl]-4-ylmethyl]-2H-imidazol-2-one;

1-phenyl-4-propyl-5-carboxy-1,3-dihydro-3-[2'-(1H-tetrazol-5-yl)[1,1'-biphenyl]-4-ylmethyl]-2H-imidazol-2-one;

1-phenylmethyl-4-propyl-5-carboxy-1,3-dihydro-3-[2'-(1H-tetrazol-5-yl)[1,1'-biphenyl]-4-ylmethyl]-2H-imidazol-2-one;

1-(2-phenylethyl)-4-propyl-5-carboxy-1,3-dihydro-3-[2'-(1H-tetrazol-5-yl)[1,1'-biphenyl]-4-ylmethyl]-2H-imidazol-2-one;

1-benzoyl-4-propyl-5-carboxy-1,3-dihydro-3-[2'-(1H-tetrazol-5-yl)[1,1'-biphenyl]-4-ylmethyl]-2H-imidazol-2-one;

1-(1-oxo-2-phenylethyl)-4-propyl-5-carboxy-1,3-dihydro-3-[2'-(1H-tetrazol-5-yl)[1,1'-biphenyl]-4-ylmethyl]-2H-imidazol-2-one;

1-(1-oxopropyl)-4-propyl-5-carboxy-1,3-dihydro-3-[2'-(1H-tetrazol-5-yl)[1,1'-biphenyl]-4-ylmethyl]-2H-imidazol-2-one;

1-(1-oxobutyl)-4-propyl-5-carboxy-1,3-dihydro-3-[2'-(1H-tetrazol-5-yl)[1,1'-biphenyl]-4-ylmethyl]-2H-imidazol-2-one;

1-(1-oxopentyl)-4-propyl-5-carboxy-1,3-dihydro-3-[2'-(1H-tetrazol-5-yl)[1,1'-biphenyl]-4-ylmethyl]-2H-imidazol-2-one;

1-ethyl-4-isopentyl-5-carboxy-1,3-dihydro-3-[2'-(1H-tetrazol-5-yl)[1,1'-biphenyl]-4-ylmethyl]-2H-imidazol-2-one;

1-propyl-4-isopentyl-5-carboxy-1,3-dihydro-3-[2'-(1H-tetrazol-5-yl)[1,1'-biphenyl]-4-ylmethyl]-2H-imidazol-2-one;

1-isopropyl-4-isopentyl-5-carboxy-1,3-dihydro-3-[2'-(1H-tetrazol-5-yl)[1,1'-biphenyl]-4-ylmethyl]-2H-imidazol-2-one;

1-butyl-4-isopentyl-5-carboxy-1,3-dihydro-3-[2'-(1H-tetrazol-5-yl)[1,1'-biphenyl]-4-ylmethyl]-2H-imidazol-2-one;

1-secbutyl-4-isopentyl-5-carboxy-1,3-dihydro-3-[2'-(1H-tetrazol-5-yl)[1,1'-biphenyl]-4-ylmethyl]-2H-imidazol-2-one;

1-isobutyl-4-isopentyl-5-carboxy-1,3-dihydro-3-[2'-(1H-tetrazol-5-yl)[1,1'-biphenyl]-4-ylmethyl]-2H-imidazol-2-one;

1-tertbutyl-4-isopentyl-5-carboxy-1,3-dihydro-3-[2'-(1H-tetrazol-5-yl)[1,1'-biphenyl]-4-ylmethyl]-2H-imidazol-2-one;

1-pentyl-4-isopentyl-5-carboxy-1,-dihydro-3-[2'-(1H-tetrazol-5-yl)[1,1'-biphenyl]-4-ylmethyl]-2H-imidazol-2-one;

1,4-diisopentyl-5-carboxy-1,3-dihydro-3-[2'-(1H-tetrazol-5-yl)[1,1'-biphenyl]-4-ylmethyl]-2H-imidazol-2-one;

1-cyclohexyl-4-isopentyl-5-carboxy-1,3-dihydro-3-[2'-(1H-tetrazol-5-yl)[1,1'-biphenyl]-4-ylmethyl]-2H-imidazol-2-one;

1-cyclohexylmethyl-4-isopentyl-5-carboxy-1,3-dihydro-3-[2'-(1H-tetrazol-5-yl)[1,1'-biphenyl]-4-ylmethyl]-2H-imidazol-2-one;

1-(2-cyclohexylethyl)-4-isopentyl-5-carboxy-1,3-dihydro-3-[2'-(1H-tetrazol-5-yl)[1,1'-biphenyl]-4-ylmethyl]-2H-imidazol-2-one;

1-cyclohexanoyl-4-isopentyl-5-carboxy-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-isopentyl-5-carboxy-1,3-dihydro-3-[2'-(1H-tetrazol-5-yl)[1,1'-biphenyl]-4-ylmethyl]-2H-imidazol-2-one;

1-phenyl-4-isopentyl-5-carboxy-1,3-dihydro-3-[2'-(1H-tetrazol-5-yl)[1,1'-biphenyl]-4-ylmethyl]-2H-imidazol-2-one;

1-phenylmethyl-4-isopentyl-5-carboxy-1,3-dihydro-3-[2'-(1H-tetrazol-5-yl)[1,1'-biphenyl]-4-ylmethyl]-2H-imidazol-2-one;

1-(2-phenylethyl)-4-isopentyl-5-carboxy-1,3-dihydro-3-[2'-(1H-tetrazol-5-yl)[1,1'-biphenyl]-4-ylmethyl]-2H-imidazol-2-one;

1-benzoyl-4-isopentyl-5-carboxy-1,3-dihydro-3-[2'-(1H-tetrazol-5-yl)[1,1'-biphenyl]-4-ylmethyl]-2H-imidazol-2-one;

1-(1-oxo-2-phenylethyl)-4-isopentyl-5-carboxy-1,3-dihydro-3-[2'-(1H-tetrazol-5-yl)[1,1'-biphenyl]-4-ylmethyl]-2H-imidazol-2-one;

1-(1-oxopropyl)-4-isopentyl-5-carboxy-1,3-dihydro-3-[2'-(1H-tetrazol-5-yl)[1,1'-biphenyl]-4-ylmethyl]-2H-imidazol-2-one;

1-(1-oxobutyl)-4-isopentyl-5-carboxy-1,3-dihydro-3-[2'-(1H-tetrazol-5-yl)[1,1'-biphenyl]-4-ylmethyl]-2H-imidazol-2-one; and 1-(1-oxopentyl)-4-isopentyl-5-carboxy-1,3-dihydro-3-[2'-(1H-tetrazol-5-yl)[1,1'-biphenyl]-4-ylmethyl]-2H-imidazol-2-one.

A family of compounds of more particular interest within Formula III consists of compounds and pharmaceutically-acceptable salts as follows:

1-ethyl-4-butyl-1,3-dihydro-3-[2'-(1H-tetrazol-5-yl)[1,1'-biphenyl]-4-ylmethyl]-2H-imidazol-2-one;

1-propyl-4-butyl-1,3-dihydro-3-[2'-(1H-tetrazol-5-yl)[1,1'-biphenyl]-4-ylmethyl]-2H-imidazol-2-one;

1-isopropyl-4-butyl-1,3-dihydro-3-[2'-(1H-tetrazol-5-yl)[1,1'-biphenyl]-4-ylmethyl]-2H-imidazol-2-one;

1,4-dibutyl-1,3-dihydro-3-[2'-(1H-tetrazol-5-yl)[1,1'-biphenyl]-4-ylmethyl]-2H-imidazol-2-one;

1-secbutyl-4-butyl-1,3-dihydro-3-[2'-(1H-tetrazol-5-yl)[1,1'-biphenyl]-4-ylmethyl]-2H-imidazol-2-one;

1-isobutyl-4-butyl-1,3-dihydro-3-[2'-(1H-tetrazol-5-yl)[1,1'-biphenyl]-4-ylmethyl]-2H-imidazol-2-one;

1-tertbutyl-4-butyl-1,3-dihydro-3-[2'-(1H-tetrazol-5-yl)[1,1'-biphenyl]-4-ylmethyl]-2H-imidazol-2-one;

1-pentyl-4-butyl-1,3-dihydro-3-[2'-(1H-tetrazol-5-yl)[1,1'-biphenyl]-4-ylmethyl]-2H-imidazol-2-one;

1-isopentyl-4-butyl-1,3-dihydro-3-[2'-(1H-tetrazol-5-yl)[1,1'-biphenyl]-4-ylmethyl]-2H-imidazol-2-one;

1-cyclohexyl-4-butyl-1,3-dihydro-3-[2'-(1H-tetrazol-5-yl)[1,1'-biphenyl]-4-ylmethyl]-2H-imidazol-2-one;

1-cyclohexylmethyl-4-butyl-1,3-dihydro-3-[2'-(1H-tetrazol-5-yl)[1,1'-biphenyl]-4-ylmethyl]-2H-imidazol-2-one;

1-(2-cyclohexylethyl)-4-butyl-1,3-dihydro-3-[2'-(1H-tetrazol-5-yl)[1,1'-biphenyl]-4-ylmethyl]-2H-imidazol-2-one;

1-cyclohexanoyl-4-butyl-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-butyl-1,3-dihydro-3-[2'-(1H-tetrazol-5-yl)[1,1'-biphenyl]-4-ylmethyl]-2H-imidazol-2-one;

1-phenyl-4-butyl-1,3-dihydro-3-[2'-(1H-tetrazol-5-yl)[1,1'-biphenyl]-4-ylmethyl]-2H-imidazol-2-one;

1-phenylmethyl-4-butyl-1,3-dihydre-3-[2'-(1H-tetrazol-5-yl)[1,1'-biphenyl]-4-ylmethyl]-2H-imidazol-2-one;

1-(2-phenylethyl)-4-butyl-1,3-dihydro-3-[2'-(1H-tetrazol-5-yl)[1,1'-biphenyl]-4-ylmethyl]-2H-imidazol-2-one;

1-benzoyl-4-butyl-1,3-dihydro-3-[2'-(1H-tetrazol-5-yl)[1,1'-biphenyl]-4-ylmethyl]-2H-imidazol-2-one;

1-(1-oxo-2-phenylethyl)-4-butyl-1,3-dihydro-3-[2'-(1H-tetrazol-5-yl)[1,1'-biphenyl]-4-ylmethyl]-2H-imidazol-2-one;

1-(1-oxopropyl)-4-butyl-1,3-dihydro-3-[2'-(1H-tetrazol-5-yl)[1,1'-biphenyl]-4-ylmethyl]-2H-imidazol-2-one;

1-(1-oxobutyl)-4-butyl-1,3-dihydro-3-[2'-(1H-tetrazol-5-yl)[1,1'-biphenyl]-4-ylmethyl]-2H-imidazol-2-one;

1-(1-oxopentyl)-4-butyl-1,3-dihydro-3-[2'-(1H-tetrazol-5-yl)[1,1'-biphenyl]-4-ylmethyl]-2H-imidazol-2-one;

1-ethyl-4-propyl-1,3-dihydro-3-[2'-(1H-tetrazol-5-yl)[1,1'-biphenyl]-4-ylmethyl]-2H-imidazol-2-one;

1,4-dipropyl-1,3-dihydro-3-[2'-(1H-tetrazol-5-yl)[1,1'-biphenyl]-4-ylmethyl]-2H-imidazol-2-one;

1-isopropyl-4-propyl-1,3-dihydro-3-[2'-(1H-tetrazol-5-yl)[1,1'-biphenyl]-4-ylmethyl]-2H-imidazol-2-one;

1-butyl-4-propyl-1,3-dihydro-3-[2'-(1H-tetrazol-5-yl)[1,1'-biphenyl]-4-ylmethyl]-2H-imidazol-2-one;

1-secbutyl-4-propyl-1,3-dihydro-3-[2'-(1H-tetrazol-5-yl)[1,1'-biphenyl]-4-ylmethyl]-2H-imidazol-2-one;
1-isobutyl-4-propyl-1,3-dihydro-3-[2'-(1H-tetrazol-5-yl)[1,1'-biphenyl]-4-ylmethyl]-2H-imidazol-2-one;
1-tertbutyl-4-propyl-1,3-dihydro-3-[2'-(1H-tetrazol-5-yl)[1,1'-biphenyl]-4-ylmethyl]-2H-imidazol-2-one;
1-pentyl-4-propyl-1,3-dihydro-3-[2'-(1H-tetrazol-5-yl)[1,1'-biphenyl]-4-ylmethyl]-2H-imidazol-2-one;
1-isopentyl-4-propyl-1,3-dihydro-3-[2'-(1H-tetrazol-5-yl)[1,1'-biphenyl]-4-ylmethyl]-2H-imidazol-2-one;
1-cyclohexyl-4-propyl-1,3-dihydro-3-[2'-(1H-tetrazol-5-yl)[1,1'-biphenyl]-4-ylmethyl]-2H-imidazol-2-one;
1-cyclohexylmethyl-4-propyl-1,3-dihydro-3-[2'-(1H-tetrazol-5-yl)[1,1'-biphenyl]-4-ylmethyl]-2H-imidazol-2-one;
1-(2-cyclohexylethyl)-4-propyl-1,3-dihydro-3-[2'-(1H-tetrazol -5-yl)[1,1'-biphenyl]-4-ylmethyl]-2H-imidazol-2-one;
1-cyclohexanoyl-4-propyl-1,3-dihydro-3-[2'-(1H-tetrazol-5-yl)[1,1'-biphenyl]-4-ylmethyl]-2H-imidazol-2-one;
1-(1-oxo-2-cyclohexylethyl)-4-propyl-1,3-dihydro-3-[2'-(1H -tetrazol-5-yl)[1,1'-biphenyl]-4-ylmethyl]-2H-imidazol-2-one;
1-phenylmethyl-4-propyl-1,3-dihydro-3-[2'-(1H-tetrazol-5-yl)[1,1'-biphenyl]-4-ylmethyl]-2H-imidazol-2-one;
1-(2-phenylethyl)-4-propyl-1,3-dihydro-3-[2'-(1H-tetrazol-5-yl)[1,1'-biphenyl]-4-ylmethyl]-2H-imidazol-2-one;
1-benzoyl-4-propyl-1,3-dihydro-3-[2'-(1H-tetrazol-5-yl)[1,1'-biphenyl]-4-ylmethyl]-2H-imidazol-2-one;
1-(1-oxo-2-phenylethyl)-4-propyl-1,3-dihydro-3-[2'-(1H -tetrazol-5-yl)[1,1'-biphenyl]-4-ylmethyl]-2H-imidazol-2-one;
1-(1-oxopropyl)-4-propyl-1,3-dihydro-3-[2'-(1H-tetrazol-5-yl)[1,1'-biphenyl]-4-ylmethyl]-2H-imidazol-2-one;
1-(1-oxobutyl)-4-propyl-1,3-dihydro-3-[2'-(1H-tetrazol-5-yl)[1,1'-biphenyl]-4-ylmethyl]-2H-imidazol-2-one;
1-(1-oxopentyl)-4-propyl-1,3-dihydro-3-[2'-(1H-tetrazol-5-yl)[1,1'-biphenyl]-4-ylmethyl]-2H-imidazol-2-one;
1-ethyl-4-cyclohexyl-1,3-dihydro-3-[2'-(1H-tetrazol-5-yl)[1,1'-biphenyl]-4-ylmethyl]-2H-imidazol-2-one;
1-propyl-4-cyclohexyl-1,3-dihydro-3-[2'-(1H-tetrazol-5-yl)[1,1'-biphenyl]-4-ylmethyl]-2H-imidazol-2-one;
1-isopropyl-4-cyclohexyl-1,3-dihydro-3-[2'-(1H-tetrazol-5-yl)[1,1'-biphenyl]-4-ylmethyl]-2H-imidazol-2-one;
1-butyl-4-cyclohexyl-1,3-dihydro-3-[2'-(1H-tetrazol-5-yl)[1,1'-biphenyl]-4-ylmethyl]-2H-imidazol-2-one;
1-secbutyl-4-cyclohexyl-1,3-dihydro-3-[2'-(1H-tetrazol-5-yl)[1,1'-biphenyl]-4-ylmethyl]-2H-imidazol-2-one;
1-isobutyl-4-cyclohexyl-1,3-dihydro-3-[2'-(1H-tetrazol-5-yl)[1,1'-biphenyl]-4-ylmethyl]-2H-imidazol-2-one;
1-tertbutyl-4-cyclohexyl-1,3-dihydro-3-[2'-(1H-tetrazol-5-yl)[1,1'-biphenyl]-4-ylmethyl]-2H-imidazol-2-one;
1-pentyl-4-cyclohexyl-1,3-dihydro-3-[2'-(1H-tetrazol-5-yl)[1,1'-biphenyl]-4-ylmethyl]-2H-imidazol-2-one;
1-isopentyl-4-cyclohexyl-1,3-dihydro-3-[2'-(1H-tetrazol-5-yl)[1,1'-biphenyl]-4-ylmethyl]-2H-imidazol-2-one;
1,4-dicyclohexyl-1,3-dihydro-3-[2'-(1H-tetrazol-5-yl)[1,1'-biphenyl]-4-ylmethyl]-2H-imidazol-2-one;
1-cyclohexylmethyl-4-cyclohexyl-1,3-dihydro-3-[2'-(1H -tetrazol-5-yl)[1,1'-biphenyl]-4-ylmethyl]-2H-imidazol-2-one;
1-(2-cyclohexylethyl)-4-cyclohexyl-1,3-dihydro-3-[2'-(1H -tetrazol-5-yl)[1,1'-biphenyl]-4-ylmethyl]-2H-imidazol-2-one;
1-cyclohexanoyl-4-cyclohexyl-1,3-dihydro-3-[2'-(1H-tetrazol-5-yl)[1,1'-biphenyl]-4-ylmethyl]-2H-imidazol-2-one;
1-(1-oxo-2-cyclohexylethyl)-4-cyclohexyl-1,3-dihydro-3-[2'-(1H-tetrazol-5-yl)[1,1'-biphenyl]-4-ylmethyl]-2H-imidazol-2-one;
1-phenyl-4-cyclohexyl-1,3-dihydro-3-[2'-(1H-tetrazol-5-yl)[1,1'-biphenyl]-4-ylmethyl]-2H-imidazol-2-one;
1-phenylmethyl-4-cyclohexyl-1,3-dihydro-3-[2'-(1H-tetrazol-5-yl)[1,1'-biphenyl]-4-ylmethyl]-2H-imidazol-2-one;
1-(2-phenylethyl)-4-cyclohexyl-1,3-dihydro-3-[2'-(1H-tetrazol -5-yl)[1,1'-biphenyl]-4-ylmethyl]-2H-imidazol-2-one;
1-benzoyl-4-cyclohexyl-1,3-dihydro-3-[2'-(1H-tetrazol-5-yl)[1,1'-biphenyl]-4-ylmethyl]-2H-imidazol-2-one;
1-(1-oxo-2-phenylethyl)-4-cyclohexyl-1,3-dihydro-3-[2'-(1H -tetrazol-5-yl)[1,1'-biphenyl]-4-ylmethyl]-2H-imidazol-2-one;
1-propyl-4-butyl-5-fluoro-1,3-dihydro-3-[2'-(1H-tetrazol-5-yl)[1,1'-biphenyl]-4-ylmethyl]-2H-imidazol-2-one;
1,4-dibutyl-5-fluoro-1,3-dihydro-3-[2'-(1H-tetrazol-5-yl)[1,1'-biphenyl]-4-ylmethyl]-2H-imidazol-2-one;
1-pentyl-4-butyl-5-fluoro-1,3-dihydro-3-[2'-(1H-tetrazol-5-yl)[1,1'-biphenyl]-4-ylmethyl]-2H-imidazol-2-one;
1-isopentyl-4-butyl-5-fluoro-1,3-dihydro-3-[2'-(1H-tetrazol-5-yl)[1,1'-biphenyl]-4-ylmethyl]-2H-imidazol-2-one;
1-cyclohexyl-4-butyl-5-fluoro-1,3-dihydro-3-[2'-(1H-tetrazol -5-yl)[1,1'-biphenyl]-4-ylmethyl]-2H-imidazol-2-one;
1-phenylmethyl-4-butyl-5-fluoro-1,3-dihydro-3-[2'-(1H -tetrazol-5-yl)[1,1'-biphenyl]-4-ylmethyl]-2H-imidazol-2-one;
1-(2-phenylethyl)-4-butyl-5-fluoro-1,3-dihydro-3-[2'-(1H -tetrazol-5-yl)[1,1'-biphenyl]-4-ylmethyl]-2H-imidazol-2-one;
1-propyl-4-butyl-5-chloro-1,3-dihydro-3-[2'-(1H-tetrazol-5-yl)[1,1'-biphenyl]-4-ylmethyl]-2H-imidazol-2-one;
1,4-dibutyl-5-chloro-1,3-dihydro-3-[2'-(1H-tetrazol-5-yl)[1,1'-biphenyl]-4-ylmethyl]-2H-imidazol-2-one;
1-pentyl-4-butyl-5-chloro-1,3-dihydro-3-[2'-(1H-tetrazol-5-yl)[1,1'-biphenyl]-4-ylmethyl]-2H-imidazol-2-one;
1-isopentyl-4-butyl-5-chloro-1,3-dihydro-3-[2'-(1H-tetrazol-5-yl)[1,1'-biphenyl]-4-ylmethyl]-2H-imidazol-2-one;
1-cyclohexyl-4-butyl-5-chloro-1,3-dihydro-3-[2'-(1H-tetrazol -5-yl)[1,1'-biphenyl]-4-ylmethyl]-2H-imidazol-2-one;
1-cyclohexylmethyl-4-butyl-5-chloro-1,3-dihydro-3-[2'-(1H -tetrazol-5-yl)[1,1'-biphenyl]-4-ylmethyl]-2H-imidazol-2-one;
1-(2-cyclohexylethyl)-4-butyl-5-chloro-1,3-dihydro-3-[2'-(1H -tetrazol-5-yl)[1,1'-biphenyl]-4-ylmethyl]-2H-imidazol-2-one;
1-phenylmethyl-4-butyl-5-chloro-1,3-dihydro-3-[2'-(1H -tetrazol-5-yl)[1,1'-biphenyl]-4-ylmethyl]-2H-imidazol-2-one;
1-(2-phenylethyl)-4-butyl-5-chloro-1,3-dihydro-3-[2'-(1H -tetrazol-5-yl)[1,1'-biphenyl]-4-ylmethyl]-2H-imidazol-2-one;

1-propyl-4-butyl-5-formyl-1,3-dihydro-3-[2'-(1H-tetrazol-5-yl)[1,1'-biphenyl]-4-ylmethyl]-2H-imidazol-2-one;

1,4-dibutyl-5-formyl-1,3-dihydro-3-[2'-(1H-tetrazol-5-yl)[1,1'-biphenyl]-4-ylmethyl]-2H-imidazol-2-one;

1-pentyl-4-butyl-5-formyl-1,3-dihydro-3-[2'-(1H-tetrazol-5-yl)[1,1'-biphenyl]-4-ylmethyl]-2H-imidazol-2-one;

1-isopentyl-4-butyl-5-formyl-1,3-dihydro-3-[2'-(1H-tetrazol-5-yl)[1,1'-biphenyl]-4-ylmethyl]-2H-imidazol-2-one;

1-phenylmethyl-4-butyl-5-formyl-1,3-dihydro-3-[2'-(1H-tetrazol-5-yl)[1,1'-biphenyl]-4-ylmethyl]-2H-imidazol-2-one;

1-(2-phenylethyl)-4-butyl-5-formyl-1,3-dihydro-3-[2'-(1H-tetrazol-5-yl)[1,1'-biphenyl]-4-ylmethyl]-2H-imidazol-2-one;

1-propyl-4-butyl-5-dimethoxymethyl-1,3-dihydro-3-[2'-(1H-tetrazol-5-yl)[1,1'-biphenyl]-4-ylmethyl]-2H-imidazol-2-one;

1,4-dibutyl-5-dimethoxymethyl-1,3-dihydro-3-[2'-(1H-tetrazol-5-yl)[1,1'-biphenyl]-4-ylmethyl]-2H-imidazol-2-one;

1-pentyl-4-butyl-5-dimethoxymethyl-1,3-dihydro-3-[2'-(1H-tetrazol-5-yl)[1,1'-biphenyl]-4-ylmethyl]-2H-imidazol-2-one;

1-isopentyl-4-butyl-5-dimethoxymethyl-1,3-dihydro-3-[2'-(1H-tetrazol-5-yl)[1,1'-biphenyl]-4-ylmethyl]-2H-imidazol-2-one;

1-cyclohexyl-4-butyl-5-dimethoxymethyl-1,3-dihydro-3-[2'-(1H-tetrazol-5-yl)[1,1'-biphenyl]-4-ylmethyl]-2H-imidazol-2-one;

1-phenylmethyl-4-butyl-5-dimethoxymethyl-1,3-dihydro-3-[2'-(1H-tetrazol-5-yl)[1,1'-biphenyl]-4-ylmethyl]-2H-imidazol-2-one;

1-(2-phenylethyl)-4-butyl-5-dimethoxymethyl-1,3-dihydro-3-[2'-(1H-tetrazol-5-yl)[1,1'-biphenyl]-4-ylmethyl]-2H-imidazol-2-one;

1-propyl-4-butyl-5-methyl-1,3-dihydro-3-[2'-(1H-tetrazol-5-yl)[1,1'-biphenyl]-4-ylmethyl]-2H-imidazol-2-one;

1,4-dibutyl-5-methyl-1,3-dihydro-3-[2'-(1H-tetrazol-5-yl)[1,1'-biphenyl]-4-ylmethyl]-2H-imidazol-2-one;

1-pentyl-4-butyl-5-methyl-1,3-dihydro-3-[2'-(1H-tetrazol-5-yl)[1,1'-biphenyl]-4-ylmethyl]-2H-imidazol-2-one;

1-isopentyl-4-butyl-5-methyl-1,3-dihydro-3-[2'-(1H-tetrazol-5-yl)[1,1'-biphenyl]-4-ylmethyl]-2H-imidazol-2-one;

1-cyclohexyl-4-butyl-5-methyl-1,3-dihydro-3-[2'-(1H-tetrazol-5-yl)[1,1'-biphenyl]-4-ylmethyl]-2H-imidazol-2-one;

1-phenylmethyl-4-butyl-5-methyl-1,3-dihydro-3-[2'-(1H-tetrazol-5-yl)[1,1'-biphenyl]-4-ylmethyl]-2H-imidazol-2-one;

1-(2-phenylethyl)-4-butyl-5-methyl-1,3-dihydro-3-[2'-(1H-tetrazol-5-yl)[1,1'-biphenyl]-4-ylmethyl]-2H-imidazol-2-one;

1-propyl-4-butyl-5-fluoromethyl-1,3-dihydro-3-[2'-(1H-tetrazol-5-yl)[1,1'-biphenyl]-4-ylmethyl]-2H-imidazol-2-one;

1,4-dibutyl-5-fluoromethyl-1,3-dihydro-3-[2'-(1H-tetrazol-5-yl)[1,1'-biphenyl]-4-ylmethyl]-2H-imidazol-2-one;

1-pentyl-4-butyl-5-fluoromethyl-1,3-dihydro-3-[2'-(1H-tetrazol-5-yl)[1,1'-biphenyl]-4-ylmethyl]-2H-imidazol-2-one;

1-isopentyl-4-butyl-5-fluoromethyl-1,3-dihydro-3-[2'-(1H-tetrazol-5-yl)[1,1'-biphenyl]-4-ylmethyl]-2H-imidazol-2-one;

1-phenylmethyl-4-butyl-5-fluoromethyl-1,3-dihydro-3-[2'-(1H-tetrazol-5-yl)[1,1'-biphenyl]-4-ylmethyl]-2H-imidazol-2-one;

1-(2-phenylethyl)-4-butyl-5-fluoromethyl-1,3-dihydro-3-[2'-(1H-tetrazol-5-yl)[1,1'-biphenyl]-4-ylmethyl]-2H-imidazol-2-one;

1-propyl-4-butyl-5-difluoromethyl-1,3-dihydro-3-[2'-(1H-tetrazol-5-yl)[1,1'-biphenyl]-4-ylmethyl]-2H-imidazol-2-one;

1,4-dibutyl-5-difluoromethyl-1,3-dihydro-3-[2'-(1H-tetrazol-5-yl)[1,1'-biphenyl]-4-ylmethyl]-2H-imidazol-2-one;

1-pentyl-4-butyl-5-difluoromethyl-1,3-dihydro-3-[2'-(1H-tetrazol-5-yl)[1,1'-biphenyl]-4-ylmethyl]-2H-imidazol-2-one;

1-isopentyl-4-butyl-5-difluoromethyl-1,3-dihydro-3-[2'-(1H-tetrazol-5-yl)[1,1'-biphenyl]-4-ylmethyl]-2H-imidazol-2-one;

1-cyclohexyl-4-butyl-5-difluoromethyl-1,3-dihydro-3-[2'-(1H-tetrazol-5-yl)[1,1'-biphenyl]-4-ylmethyl]-2H-imidazol-2-one;

1-phenylmethyl-4-butyl-5-difluoromethyl-1,3-dihydro-3-[2'-(1H-tetrazol-5-yl)[1,1'-biphenyl]-4-ylmethyl]-2H-imidazol-2-one;

1-(2-phenylethyl)-4-butyl-5-difluoromethyl-1,3-dihydro-3-[2'-(1H-tetrazol-5-yl)[1,1'-biphenyl]-4-ylmethyl]-2H-imidazol-2-one;

1-propyl-4-butyl-5-trifluoromethyl-1,3-dihydro-3-[2'-(1H-tetrazol-5-yl)[1,1'-biphenyl]-4-ylmethyl]-2H-imidazol-2-one;

1,4-dibutyl-5-trifluoromethyl-1,3-dihydro-3-[2'-(1H-tetrazol-5-yl)[1,1'-biphenyl]-4-ylmethyl]-2H-imidazol-2-one;

1-pentyl-4-butyl-5-trifluoromethyl-1,3-dihydro-3-[2'-(1H-tetrazol-5-yl)[1,1'-biphenyl]-4-ylmethyl]-2H-imidazol-2-one;

1-isopentyl-4-butyl-5-trifluoromethyl-1,3-dihydro-3-[2'-(1H-tetrazol-5-yl)[1,1'-biphenyl]-4-ylmethyl]-2H-imidazol-2-one;

1-cyclohexyl-4-butyl-5-trifluoromethyl-1,3-dihydro-3-[2'-(1H-tetrazol-5-yl)[1,1'-biphenyl]-4-ylmethyl]-2H-imidazol-2-one; 1-phenylmethyl-4-butyl-5-trifluoromethyl-1,3-dihydro-3-[2'-(1H-tetrazol-5-yl)[1,1'-biphenyl]-4-ylmethyl]-2H-imidazol-2-one;

1-(2-phenylethyl)-4-butyl-5-trifluoromethyl-1,3-dihydro-3-[2'-(1H-tetrazol-5-yl)[1,1'-biphenyl]-4-ylmethyl]-2H-imidazol-2-one;

1,4-dipropyl-5-fluoro-1,3-dihydro-3-[2'-(1H-tetrazol-5-yl)[1,1'-biphenyl]-4-ylmethyl]-2H-imidazol-2-one;

1-butyl-4-propyl-5-fluoro-1,3-dihydro-3-[2'-(1H-tetrazol-5-yl)[1,1'-biphenyl]-4-ylmethyl]-2H-imidazol-2-one;

1-pentyl-4-propyl-5-fluoro-1,3-dihydro-3-[2'-(1H-tetrazol-5-yl)[1,1'-biphenyl]-4-ylmethyl]-2H-imidazol-2-one;

1-isopentyl-4-propyl-5-fluoro-1,3-dihydro-3-[2'-(1H-tetrazol-5-yl)[1,1'-biphenyl]-4-ylmethyl]-2H-imidazol-2-one;

1-cyclohexyl-4-propyl-5-fluoro-1,3-dihydro-3-[2'-(1H-tetrazol-5-yl)[1,1'-biphenyl]-4-ylmethyl]-2H-imidazol-2-one;

1-phenylmethyl-4-propyl-5-fluoro-1,3-dihydro-3-[2'-(1H-tetrazol-5-yl)[1,1'-biphenyl]-4-ylmethyl]-2H-imidazol-2-one;

1-(2-phenylethyl)-4-propyl-5-fluoro-1,3-dihydro-3-[2'-(1H-tetrazol-5-yl)[1,1'-biphenyl]-4-ylmethyl]-2H-imidazol-2-one;
1,4-dipropyl-5-chloro-1,3-dihydro-3-[2'-(1H-tetrazol-5-yl)[1,1'-biphenyl]-4-ylmethyl]-2H-imidazol-2-one;
1-butyl-4-propyl-5-chloro-1,3-dihydro-3-[2'-(1H-tetrazol-5-yl)[1,1'-biphenyl]-4-ylmethyl]-2H-imidazol-2-one;
1-pentyl-4-propyl-5-chloro-1,3-dihydro-3-[2'-(1H-tetrazol-5-yl)[1,1'-biphenyl]-4-ylmethyl]-2H-imidazol-2-one;
1-isopentyl-4-propyl-5-chloro-1,3-dihydro-3-[2'-(1H-tetrazol-5-yl)[1,1'-biphenyl]-4-ylmethyl]-2H-imidazol-2-one;
1-cyclohexyl-4-propyl-5-chloro-1,3-dihydro-3-[2'-(1H-tetrazol-5-yl)[1,1'-biphenyl]-4-ylmethyl]-2H-imidazol-2-one;
1-phenylmethyl-4-propyl-5-chloro-1,3-dihydro-3-[2'-(1H-tetrazol-5-yl)[1,1'-biphenyl]-4-ylmethyl]-2H-imidazol-2-one;
1-(2-phenylethyl)-4-propyl-5-chloro-1,3-dihydro-3-[2'-(1H-tetrazol-5-yl)[1,1'-biphenyl]-4-ylmethyl]-2H-imidazol-2-one;
1,4-dipropyl-5-formyl-1,3-dihydro-3-[2'-(1H-tetrazol-5-yl)[1,1'-biphenyl]-4-ylmethyl]-2H-imidazol-2-one;
1-butyl-4-propyl-5-formyl-1,3-dihydro-3-[2'-(1H-tetrazol-5-yl)[1,1'-biphenyl]-4-ylmethyl]-2H-imidazol-2-one;
1-pentyl-4-propyl-5-formyl-1,3-dihydro-3-[2'-(1H-tetrazol-5-yl)[1,1'-biphenyl]-4-ylmethyl]-2H-imidazol-2-one;
1-isopentyl-4-propyl-5-formyl-1,3-dihydro-3-[2'-(1H-tetrazol-5-yl)[1,1'-biphenyl]-4-ylmethyl]-2H-imidazol-2-one;
1-cyclohexyl-4-propyl-5-formyl-1,3-dihydro-3-[2'-(1H-tetrazol-5-yl)[1,1'-biphenyl]-4-ylmethyl]-2H-imidazol-2-one;
1-phenylmethyl-4-propyl-5-formyl-1,3-dihydro-3-[2'-(1H-tetrazol-5-yl)[1,1'-biphenyl]-4-ylmethyl]-2H-imidazol-2-one;
1-(2-phenylethyl)-4-propyl-5-formyl-1,3-dihydro-3-[2'-(1H-tetrazol-5-yl)[1,1'-biphenyl]-4-ylmethyl]-2H-imidazol-2-one;
1,4-dipropyl-5-dimethoxymethyl-1,3-dihydro-3-[2'-(1H-tetrazol-5-yl)[1,1'-biphenyl]-4-ylmethyl]-2H-imidazol-2-one;
1-butyl-4-propyl-5-dimethoxymethyl-1,3-dihydro-3-[2'-(1H-tetrazol-5-yl)[1,1'-biphenyl]-4-ylmethyl]-2H-imidazol-2-one;
1-pentyl-4-propyl-5-dimethoxymethyl-1,3-dihydro-3-[2'-(1H-tetrazol-5-yl)[1,1'-biphenyl]-4-ylmethyl]-2H-imidazol-2-one;
1-isopentyl-4-propyl-5-dimethoxymethyl-1,3-dihydro-3-[2'-(1H-tetrazol-5-yl)[1,1'-biphenyl]-4-ylmethyl]-2H-imidazol-2-one;
1-cyclohexyl-4-propyl-5-dimethoxymethyl-1,3-dihydro-3-[2'-(1H-tetrazol-5-yl)[1,1'-biphenyl]-4-ylmethyl]-2H-imidazol-2-one;
1-phenylmethyl-4-propyl-5-dimethoxymethyl-1,3-dihydro-3-[2'-(1H-tetrazol-5-yl)[1,1'-biphenyl]-4-ylmethyl]-2H-imidazol-2-one;
1-(2-phenylethyl)-4-propyl-5-dimethoxymethyl-1,3-dihydro-3-[2'-(1H-tetrazol-5-yl)[1,1'-biphenyl]-4-ylmethyl]-2H-imidazol-2-one;
1,4-dipropyl-5-methyl-1,3-dihydro-3-[2'-(1H-tetrazol-5-yl)[1,1'-biphenyl]-4-ylmethyl]-2H-imidazol-2-one;
1-butyl-4-propyl-5-methyl-1,3-dihydro-3-[2'-(1H-tetrazol-5-yl)[1,1'-biphenyl]-4-ylmethyl]-2H-imidazol-2-one;
1-pentyl-4-propyl-5-methyl-1,3-dihydro-3-[2'-(1H-tetrazol-5-yl)[1,1'-biphenyl]-4-ylmethyl]-2H-imidazol-2-one;
1-isopentyl-4-propyl-5-methyl-1,3-dihydro-3-[2'-(1H-tetrazol-5-yl)[1,1'-biphenyl]-4-ylmethyl]-2H-imidazol-2-one;
1-cyclohexyl-4-propyl-5-methyl-1,3-dihydro-3-[2'-(1H-tetrazol-5-yl)[1,1'-biphenyl]-4-ylmethyl]-2H-imidazol-2-one;
1-phenylmethyl-4-propyl-5-methyl-1,3-dihydro-3-[2'-(1H-tetrazol-5-yl)[1,1'-biphenyl]-4-ylmethyl]-2H-imidazol-2-one;
1-(2-phenylethyl)-4-propyl-5-methyl-1,3-dihydro-3-[2'-(1H-tetrazol-5-yl)[1,1'-biphenyl]-4-ylmethyl]-2H-imidazol-2-one;
1,4-dipropyl-5-fluoromethyl-1,3-dihydro-3-[2'-(1H-tetrazol-5-yl)[1,1'-biphenyl]-4-ylmethyl]-2H-imidazol-2-one;
1-butyl-4-propyl-5-fluoromethyl-1,3-dihydro-3-[2'-(1H-tetrazol-5-yl)[1,1'-biphenyl]-4-ylmethyl]-2H-imidazol-2-one;
1-pentyl-4-propyl-5-fluoromethyl-1,3-dihydro-3-[2'-(1H-tetrazol-5-yl)[1,1'-biphenyl]-4-ylmethyl]-2H-imidazol-2-one;
1-isopentyl-4-propyl-5-fluoromethyl-1,3-dihydro-3-[2'-(1H-tetrazol-5-yl)[1,1'-biphenyl]-4-ylmethyl]-2H-imidazol-2-one;
1-cyclohexyl-4-propyl-5-fluoromethyl-1,3-dihydro-3-[2'-(1H-tetrazol-5-yl)[1,1'-biphenyl]-4-ylmethyl]-2H-imidazol-2-one;
1-phenylmethyl-4-propyl-5-fluoromethyl-1,3-dihydro-3-[2'-(1H-tetrazol-5-yl)[1,1'-biphenyl]-4-ylmethyl]-2H-imidazol-2-one;
1-(2-phenylethyl)-4-propyl-5-fluoromethyl-1,3-dihydro-3-[2'-(1H-tetrazol-5-yl)[1,1'-biphenyl]-4-ylmethyl]-2H-imidazol-2-one;
1,4-dipropyl-5-difluoromethyl-1,3-dihydro-3-[2'-(1H-tetrazol-5-yl)[1,1'-biphenyl]-4-ylmethyl]-2H-imidazol-2-one;
1-butyl-4-propyl-5-difluoromethyl-1,3-dihydro-3-[2'-(1H-tetrazol-5-yl)[1,1'-biphenyl]-4-ylmethyl]-2H-imidazol-2-one;
1-pentyl-4-propyl-5-difluoromethyl-1,3-dihydro-3-[2'-(1H-tetrazol-5-yl)[1,1'-biphenyl]-4-ylmethyl]-2H-imidazol-2-one;
1-isopentyl-4-propyl-5-difluoromethyl-1,3-dihydro-3-[2'-(1H-tetrazol-5-yl)[1,1'-biphenyl]-4-ylmethyl]-2H-imidazol-2-one;
1-cyclohexyl-4-propyl-5-difluoromethyl-1,3-dihydro-3-[2'-(1H-tetrazol-5-yl)[1,1'-biphenyl]-4-ylmethyl]-2H-imidazol-2-one;
1-phenylmethyl-4-propyl-5-difluoromethyl-1,3-dihydro-3-[2'-(1H-tetrazol-5-yl)[1,1'-biphenyl]-4-ylmethyl]-2H-imidazol-2-one;
1-(2-phenylethyl)-4-propyl-5-difluoromethyl-1,3-dihydro-3-[2'-(1H-tetrazol-5-yl)[1,1'-biphenyl]-4-ylmethyl]-2H-imidazol-2-one;
1,4-dipropyl-5-trifluoromethyl-1,3-dihydro-3-[2'-(1H-tetrazol-5-yl)[1,1'-biphenyl]-4-ylmethyl]-2H-imidazol-2-one;
1-butyl-4-propyl-5-trifluoromethyl-1,3-dihydro-3-[2'-(1H-tetrazol-5-yl)[1,1'-biphenyl]-4-ylmethyl]-2H-imidazol-2-one;

1-pentyl-4-propyl-5-trifluoromethyl-1,3-dihydro-3-[2'-(1H -tetrazol-5-yl)[1,1'-biphenyl]-4-ylmethyl]-2H-imidazol-2-one;

1-isopentyl-4-propyl-5-trifluoromethyl-1,3-dihydro-3-[2'-(1H -tetrazol-5-yl)[1,1'-biphenyl]-4-ylmethyl]-2H-imidazol-2-one;

1-cyclohexyl-4-propyl-5-trifluoromethyl-1,3-dihydro-3-[2'-(1H -tetrazol-5-yl)1,1 -biphenyl]-4-ylmethyl]-2H-imidazol-2-one;

1-phenylmethyl-4-propyl-5-trifluoromethyl-1,3-dihydro-3-[2'-(1H-tetrazol-5-yl)[1,1 -biphenyl]-4-ylmethyl]-2H-imidazol-2-one;

1-(2-phenylethyl)-4-propyl-5-trifluoromethyl-1,3-dihydro-3-[2'-(1H-tetrazol-5-yl)[1,1'-biphenyl]-4-ylmethyl]-2H-imidazol -2-one;

1-propyl-4-isopentyl-5-fluoro-1,3-dihydro-3-[2'-(1H-tetrazol -5-yl)[1,1'-biphenyl]-4-ylmethyl]-2H-imidazol-2-one;

1-butyl-4-isopentyl-5-fluoro-1,3-dihydro-3-[2'-(1H-tetrazol-5-yl)[1,1'-biphenyl]-4-ylmethyl]-2H-imidazol-2-one;

1-pentyl-4-isopentyl-5-fluoro-1,3-dihydro-3-[2'-(1H-tetrazol -5-yl)[1,1'-biphenyl]-4-ylmethyl]-2H-imidazol-2-one;

1,4-diisopentyl-5-fluoro-1,3-dihydro-3-[2'-(1H-tetrazol-5-yl)[1,1'-biphenyl]-4-ylmethyl]-2H-imidazol-2-one;

1-cyclohexyl-4-isopentyl-5-fluoro-1,3-dihydro-3-[2'-(1H-tetrazol-5-yl)[1,1'-biphenyl]-4-ylmethyl]-2H-imidazol-2-one;

1-phenylmethyl-4-isopentyl-5-fluoro-1,3-dihydro-3-[2'-(1H-tetrazol-5-yl)[1,1'-biphenyl]-4-ylmethyl]-2H-imidazol-2-one;

1-(2-phenylethyl)-4-isopentyl-5-fluoro-1,3-dihydro-3-[2'-(1H-tetrazol-5-yl)[1,1'-biphenyl]-4-ylmethyl]-2H-imidazol-2-one;

1-propyl-4-isopentyl-5-chloro-1,3-dihydro-3-[2'-(1H-tetrazol-5-yl)[1,1'-biphenyl]-4-ylmethyl]-2H-imidazol-2-one;

1-butyl-4-isopentyl-5-chloro-1,3-dihydro-3-[2'-(1H-tetrazol-5-yl)[1,1'-biphenyl]-4-ylmethyl]-2H-imidazol-2-one;

1-pentyl-4-isopentyl-5-chloro-1,3-dihydro-3-[2'-(1H-tetrazol-5-yl)[1,1'-biphenyl]-4-ylmethyl]-2H-imidazol-2-one;

1,4-diisopentyl-5-chloro-1,3-dihydro-3-[2'-(1H-tetrazol-5-yl)[1,1'-biphenyl]-4-ylmethyl]-2H-imidazol-2-one;

1-cyclohexyl-4-isopentyl-5-chloro-1,3-dihydro-3-[2'-(1H-tetrazol-5-yl)[1,1'-biphenyl]-4-ylmethyl]-2H-imidazol-2-one;

1-phenylmethyl-4-isopentyl-5-chloro-1,3-dihydro-3-[2'-(1H-tetrazol-5-yl)[1,1'-biphenyl]-4-ylmethyl]-2H-imidazol-2-one;

1-(2-phenylethyl)-4-isopentyl-5-chloro-1,3-dihydro-3-[2'-(1H-tetrazol-5-yl)[1,1'-biphenyl]-4-ylmethyl]-2H-imidazol-2-one;

1-propyl-4-isopentyl-5-formyl-1,3-dihydro-3-[2'-(1H-tetrazol-5-yl)[1,1'-biphenyl]-4-ylmethyl]-2H-imidazol-2-one;

1-butyl-4-isopentyl-5-formyl-1,3-dihydro-3-[2'-(1H-tetrazol-5-yl)[1,1'-biphenyl]-4-ylmethyl]-2H-imidazol-2-one;

1-pentyl-4-isopentyl-5-formyl-1,3-dihydro-3-[2'-(1H-tetrazol-5-yl)[1,1'-biphenyl]-4-ylmethyl]-2H-imidazol-2-one;

1,4-diisopentyl-5-formyl-1,3-dihydro-3-[2'-(1H-tetrazol-5-yl)[1,1'-biphenyl]-4-ylmethyl]-2H-imidazol-2-one;

1-cyclohexyl-4-isopentyl-5-formyl-1,3-dihydro-3-[2'-(1H-tetrazol-5-yl)[1,1'-biphenyl]-4-ylmethyl]-2H-imidazol-2-one;

1-phenylmethyl-4-isopentyl-5-formyl-1,3-dihydro-3-[2'-(1H-tetrazol-5-yl)[1,1'-biphenyl]-4-ylmethyl]-2H-imidazol-2-one;

1-(2-phenylethyl)-4-isopentyl-5-formyl-1,3-dihydro-3-[2'-(1H-tetrazol-5-yl)[1,1'-biphenyl]-4-ylmethyl]-2H-imidazol-2-one;

1-propyl-4-isopentyl-5-dimethoxymethyl-1,3-dihydro-3-[2'-(1H-tetrazol-5-yl)[1,1'-biphenyl]-4-ylmethyl]-2H-imidazol-2-one;

1-butyl-4-isopentyl-5-dimethoxymethyl-1,3-dihydro-3-[2'-(1H-tetrazol-5-yl)[1,1'-biphenyl]-4-ylmethyl]-2H-imidazol-2-one;

1-pentyl-4-isopentyl-5-dimethoxymethyl-1,3-dihydro-3-[2'-(1H-tetrazol-5-yl)[1,1'-biphenyl]-4-ylmethyl]-2H-imidazol-2-one;

1,4-diisopentyl-5-dimethoxymethyl-1,3-dihydro-3-[2'-(1H-tetrazol-5-yl)[1,1'-biphenyl]-4-ylmethyl]-2H-imidazol-2-one;

1-cyclohexyl-4-isopentyl-5-dimethoxymethyl-1,3-dihydro-3-[2'-(1H-tetrazol-5-yl)[1,1'-biphenyl]-4-ylmethyl]-2H-imidazol-2-one;

1-phenylmethyl-4-isopentyl-5-dimethoxymethyl-1,3-dihydro-3-[2'-(1H-tetrazol-5-yl)[1,1'-biphenyl]-4-ylmethyl]-2H-imidazol-2-one;

1-(2-phenylethyl)-4-isopentyl-5-dimethoxymethyl-1,3-dihydro-3-[2'-(1H-tetrazol-5-yl)[1,1'-biphenyl]-4-ylmethyl]-2H-imidazol-2-one;

1-propyl-4-isopentyl-5-methyl-1,3-dihydro-3-[2'-(1H-tetrazol-5-yl)[1,1'-biphenyl]-4-ylmethyl]-2H-imidazol-2-one;

1-butyl-4-isopentyl-5-methyl-1,3-dihydro-3-[2'-(1H-tetrazol-5-yl)[1,1'-biphenyl]-4-ylmethyl]-2H-imidazol-2-one;

1-pentyl-4-isopentyl-5-methyl-1,3-dihydro-3-[2'-(1H-tetrazol-5-yl)[1,1'-biphenyl]-4-ylmethyl]-2H-imidazol-2-one;

1,4-diisopentyl-5-methyl-1,3-dihydro-3-[2'-(1H-tetrazol-5-yl)[1,1'-biphenyl]-4-ylmethyl]-2H-imidazol-2-one;

5-yl)[1,1'-biphenyl]-4-ylmethyl]-2H-imidazol-2-one;

1-cyclohexyl-4-isopentyl-5-methyl-1,3-dihydro-3-[2'-(1H-tetrazol-5-yl)[1,1'-biphenyl]-4-ylmethyl]-2H-imidazol-2-one;

1-phenylmethyl-4-isopentyl-5-methyl-1,3-dihydro-3-[2'-(1H-tetrazol-5-yl)[1,1'-biphenyl]-4-ylmethyl]-2H-imidazol-2-one;

1-(2-phenylethyl)-4-isopentyl-5-methyl-1,3-dihydro-3-[2'-(1H-tetrazol-5-yl)[1,1'-biphenyl]-4-ylmethyl]-2H-imidazol-2-one;

1-propyl-4-isopentyl-5-fluoromethyl-1,3-dihydro-3-[2'-(1H-tetrazol-5-yl)[1,1'-biphenyl]-4-ylmethyl]-2H-imidazol-2-one;

1-butyl-4-isopentyl-5-fluoromethyl-1,3-dihydro-3-[2'-(1H-tetrazol-5-yl)[1,1'-biphenyl]-4-ylmethyl]-2H-imidazol-2-one;

1-pentyl-4-isopentyl-5-fluoromethyl-1,3-dihydro-3-[2'-(1H-tetrazol-5-yl)[1,1'-biphenyl]-4-ylmethyl]-2H-imidazol-2-one;

1,4-diisopentyl-5-fluoromethyl-1,3-dihydro-3-[2'-(1H-tetrazol-5-yl)[1,1'-biphenyl]-4-ylmethyl]-2H-imidazol-2-one;

1-cyclohexyl-4-isopentyl-5-fluoromethyl-1,3-dihydro-3-[2'-(1H-tetrazol-5-yl)[1,1'-biphenyl]-4-ylmethyl]-2H-imidazol-2-one;

1-phenylmethyl-4-isopentyl-5-fluoromethyl-1,3-dihydro-3-[2'-(1H-tetrazol-5-yl)[1,1'-biphenyl]-4-ylmethyl]-2H-imidazol-2-one;

1-(2-phenylethyl)-4-isopentyl-5-fluoromethyl-1,3-dihydro-3-2'-(1H-tetrazol-5-yl)[1,1'-biphenyl]-4-ylmethyl]-2H-imidazol-2-one;

1-propyl-4-isopentyl-5-difluoromethyl-1,3-dihydro-3-[2'-(1H-tetrazol-5-yl)[1,1'-biphenyl]-4-ylmethyl]-2H-imidazol-2-one;

1-butyl-4-isopentyl-5-difluoromethyl-1,3-dihydro-3-[2'-(1H-tetrazol-5-yl)[1,1'-biphenyl]-4-ylmethyl]-2H-imidazol-2-one;

1-pentyl-4-isopentyl-5-difluoromethyl-1,3-dihydro-3-[2'-(1H-tetrazol-5-yl)[1,1'-biphenyl]-4-ylmethyl]-2H-imidazol-2-one;

1,4-diisopentyl-5-difluoromethyl-1,3-dihydro-3-[2'-(1H-tetrazol-5-yl)[1,1'-biphenyl]-4-ylmethyl]-2H-imidazol-2-one;

1-cyclohexyl-4-isopentyl-5-difluoromethyl-1,3-dihydro-3-[2'-(1H-tetrazol-5-yl)[1,1'-biphenyl]-4-ylmethyl]-2H-imidazol-2-one;

1-phenylmethyl-4-isopentyl-5-difluoromethyl-1,3-dihydro-3-[2'-(1H-tetrazol-5-yl)[1,1'-biphenyl]-4-ylmethyl]-2H-imidazol-2-one;

1-(2-phenylethyl)-4-isopentyl-5-difluoromethyl-1,3-dihydro-3-[2'-(1H-tetrazol-5-yl)[1,1'-biphenyl]-4-ylmethyl]-2H-imidazol-2-one;

1-propyl-4-isopentyl-5-trifluoromethyl-1,3-dihydro-3-[2'-(1H-tetrazol-5-yl)[1,1'-biphenyl]-4-ylmethyl]-2H-imidazol-2-one;

1-butyl-4-isopentyl-5-trifluoromethyl-1,3-dihydro-3-[2'-(1H-tetrazol-5-yl)[1,1'-biphenyl]-4-ylmethyl]-2H-imidazol-2-one;

1-pentyl-4-isopentyl-5-trifluoromethyl-1,3-dihydro-3-[2'-(1H-tetrazol-5-yl)[1,1'-biphenyl]-4-ylmethyl]-2H-imidazol-2-one;

1,4-diisopentyl-5-trifluoromethyl-1,3-dihydro-3-[2'-(1H-tetrazol-5-yl)[1,1'-biphenyl]-4-ylmethyl]-2H-imidazol-2-one;

1-cyclohexyl-4-isopentyl-5-trifluoromethyl-1,3-dihydro-3-[2'-(1H-tetrazol-5-yl)[1,1'-biphenyl]-4-ylmethyl]-2H-imidazol-2-one;

1-phenylmethyl-4-isopentyl-5-trifluoromethyl-1,3-dihydro-3-[2'-(1H-tetrazol-5-yl)[1,1'-biphenyl]-4-ylmethyl]-2H-imidazol-2-one;

1-(2-phenylethyl)-4-isopentyl-5-trifluoromethyl-1,3-dihydro-3-[2'-(1H-tetrazol-5-yl)[1,1'-biphenyl]-4-ylmethyl]-2H-imidazol-2-one;

1-propyl-4-butyl-5-carboxy-1,3-dihydro-3-[2'-(1H-tetrazol-5-yl)[1,1'-biphenyl]-4-ylmethyl]-2H-imidazol-2-one;

1,4-dibutyl-5-carboxy-1,3-dihydro-3-[2'-(1H-tetrazol-5-yl)[1,1'-biphenyl]-4-ylmethyl]-2H-imidazol-2-one;

1-pentyl-4-butyl-5-carboxy-1,3-dihydro-3-[2'-(1H-tetrazol-5-yl)[1,1'-biphenyl]-4-ylmethyl]-2H-imidazol-2-one;

1-isopentyl-4-butyl-5-carboxy-1,3-dihydro-3-[2'-(1H-tetrazol-5-yl)[1,1'-biphenyl]-4-ylmethyl]-2H-imidazol-2-one;

1-cyclohexyl-4-butyl-5-carboxy-1,3-dihydro-3-[2'-(1H-tetrazol-5-yl)[1,1'-biphenyl]-4-ylmethyl]-2H-imidazol-2-one;

1-cyclohexylmethyl-4-butyl-5-carboxy-1,3-dihydro-3-[2'-(1H-tetrazol-5-yl)[1,1'-biphenyl]-4-ylmethyl]-2H-imidazol-2-one;

1-(2-cyclohexylethyl)-4-butyl-5-carboxy-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-butyl-5-carboxy-1,3-dihydro-3-2'-(1H-tetrazol-5-yl)[1,1'-biphenyl]-4-ylmethyl]-2H-imidazol-2-one;

1-phenylmethyl-4-butyl-5-carboxy-1,3-dihydro-3-[2'-(1H-tetrazol-5-yl)[1,1'-biphenyl]-4-ylmethyl]-2H-imidazol-2-one;

1-(2-phenylethyl)-4-butyl-5-carboxy-1,3-dihydro-3-[2'-(1H-tetrazol-5-yl)[1,1'-biphenyl]-4-ylmethyl]-2H-imidazol-2-one;

1-benzoyl-4-butyl-5-carboxy-1,3-dihydro-3-[2'-(1H-tetrazol-5-yl)[1,1'-biphenyl]-4-ylmethyl]-2H-imidazol-2-one;

1-(1-oxo-2-phenylethyl)-4-butyl-5-carboxy-1,3-dihydro-3-[2'-(1H-tetrazol-5-yl)[1,1'-biphenyl]-4-ylmethyl]-2H-imidazol-2-one;

1-butyl-4-propyl-5-carboxy-1,3-dihydro-3-[2'-(1H-tetrazol-5-yl)[1,1'-biphenyl]-4-ylmethyl]-2H-imidazol-2-one;

1,4-dipropyl-5-carboxy-1,3-dihydro-3-[2'-(1H-tetrazol-5-yl)[1,1'-biphenyl]-4-ylmethyl]-2H-imidazol-2-one;

1-pentyl-4-propyl-5-carboxy-1,3-dihydro-3-[2'-(1H-tetrazol-5-yl)[1,1'-biphenyl]-4-ylmethyl]-2H-imidazol-2-one;

1-isopentyl-4-propyl-5-carboxy-1,3-dihydro-3-[2'-(1H-tetrazol-5-yl)[1,1'-biphenyl]-4-ylmethyl]-2H-imidazol-2-one;

1-cyclohexyl-4-propyl-5-carboxy-1,3-dihydro-3-[2'-(1H-tetrazol-5-yl)[1,1'-biphenyl]-4-ylmethyl]-2H-imidazol-2-one;

1-cyclohexylmethyl-4-propyl-5-carboxy-1,3-dihydro-3-[2'-(1H-tetrazol-5-yl)[1,1'-biphenyl]-4-ylmethyl]-2H-imidazol-2-one;

1-(2-cyclohexylethyl)-4-propyl-5-carboxy-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-propyl-5-carboxy-1,3-dihydro-3-[2'-(1H-tetrazol-5-yl)[1,1'-biphenyl]-4-ylmethyl]-2H-imidazol-2-one;

1-phenylmethyl-4-propyl-5-carboxy-1,3-dihydro-3-[2'-(1H-tetrazol-5-yl)[1,1'-biphenyl]-4-ylmethyl]-2H-imidazol-2-one;

1-(2-phenylethyl)-4-propyl-5-carboxy-1,3-dihydro-3-[2'-(1H-tetrazol-5-yl)[1,1'-biphenyl]-4-ylmethyl]-2H-imidazol-2-one;

1-benzoyl-4-propyl-5-carboxy-1,3-dihydro-3-[2'-(1H-tetrazol-5-yl)[1,1'-biphenyl]-4-ylmethyl]-2H-imidazol-2-one;

1-(1-oxo-2-phenylethyl)-4-propyl-5-carboxy-1,3-dihydro-3-[2'-(1H-tetrazol-5-yl)[1,1'-biphenyl]-4-ylmethyl]-2H-imidazol-2-one;

1-propyl-4-isopentyl-5-carboxy-1,3-dihydro-3-[2'-(1H-tetrazol-5-yl)[1,1'-biphenyl]-4-ylmethyl]-2H-imidazol-2-one;

1,4-diisopentyl-5-carboxy-1,3-dihydro-3-[2'-(1H-tetrazol-5-yl)[1,1'-biphenyl]-4-ylmethyl]-2H-imidazol-2-one;

1-pentyl-4-isopentyl-5-carboxy-1,3-dihydro-3-[2'-(1H-tetrazol-5-yl)[1,1'-biphenyl]-4-ylmethyl]-2H-imidazol-2-one;

1-butyl-4-isopentyl-5-carboxy-1,3-dihydro-3-[2'-(1H-tetrazol-5-yl)[1,1'-biphenyl]-4-ylmethyl]-2H-imidazol-2-one;

1-cyclohexyl-4-isopentyl-5-carboxy-1,3-dihydro-3-[2'-(1H-tetrazol-5-yl)[1,1'-biphenyl]-4-ylmethyl]-2H-imidazol-2-one;

1-cyclohexylmethyl-4-isopentyl-5-carboxy-1,3-dihydro-3-[2'-(1H-tetrazol-5-yl)[1,1'-biphenyl]-4-ylmethyl]-2H-imidazol-2-one;

1-(2-cyclohexylethyl)-4-isopentyl-5-carboxy-1,3-dihydro-3-[2'-(1H-tetrazol-5-yl)[1,1'-biphenyl]-4-ylmethyl]-2H-imidazol-2-one;

1-(1-oxo-2-cyclohexylethyl)-4-isopentyl-5-carboxy-1,3-dihydro-3-[2'-(1H-tetrazol-5-yl)[1,1'-biphenyl]-4-ylmethyl]-2H-imidazol-2-one;

1-phenylmethyl-4-isopentyl-5-carboxy-1,3-dihydro-3-[2'-(1H-tetrazol-5-yl)[1,1'-biphenyl]-4-ylmethyl]-2H-imidazol-2-one;

1-(2-phenylethyl-4-isopentyl-5-carboxy-1,3-dihydro-3-[2'-(1H-tetrazol-5-yl)[1,1'-biphenyl]-4-ylmethyl]-2H-imidazol-2-one;

1-benzoyl-4-isopentyl-5-carboxy-1,3-dihydro-3-[2'-(1H-tetrazol-5-yl)[1,1'-biphenyl]-4-ylmethyl]-2H-imidazol-2-one; and 1-(1-oxo-2-phenylethyl)-4-isopentyl-5-carboxy-1,3-dihydro-3-[2'-(1H-tetrazol-5-yl)[1,1'-biphenyl]-4-ylmethyl]-2H-imidazol-2-one.

The term "hydrido" denotes a single hydrogen atom (H) which may be attached, for example, to a carbon atom to form a hydrocarbyl group or attached to an oxygen atom to form an hydroxyl group. Where the term "alkyl" is used, either alone or within other terms such as "haloalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about five carbon atomms. The term "cycloalkyl" embraces cyclic radicals having three to about ten ring carbon atoms, preferably three to about six carbon atoms, such as cyclopropyl and cyclobutyl. The term "cycloalkylalkyl" is exemplified by cyclohexylmethyl and cyclohexylethyl, either of which may be optionally attached to a substitutable position of Formula I through a carbonyl moiety. The term "haloalkyl" embraces radicals wherein any one or more of the alkyl carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two fluoro atoms, such as difluoromethyl and difluorobutyl groups, or two chloro atoms, such as a dichloromethyl group, or one fluoro atom and one chloro atom, such as a fluorochloromethyl group. Examples of a polyhaloalkyl are trifluoromethyl, 1,1-difluoroethyl, 2,2,2-trifluoroethyl, perfluoroethyl and 2,2,3,3-tetrafluoropropyl groups. The term "difluoroalkyl" embraces alkyl groups having two fluoro atoms substituted on any one or two of the alkyl group carbon atoms. Preferably, when the difluoroalkyl group is attached at the triazole ring $R^1$ and $R^2$ positions of Formula I, the two fluoro atoms are substituted on the carbon atom which is attached directly to the triazole ring. Such preferred difluoroalkyl group may be characterized as an "alpha-carbon difluoro-substituted difluoroalkyl group". The terms "alkylol" and "hydroxyalkyl" embrace linear or branched alkyl groups having one to about ten carbon atoms any one of which may be substituted with one or more hydroxyl groups. The term "alkenyl" embraces linear or branched radicals having two to about twenty carbon atoms, preferably three to about ten carbon atoms, and containing at least one carbon-carbon double bond, which carbon-carbon double bond may have either cis or trans geometry within the alkenyl moiety. The term "alkynyl" embraces linear or branched radicals having two to about twenty carbon atoms, preferably two to about ten carbon atoms, and containing at least one carbon-carbon triple bond. The terms "cycloalkenyl" and "cycloalkynyl" embrace cyclic radicals having three to about ten ring carbon atoms including, respectively, one or more double or triple bonds involving adjacent ring carbons. The terms "alkoxy" and "alkoxyalkyl" embrace linear or branched oxy-containing radicals each having alkyl portions of one to about ten carbon atoms, such as methoxy group. The term "alkoxyalkyl" also embraces alkyl radicals having two or more alkoxy groups attached to the alkyl radical, that is, to form monoalkoxyalkyl and dialkoxyalkyl groups. The "alkoxy" or "alkoxyalkyl" radicals may be further substituted with one or more halo atoms, such as fluoro, chloro or bromo, to provide haloalkoxy or haloalkoxyalkyl groups. The term "alkylthio" embraces radicals containing a linear or branched alkyl group, of one to about ten carbon atoms attached to a divalent sulfur atom, such as a methythio group. The term "aryl" embraces aromatic radicals such as phenyl, naphthyl and biphenyl. The terms "aralkyl" and "arylalkyl" embrace aryl-substituted alkyl radicals such as benzyl, diphenylmethyl, triphenylmethyl, phenylethyl, phenylbutyl and diphenylethyl. Aralkyl groups may be attached to a carbonyl to form a radical attachable through the carbonyl to a substitutable position on Formula I. The terms "benzyl" and "phenylmethyl" are interchangeable. The terms "aryloxy" and "arylthio" denote radical respectively, aryl groups having an oxygen or sulfur atom through which the radical is attached to a nucleus, examples of which are phenoxy and phenylthio. The terms "sulfinyl" and "sulfonyl", whether used alone or linked to other terms, denotes respectively divalent radicals SO and $SO_2$. The term "aralkoxy", alone or within another term, embraces an aryl group attached to an alkoxy group to form, for example, benzyloxy. The term "acyl" whether used alone, or within a term such as acyloxy, denotes a radical provided by the residue after removal of hydroxyl from an organic acid, examples of such radical being acetyl and benzoyl. The term "heteroaryl" embraces aromatic ring systems containing one or two hetero atoms selected from oxygen, nitrogen and sulfur in a ring system having five or six ring members, examples of which are thienyl, furanyl, pyridinyl, thiazolyl, pyrimidyl and isoxazolyl. Such heteroaryl may be attached as a substituent through a carbon atom of the heteroaryl ring system, or may be attached through a carbon atom of a moiety substituted on a heteroaryl ring-member carbon atom, for example, through the methylene substituent of imidazolemethyl moiety. Also, such heteroaryl may be attached through a ring nitrogen atom as long as aromaticity of the heteroaryl moiety is preserved after attachment.

Specific examples of alkyl groups are methyl, ethyl, n-propyl, isopropyl, n-butyl, sec-butyl, isobutyl, tert-butyl, n-pentyl, isopentyl and neopentyl. Typical alkenyl and alkynyl groups may have one unsaturated bond, such as an allyl group, or may have a plurality or unsaturated bonds, with such plurality of bonds either adjacent, such as allene-type structures, or in conjugation, or separated by several saturated carbons.

Compounds of Formula I have been found to inhibit the action of angiotensin II in mammals. Angiotensin II is a potent vasoconstrictor and participates in the formation of aldosterone which regulates sodium and water balance in mammals. Thus, compounds of Formula I are therapeutically useful in methods for treating hypertension by administering to a hypertensive patient a therapeutically-effective amount of a compound of Formula I. The phrase "hypertensive patient" means, in this context, a mammalian subject suffering from the effects of hypertension or susceptible to a hypertensive condition if not treated to prevent or control such hypertension.

The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methansulfonic, ethanesulfonic, 2-hydroxyethanesulfonic, pantothenic, benzenesulfonic, toluenesulfonic, sulfanilic, mesylic, cyclohexylaminosulfonic, stearic, algenic, b-hydroxybutyric, malonic, galactaric and galacturonic acid. Suitable pharmaceutically-acceptable base addition salts of compounds of Formula I include metallic salts made from aluminium, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

GENERAL SYNTHETIC PROCEDURES

Compounds embraced by Formula I may be prepared in accordance with Schemes I-VIII, which follow:

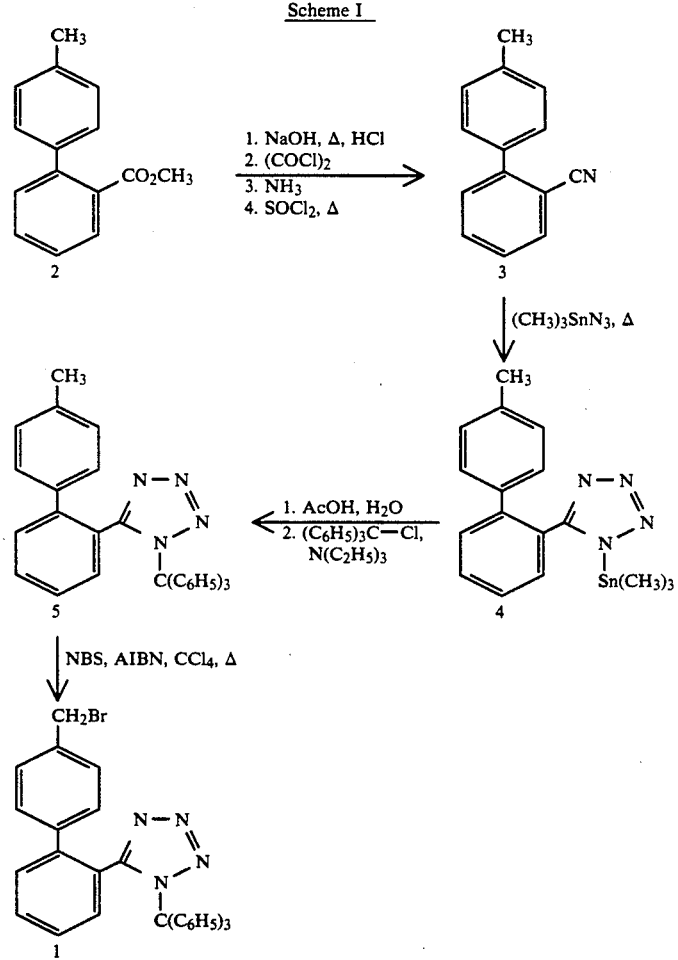

Synthetic Scheme I shows the preparation of the alkylating agent 1 where $R^5$ equal $CN_4C(C_6H_5)_3$ from the corresponding methyl ester 2 ($R^5=CO_2CH_3$). In step 1, the methyl ester is converted to the corresponding acid ($R^5=CO_2H$) by the action of sodium hydroxide/hydrochloric acid. In step 2, the acid is converted to the corresponding acid chloride ($R^5=COCl$) by the action of oxalyl chloride. In step 3, the acid chloride is converted to the corresponding primary amide ($R^5=CONH_2$) by the action of ammonia. In step 4, the amide is converted to the corresponding nitrile 3 by the action of thionyl chloride at reflux. In step 5, the nitrile 3 is reacted with trimethyltinazide in xylene at reflux to give the corresponding trimethytin protected tetrazole 4. In step 5, 6, and 7 deprotection with acetic acid/water and reprotection with triphenylmethyl chloride/triethylamine gives the N-trityltetrazole 5 ($R^5=CN_4C(C_6H_5)3$). In step 8, bromination with N-bromosuccinimide (NBS) provides the N-trityltetrazole alkylating agent 1.

Scheme II

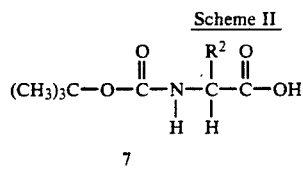

7

-continued
Scheme II

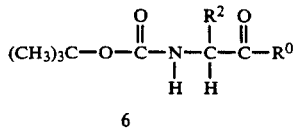

6

Synthetic Scheme II shows the preparation of N-Boc-amino ketones 6 (or aldehydes when $R^o=H$) from the corresponding N-Boc-amino acides 7. In step 1, the amino acid 7 is reacted with isobutyl chloroformate in the presence of triethylamine and subsequently with N,O-dimethylhydroxylamine to give the corresponding N-methoxy-N-methylamide 8. In step 2, the amide 8 is reacted with an organolithium reagent $R^o$-Li (or lithium aluminum hydride (LAH) when $R^o=H$) to give the desired ketone 6 (or aldehyde when $R^o=H$).

Scheme III

METHOD A:

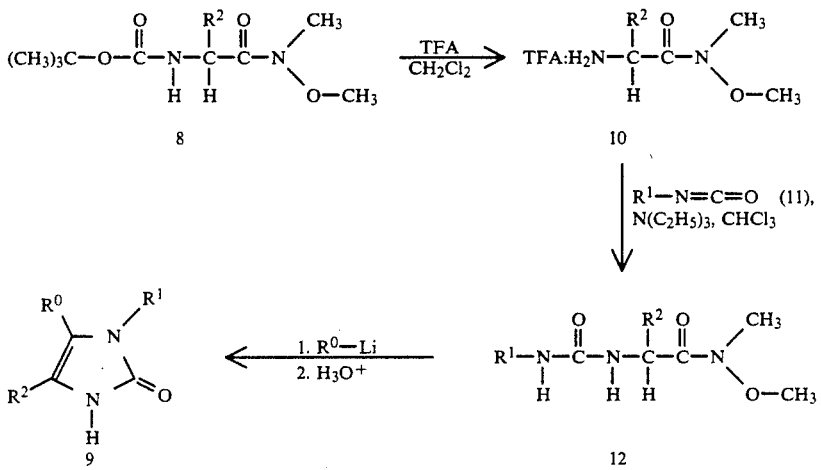

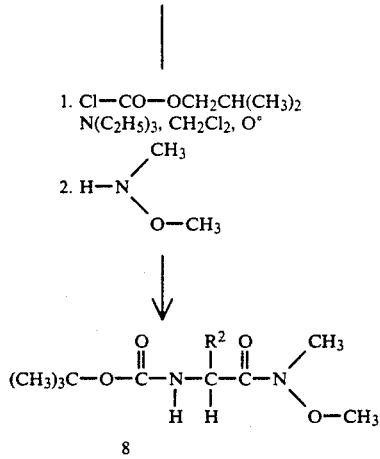

Synthetic Scheme III shows the preparation of imidazol-2-ones 9 from the corresponding amides 8 via Method A. In step 1, the protected amide 8 (prepared in Scheme II) is reacted with trifluoroacetic acid (TFA) to give the TFA salt 10 of the free amine. In step 2, the salt 10 is reacted with the appropriate isocyanate 11 in the presence of triethylamine to give the urea 12. In step 3, the urea 12 is reacted with an organolithium reagent $R^o$-Li (or lithium aluminum hydride (LAH) when $R^o=H$) and subsequently cyclized to the imidazole-2-one 9 on treatment with dilute acid during the work-up procedure.

Scheme IV

METHOD B:

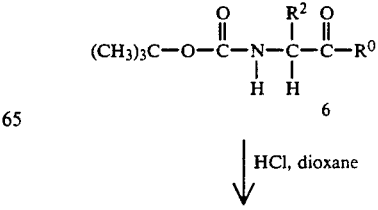

-continued
Scheme IV

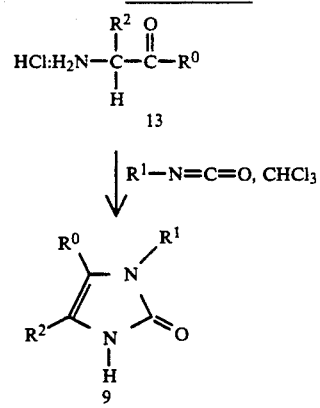

Synthetic Scheme IV shows the preparation of imidazol-2-ones 9 from the corresponding N-Boc-protected amino ketones 6 (or aldehydes when $R^o=H$) via Method B. In step 1, the carbonyl compound 6 (prepared in Scheme II) is reacted with anhydrous hydrogen chloride in dioxane to give the HCl salt 13. In step 2, the salt 13 is reacted with the appropriate isocyanate 11 in chloroform to give the imidazol-2-one 9 directly.

Scheme V

METHOD C:

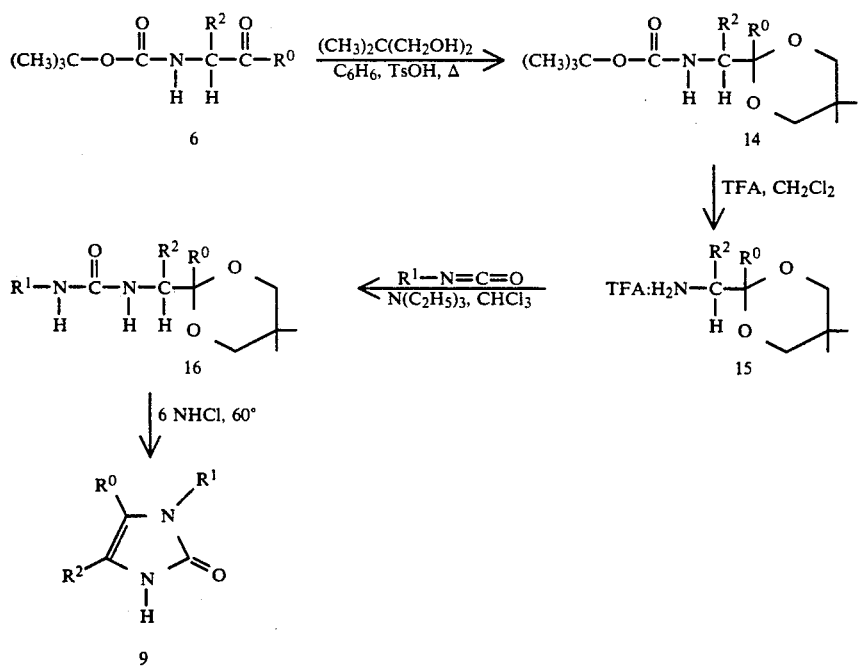

Synthetic Scheme V shows the preparation of imidazol-2-ones 9 from the corresponding N-Boc-protected amino ketones 6 (or aldehydes when $R^o=H$) via Method C. In step 1, the carbonyl compound 6 (prepared in Scheme II) is reacted with 2,2-dimethyl-1,3-propandiol to give the cyclic ketal 14. In step 2, the ketal 14 is reacted with TFA to give the TFA salt 15 of the free amine. In step 3, the salt 15 is reacted with the appropriate isocyanate 11 in the presence of triethylamine to give the urea ketal 16. In step 4, the urea ketal 16 is reacted with 6N hydrochloric acid at 60° C. to give the desired imidazol-2-one 9 directly.

Scheme VI

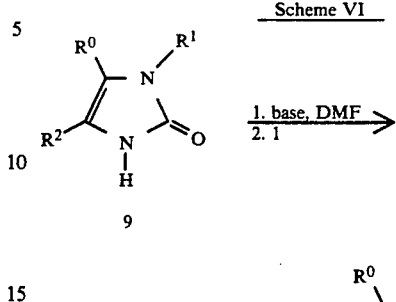

-continued
Scheme VI treated with a base, such as potassium t-butoxide, and subsequently with the alkylating agent 1 (prepared in Scheme I) to give the protected coupled imidazol-2-one In step 2, the N-trityl (triphemylmethyl) protected 18 is deprotected with acetic acid/water to give the desired angiotensin II antagonist 17.

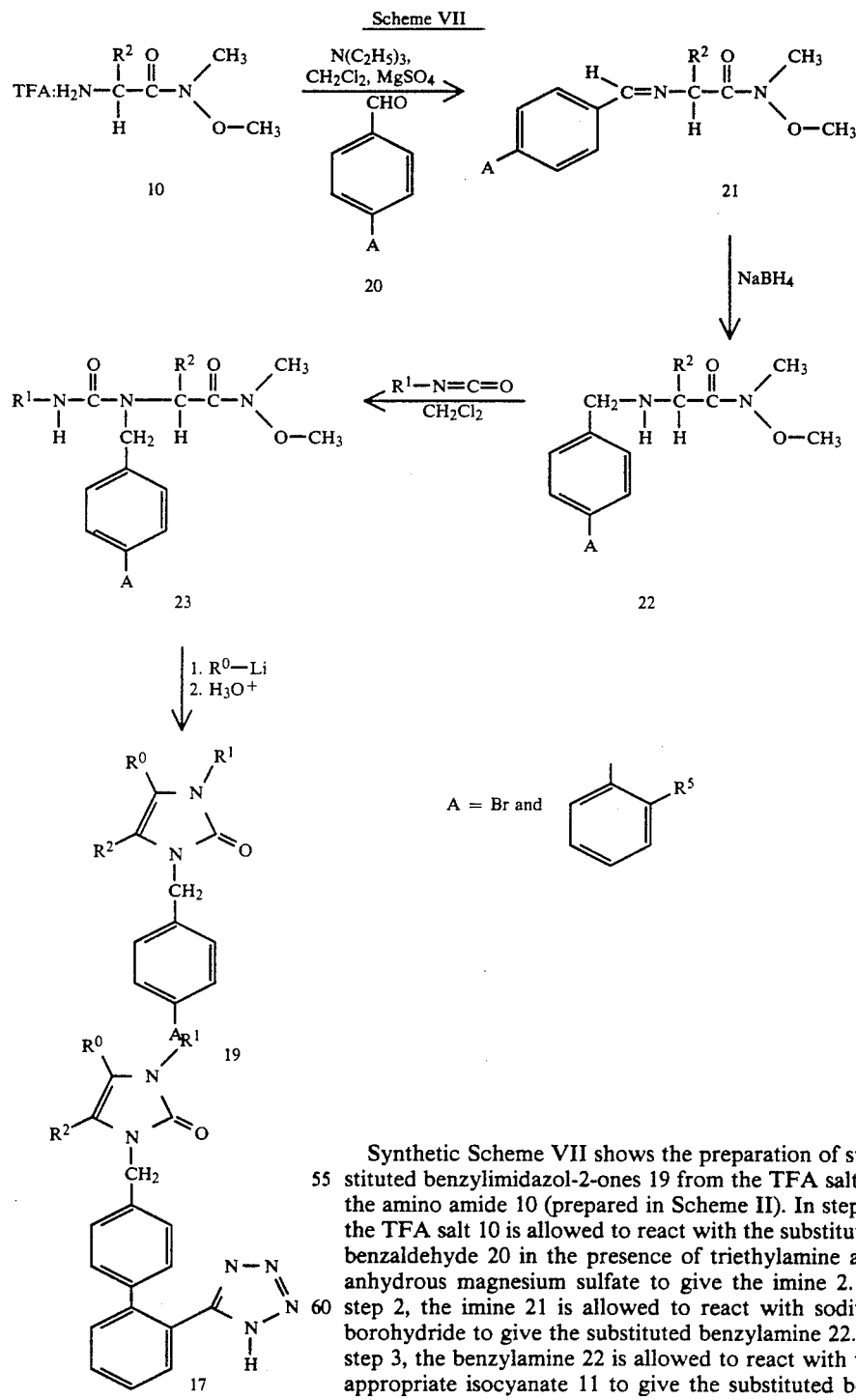

Synthetic Scheme VI shows the preparation of biphenylmethylimidazol-2-ones 17 from the parent imidazol-2-ones 9 (prepared in Scheme III, Scheme IV, or Scheme V). In step 1, the imidazol-2-one 9 is first Synthetic Scheme VII shows the preparation of substituted benzylimidazol-2-ones 19 from the TFA salt of the amino amide 10 (prepared in Scheme II). In step 1, the TFA salt 10 is allowed to react with the substituted benzaldehyde 20 in the presence of triethylamine and anhydrous magnesium sulfate to give the imine 2. In step 2, the imine 21 is allowed to react with sodium borohydride to give the substituted benzylamine 22. In step 3, the benzylamine 22 is allowed to react with the appropriate isocyanate 11 to give the substituted benzylurea 23. In step 4, the urea 23 is first allowed to react with an organolithium reagent $R^o$-Li (or lithium aluminum hydride (LAH) when $R^o$=H) and subsequently with dilute aqueous acid to give the desired substituted benzylimidazol-2-one 19.

Scheme VIII

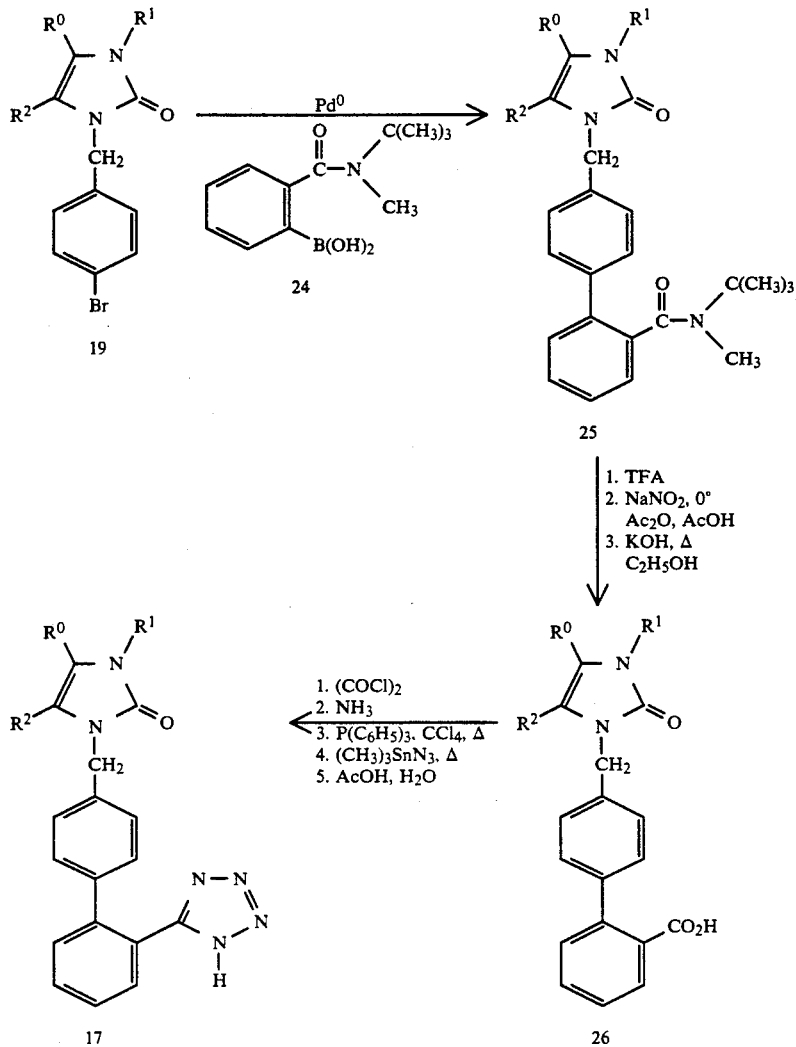

Synthetic Scheme VIII shows the preparation of biphenylmethylimidazol-2-ones 17-from 4-bromobenzylimidazol-2-ones 19 (prepared in Scheme VII). In step 1, the bromobenzylimidazol-2-one 19 is allowed to react with the boronic acid amide 24 (which can be prepared from N-t-butyl-N-methylbenzamide via ortho metalation) in the presence of a palladium catalyst, such as tetrakis(triphenylphospine) palladium, to give the biphenylmethylimidazol-2-one amide 25. In step 2, the N-t-butyl-N-methylamide 25 is allowed to react with TFA to give the N-methylamide, sodium nitrite to give the N-nitrosoamide, and ethanolic potassium hydroxide to give the biphenylmethylimidazol-2-one carboxylic acid 26. In step 3, the acid 26 is allowed to react with oxalyl chloride to give the acid chloride, anhydours ammonia to give the primary amide, triphenylphospine/carbon tetrachloride to give the nitrile, and acetic acid/water to give the desired angiotensin II antagonist 17.

The following Example contains detailed descriptions of the methods of preparation of compounds of Formula I. These detailed descriptions fall within the scope of, and serve to exemplify, the above described General Synthetic Procedures which form part of the invention. These detailed descriptions are presented for illustrative purposes only and are not intended as a restriction on the scope of the invention. All parts are by weight and temperatures are in degrees Centigrade, unless otherwise indicated.

Example 1

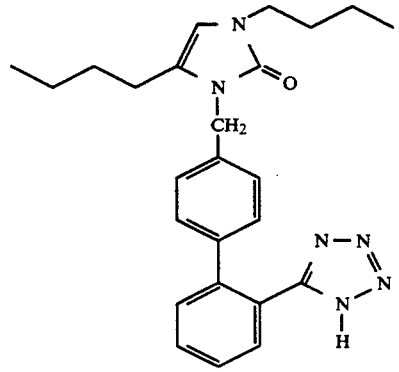

1,4-dibutyl-1,3-dihydro-3-[2'-(1H-tetrazol-5-yl)[1,1'biphenyl]-4-ylmethyl]-2H-imidazol-2-one

STEP 1

Preparation of N-Triphenylmethyl-5-2-(4'-bromomethylbiphen-2-yl)tetrazole.

A 542.5 g (2.4 mol) sample of methyl 2-(p-tolyl)benzoate (Chemo Dynamics Inc.) was dissolved in 5.5 L of ethanol and treated with 3 L (7.5 mol) of 2.5 N sodium hydroxide. The reaction was stirred overnight at ambient temperature and treated with an additional 480 ml (6.0 mol) of sodium hydroxide; stirring was continued for an additional 24 h and the ethanol removed in vacuo. The remaining solution was cooled in ice and acidified to pH 1 with hydrochloric acid which caused the product to precipitate; filtration and drying in vacuo gave 510 g (100%) of crude 2-(p-tolyl)benzoic acid: mp 145.0°–147.5° C; NMR (CDCl$_3$) δ2.40 (s, 3H), 7.17–7.28 (m, 4H), 7.35–7.45 (m, 2H), 7.51–7.59 (m, 1H), 7.90–7.97 (m, 1H). The crude acid was suspended in 1 L of toluene and slowly treated with 400 g (3.15 mol) of oxalyl chloride under nitrogen. The reaction was allowed to stir at ambient temperature for 4.5 h and concentrated in vacuo to remove excess oxalyl chloride. The residue was redissolved in 2 L of toluene and treated with 92.8 g (5.46 mol) of anhydrous ammonia. The reaction was filtered and the filtrate concentrated in vacuo producing 424 g (84%) of crude 2-(p-tolyl)benzamide: mp 128°–130° C.; NMR (CDCl$_3$) δ2.40 (s, 3H), 5.28 (br s, 1H), 5.77 (br s, 1H), 7.21–7.53 (m, 7H), 7.76–7.83 (m, 1H). The crude amide was treated with 1420 ml (19.5 mol) of thionyl chloride at reflux for 3.5 h. The reaction was filtered and the thionyl chloride removed in vacuo. The residue was dossolved in 800 ml of toluene and reconcentrated in vacuo. On standing overnight, the residue crystallized. The crystals were collected and washed with hexane to give 296 g (64%) of 2-(p-tolyl)-benzonitrile: mp 50.5°–52.0° C.; NMR (CDCl$_3$) δ2.42 (s, 3H), 7.22–7.34 (m, 2H), 7.37–7.52 (m, 3H), 7.58–7.66 (m, 1H), 7.72–7.78 (m, 1H). A 286 g (1.48 mol) sample of the crude nitrile was dissolved in 1630 mL to toluene and treated with 377 g (1.8 mol) of trimethyltinazide at reflux for 24 h. The reaction was cooled; filtration gave 600 g of crude N-trimethylstannyl-5-[2-(4'-methylbiphen-2-yl]tetrazole: mp 271°–272° C. (dec.); NMR (DMSO-d$_6$) δ0.36 (br t, J=34 Hz, 9H), 2.24 (s, 3H), 6.89–7.06 (m, 4H), 7.35–7.55 (m, 4H). The crude N-trimethylstannyl tetrazole was suspended in 4270 mL of toluene and 287 mL of anhydrous tetrahydrofuran (THF) and treated with 6.34 g (173 mol) of anhydrous hydrogen chloride at ambient temperature under nitrogen with stirring. The reaction was allowed to stand overnight and filtered; recrystallization from toluene gave 217 g (62%) of 5-[2-(4'-methylbiphen-2-yl)]tetrazole as a solid: mp 149°–152 ° C.; NMR (DMSO-d$_6$) δ2.28 (s, 3H), 6.94–7.02 (m, 2H), 7.08–7.15 (m, 2H), 7.50–7.59 (m, 2H), 7.62–7.72 (m, 2H). A 200 g (0.85 mol) sample of the tetrazole was suspended in 3.3 L of dichloromethane and treated with 262 g (0.91 mol) of triphenylmethyl chloride and 141 mL (1.0 mol) of anhydrous triethylamine. The reaction was stirred at reflux for 3 h under nitrogen, washed with water, dried (MgSO$_4$), and concentrated Recrystallization gave 338 g (83%) of N-triphenylmethyl-5-[2-4'-methylbiphen-2-yl)]tetrazole as a colorless solid: mp 170°–173° C.; NMR (CDCl$_3$) δ2.27 (s, 3H), 6.86–6.96 (m, 8H), 6.98–7.04 (m, 2H), 7.09–7.52 (m, 12H), 7.86–7.94 (m, 1H). The N-triphenylmethyl tetrazole was dissolved in 4260 mL of carbon tetrachloride and treated with 126.4 g (0.71 mol) of N-bromosuccinimide (NBS) of 11.9 g (49 mmol) of benzoyl peroxide at reflux for 3.5 h. The reaction was filtered and the solvent removed in vacuo. Recrystallization from toluene gave 277 g (59%) of N-triphenyl-methyl-5-[2-4'-bromomethylbiphen-2-yl)]tetrazole as a colorless solid: mp 140°–142° C.; NMR (CDCl$_3$) δ4.39 (s, 2H), 6.85–6.95 (m, 7H), 7.06–7.15 (m, 4H), 7.22–7.43 (m, 9H), 7.45–7.55 (m, 2H), 7.94–8.01 (m, 1H). NMR indicated that this material was only 85% pure; it contained 7% of corresponding dibromocompound (δ6.50) and 8% of starting material (δ2.27); however, no further attempts at purification were made and this mixture was used as is for the subsequent alkylation reaction.

STEP 2

Preparation of N-t-Boc-L-norleucine-N-methoxy-N-methylamide

Under nitrogen, a stirred solution of 70.25 g (0.3 mol) of N-t-Boc-norleucine and 30.8 g (0.3 mol) of triethylamine (TEA) in 750 mL of dichloromethane (DCM) at −15° C. was treated with 44.2 g (0.32 mol) of isobutyl chlorformate. After 15 min, a slurry of 32.6 g (0.33 mol) of N,O-dimethylhydroxylamine in 100 mL of DCM was added followed by 33.8 g (0.33 mol) of TEA at such a rate as to maintain the reaction temperature at −5 ° C. The reaction was stirred at −1020 C. for 1 h and then allowed to warm to ambient temperature and stir overnight. The reaction was diluted with 1 L of chloroform and washed with 1 M citric acid, NaHCO$_3$ (sat), and brine. The solution was dried (Na$_2$SO$_4$) and concentrated an vacuo to give 80.2 g of crude product as a yellow oil. Purification by silica gel chromatography (Waters Prep-500A) using ethyl acetate/hexane (75:25) gave 58.1 g (74%) of colorless product as an oil: NMR (CDCl$_3$) δ0.88 (t, J=7 Hz, 3H), 1.28–1.38 (m, 4H), 1.43 (s, 9H), 1.49–1.57 (m, 1H), 1.63–1.75 (m, 1H), 3.20 (s, 3H), 3.76 (s, 3H), 4.60–4.72 (m, 1H), 5.13 (d, J=8 Hz, 1H).

Step 3A

Preparation of 3,5-dibutylimidazol-2-one: Method A

Under nitrogen, a stirred solution of 10.0 g (36.5 mmol) of N-t-Boc-L-norleucine-N-methoxy-N-methylamide from Step 2 in 100 mL of methylene chloride at 0° C. was treated with 100 mL of trifluoroacetic acid (TFA). The reaction was allowed to warm to ambient temperature and stir. After 2 h, the reaction was concentrated in vacuo to give the TFA salt of L-norleucine-N-methoxy-N-methylamide as a viscous colorless oil: NMR (CDCl$_3$) δ0.88 (t, J=7 Hz, 3H), 1.30–1.40 (m, 4H), 1.88 (t, J=7 Hz, 2H), 3.25 (s, 3H), 3.75 (s, 3H), 4.35–4.46 (m, 1H), 7.55–7.76 (br s, 3H). Under nitrogen, the TFA salt was dissolved in 150 mL of chloroform at 0° C. and sequentially treated with 7.37 g (73 mmol) of triethylamine and 5.42 g (55 mmol) of butyl isocyanate. The reaction was allowed to warm to ambient temperature and stir overnight; concentration in vacuo provided the crude product. Purification by silica gel chromatography (Waters Prep-500A) using ethyl acetate gave 9.0 g (90% from N-t-Boc-L-norleucine-N-methoxy-N-methylamide) of the N-butylurea of L-norleucine-N-methoxy-N-methylamide as a colorless oil: NMR (CDCl$_3$) δ0.83–0.95 (m, 6H), 1.25–1.47 (m, 8H), 1.48–1.60 (m, 1H), 1.63–1.75 (m, 1H), 3.02–3.26 (m, 2H), 3.21 (s, 3H), 3.84 (s, 3H), 4.82–4.93 (m, 1H). Under nitrogen, a 9.0 g (32.5 mmol) sample of the urea was dissolved in 150 mL of anhydrous diethyl ether; the solution was cooled to 0° C. and slowly treated with 41 mL (41 mmol, 1.25 equiv) of a 1.0 M solution of lithium aluminum hydride (LAH) in ether. The reaction was allowed to warm to ambient temperature and stir overnight. A solution of 7.87 g (58 mmol) of potassium bisulfate in 165 mL of water was added cautiously and the reaction stirred for 4 h. The reaction mixture was transferred to a separatory funnel and the phases separated. The aqueous phase was extracted 3 times with additional ether. The combined ether extracts were washed 3 times each with 3N hydrochloric acid, saturated sodium bicarbonate, and brine. The ether extracts were then dried (MgSO$_4$) and concentrated in vacuo to give 5.40 (85%) of 3,5-dibutylimidazol-2-one as a viscous colorless oil which solidified on storage in the refrigerator: NMR (CDCl$_3$) δ0.91 (t,=7 Hz, 3H), 0.93 (t, J=7 Hz, 3H), 1.28–1.41 (m, 4H), 1.47–1.65 (m, 4H), 2.36 (td, J=7 and 1 Hz, 2H), 3.55 (t, J=7 Hz, 2H), 5.84 (t, J=1 Hz, 1H), 9.78 (br s, 1H).

STEP 3B

Preparation of 3,5-dibutylimidazol-2-one: Method B.

Under nitrogen, a stirred solution of 67.8 g (0.26 mol) of N-t-Boc-norleucine-N-methoxy-N-methylamide from Step 2 in 550 mL of anhydrous diethyl ether at 0° C. was treated with 145 mL (0.145 mol) of 1 M solution of lithium aluminum hydride (LAH) in ether over a 30 min period. The reaction was allowed to stir for an additional 30 min and then was quenched with the addition of 10 mL of ethyl acetate. The reaction was diluted with 1 L of cold water to which 63 g (0.46 mol) of potassium hydrogen sulfate had been added and the mixture stirred vigorously for 15 min. The phases were separated and the aqueous phase extracted 4 times with ether; the extracts were combined, washed 3 times with 3 N hydrochloric acid, once with saturated sodium bicarbonate, and once with brine, dried (Na$_2$SO$_4$), and concentrated in vacuo to give 47.6 g (84%) of N-t-Boc-L-norleucinal as a colorless waxy solid: NMR (CDCl$_3$) δ0.91 (t, J=7 Hz, 3H), 1.34–1.41 (m, 4H), 1.46 (s, 9H), 1.55–1.64 (m, 1H), 1.80–1.95 (m, 1H), 4.16–4.30 (m, 1H), 5.07–5.15 (m, 1H), 9.59 (s, 1H). Under nitrogen, a stirred solution of 10.0 g (46.4 mmol) of this material in 10 mL of dioxane (anhydrous) at 0° C. was treated with 120 mL (480 mmol) of 4 N hydrogen chloride in dioxane over a 10 min period. The reaction was allowed to stir at 0° C. for an additional 20 min after the addition was complete and then concentrated in vacuo. The residue was dissolved in 200 mL of chloroform and treated with 77.4 g (0.78 mol) of butyl isocyanate. The mixture was stirred at ambient temperature for 24 h, stirred at 40° C. for 24 h, and concentrated in vacuo. Purification of the reddish colored residue by silica gel chromatography (Harrison Chromatotron) using ethyl acetate/2-propanol (95:5) gave 160 mg (1.7% from N-t-Boc-L-norleucinal) of 3,5-dibutylimidazol-2-one as an yellowish oil: NMR (CDCl$_3$) δ0.91 (t, J=7 Hz, 3H), 0.93 (t, J=7 Hz, 3H), 1.28–1.41 (m, 4H), 1.47–1.65 (m, 4H), 2.36 (td, J=7 and 1 Hz, 2H), 3.55 (t, J=7 Hz, 2H), 5.84 (t, J=1 Hz, 1H), 9.78 (br s, 1H); MS (FAB) m/e (rel intensity) 197 (100), 153 (12), 141 (12), 125 (8), 111 (7).

STEP 3C

Preparation of 3,5-dibutylimidazol-2-one: Method C.

Under nitrogen, a solution of 27.0 g (125 mmol), 39.1 g (376 mmol) of 2,2-dimethyl-1,3-propanediol, and 1.18 g (6.2 mmol) of p-toluenesulfonic acid monohydrate in 220 mL of benzene was stirred at reflux for 22 h over a Dean-Stark trap. The reaction was cooled, diluted with 300 mL of ethyl acetate, washed sequentially with saturated sodium bicarbonate and brine, dried (Na$_2$SO$_4$), and concentrated in vacuo to give 38.27 g of crude ketal which was a red oil: NMR (CDCl$_3$) δ0.71 (s, 3H), 0.89 (t, J=7 Hz 3H), 1.16 (s, 3H), 1.20–1.52 (m, 5H), 1.45 (s, 9H), 1.58–1.72 (m, 1H), 3.35–3.46 (m, 2H), 3.56–3.63 (m, 2H), 4.43 (s, 1H), 4.66 (d, J=9 Hz, 1H). Under nitrogen, a 38.2 g sample of the crude ketal was dissolved in 200 mL of methylene chloride; the solution was cooled to 0° C. and treated with 200 mL of trifluoracetic acid. The reaction was allowed to warm to ambient temperature and stir for 2 h. Concentration in vacuo gave the crude TFA salt of the free amino ketal as a red viscous oil: NMR (CDCl$_3$) δ0.75 (s, 3H), 0.90 (t, J=7 Hz, 3H), 1.13 (s, 3H), 1.27–1.42 (m, 4H), 1.60–1.82 (m, 2H), 3.27–3.38 (m, 1H), 3.42–3.52 (m, 2H), 3.63–3.72 (m, 2H), 4.58 (d, J=3 Hz, 1H), 7.1–7.5 (br s, 3H). Under nitrogen, the crude TFA salt was redissolved in 100 mL of methylene chloride and treated with 264 g (2.66 mol) of butyl isocyanate. The reaction was stirred at ambient temperature for 17 h. The reaction was concentrated in vacuo to give the crude N-butyl urea of the ketal as a red oil. Purification of a small sample by silica gel chromatography (Harrison Chromatotron) using ethyl acetate/hexane (1:1) gave the pure N-butyl urea as a pale yellow oil: NMR (CDCl$_3$) δ0.71 l (s, 3H), 0.89 (t, J=7 Hz, 3H), 0.92 (t, J=7 Hz, 3H), 1.16 (s, 3H), 1.23–1.54 (m, 9H), 1.61–1.75 (m, 1H), 3.09–3.21 (m, 2H), 3.37–3.46 (m, 2H), 3.56–3.64 (m, 2H), 3.68–3.79 (m, 1H), 4.32–4.47 (br s, 1H), 4.42 (d, J=3 Hz, 1H). Under nitrogen, a solution of the crude N-butyl urea ketal in 1 L of 1,4-dioxane was treated with 1 L of 6 N hydrochloric acid. The reaction was allowed to stir at ambient temperature for 16 h and then warmed to 60° C. and stirred for an additional 24 h. The reaction was concentrated in vacuo; the residue was treated with ethyl acetate and filtered. The ethyl acetate solution was dried (MgSO$_4$) and concentrated in vacuo to give the crude product. Purification by silica gel chromatography (Waters Prep-500A) using methylene chloride/2-propanol (95:5) gave 4.95 g (20% from N-t-Boc-L-norleucinal) of 3,5-dibutylimidazol-2-one as a pale yellow oil: NMR (CDCl$_3$) δ0.91 (t, J=7 Hz, 3H), 1.28–1.41 (m, 4H), 1.47–1.65 (m, 4H), 2.36 (td, J=7 and 1 Hz, 2H), 3.55 (t, J=7 Hz, 2H), 5.84 (t, J=1 Hz, 1H), 9.78 (br s, 1H).

STEP 4

Preparation of 1,4-dibutyl-1,3-dihydro-3-2'-(1H-tetrazol-5-yl)[1,1'-biphenyl]-4-ylmethyl]-2H-imidazol-2-one Under nitrogen, a stirred suspension of 0.92 mmol of sodium hydride in 1 mL of dimethylformamide (DMF) at 0° C. was slowly treated with a solution of 150 mg (0.76 mmol) of 3,5-dibutylimidazol-2-one from Step 3 in 1 mL of DMF. The reaction was stirred for 20 min prior to the portionwise addition of 429 mg (0.77 mmol) of solid N-triphenylmethyl-5-[2-(4'bromomethylbiphenyl-2-yl)]tetrazole from Step 1. The reaction was stirred at 0° C. for 3.5 h and then allowed to warm to ambient temperature and stir overnight. The reaction was concentrated in vacuo and the residue dissolved in ethyl acetate; the resulting solution was washed with water followed by brine, dried (MgSO$_4$), and reconcentrated to give a yellowish-orange oil. Purification by silica gel chromatography (Harrison Chromatotron) using ethyl acetate/chloroform/hexane (25:25:50) gave 157 mg (31%) of colorless N-triphenylmethyl protected product: NMR (CDCl$_3$) δ 0.83 (t, J=7 Hz, 3H), 0.95 (t, J=7 Hz, 3H), 1.16-1.28 (m, 2H), 1.29-1.45 (m, 4H), 1.58-1.73 (m, 2H), 2.12 (t, J=7 Hz, 2H), 3.53 (t, J=7 Hz, 2H), 4.73 (s, 2H), 5.87 (s, 1H), 6.85-7.15 (m, 11H), 7.21-7.38 (m, 9H), 7.40-7.52 (m, 2H), 7.86-7.92 (m, 1H). A 150 mg (0.22 mmol) sample of this material was dissolved in 4 mL of acetic acid to which 0.44 mL of water was added and allowed to stir at ambient temperature for 20 h. All volatiles were removed in vacuo and the residue purified by reverse phase chromatography (Waters Delta-Prep-3000) using isocratic acetonitrile/water (40:60) (0.05% TFA). The acetonitrile was removed in vacuo and aqueous layer extracted with chloroform. The extracts were combined, dried (MgSO$_4$), and concentrated in vacuo to give 51 mg (53%) of colorless 1,4-dibutyl-1,3-dihydro-3-[2'-(1H-tetrazol-5-yl)[1,1'biphenyl]-4-ylmethyl]-2H-imidazol-2-one: mp 153°-155° C. (dec); NMR (CDCl$_3$) δ0.84 (t, δ=7 Hz, 3H), 0.86 (t, J=7 Hz, 3H), 1.14-1.59 (m, 8H), 2.23 (t, J=7 Hz, 2H), 3.47 (t, J=7 Hz, 2H), 4.67 (s, 2H), 5.88 (s, 1H), 6.95-7.13 (m, 4H), 7.38-7.63 (m, 3H), 7.81-7.89 (m, 1H); MS (FAB) m/e (rel intensity) 431 (22), 207 (100), 192 (26); HRMS. Calc'd for M+H: 431.2559. Found: 431.2550.

BIOLOGICAL EVALUATION

Assay A: Angiotensin II Binding Activity

Compounds of the invention were tested for ability to bind to the smooth muscle angiotensin II receptor using a rat uterine membrane preparation. Angiotensin II (AII) was purchased from Peninsula Labs. $^{125}$I-angiotensin II (specific activity of 2200 Ci/mmol) was purchased from Du Pont-New England Nuclear. Other chemicals were obtained from Sigma Chemical Co. This assay was carried out according to the method of Douglas et al [*Endocrinology*, 106, 120-124 (1980)]. Rat uterine membranes were prepared from fresh tissue. All procedures were carried out at 4° C. Uteri were stripped of fat and homogenized in phosphate-buffered saline at pH 7.4 containing 5 mM EDTA. The homogenate was centrifuged at 1500×g for 20 min., and the supernatant was recentrifuged at 100,000×g for 60 min. The pellet was resuspended in buffer consisting of 2 mM EDTA and 50 mM Tris-HCl (pH 7.5) to a final protein concentration of 4 mg/ml. Assay tubes were charged with 0.25 ml of a solution containing 5 mM MgCl$_2$, 2 mM EDTA, 0.5% bovine serum albumin, 50 mM Tris-HCl, pH 7.5 and $^{125}$I-AII (approximately 105 cpm) in the absence or in the presence of unlabelled ligand. The reaction was initiated by the addition of membrane protein and the mixture was incubated at 25° C. for 60 min. The incubation was terminated with ice-cold 50 mM Tris-HCl (pH 7.5) and the mixture was filtered to separate membrane-bound labelled peptide from the free ligand. The incubation tube and filter were washed with ice-cold buffer. Filters were assayed for radioactivity in a Micromedic gamma counter. Nonspecific binding was defined as binding in the presence of 10 μM of unlabelled AII. Specific binding was calculated as total binding minus nonspecific binding. The receptor binding affinity of an AII antagonist compound was indicated by the concentration (IC$_{50}$) of the tested AII antagonist which gives 50% displacement of the total specifically bound $^{125}$I-AII from the high affinity AII receptor. Binding data were analyzed by a nonlinear least-squares curve fitting program. The compound of Example 1 was found to have IC$_{50}$ value of 6.4 nM.

Assay B: In Vitro Vascular Smooth Muscle-Response for AII

The compounds of the invention were tested for antagonist activity in rabbit aortic rings. Male New Zealand white rabbits (2-2.5 kg) were sacrificed using an overdose of pentobarbital and exsanguinated via the carotid arteries. The thoracic aorta was removed, cleaned of adherent fat and connective tissue and then cut into 3-mm ring segments. The endothelium was removed from the rings by gently sliding a rolled-up piece of filter paper into the vessel lumen. The rings were then mounted in a water-jacketed tissue bath, maintained at 37° C., between moveable and fixed ends of a stainless steel wire with the moveable end attached to an FT03 Grass transducer coupled to a Model 7D Grass Polygraph for recording isometric force responses. The bath was filled with 20 ml of oxygenated (95% oxygen/5% carbon dioxide) Krebs solution of the following composition (mM): 130 NaCl, 15 NaHCO$_3$, 15 KCl, 1.2 NaH$_2$PO$_4$, 1.2 MgSO$_4$, 2.5 CaCl$_2$, and 11.4 glucose. The preparations were equilibrated for one hour before approximately one gram of passive tension was placed on the rings. Angiotensin II concentration-response curves were then recorded ($3 \times 10^{-10}$ to $1 \times 10^{-5}$ M). Each concentration of AII was allowed to elicit its maximal contraction, and then rechallenging with a higher concentration of AII. Aorta rings were exposed to the test antagonist at $10^{-5}$ M for 5 minutes before challenging with AII. Adjacent segments of the same aorta ring were used for all concentration-response curves in the presence or absence of the test antagonist. The effectiveness of the test compound was expressed in terms of pA$_2$ values and were calculated according to H. O. Schild [*Br. J. Pharmacol Chemother.*, 2, 189-206 (1947)]. The pA$_2$ value is the concentration of the antagonist which increases the EC$_{50}$ value for AII by a factor of two. Each test antagonist was evaluated in aorta rings from two rabbits. The compound of Example 1 was found to have a pA$_2$ value of 8.6.

Assay C: In Vivo Intragastric Pressor Assay Response for AII Antagonists

Male Sprague-Dawley rats weighing 225-300 grams were anesthetized with methohexital (30 mg/kg, i.p.) and catheters were implanted into the femoral artery and vein. The catheters were tunneled subcutaneously to exit dorsally, posterior to the head and between the scapulae. The catheters were filled with heparin (1000 units/ml of saline). The rats were returned to their cage and allowed regular rat chow and water ad libitum. After full recovery from surgery (3-4 days), rats were placed in Lucite holders and the arterial line was connected to a pressure transducer. Arterial pressure was recorded on a Gould polygraph (mmHg). After 1-2 hours of stable baseline recording, the intravenous infusion of angiotensin II (50 ng/kg/min) was given at a rate of 0.0096 ml/min. After allowing one hour for pressure to stabilize, the test compound (suspended in 0.5% methylcellulose in water) was administered by gavage. The volume administered was 2 ml/kg body weight. Arterial pressure was monitored for 5 hours post-dosing. The angiotensin II infusion was then discontinued and pressure was allowed to reach a stable recovery level. Percent inhibition (%I) of the angiotensin II pressor response was calculated from the difference in pressure at a given timepoint post-dosing with the test compound and the antiotensin II-infused pressure, divided by the difference in pressure with and without the angiotensin II infusion; this value was multiplied by 100. Duration of action of a test compound was defined as the time taken for pressure to return to angiotensin II-infused baseline levels after compound administration. One compound at one dose was tested in each rat. The compound of Example I was tested in two rats. Results are reported in Table I.

TABLE I

Blood Pressure Response of Angiotensin II Infused Rats Following Treatment With Angiotensin II Antagonist of the Invention

| DOSE | BASELINE BLOOD PRESSURE | BLOOD PRESSURE AFTER AII ADMINISTRATION (mmHg) | | ADMINISTRATION OF EX. #1 COMPOUND | | | | | | |
|---|---|---|---|---|---|---|---|---|---|---|
| | | | | 10 | 20 | 30 | 40 | 50 | 60 | 90 |
| 10 | 116 | 168 | mmHg: | 165 | 163 | 159 | 146 | 144 | 140 | 123 |
| | | | % I: | 6 | 9 | 17 | 41 | 45 | 54 | 86 |
| 10 | 126 | 175 | mmHg: | 166 | 155 | 147 | 147 | 132 | 132 | 128 |
| | | | % I: | 19 | 40 | 58 | 58 | 89 | 88 | 96 |

| DOSE | BASELINE BLOOD PRESSURE | BLOOD PRESSURE AFTER AII ADMINISTRATION (mmHg) | | ADMINISTRATION OF EX. #1 COMPOUND | | | | | | |
|---|---|---|---|---|---|---|---|---|---|---|
| | | | | 120 | 150 | 180 | 210 | 240 | 270 | 300 |
| 10 | 116 | 168 | mmHg: | 124 | 119 | 117 | 113 | 115 | 117 | 117 |
| | | | % I: | 85 | 93 | 96 | 106 | 102 | 96 | 97 |
| 10 | 126 | 175 | mmHg: | 125 | 128 | 127 | 127 | 131 | 130 | 133 |
| | | | % I: | 103 | 97 | 97 | 98 | 89 | 92 | 87 |

[1]Values are mean arterial pressure, MAP (mmHg) and % inhibition, % I, of the AII pressor response.

Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A therapeutic method for treating a glaucoma disorder mediated by angiotensin II receptors, said method comprising administering to a subject susceptible to or afflicted with said disorder a therapeutically-effective amount of a compound of Formula I:

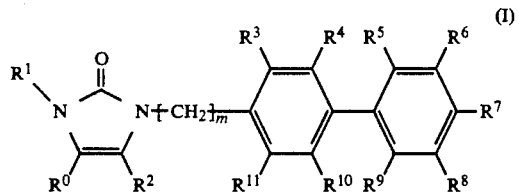

wherein m is one; wherein $R^1$ is selected from methyl; ethyl, n-propyl, isopropyl, n-butyl, sec-butyl, isobutyl, tert-butyl, 4-metylbutyl, n-pentyl, neopentyl, phenyl, benzyl, phenethyl, cyclohexyl, cyclohexyl-methyl, cyclohexylethyl, cyclohexanoyl, 1-oxo-2-cyclohexylethyl, benzoyl, 1-oxo-2-phenethyl, 1-oxoethyl, 1-oxopropyl, 1-oxobutyl, 1-oxopentyl, 2-butenyl, 3-butenyl, 2-butynyl, 3-butynyl and 2-hydroxybutyl; wherein $R^0$ is selected from hydrido, methyl, ethyl, fluoro, chloro, monofluoromethyl, difluoromethyl, trifluoromethyl, formyl, carboxyl, dimethoxymethyl, 1,1-dimethoxybutyl, 1,1-difluoroethyl and 1,1-difluoropropyl;
wherein $R^2$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, cyclohexylethyl, 2-butenyl, 3-butenyl, 2-butynyl, 3-butynyl, propylthio, butylthio and 2-hydroxybutyl; wherein each of $R^3$ through $R^{11}$ is hydrido with the proviso that at least one of $R^5$, $R^6$, $R^8$ and $R^9$ is an acidic group selected from COOH and

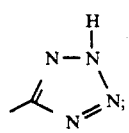

or a tautomer or a stereoisomer thereof or a pharmaceutically-acceptable salt thereof.

2. The method of claim 4 wherein m is one; wherein $R^1$ is selected from methyl, ethyl, n-propyl, isopropyl, n-butyl, sec-butyl, isobutyl, tertbutyl, 4-methylbutyl, n-pentyl, neopentyl, phenyl, benzyl, phenethyl, cyclohexyl, cyclohexylmethyl, cyclohexylethyl, cyclohexanoyl, 1-oxo-2-cyclohexylethyl, benzoyl, 1-oxo-2-phenethyl, 1-oxopropyl, 1-oxobutyl, 1-oxopentyl and 2-hydroxybutyl; wherein $R^0$ is selected from hydrido, methyl, ethyl, fluoro, chloro, monofluoromethyl, difluoromethyl, trifluoromethyl, 1,1-difluoroethyl and 1,1-difluoropropyl;
wherein $R^2$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, cyclohexylethyl, 2-butenyl, 3-butenyl, 2-butynyl, 3-butynyl, propylthio, butylthio and 2-hydroxybutyl; wherein each of $R^3$, $R^4$, $R^6$, $R^7$, $R^8$, $R^{10}$ and $R^{11}$ is hydrido; wherein one of $R^5$ and $R^9$ is hydrido and the other of $R^5$ and $R^9$ is an acidic group selected from COOH and

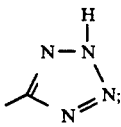

or a tautomer or a stereoisomer thereof or a pharmaceutically-acceptable salt thereof.

3. The method of claim 2 wherein m is one; wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, cyclohexylethyl, cyclohexanoyl, 1-oxo-2-cyclohexylethyl, benzoyl, 1-oxo-2-phenethyl, 1-oxopropyl, 1-oxobutyl, 1-oxopentyl and 2-hydroxybutyl; wherein $R^0$ is selected from hydrido, methyl, fluoro, chloro, monofluoromethyl, difluoromethyl, trifluoromethyl, formyl, carboxyl and dimethoxymethyl; wherein $R^2$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, cyclohexylethyl, 2-butenyl, 3-butenyl, 2-butynyl, 3-butynyl, propylthio, butylthio and 2-hydroxybutyl; wherein each of $R^3$, $R^4$, $R^6$, $R^7$, $R^8$, $R^{10}$ and $R^{11}$ is hydrido; with the proviso that at least one of $R^5$ and $R^9$ must be selected from COOH and

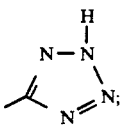

or a tautomer or a stereoisomer thereof or a pharmaceutically-acceptable salt thereof.

4. The method of claim 3 wherein m is one; wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, cyclohexylethyl, cyclohexanoyl, 1-oxo-2-cyclohexylethyl, benzoyl, 1-oxo-2-phenethyl, 1-oxopropyl, 1-oxobutyl, 1-oxopentyl and 2-hydroxybutyl; wherein $R^0$ is selected from hydrido, methyl, fluoro, chloro, monofluoromethyl, difluoromethyl, trifluoromethyl, formyl, carboxyl and dimethoxymethyl; wherein $R^2$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, cyclohexylethyl, 2-butenyl, 3-butenyl, 2-butynyl, 3-butynyl, propylthio, butylthio and 2-hydroxybutyl; wherein each of $R^3$, $R^4$, $R^6$, $R^7$, $R^8$, $R^{10}$ and $R^{11}$ is hydrido; wherein one of $R^5$ and $R^9$ is hydrido and the other of $R^5$ and $R^9$ is an acidic group selected from $CO_2H$ and

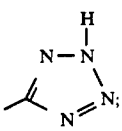

or a tautomer or a stereoisomer thereof or a pharmaceutically-acceptable salt thereof.

5. The method of claim 4 wherein said compound is of Formula II:

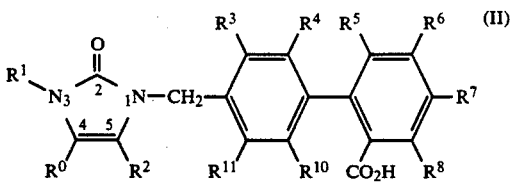

wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, cyclohexylethyl, cyclohexanoyl, 1-oxo-2-cyclohexylethyl, benzoyl, 1-oxo-2-phenethyl, 1-oxopropyl, 1-oxobutyl, 1-oxopentyl and 2-hydroxybutyl; wherein $R^0$ is selected from hydrido, methyl, fluoro, chloro, monofluoromethyl, difluoromethyl, trifluoromethyl, formyl, carboxyl and dimethoxymethyl wherein $R^2$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, cyclohexylethyl, 2-butenyl, 3-butenyl, 2-butynyl and 3-butynyl; wherein each of $R^3$, $R^4$, $R^5$, $R^6$, $R^8$, $R^{10}$ and $R^{11}$ is hydrido; or a tautomer or a stereoisomer thereof or a pharmaceutically-acceptable salt thereof.

6. The method of claim 5 wherein said compound is selected from compounds and the tautomers and stereoisomer thereof, and their pharmaceutically-acceptable salts, of the group consisting of 4'-[(3-propyl-5-butyl-2,3-dihydro-2-oxo-1H-imidazol-1-yl)methyl][1,1'-biphenyl]-2-carboxylic acid;
4'-[(3,5-dibutyl-2,3-dihydro-2-oxo-1H-imidazol-1-yl)methyl](1,1'-biphenyl]-2-carboxylic acid;
4'-[(3-(2-phenylethyl)-5-butyl-2,3-dihydro-2-oxo-1H-imidazol-1-yl)methyl][1,1'-biphenyl]-2-carboxylic acid;
4'-[(3,5-dipropyl-2,3-dihydro-2-oxo-1H-imidazol-1-yl)methyl][1,1'-diphenyl]-2-carboxylic acid;
4'-[(3-butyl-5-propyl-2,3-dihydro-2-oxo-1H-imidazol-1-yl)methyl][1,1'-biphenyl]-2-carboxylic acid;
4'-[(3-(2-phenylethyl)-5-propyl-2,3-dihydro-2-oxo-1H-imidazol-1-yl)methyl][1,1'-biphenyl]-2-carboxylic acid;
4'-[(3-butyl-5-ethyl-2,3-dihydro-2-oxo-1H-imidazol-1-yl)methyl][1,1'-biphenyl]-2-carboxylic acid;
4'-[(3-butyl-5-secbutyl-2,3-dihydro-2-oxo-1H-imidazol-1-yl)methyl][1,1'-biphenyl]-2-carboxylic acid;
4'-[(3-butyl-5-isobutyl-2,3-dihydro-2-oxo-1H-imidazol-1-yl)methyl][1,1'-biphenyl]-2-carboxylic acid;
4'-[(3-butyl-5-(2-butenyl)-2,3-dihydro-2-oxo-1H-imidazol-1-yl)methyl][1,1'-biphenyl]-2-carboxylic acid;
4'-[(3-butyl-4-chloro-5-propyl-2,3-dihydro-2-oxo-1H-imidazol-1-yl)methyl][1,1'-biphenyl]-2-carboxylic acid;
4'-[(3-butyl-4-formyl-5-propyl-2,3-dihydro-2-oxo-1H-imidazol-1-yl)(methyl)[1,1'-biphenyl]-2-carboxylic acid;
4'-[(3-butyl-4-dimethoxymethyl-5-propyl-2,3-dihydro-2-oxo-1H-imidazol-1-yl)methyl][1,1'-biphenyl]-2-carboxylic acid;
4'-[(3-butyl-4-methyl-5-propyl-2,3-dihydro-2-oxo-1H-imidazol-1-yl)methyl][1,1'-biphenyl]-2-carboxylic acid;
4'-[(3-butyl-4-fluoromethyl-5-propyl-2,3-dihydro-2-oxo-1H-imidazol-1-yl)methyl[]1,1'-biphenyl-2-carboxylic acid,
4'-[(3-butyl-4-difluoromethyl-5-propyl-2,3-dihydro-2-oxo-1H-imidazol-1-yl)methyl)[]1,1'-biphenyl]-2-carboxylic acid;
4'-[(3-butyl-4-trifluoromethyl-5-propyl-2,3-dihydro-2-oxo-1H-imidazol-1-yl)methyl][1,1'-biphenyl]-2-carboxylic acid;
4'-[(3-propyl-4-carboxy-5-butyl-2,3-dihydro-2-oxo-1H-imidazol-1-yl)methyl][1,1'-biphenyl]-2-carboxylic acid;
4'-[(3,5-dibutyl-4-carboxy-2,3-dihydro-2-oxo-1H-imidazol-1-yl)methyl][1,1'-biphenyl]-2-carboxylic acid;
4'-[(3,5-dipropyl-4-carboxy-2,3-dihydro-2-oxo-1H-imidazol-1-yl)methyl]1,1'-biphenyl]-2-carboxylic acid; and
4'-[(3-butyl-4-carboxy-5-propyl-2,3-dihydro-2-oxo-1H-imidazol-1-yl)methyl][1,1'-biphenyl]-2-carboxylic acid.

7. The method of claim 4, wherein said compound is Formula III:

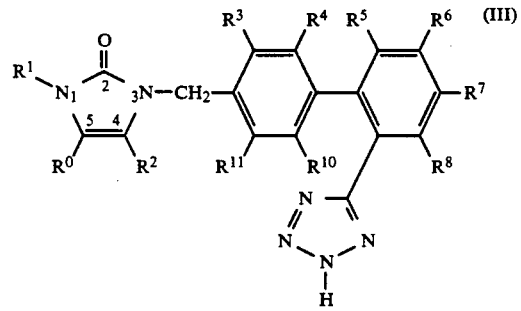

wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, cyclohexylethyl, cyclohexanoyl, 1-oxo-2-cyclohexylethyl, benzoyl, 1-oxo-2-phenethyl, 1-oxopropyl, 1-oxobutyl, 1-oxopentyl and 2-hydroxybutyl; wherein $R^0$ is selected from hydrido, methyl, fluoro, chloro, monofluoromethyl, difluoromethyl, trifluoromethyl, formyl, carboxyl and dimethoxymethyl; wherein $R^2$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, cyclohexylethyl, 2-butenyl, 3-butenyl, 2-butynyl and 3-butynyl; wherein each of $R^3$, $R^4$, $R^5$, $R^6$, $R^7$, $R^8$, $R^{10}$ and $R^{11}$ is hydrido; or a tautomer or a stereoisomer thereof or a pharmaceutically-acceptable salt thereof.

8. The method of claim 7 wherein said compound is selected from compounds and the tautomers and stereoisomers thereof, and their pharmaceutically-acceptable salts, of the group consisting of 1-ethyl-4-butyl-1,3-dihydro-3-[2'-(1H-tetrazol-5-yl)[1,1'-biphenyl]-4-ylmethyl]-2-H-imidazol-2-one;
1-propyl-4-butyl-1,3-dihydro-3-[2'-(1H-tetrazol-5-yl)[1,1'-biphenyl]-4-ylmethyl]-2H-imidazol-2-one;
1-isopropyl-4-butyl-1,3-dihydro-3-[2'-(1H-tetrazol-5-yl)[1,1'-biphenyl]-4-ylmethyl]-2H-imidazol-2-one;
1,4-dibutyl-1,3-dihydro-3-[2'-(1H-tetrazol-5-yl)[1,1-biphenyl]'-4-ylmethyl]-2H-imidazol-2-one;

1-secbutyl-4-butyl-1,3-dihydro-3-[2'-(1H-tetrazol-5-yl)[1,1'-biphenyl]-4-ylmethyl]-2H-imidazol-2-one;
1-isobutyl-4-butyl-1,3-dihydro-3-[2'-(1H-tetrazol-5-yl)[1,1'-biphenyl]-4-ylmethyl]-2H-imidazol-2-one;
1-tertbutyl-4-butyl-1,3-dihydro-3-[2'-(1H-tetrazol-5-yl)[1,1'-biphenyl]-4-ylmethyl9 -2H-imidazol-2-one;
1-pentyl-4-butyl-1,3-dihydro-3-[2'-(1H-tetrazol-5-yl)[1,1'-biphenyl]-4-ylmethyl]-2H-imidazol-2-one;
1-isopentyl-4-butyl-1,3-dihydro-3-[2'-(1H-tetrazol-5-yl)[1,1'-biphenyl]-4-ylmethyl]-2H-imidazol-2-one;
1-cyclohexyl-4-butyl-1,3-dihydro-3-[2'-(1H-tetrazol-5-yl)[1,1'-biphenyl]-4-ylmethyl]-2H-imidazol-2-one;
1-cyclohexylmethyl-4-butyl-1,3-dihydro-3-[2'-(1H-tetrazol-5-yl)[1,1'-biphenyl]-4-ylmethyl)-2-H-imidazol-2-one;
1-(2-cyclohexylethyl)-4-butyl-1,3-dihydro-3-[2'-(1H-tetrazol-5-yl)[1,1'-biphenyl]-4-ylmethyl]-2H-imidazol-2-one;
1-phenyl-4-butyl-1,3-dihydro-3-[2'-(1H-tetrazol-5-yl)[1,1'-biphenyl]-4-ylmethyl]-2H-imidazol-2-one;
1-phenylmethyl-4-butyl-1,3-dihydro-3-[2'-(1H-tetrazol-5-yl)[1,1'-biphenyl]-4-ylmethyl]-2H-imidazol-2-one;
1-(2-phenylmethyl)-4-butyl-1,3-dihydro-3-[2'-(1H-tetrazol-5-yl)[1,1'-biphenyl]-4-ylmethyl)-2H-imidazol-2-one;
1-ethyl-4-propyl-1,3-dihydro-3-[2'-(1H-tetrazol-5-yl)[1,1'-biphenyl]-4-ylmethyl]-2H-imidazol-2-one;
1,4-dipropyl-1,3-dihydro-3-[2'-(1H-tetrazol-5-yl)[1,1'-biphenyl]-4-ylmethyl]-2H-imidazol-2-one;
1-isopropyl-4-propyl-1,3-dihydro-3-[2'-(1H-tetrazol-5-yl)[1,1'-biphenyl]-4-ylmethyl]-2H-imidazol-2-one;
1-butyl-4-propyl-1,3-dihydro-3-[2'-(1H-tetrazol-5-yl)(1,1'-biphenyl]-4-ylmethyl]-2H-imidazol-2-one;
1-secbutyl-4-propyl-1,3-dihydro-3-[2'-(1H-tetrazol-5-yl[1,1'-biphenyl]-4-ylmethyl]-2H-imidazol-2-one;
1-isobutyl-4-propyl-1,3-dihydro-3-[2'-(1H-tetrazol-5-yl)[1,1'-biphenyl]-4-ylmethyl]-2H-imidazol-2-one;
1-tertbutyl-4-propyl-1,3-dihydro-3-[2'-(1H-tetrazol-5-yl)[1,1'-biphenyl]-4-ylmethyl]-2H-imidazol-2-one;
1-pentyl-4-propyl-1,3-dihydro-3-[2'-(1H-tetrazol-5-yl)[1,1'-biphenyl]-4-ylmethyl]-2H-imidazol-2-one;
1-isopentyl-4-propyl-1,3-dihydro-3-[2'-(1H-tetrazol-5-yl)[1,1'-biphenyl]-4-ylmethyl]-2H-imidazol-2-one;
1-cyclohexyl-4-proyl-1,3-dihydro-3-[2'-(1H-tetrazol-5-yl)[1,1'-biphenyl]-4-ylmethyl]-2H-imidazol-2-one;
1-cyclohexylmethyl-4-propyl-1,3-dihydro-3-[2'-(1H-tetrazol-5-yl)[1,1'-biphenyl]-4-ylmethyl]-2H-imidazol-2-one;
1-(2-cyclohexylmethyl)-4-propyl-1,3-dihydro-3-[2'-(1H-tetrazol-5-yl)[1,1'-biphenyl]-4-ylmethyl]-2H-imidazol-2-one;
1-phenylmethyl-4-propyl-1,3-dihydro-3-[2'-(1H-tetrazol-5-yl)[1,1'-biphenyl]-4-ylmethyl]-2H-imidazol-2-one;
1-(2-phenylethyl)-4-propyl-1,3-dihydro-3-[2'-(1H-tetrazol-5-yl)[1,1'-biphenyl]-4-ylmethyl]-2H-imidazol-2-one;
1-(2-phenyl)-4-propyl-1,3-dihydro-3-[2'-(1H-tetrazol-5-yl)[1,1'-biphenyl]-4-ylmethyl]-2H-imidazol-2-one;
1-ethyl-4-cyclohexyl-1,3-dihydro-3-[2'-(1H-tetrazol-5-yl)[1,1'-biphenyl]-4-ylmethyl]-2H-imidazol-2-one;
1-propyl-4-cyclohexyl-1,3-dihydro-3-[2'-(1H-tetrazol-5-yl)[1,1'-biphenyl]-4-ylmethyl]-2H-imidazol-2-one;
1-isopropyl-4-cyclohexyl-1,3-dihydro-3-[2'-(1H-tetrazol-5-yl)[1,1'-biphenyl]-4-ylmethyl]-2H-imidazol-2-one;
1-butyl-4-cyclohexyl-1,3-dihydro-3-[2'-(1H-tetrazol-5-yl)[1,1'-biphenyl]-4-ylmethyl]-2H-imidazol-2-one;
1-secbutyl-4-cyclohexyl-1,3-dihydro-3-[2'-(1H-tetrazol-5-yl)[1,1'-biphenyl]-4-ylmethyl]-2H-imidazol-2-one;
1-isobutyl-4-cyclohexyl-1,3-dihydro-3-[2'-(1H-tetrazol-5-yl)[1,1'-biphenyl]-4-ylmethyl]-2H-imidazol-2-one;
1-tertbutyl-4-cyclohexyl-1,3-dihydro-3-[2'-(1H-tetrazol-5-yl)[1,1'-biphenyl]-4-ylmethyl]-2H-imidazol-2-one;
1-pentyl-4-cyclohexyl-1,3-dihydro-3-[2'-(1H-tetrazol-5-yl)[1,1'-biphenyl]-4-ylmethyl]-2H-imidazol-2-one;
1-isopentyl-4-cyclohexyl-1,3-dihydro-3-[2'-(1H-tetrazol-5-yl)[1,1'-biphenyl]-4-ylmethyl]-2H-imidazol-2-one;
1,4-dicyclohexyl-1,3-dihydro-3-[2'-(1H-tetrazol-5-yl)[1,1'-biphenyl]-4-ylmethyl]-2H-imidazol-2-one;
1-cyclohexylmethyl-4-cyclohexyl-1,3-dihydro-3-[2'-(1H-tetrazol-5-yl)[1,1'-biphenyl]-4-ylmethyl]-2H-imidazol-2-one;
1-(2-cyclohexylethyl)-4-cyclohexyl-1,3-dihydro-3-[2'-(1H-tetrazol-5yl)[1,1'-biphenyl]-4-ylmethyl]-2H-imidazol-2-one;
1-phenyl-4-cyclohexyl-1,3-dihydro-3-[2'-(1H-tetrazol-5-yl)[1,1'-biphenyl]-4-ylmethyl]-2H-imidazol-2-one;
1-phenylmethyl-4-cyclohexyl-1,3-dihydro-3-[2'-(1H-tetrazol-5-yl)[1,1'-biphenyl]-4-ylmethyl]-2H-imidazol-2-one;
1-(2-phenylethyl)-4-cyclohexyl-1,3-dihydro-3-[2'-(1H-tetrazol-5-yl)[1,1'-biphenyl]-4-ylmethyl]-2H-imidazol-2-one;
1-propyl-4-butyl-5-fluoro-1,3-dihydro-3-[2'-(1H-tetrazol-5-yl)[1,1'-biphenyl]-4-ylmethyl]-2H-imidazol-2-one;
1,4-dibutyl-5-fluoro-1,3-dihydro-3-[2'-(1H-tetrazol-5-yl)[1,1'-biphenyl]-4-ylmethyl]-2H -imidazol-2-one;
1-(2-phenylmethyl)-4-butyl-5-fluoro-1,3-dihydro-3-[2'-(1H-tetrazol-5-yl)[1,1'-biphenyl]-4-ylmethyl]-2H-imidazol-2-one;
1-propyl-4-butyl-5-chloro-1,3-dihydro-3-[2'-(1H-tetrazol-5-yl)[1,1'-biphenyl]-4-ylmethyl]-2H-imidazol-2-one;
1,4-dibutyl-5-chloro-1,3-dihydro-3-[2'-(1H-tetrazol-5-yl)[1,1'-biphenyl]-4-ylmethyl]-2H-imidazol-2-one;
1-(2-phenylmethyl)-4-butyl-5-chloro-1,3-dihydro-3-[2'-(1H-tetrazol-5-yl)[1,1'-biphenyl]-4-ylmethyl]-2H-imidazol-2-one;
1-propyl-4-butyl-5-formyl-1,3-dihydro-3-[2'-(1H-tetrazol-5-yl)[1,1'-biphenyl]-4-ylmethyl]-2H-imidazol-2-one;
1,4-dibutyl-5-formyl-1,3-dihydro-3-[2'-(1H-tetrazol-5-yl)[1,1'-biphenyl]-4-ylmethyl]-2H-imidazol-2-one;
1-(2-phenylethyl)-4-butyl-5-formyl-1,3-dihydro-3-[2'-(1H-tetrazol-5-yl)[1,1'-biphenyl]-4-ylmethyl]-2H-imidazol-2-one;
1-propyl-4-butyl-5-dimethoxymethyl-1,3-dihydro-3-[2'-(1H-tetrazol-5yl)[1,1'-biphenyl]-4-ylmethyl]-2H-imidazol-2-one;
1,4-dibutyl-5-dimethoxymethyl-1,3-dihydro-3-[2'-(1H-tetrazol-5-yl)[1,1'-biphenyl]-4-ylmethyl]-2H-imidazol-2-one;
1-(2-phenylethyl)-4-butyl-5-dimethoxymethyl-1,3-dihydro-3-[2'-(1H-tetrazol-5-yl)[1,1'-biphenyl]-4-ylmethyl]-2H-imidazol-2-one;
1-propyl-4-butyl-5-methyl-1,3-dihydro-3-[2'-(1H-tetrazol-5-yl)[1,1'-biphenyl]-4-ylmethyl]-2H-imidazol-2-one;
1,4-dibutyl-5-methyl-1,3-dihydro-3-[2'-(1H-tetrazol-5-yl)[1,1'-biphenyl]-4-ylmethyl]-2H-imidazol-2-one;
1-propyl-4-butyl-5-fluoromethyl-1,3-dihydro-3-[2'-(1H-tetrazol-5-yl)[1,1'-biphenyl]-4-ylmethyl]-2H-imidazol-2-one;

1,4-dibutyl-5-fluoromethyl-1,3-dihydro-3-[2'-(1H-tetrazol-5-yl)[1,1'-biphenyl]-4-ylmethyl]-2H-imidazol-2-one;

1-(2-phenylethyl)-4-butyl-5-fluoromethyl-1,3-dihydro-3-[2'-(1H-tetrazol-5-yl)[1,1'-biphenyl]-4-ylmethyl]-2H-imidazol-2-one;

1-propyl-4-butyl-5-difluoromethyl-1,3-dihydro-3-[2'-(1H-tetrazol-5-yl)[1,1'-biphenyl]-4-ylmethyl]-2H-imidazol-2-one;

1,4-dibutyl-5-difluoromethyl-1,3-dihydro-3-[2'-(1H-tetrazol-5-yl)[1,1'-biphenyl]-4-ylmethyl]-2H-imidazol-2-one;

1-(2phenylethyl)-4-butyl-5-difluoromethyl-1,3-dihydro-3-[2'-(1H-tetrazol-5-yl)[1,1'-biphenyl]-4-ylmethyl]-2H-imidazol-2-one;

1-propyl-4-butyl-5-trifluoromethyl-1,3-dihydro-3-[2'-(1H-tetrazol-5-yl)[1,1'-biphenyl]-4-ylmethyl]-2H-imidazol-2-one;

1,4-dibutyl-5-trifluoromethyl-1,3-dihydro-3-[2'-(1H-tetrazol-5-yl)[1,1'-biphenyl]-4-ylmethyl]-2H-imidazol-2-one;

1-(2-phenylmethyl)-4-butyl-5-trifluoromethyl-1,3-dihydro-3-[2'-(1H-tetrazol-5yl)[1,1'-biphenyl]-4-ylmethyl]-2H-imidazol-2-one;

1,4-dipropyl-5-fluoro-1,3-dihydro-3-[2'-(1H-tetrazol-5-yl)[1,1'-biphenyl]-4-ylmethyl]-2H-imidazol-2-one;

1-butyl-4-5-fluoro-1,3-dihydro-3-[2'-(1H-tetrazol-5-yl)[1,1'-biphenyl]-4-ylmethyl]-2H-imidazol-2-one;

1-(2-phenylethyl)-4-propyl-5-fluoro-1,3-dihydro-3-[2'-(1H-tetrazol-5-yl)[1,1'-biphenyl)-4-ylmethyl]-2H-imidazol-2-one;

1,4-dipropyl-5-chloro-1,3-dihydro-3-[2'-(1H-tetrazol-5-yl)[1,1'-biphenyl]-4-ylmethyl]-2H-imidazol-2-one;

1-butyl-4-propyl-5-chloro-1,3-dihydro-3-[2'-(1H-tetrazol-5-yl)[1,1'-biphenyl]-4-ylmethyl]-2H-imidazol-2-one;

1-(2-phenylethyl)-4-propyl-5-chloro-1,3-dihydro-3-[2'-(1H-tetrazol-5-yl)[1,1'-biphenyl]-4-ylmethyl]-2H-imidazol-2-one;

1,4-dipropyl-5-formyl-1,3-dihydro-3-[2'-(1H-tetrazol-5-yl)[1,1'-biphenyl]-4-ylmethyl]-2H-imidazol-2-one;

1-butyl-4-propyl-5-formyl-1,3-dihydro-3-[2'-(1H-tetrazol-5-yl)[1,1'-biphenyl]-4-ylmethyl]-2H-imidazol-2-one;

1-(2-phenylethyl)-4-propyl-5-formyl-1,3-dihydro-3-[2'-(1H-tetrazol-5-yl)[1,1'-biphenyl]-4-ylmethyl]-2H-imidazol-2-one;

1,4-dipropyl-5-dimethoxymethyl-1,3-dihydro-3-[2'-(1H-tetrazol-5yl)[1,1'-biphenyl]-4-ylmethyl]-2H-imidazol-2-one;

1-butyl-4-propyl-5-dimethoxymethyl-1,3-dihydro-3-[2'-(1H-tetrazol-5-yl)[1,1'-biphenyl]-4-ylmethyl]-2H-imidazol-2-one;

1-(2-phenylethyl)-4-propyl-5-dimethoxymethyl-1,3-dihydro-3-[2'-(1H-tetrazol-5-yl)[1,1'-biphenyl -4-ylmethyl]-2H-imidazol-2-one;

1,4-dipropyl-5-methyl-1,3-dihydro-3-[2'-(1H-tetrazol-5-yl)[1,1'-biphenyl]-4-ylmethyl]-2H-imidazol-2-one;

1-butyl-4-propyl-5-methyl-1,3-dihydro-3-[2'-(1H-tetrazol-5-yl)[1,1'-biphenyl]-4-ylmethyl]-2H-imidazol-2-one;

1-[2-phenylethyl)-4-propyl-5-methyl-1,3-dihydro-3-[2'-(1H-tetrazol-5-yl)[1,1'-biphenyl]-4-ylmethyl]-2H-imidazol-2-one;

1,4-dipropyl-5-fluoromethyl-1,3-dihydro-3-[2'-(1H-tetrazol-5-yl)[1,1'-biphenyl]-4-ylmethyl]-2H-imidazol-2-one;

1-butyl-4-propyl-5-fluoromethyl-1,3-dihydro-3-[2'-(1H-tetrazol-5-yl)[1,1'-biphenyl]-4-ylmethyl]-2H-imidazol-2-one;

1-(2-phenylethyl)-4-propyl-5-fluoromethyl-1,3-dihydro-3-[2'-(1H-tetrazol-5-yl)[1,1'-biphenyl]-4-ylmethyl]-2H-imidazol-2-one;

1-propyl-4-isopentyl-5-difluoromethyl-1,3-dihydro-3-[2'-(1H-tetrazol-5-yl)[1,1'-biphenyl]-4-ylmethyl]-2H-imidazol-2-one;

1-butyl-4-proyl-5-difluoromethyl-1,3-dihydro-3-[2'-(1H-tetrazol-5-yl)[1,1'-biphenyl]-4-ylmethyl]-2H-imidazol-2-one;

1-(2-phenylethyl)-4-propyl-5-difluoromethyl-1,3-dihydro-3-[2'-(1H-tetrazol-5-yl)[1,1'-biphenyl]-4-ylmethyl]-2H-imidazol-2-one;

1,4-dipropyl-5-trifluoromethyl-1,3-dihydro-3-[2'-(1H-tetrazol-5-yl)[1,1'-biphenyl]-4-ylmethyl]-2H-imidazol-2-one;

1-butyl-4-propyl-5-trifluoromethyl-1,3-dihydro-3-[2'-(1H-tetrazol-5-yl)[1,1'-biphenyl]-4-ylmethyl]-2H-imidazol-2-one;

1-(2phenylethyl)-4-propyl-5-trifluoromethyl-1,3-dihydro-3-[2'-(1H-tetrazol-5-yl)[1,1'-biphenyl]-4-ylmethyl]-2H-imidazol-2-one;

1-propyl-4-butyl-5-carboxy-1,3-dihydro-3-[2'-(1H-tetrazol-5-yl)[1,1'-biphenyl]-4-ylmethyl]-2H-imidazol-2-one;

1,4-dibutyl-5-carboxy-1,3-dihydro-3-[2'-(1H-tetrazol-5-yl)[1,1'-biphenyl]-4-ylmethyl]-2H-imidazol-2-one;

1-(2-phenylethyl)-4-butyl-5-carboxy-1,3-dihydro-3-[2'-(1H-tetrazol-5-yl)[1,1'-biphenyl]-4-ylmethyl]-2H-imidazol-2-one;

1-butyl-4-propyl-5-carboxy-1,3-dihydro-3-[2'-(1H-tetrazol-5-yl)[1,1'-biphenyl]-4-ylmethyl]-2H-imidazol-2-one; and 1,4-dipropyl-5-carboxy-1,3-dihydro-3-[2'-(1H-tetrazol-5-yl)[1,1'-biphenyl]-4-ylmethyl]-2H-imidazol-2-one.

9. The method of claim 8 wherein said compound is 1,4-dipropyl-1,3-dihydro-3-[2'-(1H-tetrazol-5-yl)[1,1-biphenyl]-4-ylmethyl]-2H-imidazol-2-one or a pharmaceutically-acceptable salt thereof.

10. The method of claim 8 wherein said compound is 1,4-dibutyl-1,3-dihydro-3-[2'-(1H-tetrazol-5-yl)[1,1'biphenyl]-4-ylmethyl]-2H-imidazol-2-one or a pharmaceutically-acceptable salt thereof.

* * * * *